US012116364B2

(12) United States Patent
Jang et al.

(10) Patent No.: US 12,116,364 B2
(45) Date of Patent: Oct. 15, 2024

(54) HETEROARYL COMPOUNDS AND USES THEREOF

(71) Applicant: APRINOIA THERAPEUTICS INC., Taipei (CN)

(72) Inventors: Ming-Kuei Jang, Taipei (CN); Paul Tempest, Taipei (CN)

(73) Assignee: APRINOIA THERAPEUTICS INC., Taipei (CN)

( * ) Notice: Subject to any disclaimer, the term of this patent is extended or adjusted under 35 U.S.C. 154(b) by 1011 days.

(21) Appl. No.: 17/054,015

(22) PCT Filed: May 9, 2019

(86) PCT No.: PCT/CN2019/086201
§ 371 (c)(1),
(2) Date: Nov. 9, 2020

(87) PCT Pub. No.: WO2019/214681
PCT Pub. Date: Nov. 14, 2019

(65) Prior Publication Data
US 2021/0253569 A1    Aug. 19, 2021

(30) Foreign Application Priority Data
May 9, 2018   (WO) ................ PCT/CN2018/086144

(51) Int. Cl.
| | |
|---|---|
| *C07D 471/04* | (2006.01) |
| *A61K 49/00* | (2006.01) |
| *A61K 51/04* | (2006.01) |
| *C07D 401/10* | (2006.01) |
| *C07D 413/10* | (2006.01) |
| *C07D 417/10* | (2006.01) |
| *C07D 417/14* | (2006.01) |
| *C07D 495/04* | (2006.01) |
| *G01N 33/68* | (2006.01) |

(52) U.S. Cl.
CPC ........ *C07D 471/04* (2013.01); *A61K 49/0021* (2013.01); *A61K 51/0455* (2013.01); *C07D 401/10* (2013.01); *C07D 413/10* (2013.01); *C07D 417/10* (2013.01); *C07D 417/14* (2013.01); *C07D 495/04* (2013.01); *G01N 33/6896* (2013.01); *G01N 2800/2821* (2013.01)

(58) Field of Classification Search
CPC ............... C07D 401/02; C07D 401/01; C07D 471/04; A61K 49/0021
See application file for complete search history.

(56) References Cited

U.S. PATENT DOCUMENTS

| | | |
|---|---|---|
| 3,833,863 A | 9/1974 | Webster et al. |
| 5,130,228 A | 7/1992 | Wade et al. |
| 5,264,329 A | 11/1993 | Wade et al. |
| 7,060,697 B2 | 6/2006 | Marsilje et al. |
| 7,910,579 B2 | 3/2011 | Kudo et al. |
| 9,750,816 B2 | 9/2017 | Bradner et al. |
| 9,770,512 B2 | 9/2017 | Bradner et al. |
| 9,808,542 B2 | 11/2017 | Walji et al. |
| 9,821,068 B2 | 11/2017 | Bradner et al. |
| 10,125,114 B2 | 11/2018 | Bradner et al. |
| 10,308,871 B2 | 6/2019 | Yano |
| 10,464,925 B2 | 11/2019 | Bradner et al. |
| 10,604,516 B2 | 3/2020 | Higuchi et al. |
| 10,669,253 B2 | 6/2020 | Bradner et al. |
| 10,730,870 B2 | 8/2020 | Crew et al. |
| 10,772,962 B2 | 9/2020 | Qian et al. |
| 10,849,980 B2 | 12/2020 | Bradner et al. |
| 2006/0018825 A1 | 1/2006 | Kudo et al. |
| 2009/0028787 A1 | 1/2009 | Gravenfors et al. |
| 2009/0257949 A1 | 10/2009 | Hefti et al. |
| 2010/0239496 A1 | 9/2010 | Gangadharmath et al. |
| 2011/0130305 A1 | 6/2011 | Patton et al. |
| 2012/0214994 A1 | 8/2012 | Chi et al. |
| 2014/0147428 A1 | 5/2014 | Shchepinov |
| 2015/0197498 A1 | 7/2015 | Song et al. |
| 2017/0189566 A1 | 7/2017 | Tu et al. |
| 2017/0233655 A1 | 8/2017 | Saito |
| 2017/0362507 A1 | 12/2017 | Okabe |
| 2018/0125821 A1 | 5/2018 | Crew et al. |
| 2020/0085793 A1 | 3/2020 | Crew et al. |
| 2023/0047178 A1 | 2/2023 | Jang et al. |
| 2023/0374006 A1 | 11/2023 | Jang et al. |

FOREIGN PATENT DOCUMENTS

| | | |
|---|---|---|
| AU | 2017204357 A1 | 8/2017 |
| CN | 1791592 A | 6/2006 |
| CN | 1867552 A | 11/2006 |
| CN | 102639135 B | 3/2015 |

(Continued)

OTHER PUBLICATIONS

Notice of Allowance on U.S. Appl. No. 17/477,479 DTD Feb. 15, 2023.
International Preliminary Report on Patentability dated Nov. 23, 2023 issued in International Application No. PCT/IB2021/054167, 9 pages.
Final Office Action on U.S. Appl. No. 17/477,479 DTD Nov. 28, 2022.
Non-Final Office Action on U.S. Appl. No. 17/687,570 DTD Nov. 7, 2022.
Notice of Allowance on U.S. Appl. No. 17/687,570 DTD Dec. 7, 2022.
International Report on Patentability dated May 17, 2022 issued in International Application No. PCT/US2020/060459 by the International Bureau of WIPO, 5 pages.

(Continued)

*Primary Examiner* — James W Rogers
(74) *Attorney, Agent, or Firm* — FOLEY & LARDNER LLP

(57) ABSTRACT

Described herein are compounds of formula (I), and pharmaceutically acceptable salts, solvates, hydrates, isotopically labeled derivatives and radiolabeled derivative thereof, and pharmaceutical compositions thereof. Also provided are methods and kits involving the inventive compounds or compositions for detecting and imaging Tau aggregates in the brain for detection of Alzheimer's disease (AD) in a subject.

14 Claims, 1 Drawing Sheet

(56) References Cited

FOREIGN PATENT DOCUMENTS

| | | |
|---|---|---|
| CN | 107207459 A | 9/2017 |
| EP | 1 655 287 A1 | 5/2006 |
| EP | 2 397 139 A1 | 12/2011 |
| JP | S4874796 A | 10/1973 |
| JP | S55-053333 A | 4/1980 |
| JP | S61-275836 A | 12/1986 |
| JP | H03-144569 A | 6/1991 |
| JP | 2007-106755 A | 4/2007 |
| JP | 2009-519239 A | 5/2009 |
| JP | 2011-512354 A | 4/2011 |
| JP | 2011-516866 A | 5/2011 |
| JP | 2012-102106 A | 5/2012 |
| TW | 201722957 A | 7/2017 |
| TW | 201722958 A | 7/2017 |
| WO | WO-2005/016888 A1 | 2/2005 |
| WO | WO-2007/034282 A2 | 3/2007 |
| WO | WO-2008/078424 A1 | 7/2008 |
| WO | 2010011964 A2 | 1/2010 |
| WO | WO-2010/024769 A1 | 3/2010 |
| WO | WO-2010/087315 A1 | 8/2010 |
| WO | 2011045415 A2 | 4/2011 |
| WO | WO-2011/065980 A2 | 6/2011 |
| WO | WO-2011/119565 A1 | 9/2011 |
| WO | 2015188368 A1 | 12/2015 |
| WO | WO-2016/105518 A1 | 6/2016 |
| WO | WO-2016/149668 A1 | 9/2016 |
| WO | WO-2017/007612 A1 | 1/2017 |
| WO | WO-2017/030814 A1 | 2/2017 |
| WO | WO-2018/011073 A1 | 1/2018 |
| WO | WO-2018/017370 A1 | 1/2018 |
| WO | WO-2018/102067 A2 | 6/2018 |
| WO | WO-2018/119448 A1 | 6/2018 |
| WO | WO-2019/014429 A1 | 1/2019 |
| WO | WO-2019/214681 A1 | 11/2019 |
| WO | WO-2020/006264 A1 | 1/2020 |
| WO | WO-2020/041331 A1 | 2/2020 |
| WO | WO-2021/011913 A1 | 1/2021 |

OTHER PUBLICATIONS

Non-Final Office Action on U.S. Appl. No. 17/477,411 DTD Jun. 14, 2022.
Yang, Yanping, et al., "Radiolabeled bioactive benzoheterocycles for imaging Beta-amyloid plaques in Alzheimer's disease," European Journal of Medicinal Chemistry, vol. 87, 2014, pp. 703-721.
Non-Final Office Action on U.S. Appl. No. 17/477,411 DTD Apr. 3, 2023.
STN RN 860-260-26-0, entered Aug. 15, 2005.
Aakeroy, C.B. et al., Directed Supramolecular Assembly of Cu(II)-based "paddlewheels" into Infinite 1-D Chains Using Structurally Bifunctional Ligands, The Royal Society of Chemistry, Dalton Trans. 2006, pp. 1627-1635.
Arriagada et al., Neurofibrillary Tangles but not Senile Plaques Parallel Duration and Severity of Alzheimer's Diseases, Neurology, 1992, vol. 42, pp. 631-639.
Ballatore, et al., "Tau-mediated Neurodegeneration in Alzheimer's Disease and related Disorders," Nature Reviews/Neuroscience, Sep. 2007, vol. 8, pp. 663-672.
Braak, Heiko, et al., "Staging of Alzheimer disease-associated neurofibrillary pathology using paraffin sections and immunocytochemistry," Acta Neuropathol (2006), vol. 112, pp. 389-404.
Braak, Heiko, et al., "Staging of Alzheimer's Disease-Related Neurofibrillary Changes," Neurobiology of Aging, vol. 16, No. 3, (1995), pp. 271-284.
Braymer, Joseph J., et al., "Recent Development of Bifunctional Small Molecules to Study Metal-Amyloid-B Species in Alzheimer's Disease," International Journal of Alzheimer's Disease, vol. 2011, Article ID 623051, (2011), doi: 10.4061/2011/623051, 9 pages.
DeVos, Sarah L., et al., "Synaptic Tau Seeding Precedes Tau Pathology in Human Alzheimer's Disease Brain," Frontiers in Neuroscience, Apr. 2018, vol. 12, Article 267, 15 pages.
Ehrenberg, Benjamin, et al., "Surface potential on purple membranes and its sidedness studied by a resonance Raman dye probe", Biophysical Journal, 1984, vol. 45, pp. 663-670.
Etaiw et al., "Photophysics of benzazole derived push-pull butadienes: A highly sensitive fluorescence probes", Journal of Photochemistry and Photobiology, A: Chemistry, 2006, vol. 177, No. 2-3, pp. 238-247.
Final Office Action on U.S. Appl. No. 16/798,226 DTD Feb. 16, 2021.
Final Office Action on U.S. Appl. No. 16/798,226 DTD Sep. 7, 2021.
Final Office Action on U.S. Appl. No. 17/320,882 DTD Dec. 20, 2021.
International Search Report dated Feb. 9, 2021 issued in International Application No. PCT/US2020/060459, 3 pages.
International Search Report dated May 12, 2021 issued in International Application No. PCT/IB2020/057415, 10 pages.
International Search Report for PCT/JP2012/083286, mailed Mar. 5, 13, 3 pgs.
Kfoury, Najla, et al., "Trans-cellular Propagation of Tau Aggregation by Fibrillar Species," The Journal of Biological Chemistry, vol. 287, No. 23, (2012), pp. 19440-19451.
Kung, H.F. et al. (Dec. 19, 2001). "Novel stilbenes as probes for amyloid plaques," J Am Chem Soc 123(50):12740-12741.
La Clair, James J., "Selective Detection of the Carbohydrate-Bound State of Concanavalin A at the Single Molecule Level", Journal of the American Chemical Society, 1997, vol. 119, No. 33, pp. 7676-7684.
Matsumura, K. et al. (2011). "Phenyldiazenyl benzothiazole derivatives as probes for in vivo imaging of neurofibrillary tangles in Alzheimer's disease brains," Med. Chem. Comm. 2:596-600.
Non-Final Office Action on U.S. Appl. No. 16/798,226 DTD Oct. 26, 2020.
Non-Final Office Action on U.S. Appl. No. 17/320,882 DTD Oct. 7, 2021.
Non-Final Office Action on U.S. Appl. No. 17/320,913 DTD Sep. 21, 2021.
Notice of Allowance on U.S. Appl. No. 14/346,914 DTD Nov. 1, 2019.
Notice of grant for patent dated Jul. 30, 2019 issued in Australian Application No. 2017204357, 1 page.
Rudikoff, Stuart, et al., "Single amino acid substitution altering antigen-binding specificity," Proc. Natl. Acad. Sci. USA, vol. 79, (1982), pp. 1979-1983.
Sanders, David W., et al., "Distinct Tau Prion Strains Propagate in Cells and Mice and Define Different Tauopathies," Neuron, vol. 82, (2014), pp. 1271-1288.
Silva, Catarina, et al., "Targeted degradation of aberrant tau in frontotemporal dementia patient-derived neuronal cell models," eLife, 2019, 8e45457, 31 pages.
Song, Lixin, et al., "Analysis of tau post-translational modifications in rTg4510 mice, a model of tau pathology," Molecular Neurodegeneration, (2015), 10:14, 11 pages.
U.S. Notice of Allowance on U.S. Appl. No. 17/320,913 DTD Nov. 29, 2021.
Wang, et al., "A near infrared dye laser pumped by nitrogen laser light", Zhongguo Jiguang, 1989, vol. 16, No. 8, pp. 492-495.
Written Opinion of the International Searching Authority dated Feb. 9, 2021 issued in International Application No. PCT/US2020/060459, 4 pages.
Xu et al. "Tau protein, aβprotein and Alzheimer's disease A protein and its role", Journal of Practice on Clinical Medicines, 2008, vol. 12, No. 3, pp. 118-120, Chinese language.
Yoshiyama, et al., Synapse Loss and Microglial Activation Precede Tangles in a P301S Tauopathy Mouse Model, Neuron, Feb. 1, 2007, vol. 53, pp. 337-351.
Zhuang, Z.P., et al., Radioiodinayed Styrylbenzenes ang Thioflavins as Probes for Amyloid Aggregates, J. Med. Chem. 2001, vol. 44, pp. 1905-1914.
International Preliminary Report on Patentability dated Sep. 18, 2020 issued in International Application No. PCT/CN2019/086201, 72 pages.

(56) References Cited

OTHER PUBLICATIONS

Final Office Action on U.S. Appl. No. 17/477,411 DTD Sep. 30, 2022.
Non-Final Office Action on U.S. Appl. No. 17/320,882 DTD Sep. 14, 2022.
Non-Final Office Action on U.S. Appl. No. 17/477,479 DTD Aug. 19, 2022.
International Search Report dated Aug. 12, 2019 issued in International Application No. PCT/CN2019/0826201, 7 pages.
Written Opinion of the International Searching Authority dated Aug. 12, 2019 issued in International Application No. PCT/CN2019/086201, 4 pages.
Klunk, William E., et al., "Uncharged thioflavin-T derivatives bind to amyloid-beta protein with high affinity and readily enter the brain," Life Sciences, vol. 69, (2001), pp. 1471-1484.
Cary, Brian P., et al., "Targeting Metal-Aβ Aggregates with Bifunctional Radioligand [11 C]L2-b and a Flourine-18 Analogue [18 F]FL2-b," ACS Medicinal Chemistry Letters, vol. 6, Nov. 9, 2014, pp. 112-116.
Nakazono, Manabu, et al., "Novel styrylbenzene derivatives for detecting amyloid deposits," Clinica Chimica Acta, vol. 436, May 9, 2014, pp. 27-34.
Ono, Maiko, et al., "Distinct binding of PET ligands PBB3 and AV-1451 to tau fibril strains in neurodegenerative tauopathies," Brain, (2017), 140(3), pp. 764-780, doi: 10.1093/brain/aww339.
Maruyama, Masahiro, et al., "Imaging of Tau Pathology in a Tauopathy Mouse Model and in Alzheimer Patients Compared to Normal Controls," Neuron, (2013), 79(6), pp. 1094-1108, doi:10.1016/j.neuron.2013.07.037.
Santacruz, K., et al., "Tau Suppression in a Neurodegenerative Mouse Model Improves Memory Function," Science, (2005), 309(5733), pp. 476-481.
Wilen, Samuel H., et al., "Strategies in Optical Resolutions," Tetrahedron Report No. 38, Tetrahedron, vol. 33, Pergamon Press, (1977), pp. 2725-2736.
Takuwa, Hiroyuki, et al., "Hemodynamic changes during neural deactivation in awake mice: A measurement by laser-Doppler flowmetry in crossed cerebellar diaschisis," Brain Research, (2013), vol. 1537, pp. 350-355, doi: 10.1016/j.brainres.2013.09.023.
Tomita, Yutaka, et al., "Long-term in vivo investigation of mouse cerebral microcirculation bymicroscopy in the area of focal ischemia," Journal of Cerebral Blood Flow & Metabolism, (2005),858-867, doi:10.1038/sj.jcbfm.9600077.
Allowance Decision from the Intellectual Property Office dated Dec. 9, 2021 issued in TW Application No. 109139798, with English translation, 4 pages.
Examination Report No. 2 for Standard patent application dated Sep. 27, 2021 issued in AU Patent Application No. 2019265346, 11 pages.
Feng, Xun, et al., "Aerobic Oxidation of Alcohols and the Synthesis of Benzoxazoles Catalyzed by a Cuprocupric Coordination Polymer (Cu+-CP) Assisted by TEMPO," Inorganic Chemistry, 2015, vol. 54, Issue No. 5, pp. 2088-2090. (Author's copy).
International Search Report and Written Opinion of the International Searching Authority dated Feb. 9, 2022 issued in International Application No. PCT/IB2021/054167, 13 pages.
Perry, Robert, J., et al., "Palladium-Catalyzed Syntheses of 2-Arylbenzothiazoles," Organometallics, 1994, vol. 13, pp. 3346-3350.
Rao, R Nishanth, et al., "Efficient access to imidazo[1,2-a]pyridines/pyrazines/pyrimidines via catalyst free annulation reaction under microwave irradiation in green solvent, "ACS Combinatorial Science, 2018, vol. 20, Issue No. 3, pp. 164-171 (Accepted Manuscript).
Santra, Sourav Kumar, et al., "Peroxide Free Pd(II)-Catalyzed ortho-Aroylation and ortho-Halogenation of Directing Arenes," J. Org. Chem., 2016, vol. 81, Issue No. 14, pp. 6066-6074. (Accepted manuscript).
Xie, Yuan-Yuan, et al., "Organic reactions in ionic liquids: cyclocondensation of a-bromoketones with 2-aminopyridine", J. Chem. Research (S), 2003, pp. 614-615. (Short Paper).

|  | Compound J | PBB3 |
|---|---|---|
| pre | 100.00% | 100.00% |
| 1min | 1078.05% | 302.38% |
| 30min | 8212.65% | 1740.44% |
| 60min | 9531.46% | 925.41% |

HETEROARYL COMPOUNDS AND USES THEREOF

CROSS-REFERENCE TO RELATED APPLICATIONS

The present application is a 371 of PCT/CN2019/086201, filed May 9, 2019, which is based upon and claims priority to PCT application PCT/CN2018/086144, filed on May 9, 2018, both of which are incorporated herein by reference in their entireties.

FIELD OF INVENTION

The present invention relates to a series of novel heteroaryl compounds, processes for preparing the compounds, intermediates and uses thereof.

PRIOR ARTS

Alzheimer's is a devastating and incurable disease marked by β-Amyloid (Aβ) and tau protein aggregations in the brain. The accumulation of β-Amyloid (Aβ) and tau proteins in the brain is hallmark pathology for Alzheimer disease. Recently developed positron emission tomography (PET) tracers, including [18F]-AV-1451, bind to tau in neurofibrillary tangles in the brain. Tau PET is a promising imaging method for Alzheimer's disease, and the imaging method can be of great significance in the development of new drugs to combat Alzheimer's disease.

The aggregation of Tau protein is also linked in many studies to other memory-related neurodegenerative disorders. Tau PET imaging is considered interesting for other neurological diseases such as frontal lobe dementia and Parkinson's-like diagnoses such as PSP (progressive supranuclear palsy) and CBD (corticobasal degeneration).

The amount of Tau aggregates present in the brain may correlate with the stage of Alzheimer's disease. New Tau PET tracer carries potential to advance the diagnosis and treatment for Alzheimer's disease and other neurodegenerative disorders. Therefore, development of new tau PET tracer is greatly needed.

CONTENT OF THE PRESENT INVENTION

The present disclosure relates to a series of novel heteroaryl compounds having a structure of formula (I), or a pharmaceutically acceptable salt, a solvate, a hydrate, an isotopically labeled derivative or a radiolabeled derivative thereof,

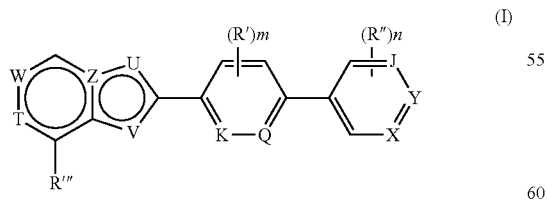

(I)

wherein, W is N—R or C—R$^1$;
R is absent or C$_{1-6}$ alkyl, and the C$_{1-6}$ alkyl of which is optionally substituted by the substituent selected from the group consisting of OH, halogen, C$_{2-6}$ heterocycloalkyloxy, toluenesulfonyloxy and phenyl which is further optionally substituted by C$_{1-3}$ alkoxy, OH or C$_{1-3}$ alkyl; the heteroatom contained in the C$_{2-6}$ heterocycloalkyloxy is selected from the group consisting of N, O and S; the number of the heteroatom contained in the C$_{2-6}$ heterocycloalkyloxy is 1, 2, 3 and 4;
R$^1$ is H, halogen, OH, NH$_2$, C$_{1-6}$ alkoxycarbonyl, C$_{1-6}$ alkyl, C$_{1-6}$ alkylamino or C$_{1-6}$ alkoxy, and OH, NH$_2$, C$_{1-6}$ alkoxycarbonyl, C$_{1-6}$ alkyl, C$_{1-6}$ alkylamino or C$_{1-6}$ alkoxy of which is optionally substituted by the substituent selected from the group consisting of halogen, OH, C$_{2-6}$ heterocycloalkyloxy and toluenesulfonyloxy;
T is C—R$^3$ or N;
R$^3$ is H, OH, C$_{1-6}$ alkoxy or halogen;
Z is N or CH;
U is N—R$^4$, S, O or C—R$^5$;
R$^4$ is absent, H, C$_{1-6}$ alkyl, C$_{1-6}$ alkoxycarbonyl, C$_{1-6}$ alkylcarbonyl or benzoyl, and the C$_{1-6}$ alkyl, C$_{1-6}$ alkoxycarbonyl, C$_{1-6}$ alkylcarbonyl and benzoyl of which is optionally substituted by the substituents selected from the group consisting of halogen, OH, C$_{1-3}$ alkoxy, C$_{2-6}$ heterocycloalkyloxy and toluenesulfonyloxy;
R$^5$ is H or C$_{1-6}$ alkyl, and the C$_{1-6}$ alkyl is optionally substituted by halogen and/or OH;
V is CH, N or NH;
Q is CH or N;
X is CH or N;
Y is CR$^6$ or N;
R$^6$ is selected from the group consisting of H, NH$_2$ and a C$_{1-6}$ alkoxy, and NH$_2$ and the C$_{1-6}$ alkoxy is optionally substituted by C$_{1-3}$ alkyl, halogenated C$_{1-3}$ alkyl and/or halogen;
J is CH or N;
K is CH or N;
provided that X and Y are not N simultaneously, and J and Y are not N simultaneously;
R' is halogen, OH, C$_{1-6}$ alkyl or C$_{1-6}$ alkoxy;
R" is halogen, OH, NH$_2$, C$_{1-6}$ alkoxy, C$_{1-6}$ alkylamino or C$_{2-6}$ heterocycloalkyl, and OH, NH$_2$, C$_{1-6}$ alkoxy, C$_{1-6}$ alkylamino and C$_{2-6}$ heterocycloalkyl of which is optionally substituted by the substituent selected from the group consisting of oxo, OH, halogen, C$_{3-6}$ cycloalkyl, C$_{1-4}$ alkoxy carbonyl, C$_{2-6}$ heterocycloalkyloxy, toluenesulfonyloxy and phenyl which is further optionally substituted by OH and/or C$_{1-3}$ alkoxy;
R'" is H, OH or halogen;
m is 0, 1, 2;
n is 0, 1, 2;
provided that U and V are both containing N atom, R$^1$ and R$^3$ are not CF$_3$ or C$_1$.
Preferably, the moiety of

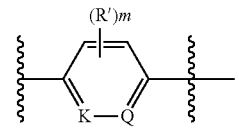

is selected from the group consisting of

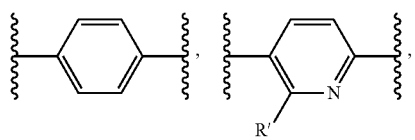

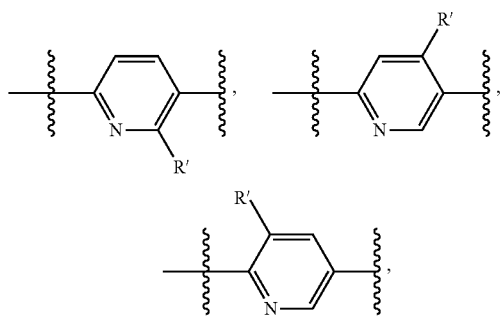

wherein R' is H or F.

Preferably, the heteroaryl compounds having a structure of formula (I), or a pharmaceutically acceptable salt, a solvate, a hydrate, an isotopically labeled derivative or a radiolabeled derivative thereof has a structure of formula (II),

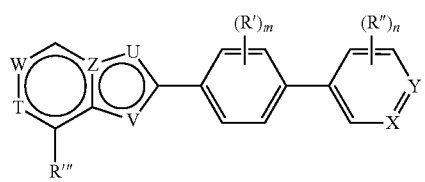

(II)

wherein, X is CH or N; Y is CH or N, provided that X and Y are not N simultaneously;

the structural unit

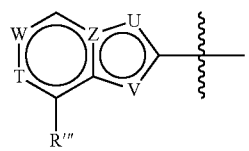

is selected from the group consisting of

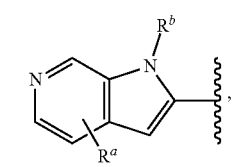

Formula I-(a)

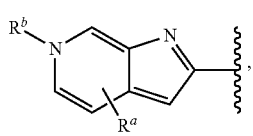

Formula I-(b)

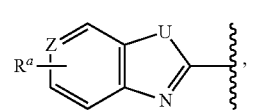

Formula I-(c)

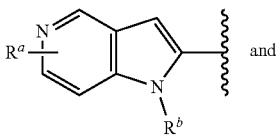

Formula I-(d)

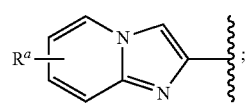

Formula I-(e)

wherein, in Formula I-(c), U is O or S; Z is CH or N;

$R^a$ is selected from the group consisting of H, OH, halogen, $C_{1-3}$ alkyl, $C_{1-3}$ alkoxy, $NH_2$, $C_{1-3}$ alkylamino and $C_{1-6}$ alkoxycarbonyl, and OH, $C_{1-3}$ alkyl, $C_{1-3}$ alkoxy, $NH_2$, $C_{1-3}$ alkylamino or $C_{1-6}$ alkoxycarbonyl of which is optionally substituted by OH, halogen, $C_{2-6}$ heterocycloalkyloxy or toluenesulfonyloxy;

$R^b$ is selected from the group consisting of H, $C_{1-6}$ alkyl, $C_{1-6}$ alkoxycarbonyl, $C_{1-3}$ alkylcarbonyl, benzyl and benzoyl, and the $C_{1-6}$ alkyl, $C_{1-6}$ alkoxycarbonyl, $C_{1-3}$ alkylcarbonyl or benzoyl of which is optionally substituted by halogen, OH, $C_{1-3}$ alkoxy, $C_{2-6}$ heterocycloalkyloxy or toluenesulfonyloxy.

Preferably, at least one of K and Q is N. In one embodiment of the present invention, K is N while Q is CH. In another embodiment of the present invention, K is CH while Q is N. In another embodiment of the present invention, K is N while Q is N.

Preferably, the structural unit

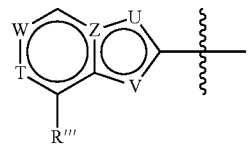

is selected from the group consisting of

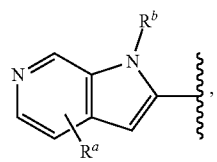

Formula I-(a)

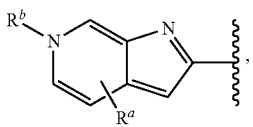

Formula I-(b)

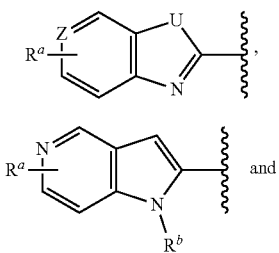

Formula I-(c)

Formula I-(d)

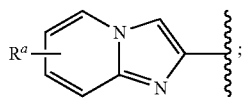

Formula I-(e)

wherein, in Formula I-(c), U is O or S; Z is CH or N;

$R^a$ is selected from the group consisting of H, OH, halogen, $C_{1-3}$ alkyl, $C_{1-3}$ alkoxy, $NH_2$, $C_{1-3}$ alkylamino and $C_{1-6}$ alkoxycarbonyl, and OH, $C_{1-3}$ alkyl, $C_{1-3}$ alkoxy, $NH_2$, $C_{1-3}$ alkylamino or $C_{1-6}$ alkoxycarbonyl of which is optionally substituted by OH, halogen, $C_{2-6}$ heterocycloalkyloxy or toluenesulfonyloxy;

$R^b$ is selected from the group consisting of H, $C_{1-6}$ alkyl, $C_{1-6}$ alkoxycarbonyl, $C_{1-3}$ alkylcarbonyl, benzyl and benzoyl, and the $C_{1-6}$ alkyl, $C_{1-6}$ alkoxycarbonyl, $C_{1-3}$ alkylcarbonyl or benzoyl of which is optionally substituted by halogen, OH, $C_{1-3}$ alkoxy, $C_{2-6}$ heterocycloalkyloxy or toluenesulfonyloxy.

Preferably, R is $C_{1-3}$ alkyl which is optionally substituted by the substituent selected from the group consisting of F, OH, p-toluenesulfonyloxy, $C_{3-5}$ heterocycloalkyloxy and phenyl which is optionally substituted by OH or methoxy.

Preferably, $R^1$ is H, F, OH, $NH_2$, $C_{1-3}$ alkoxycarbonyl, $C_{1-3}$ alkyl, $C_{1-3}$ alkylamino or $C_{1-3}$ alkoxy; and OH, $NH_2$, $C_{1-3}$ alkoxycarbonyl, $C_{1-3}$ alkyl, $C_{1-3}$ alkylamino or $C_{1-3}$ alkoxy of which is optionally substituted by the substituent selected from the group consisting of F, OH, p-toluenesulfonyloxy and $C_{3-5}$ heterocycloalkyloxy.

Preferably, $R^3$ is $C_{1-3}$ alkoxy, F or $C_1$.

Preferably, $R^4$ is $C_{1-3}$ alkyl, $C_{1-4}$ alkoxycarbonyl, $C_{1-3}$ alkylcarbonyl or benzoyl, and $C_{1-3}$ alkyl, $C_{1-4}$ alkoxycarbonyl, $C_{1-3}$ alkylcarbonyl or benzoyl of which is optionally substituted by the substituents selected from the group consisting of F, OH, methoxy, $C_{3-5}$ heterocycloalkyloxy and p-toluenesulfonyloxy.

Preferably, $R^5$ is $C_{1-3}$ alkyl.

Preferably, $R^6$ is selected from the group consisting of H, $NH_2$ and a $C_{1-3}$ alkoxy, and $NH_2$ and the $C_{1-3}$ alkoxy is optionally substituted by $C_{1-3}$ alkyl and/or F.

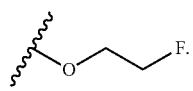

More preferably, $R^6$ is $NH_2$, methoxy, dimethylamino or

Preferably, R' is F, $C_{1-3}$ alkyl or $C_{1-3}$ alkoxy.

Preferably, R" is F, $C_{1-3}$ alkoxy, $C_{1-3}$ alkylamino or $C_{3-5}$ heterocycloalkyl, and OH, $NH_2$, $C_{1-3}$ alkoxy, $C_{1-3}$ alkylamino or $C_{3-5}$ heterocycloalkyl of which is optionally substituted by the substituent selected from the group consisting of oxo, OH, F, Cl, $C_{3-5}$ cycloalkyl, $C_{1-3}$ alkoxy carbonyl, $C_{3-5}$ heterocycloalkyloxy, p-toluenesulfonyloxy and phenyl which is further optionally substituted by OH, methoxy or ethoxy.

Preferably, R'" is F or $C_1$.

Preferably, in formula I-(c), Z is CH, U is S or O.

Preferably, $R^a$ is selected from the group consisting of H, OH, F, Cl, methyl, ethyl, methoxy, ethoxy, n-propoxy, $NH_2$, N-methylamino, N-ethylamino, N-n-propylamino, N,N-dimethylamino, methylethylamino, methoxycarbonyl and tert-butoxy carbonyl, and OH, methyl, ethyl, methoxy, ethoxy, n-propoxy, $NH_2$, N-methylamino, N-ethylamino, N-n-propylamino, N,N-dimethylamino, methylethylamino, methoxycarbonyl and tert-butoxy carbonyl of which is optionally substituted by OH, F, Cl, $C_{3-5}$ heterocycloalkyloxy or toluenesulfonyloxy.

Preferably, $R^b$ is H, $C_{1-3}$ alkyl, $C_{1-4}$ alkoxycarbonyl, $C_{1-3}$ alkylcarbonyl, benzyl or benzoyl, and the $C_{1-3}$ alkyl, $C_{1-4}$ alkoxycarbonyl, $C_{1-3}$ alkylcarbonyl or benzoyl of which is optionally substituted by F, Cl, OH, $C_{1-3}$ alkoxy, $C_{3-5}$ heterocycloalkyloxy or toluenesulfonyloxy.

Preferably, $R^a$ is H, F, OH, $NH_2$, methoxy, ethoxy,

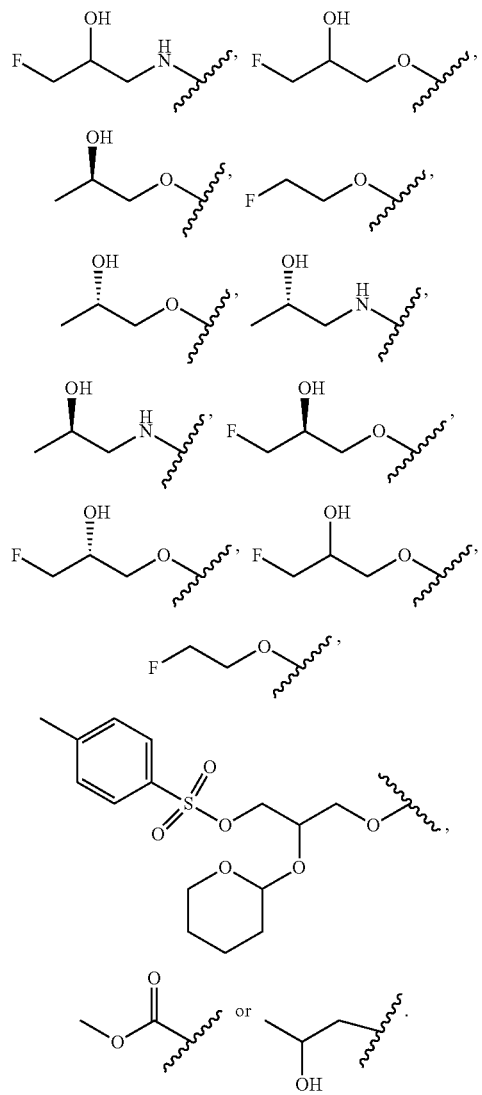

Preferably, $R^b$ is H, methyl,

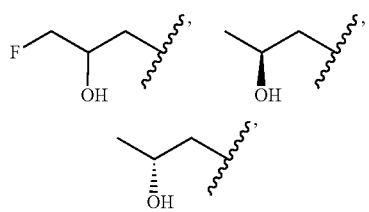

-continued
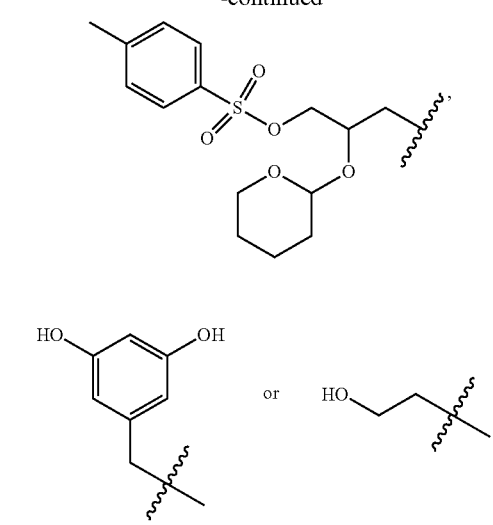
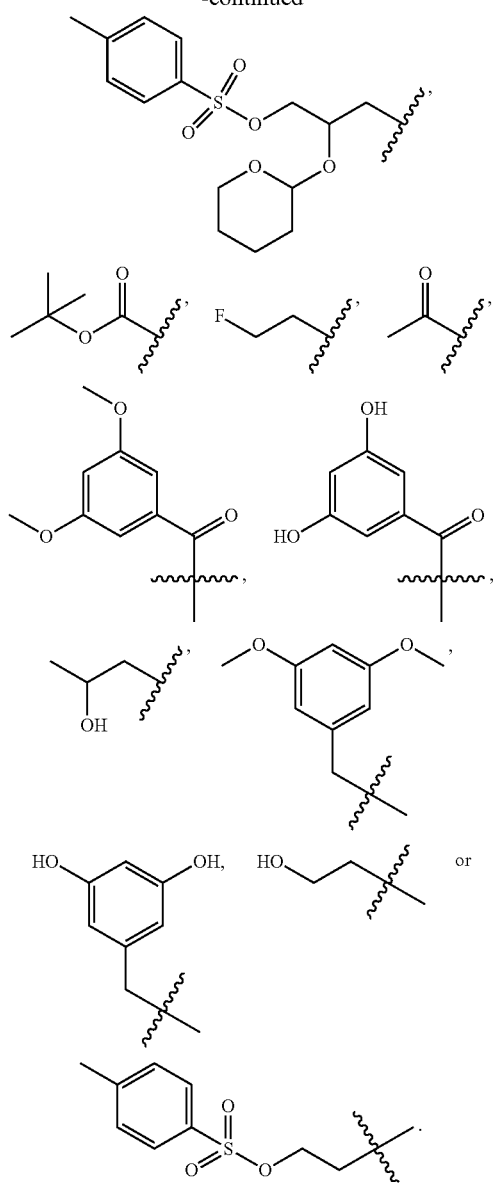
Preferably, $R^1$ is F, OH, $NH_2$.
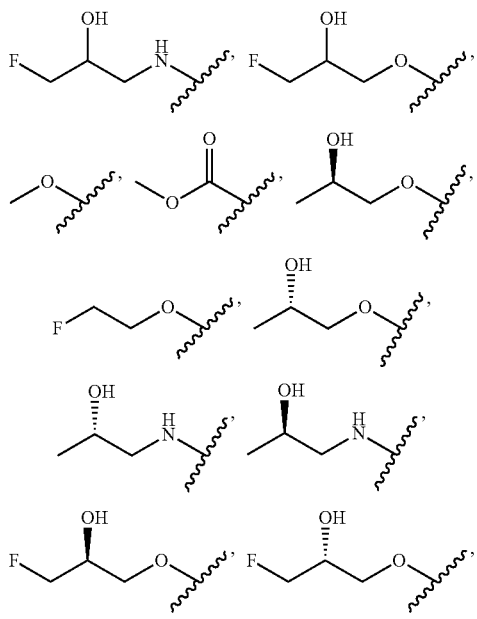
Preferably, R is
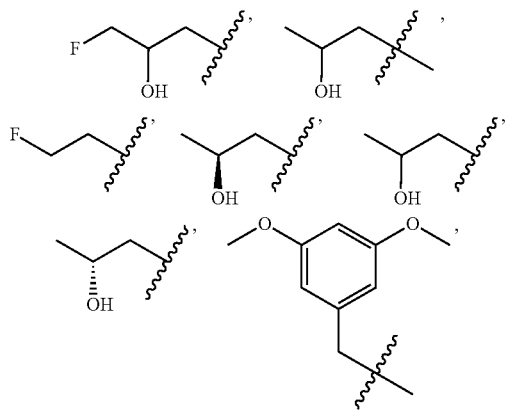
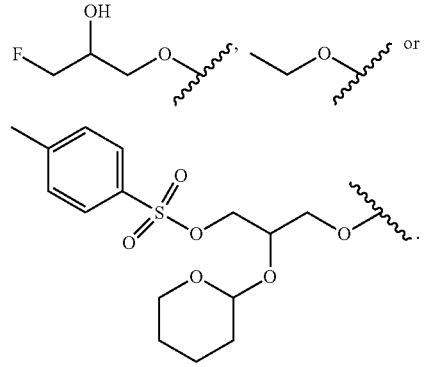
Preferably, $R^3$ is F, OH, methoxy.
Preferably, $R^4$ is H, methyl, methoxy, ethoxy,

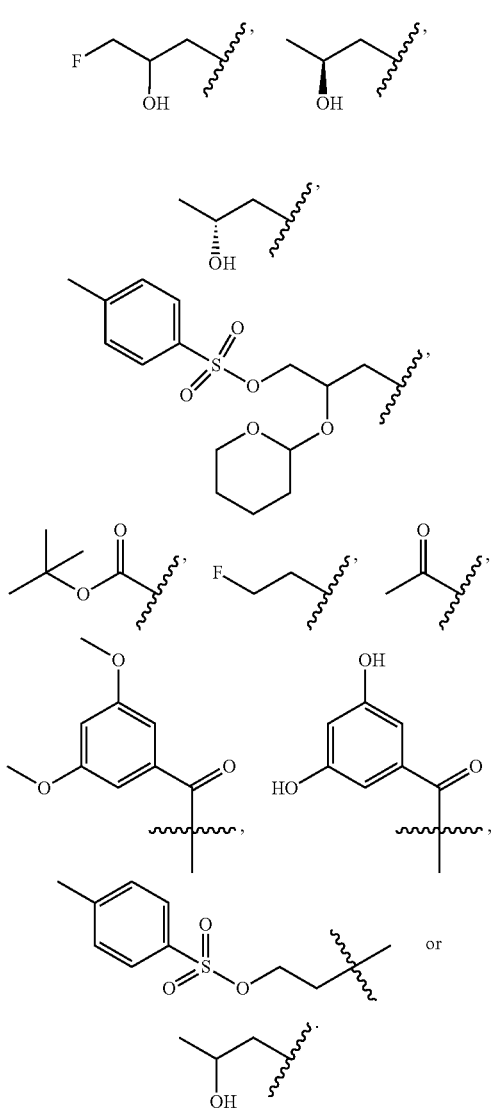
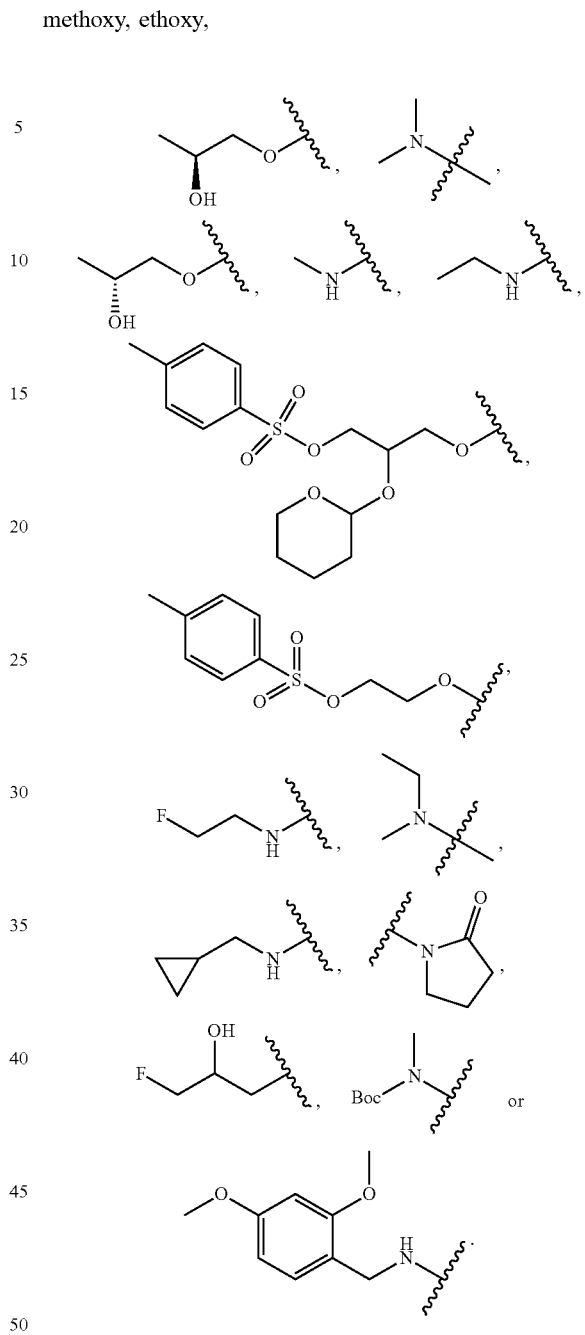

Preferably, R⁵ is H, methyl or ethyl.
Preferably, R' is F, OH, methyl or methoxy.
Preferably, R" is F, Cl, OH, NH₂, methyl,

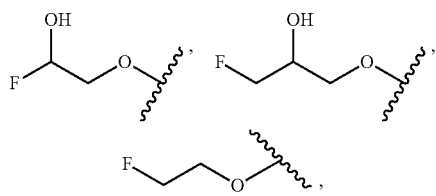

Preferably, R'" is H or F.

Preferably, the heteroaryl compounds having a structure of formula (I), or a pharmaceutically acceptable salt, a solvate, a hydrate, an isotopically labeled derivative or a radiolabeled derivative thereof is selected from the group consisting of the compounds in Table (I).

TABLE (I)

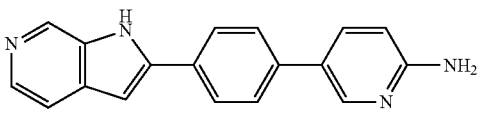 [SMILES: Nc1ccc(-c2ccc(-c3cc4ccncc4[nH]3)cc2)cn1]

TABLE (I)-continued
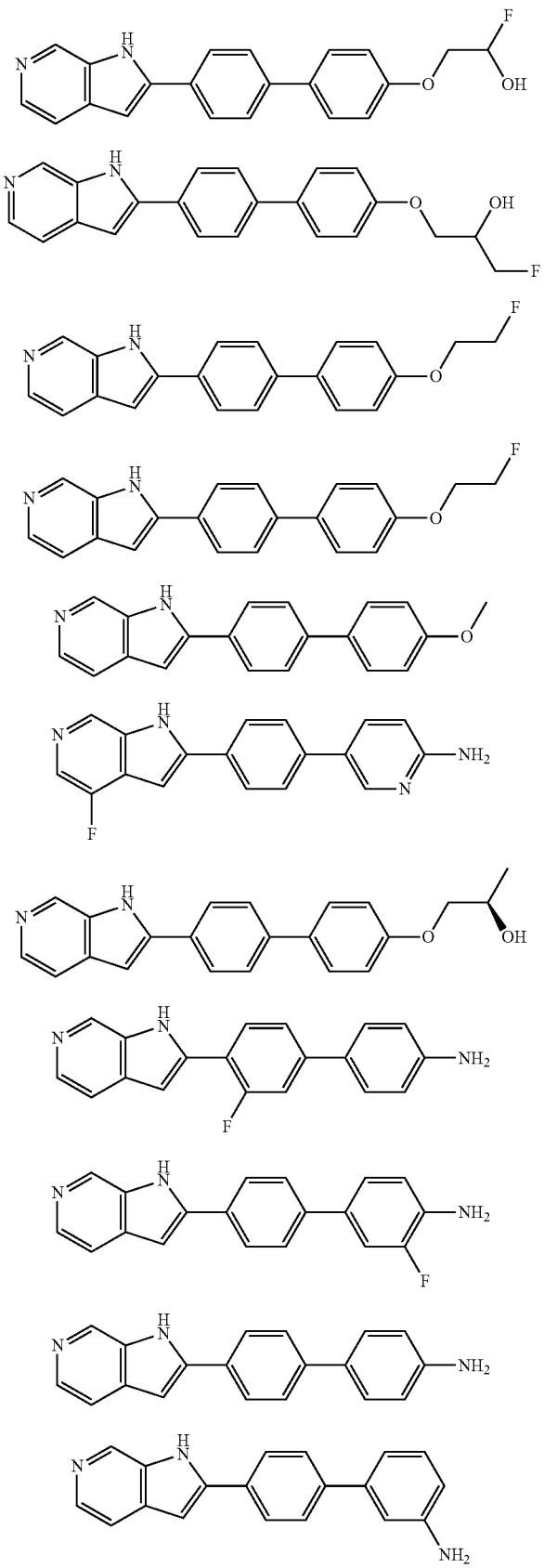

TABLE (I)-continued
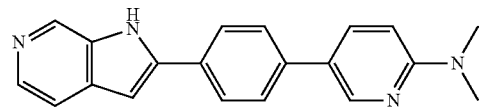 [SMILES: CN(C)c1ccc(-c2ccc(-c3cc4ccncc4[nH]3)cc2)cn1]
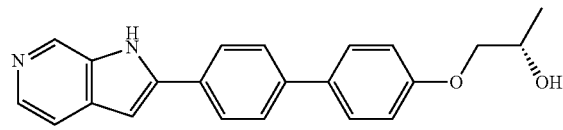 [SMILES: C[C@H](O)COc1ccc(-c2ccc(-c3cc4ccncc4[nH]3)cc2)cc1]
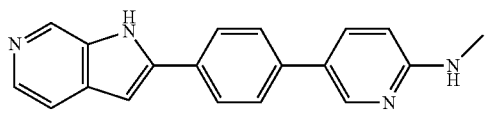 [SMILES: CNc1ccc(-c2ccc(-c3cc4ccncc4[nH]3)cc2)cn1]
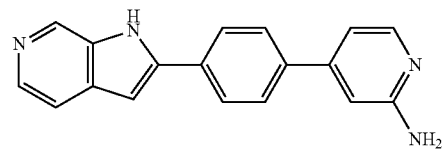
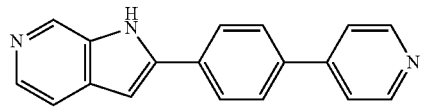 [SMILES: c1cc(-c2ccc(-c3cc4ccncc4[nH]3)cc2)ccn1]
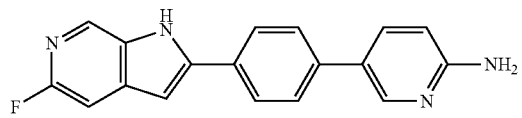 [SMILES: Nc1ccc(-c2ccc(-c3cc4cc(F)ncc4[nH]3)cc2)cn1]
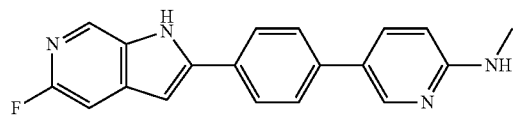 [SMILES: CNc1ccc(-c2ccc(-c3cc4cc(F)ncc4[nH]3)cc2)cn1]
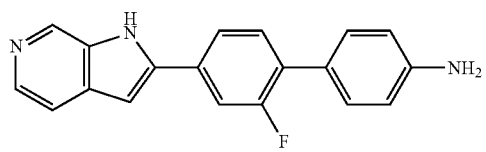 [SMILES: Nc1ccc(-c2ccc(-c3cc4ccncc4[nH]3)cc2F)cc1]
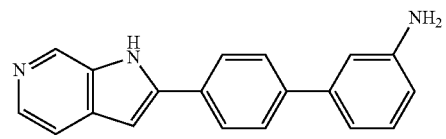 [SMILES: Nc1cccc(-c2ccc(-c3cc4ccncc4[nH]3)cc2)c1]
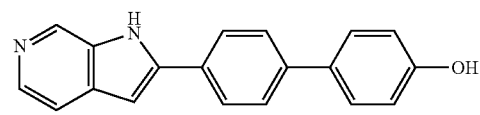 [SMILES: Oc1ccc(-c2ccc(-c3cc4ccncc4[nH]3)cc2)cc1]
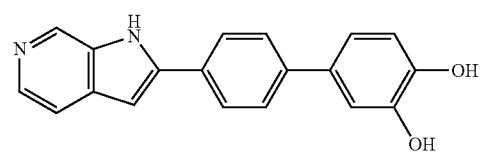 [SMILES: Oc1ccc(-c2ccc(-c3cc4ccncc4[nH]3)cc2)cc1O]
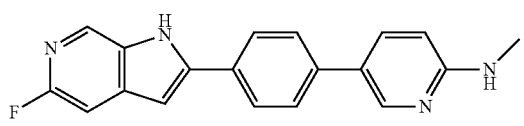

TABLE (I)-continued
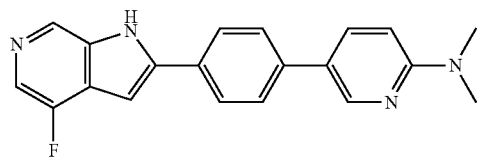 [SMILES: CN(C)c1ccc(-c2ccc(-c3cc4c(F)cncc4[nH]3)cc2)cn1]
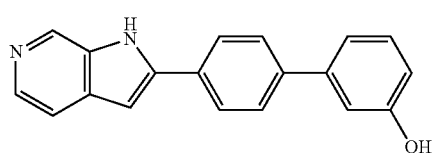
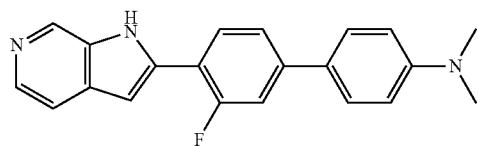
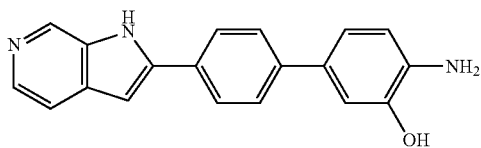 [SMILES: Nc1ccc(-c2ccc(-c3cc4ccncc4[nH]3)cc2)cc1O]
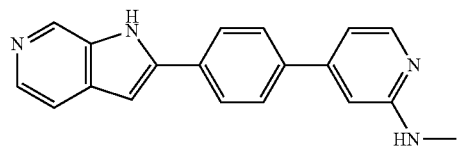 [SMILES: CNc1cc(-c2ccc(-c3cc4ccncc4[nH]3)cc2)ccn1]
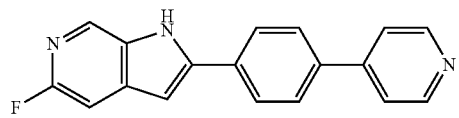 [SMILES: Fc1cc2cc(-c3ccc(-c4ccncc4)cc3)[nH]c2cn1]
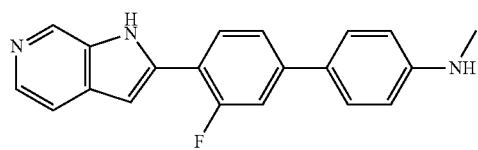 [SMILES: CNc1ccc(-c2ccc(-c3cc4ccncc4[nH]3)c(F)c2)cc1]
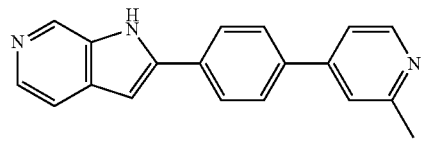 [SMILES: Cc1cc(-c2ccc(-c3cc4ccncc4[nH]3)cc2)ccn1]
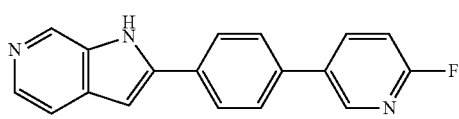 [SMILES: Fc1ccc(-c2ccc(-c3cc4ccncc4[nH]3)cc2)cn1]
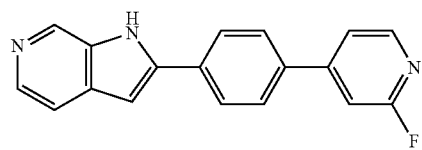 [SMILES: Fc1cc(-c2ccc(-c3cc4ccncc4[nH]3)cc2)ccn1]

TABLE (I)-continued
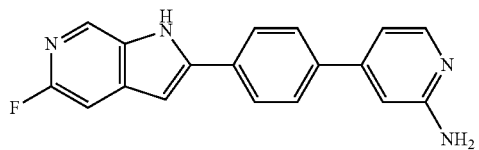 [SMILES: Nc1cc(-c2ccc(-c3cc4cc(F)ncc4[nH]3)cc2)ccn1]
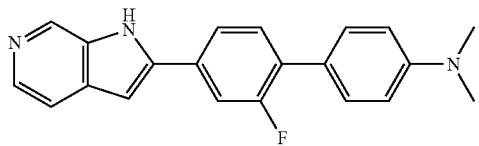
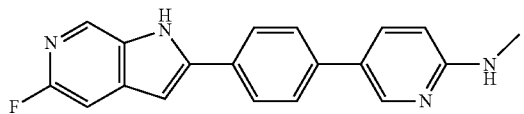
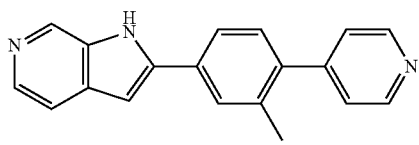 [SMILES: Cc1cc(-c2cc3ccncc3[nH]2)ccc1-c1ccncc1]
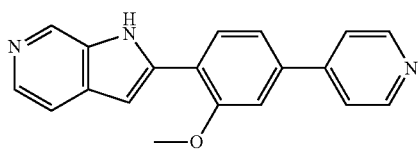 [SMILES: COc1cc(-c2ccncc2)ccc1-c1cc2ccncc2[nH]1]
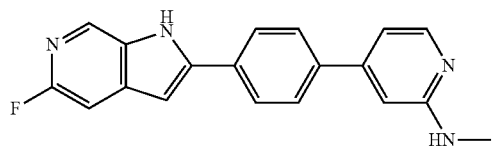 [SMILES: CNc1cc(-c2ccc(-c3cc4cc(F)ncc4[nH]3)cc2)ccn1]
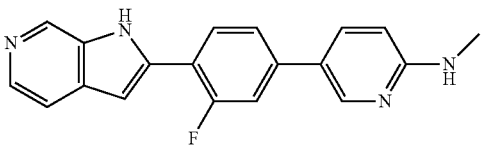 [SMILES: CNc1ccc(-c2ccc(-c3cc4ccncc4[nH]3)c(F)c2)cn1]
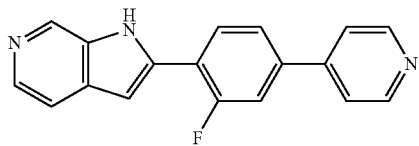 [SMILES: Fc1cc(-c2ccncc2)ccc1-c1cc2ccncc2[nH]1]
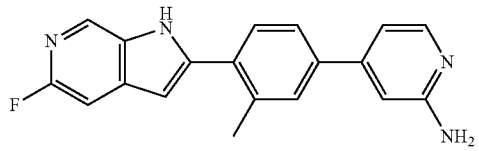 [SMILES: Cc1cc(-c2ccnc(N)c2)ccc1-c1cc2cc(F)ncc2[nH]1]
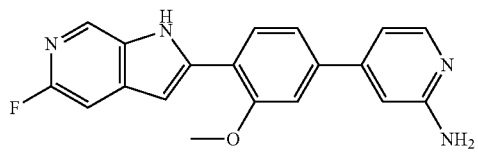 [SMILES: COc1cc(-c2ccnc(N)c2)ccc1-c1cc2cc(F)ncc2[nH]1]

TABLE (I)-continued
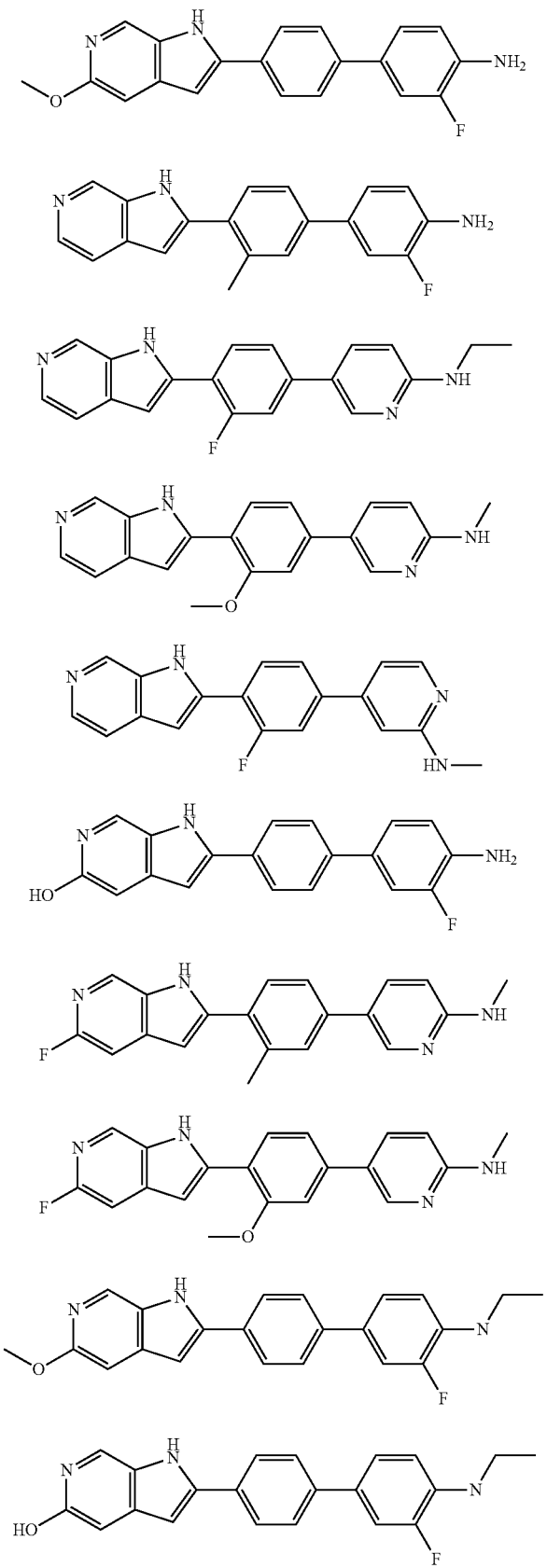

TABLE (I)-continued
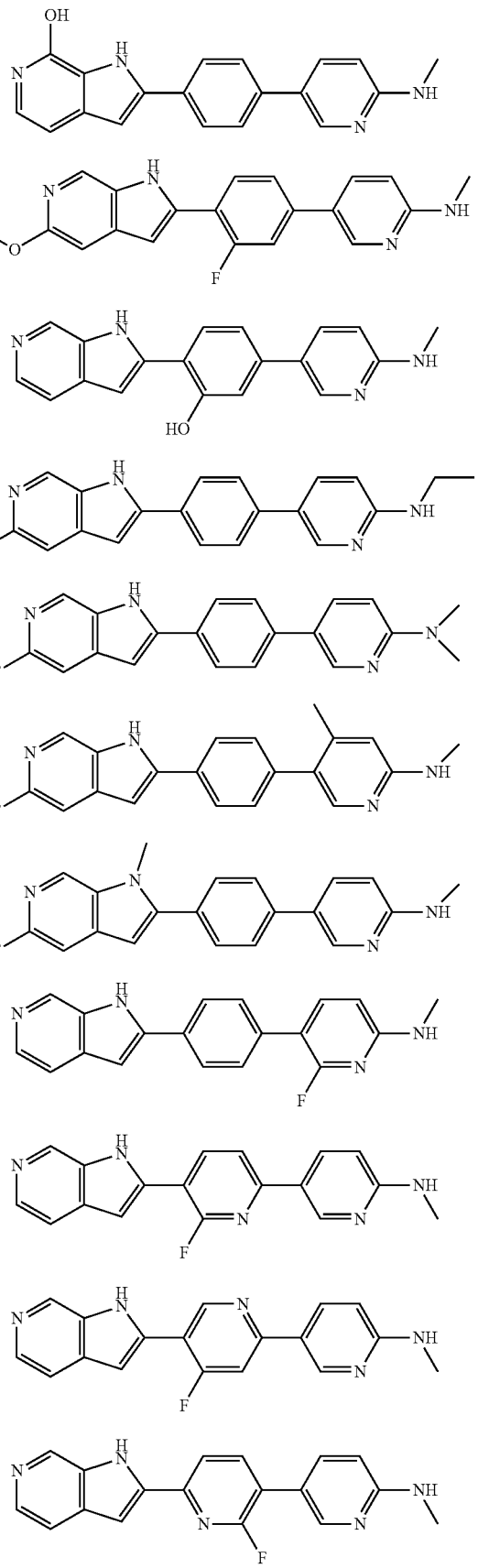

TABLE (I)-continued
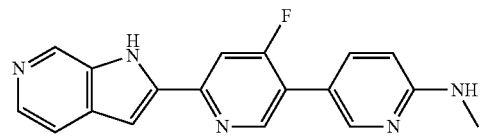 [SMILES: CNc1ccc(-c2cnc(-c3cc4ccncc4[nH]3)cc2F)cn1]
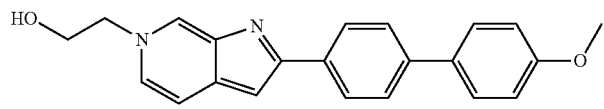 [SMILES: COc1ccc(-c2ccc(-c3cc4ccn(CCO)cc-4n3)cc2)cc1]
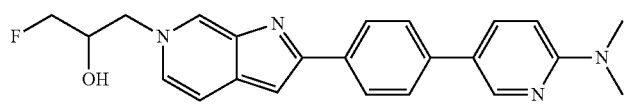
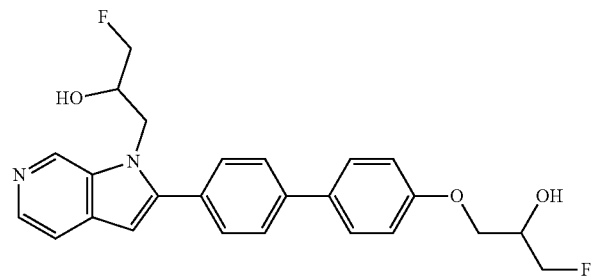 [SMILES: OC(CF)COc1ccc(-c2ccc(-c3cc4ccncc4n3CC(O)CF)cc2)cc1]
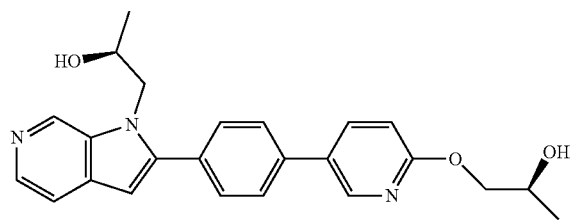 [SMILES: C[C@H](O)COc1ccc(-c2ccc(-c3cc4ccncc4n3C[C@H](C)O)cc2)cn1]
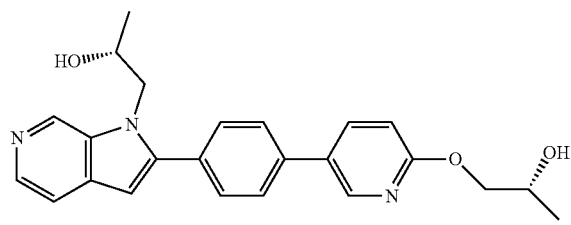 [SMILES: C[C@@H](O)COc1ccc(-c2ccc(-c3cc4ccncc4n3C[C@@H](C)O)cc2)cn1]
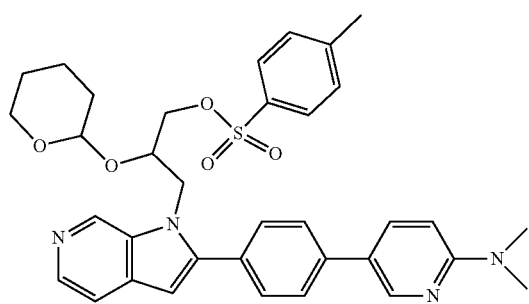 [SMILES: Cc1ccc(S(=O)(=O)OCC(Cn2c(-c3ccc(-c4ccc(N(C)C)nc4)cc3)cc3ccncc32)OC2CCCCO2)cc1]

TABLE (I)-continued
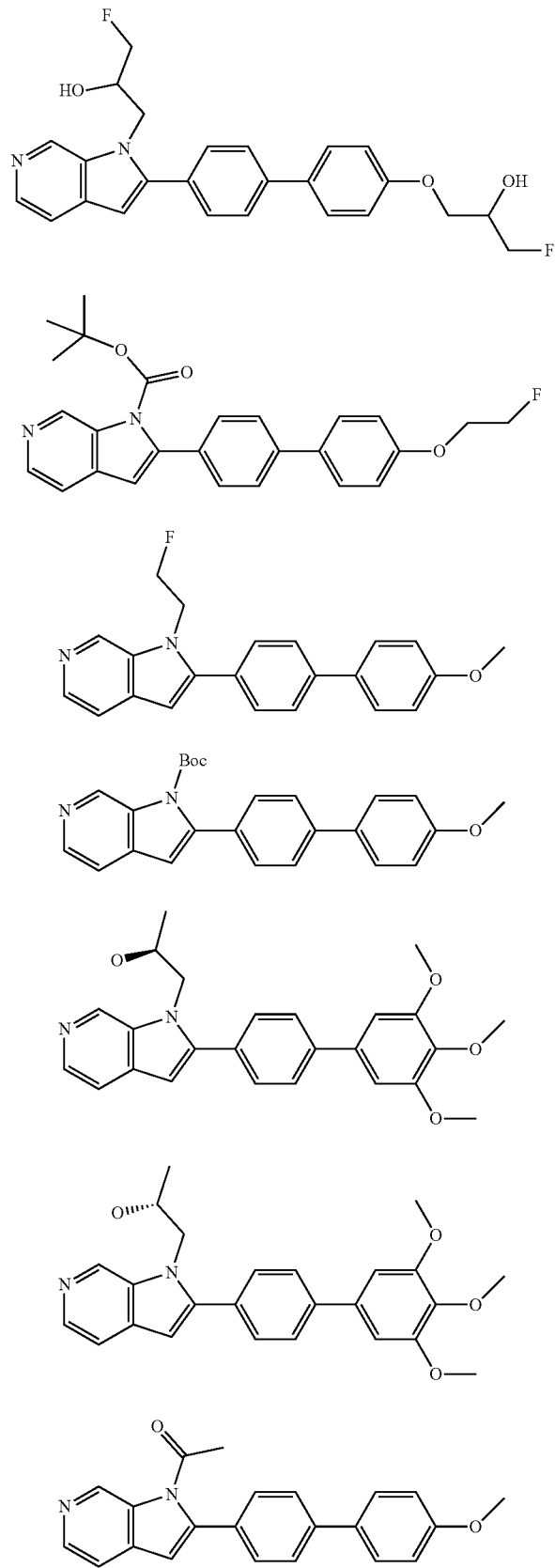

TABLE (I)-continued
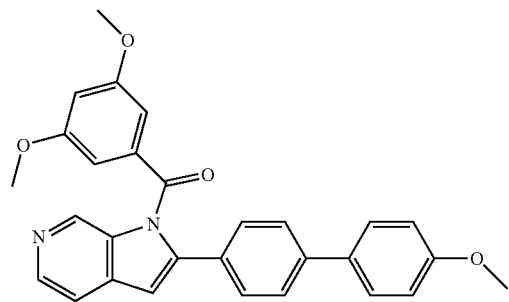
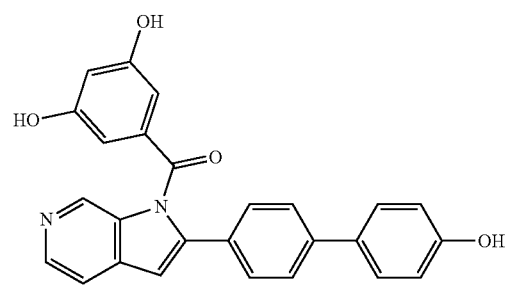 [SMILES: O=C(c1cc(O)cc(O)c1)n1c(-c2ccc(-c3ccc(O)cc3)cc2)cc2ccncc21]
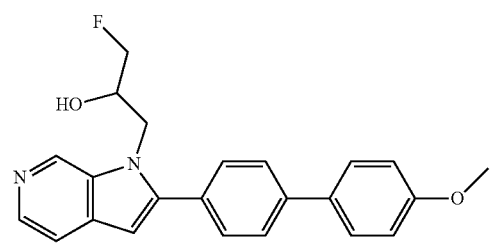 [SMILES: COc1ccc(-c2ccc(-c3cc4ccncc4n3CC(O)CF)cc2)cc1]
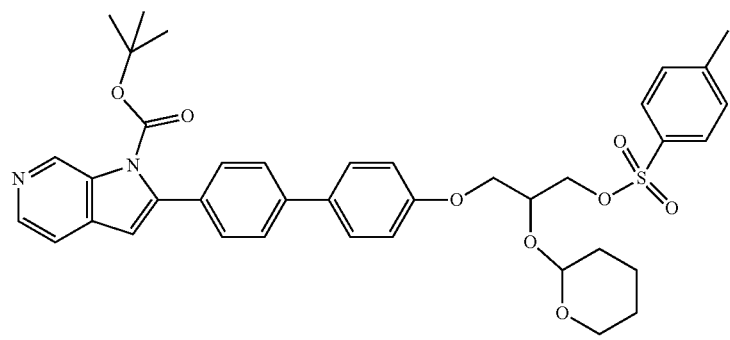 [SMILES: Cc1ccc(S(=O)(=O)OCC(COc2ccc(-c3ccc(-c4cc5ccncc5n4C(=O)OC(C)(C)C)cc3)cc2)OC2CCCCO2)cc1]
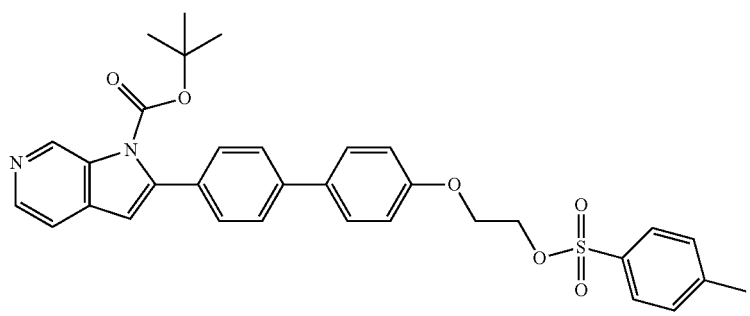 [SMILES: Cc1ccc(S(=O)(=O)OCCOc2ccc(-c3ccc(-c4cc5ccncc5n4C(=O)OC(C)(C)C)cc3)cc2)cc1]

TABLE (I)-continued
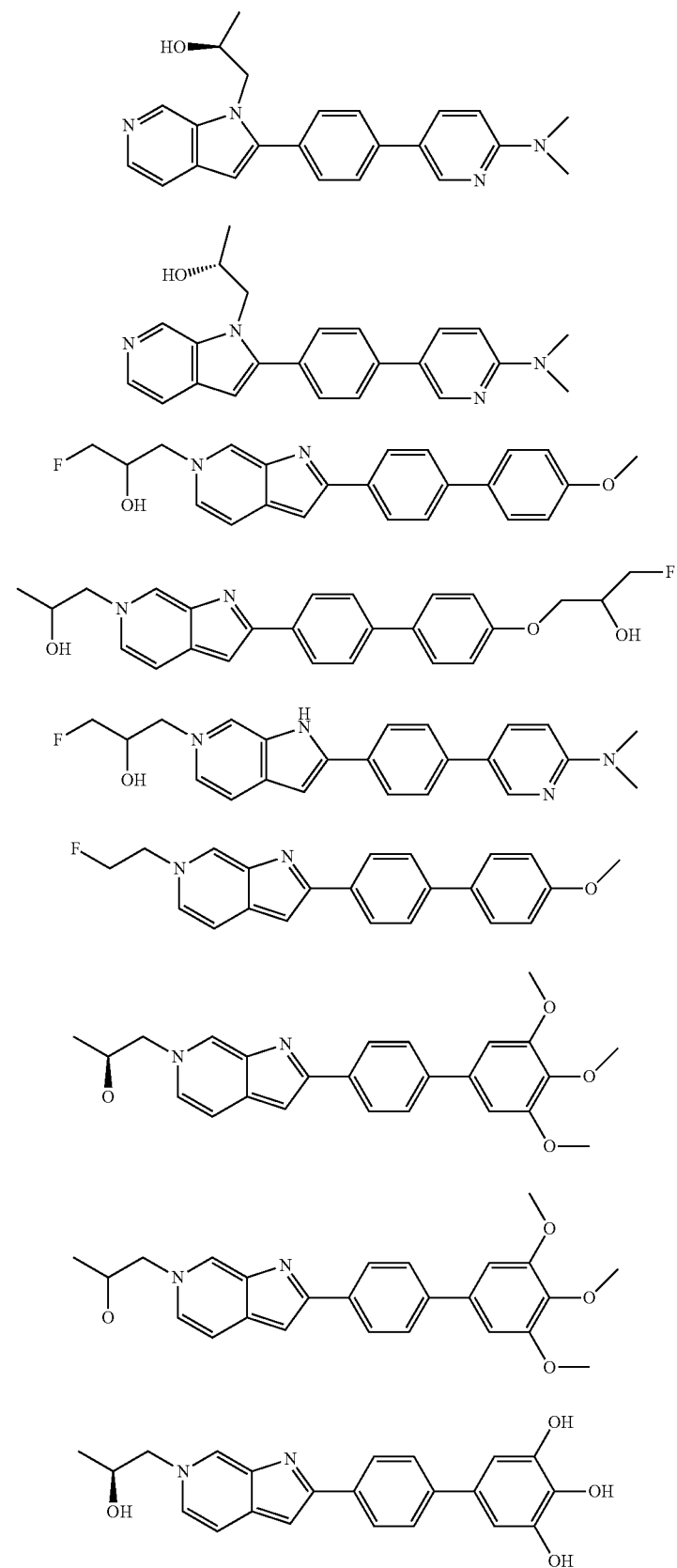

TABLE (I)-continued
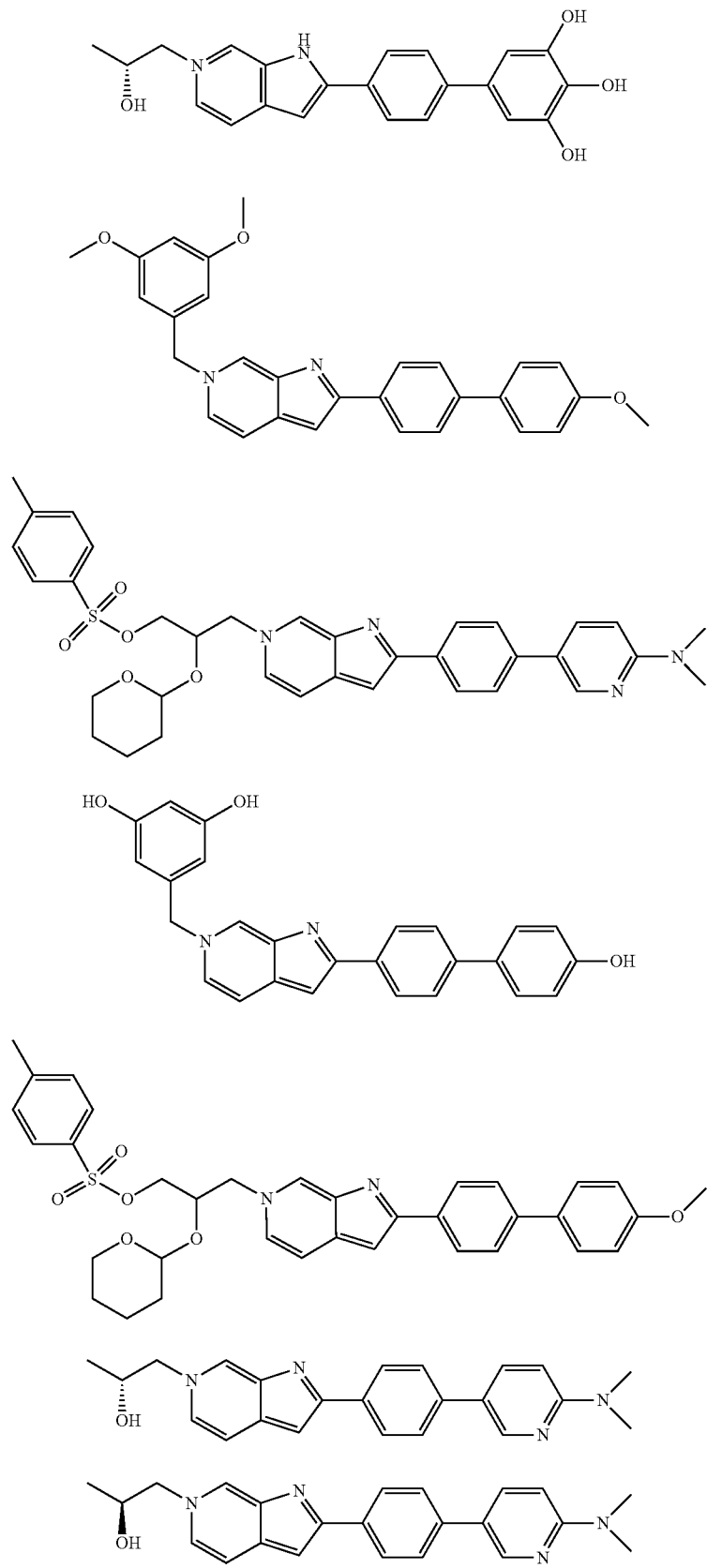

TABLE (I)-continued
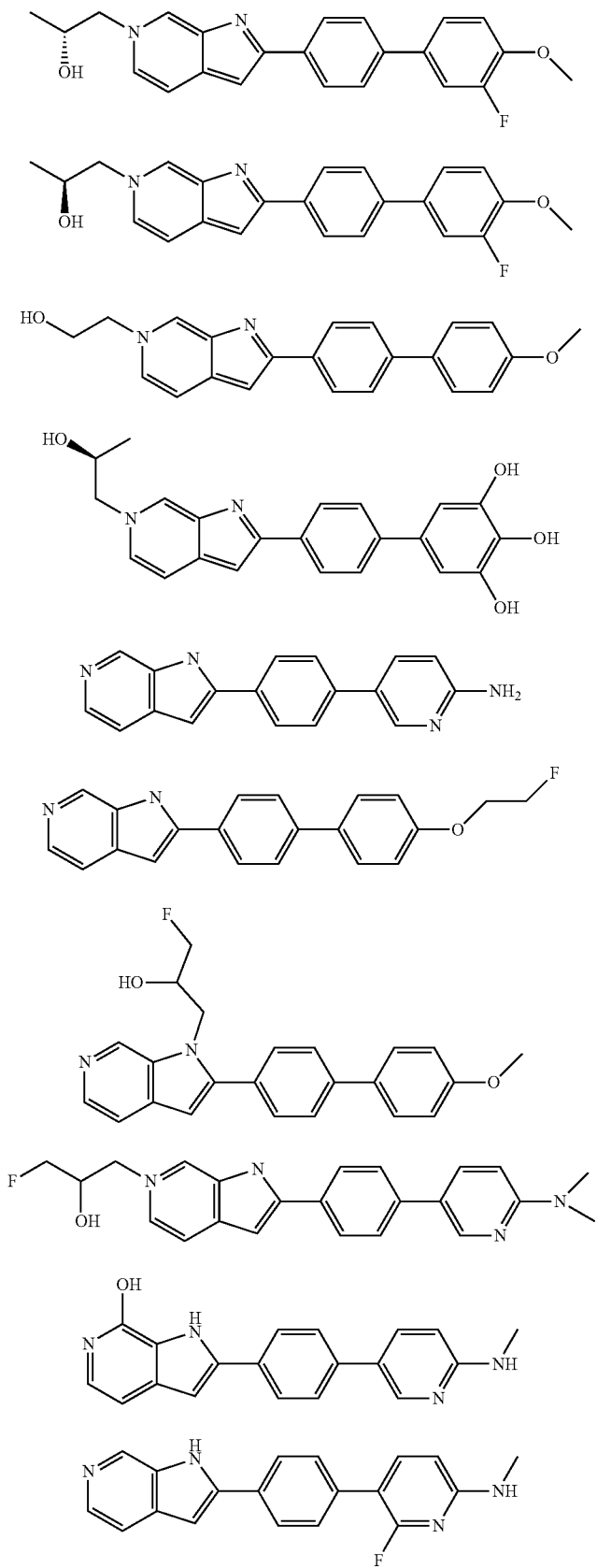

TABLE (I)-continued
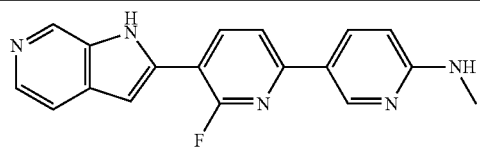
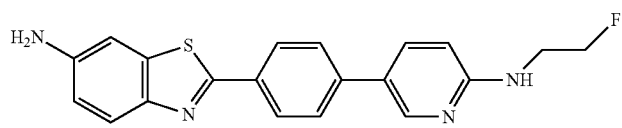 [SMILES: Nc1ccc2nc(-c3ccc(-c4ccc(NCCF)nc4)cc3)sc2c1]
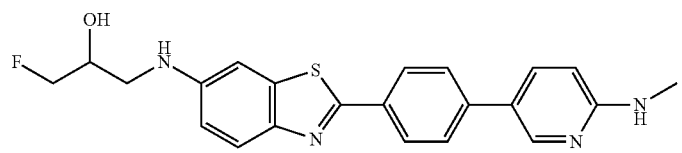 [SMILES: CNc1ccc(-c2ccc(-c3nc4ccc(NCC(O)CF)cc4s3)cc2)cn1]
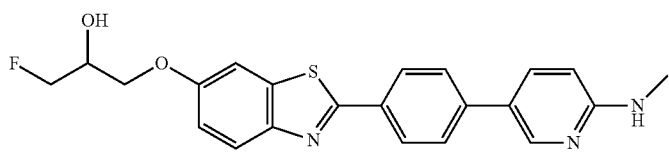 [SMILES: CNc1ccc(-c2ccc(-c3nc4ccc(OCC(O)CF)cc4s3)cc2)cn1]
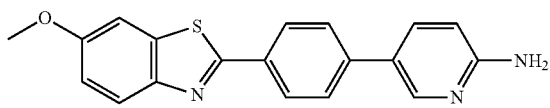
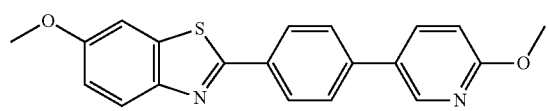
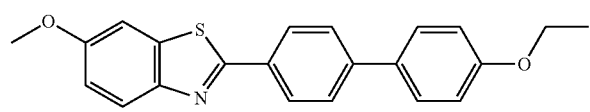 [SMILES: CCOc1ccc(-c2ccc(-c3nc4ccc(OC)cc4s3)cc2)cc1]
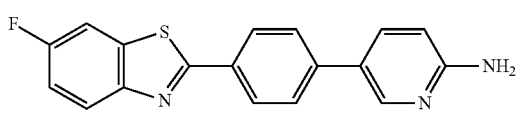 [SMILES: Nc1ccc(-c2ccc(-c3nc4ccc(F)cc4s3)cc2)cn1]
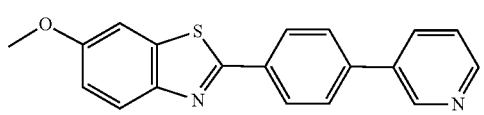
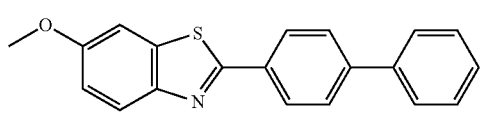 [SMILES: COc1ccc2nc(-c3ccc(-c4ccccc4)cc3)sc2c1]
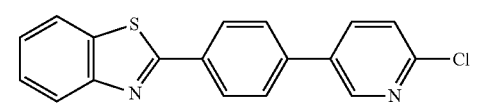 [SMILES: Clc1ccc(-c2ccc(-c3nc4ccccc4s3)cc2)cn1]
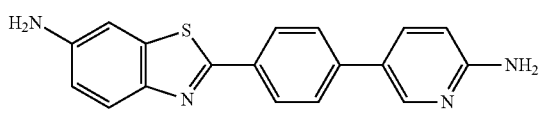 [SMILES: Nc1ccc2nc(-c3ccc(-c4ccc(N)nc4)cc3)sc2c1]
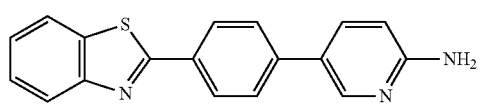

TABLE (I)-continued
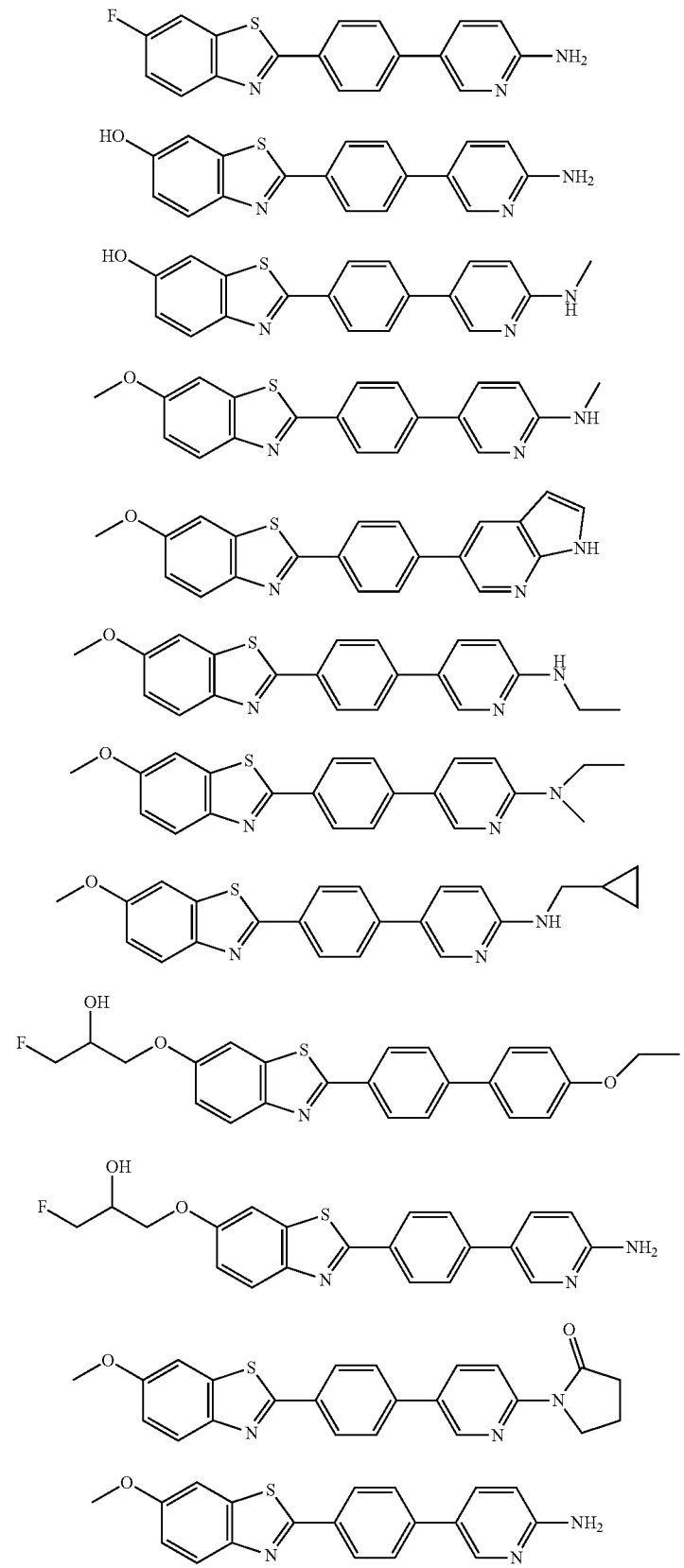

TABLE (I)-continued
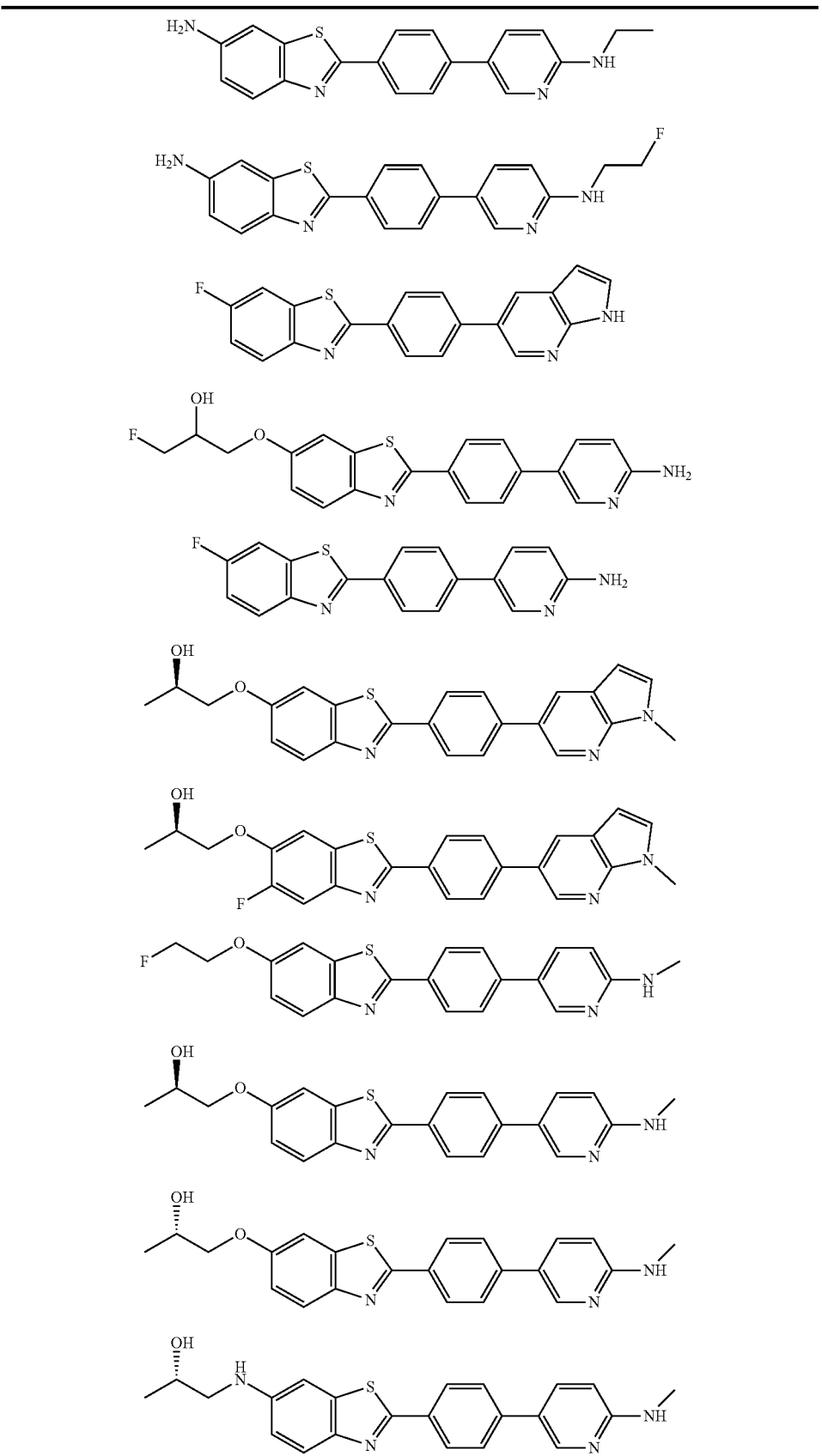

TABLE (I)-continued
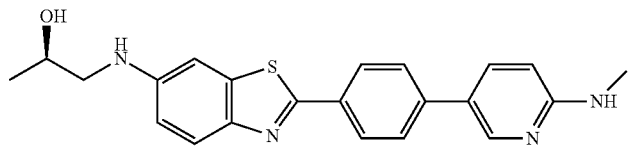 [SMILES: CNc1ccc(-c2ccc(-c3nc4ccc(NC[C@H](C)O)cc4s3)cc2)cn1]
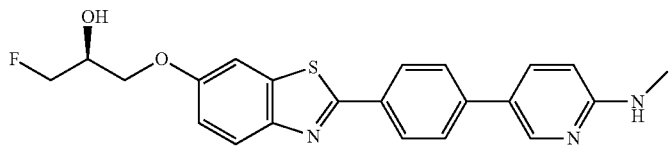
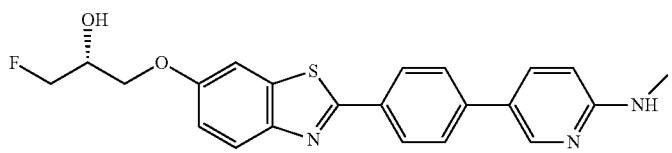 [SMILES: CNc1ccc(-c2ccc(-c3nc4ccc(OC[C@@H](O)CF)cc4s3)cc2)cn1]
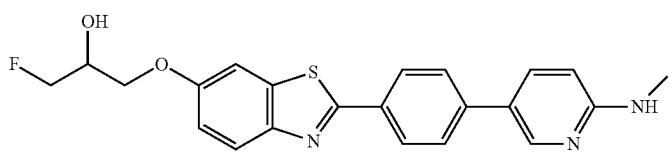
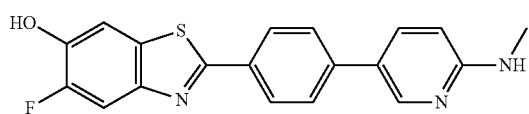 [SMILES: CNc1ccc(-c2ccc(-c3nc4cc(F)c(O)cc4s3)cc2)cn1]
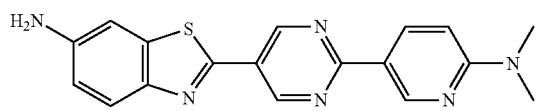
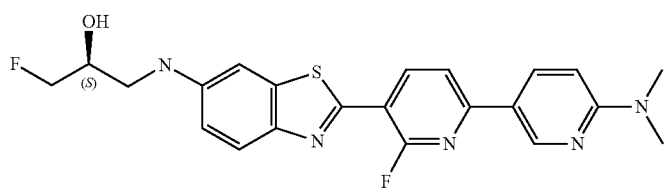
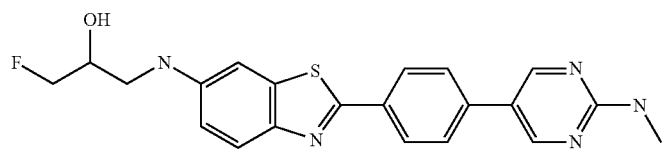
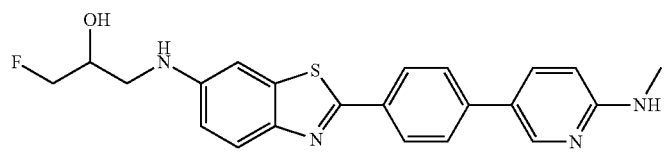 [SMILES: CNc1ccc(-c2ccc(-c3nc4ccc(NCC(O)CF)cc4s3)cc2)cn1]
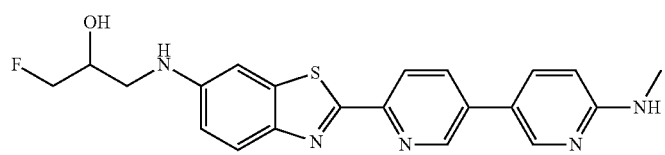 [SMILES: CNc1ccc(-c2ccc(-c3nc4ccc(NCC(O)CF)cc4s3)nc2)cn1]

TABLE (I)-continued
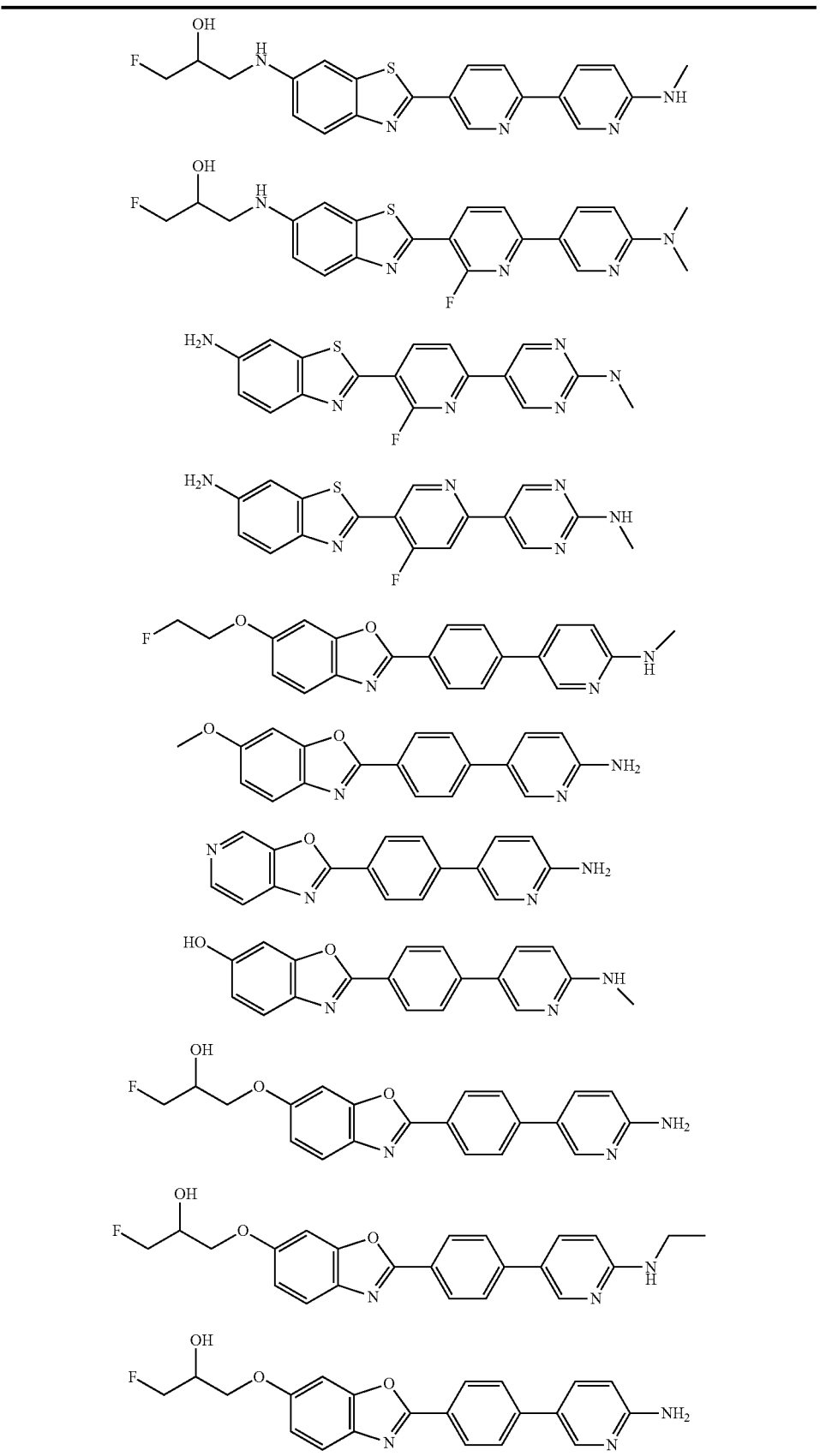

TABLE (I)-continued
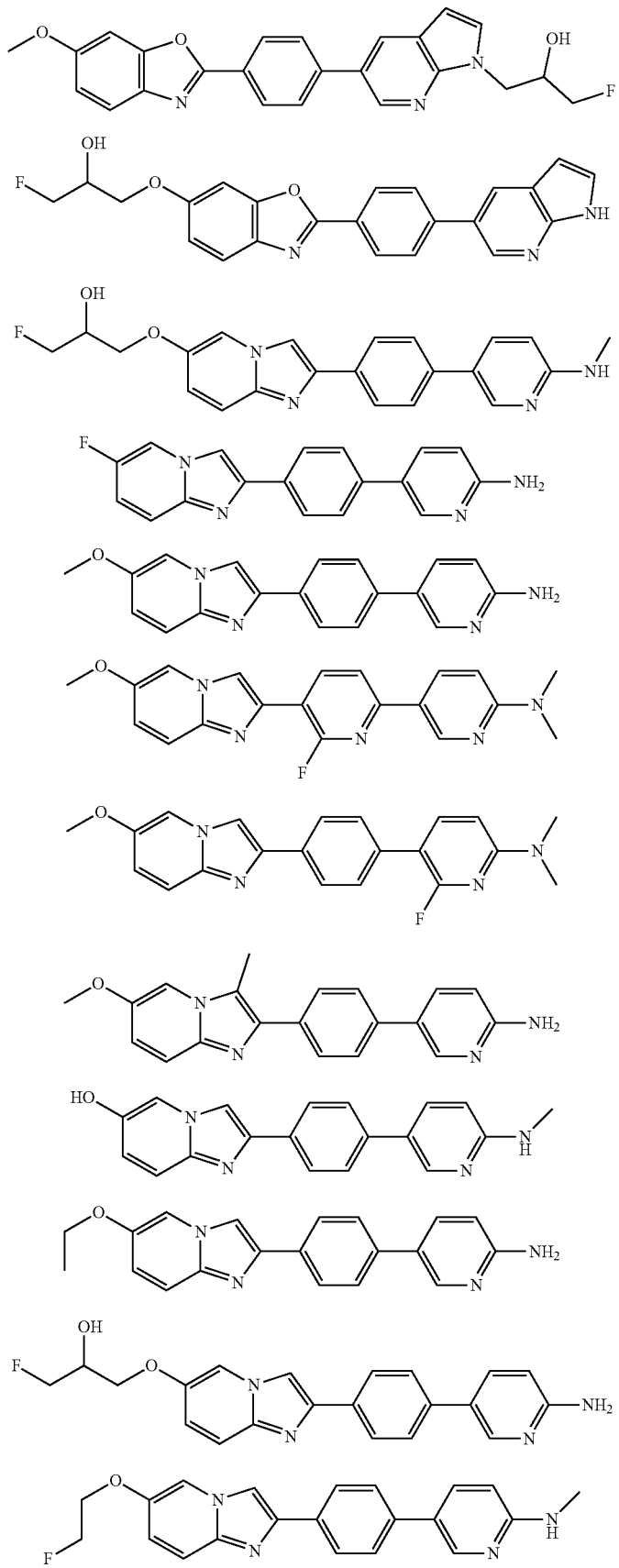

TABLE (I)-continued
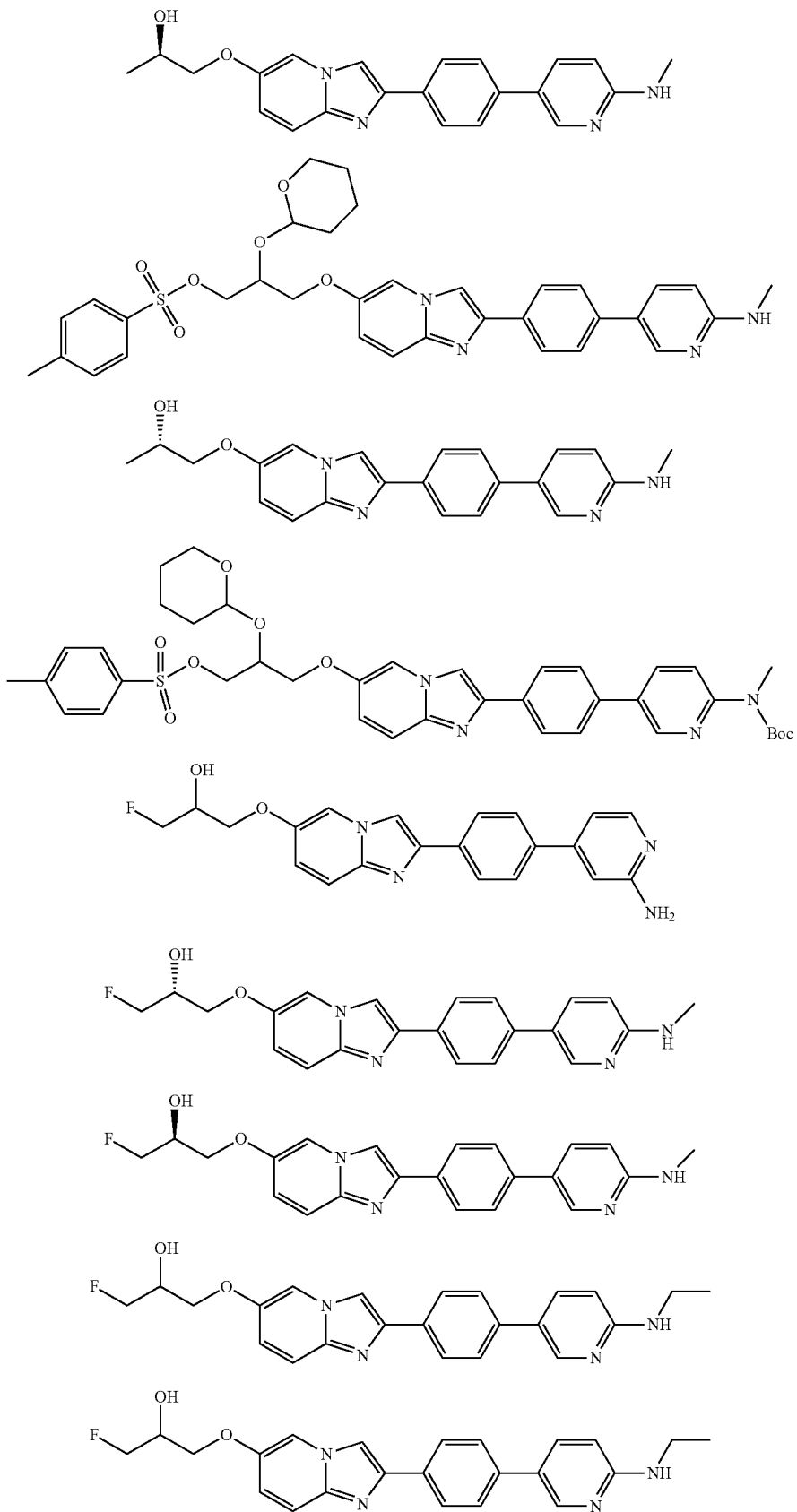

TABLE (I)-continued
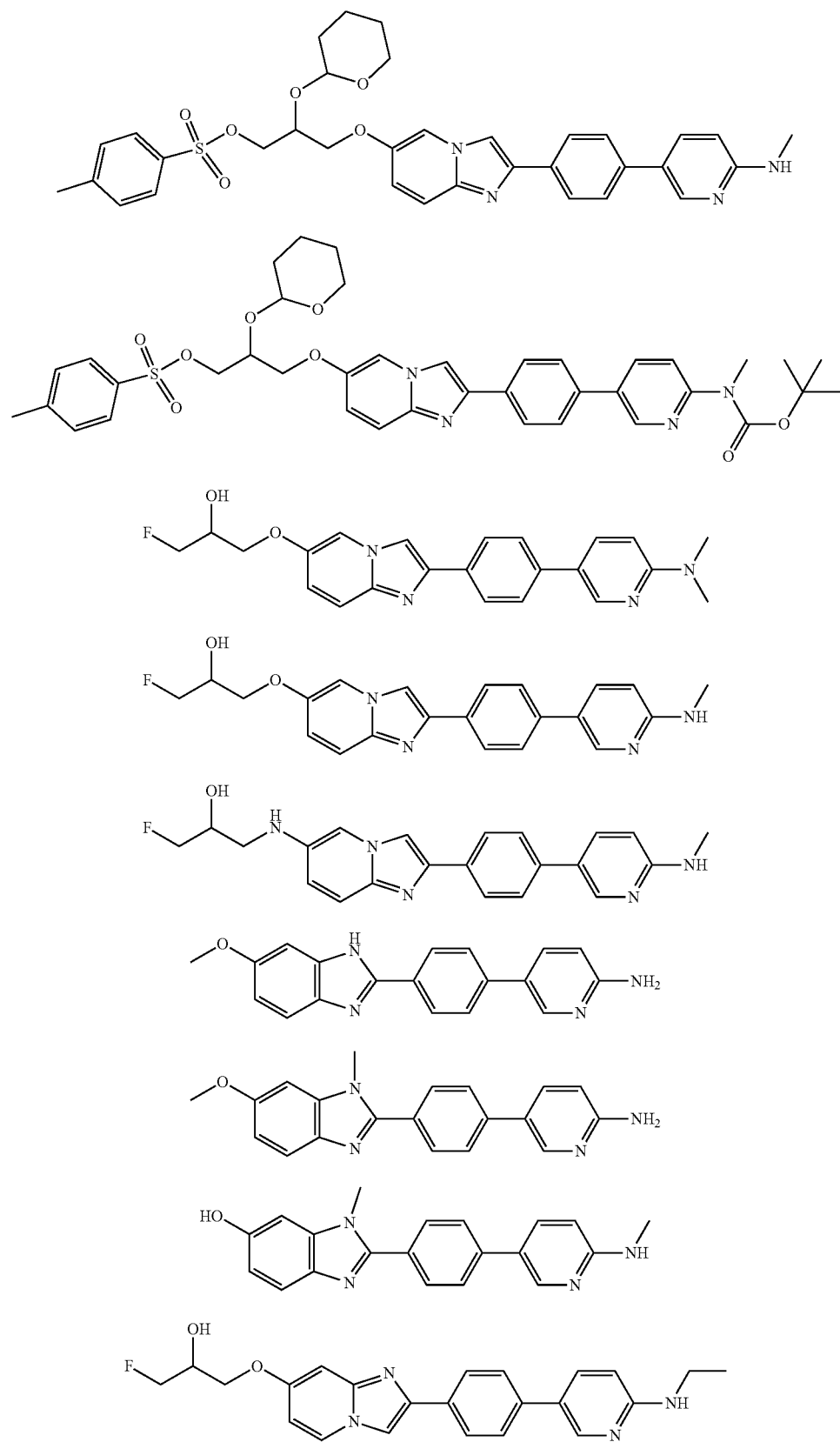

TABLE (I)-continued
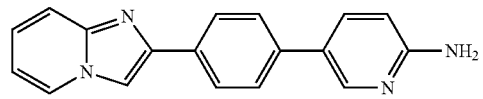
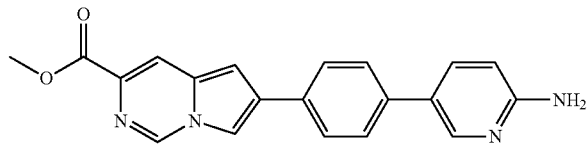
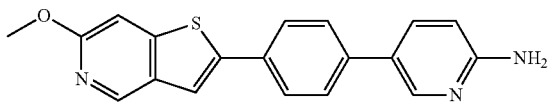 [SMILES: COc1ccc2nc(-c3ccc(-c4ccc(N)nc4)cc3)oc2c1]
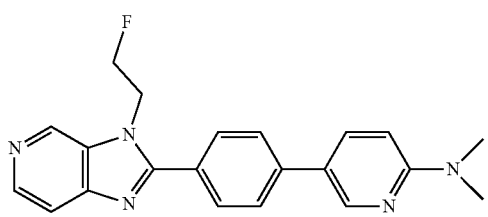 [SMILES: CN(C)c1ccc(-c2ccc(-c3nc4ccncc4n3CCF)cc2)cn1]
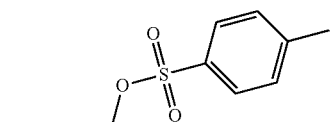
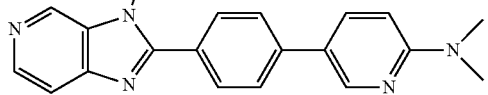
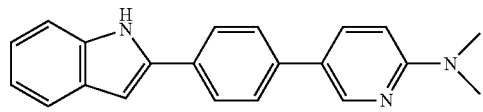 [SMILES: CN(C)c1ccc(-c2ccc(-c3cc4ccccc4[nH]3)cc2)cn1]
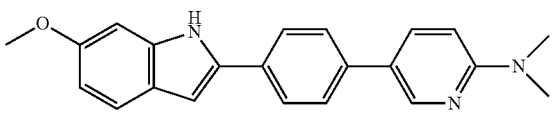
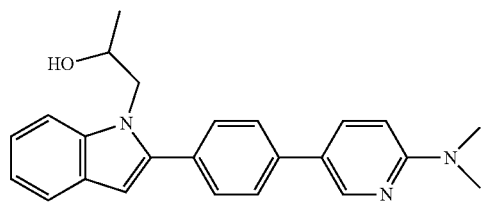 [SMILES: CC(O)Cn1c(-c2ccc(-c3ccc(N(C)C)nc3)cc2)cc2ccccc21]
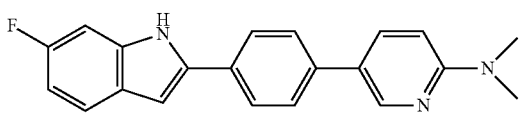
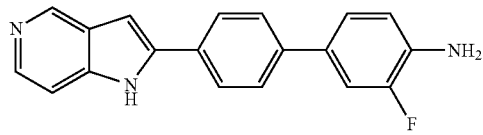 [SMILES: Nc1ccc(-c2ccc(-c3cc4cnccc4[nH]3)cc2)cc1F]

TABLE (I)-continued
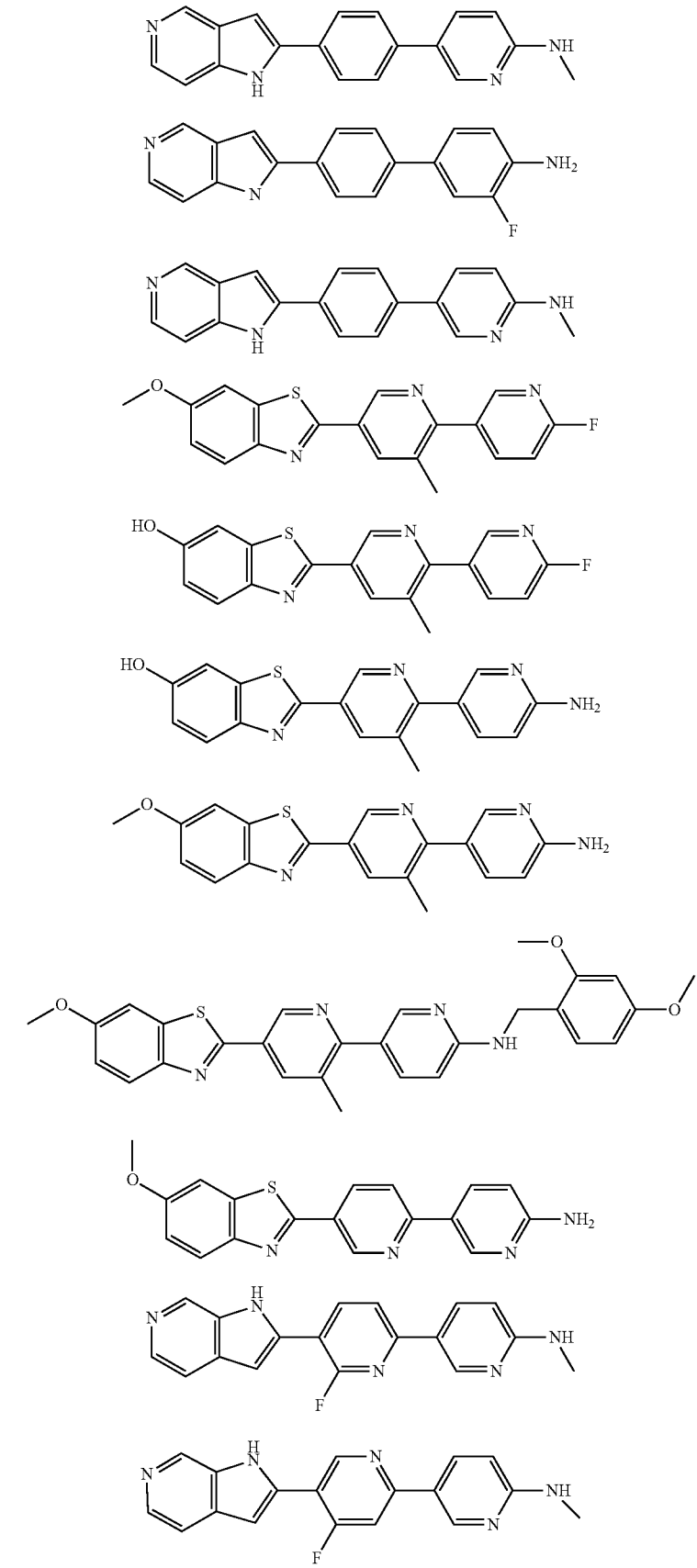

TABLE (I)-continued
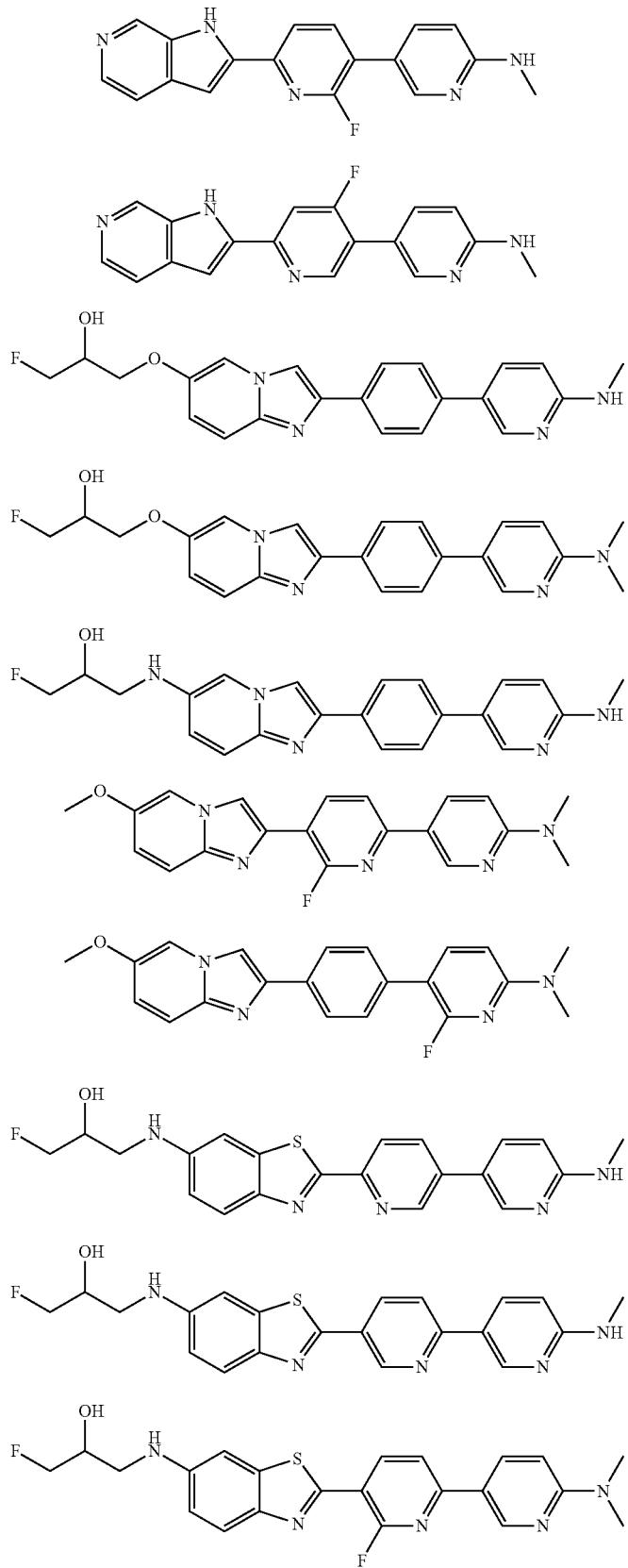

TABLE (I)-continued

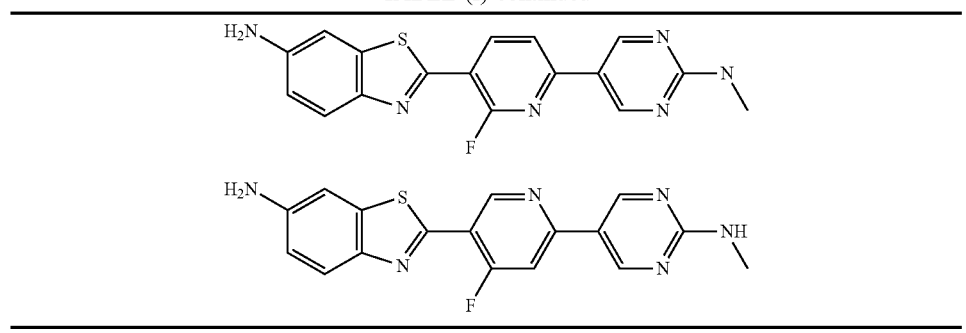

The present invention also provides a process for preparing the heteroaryl compounds having a structure of formula (I), or a pharmaceutically acceptable salt, a solvate, a hydrate, an isotopically labeled derivative or a radiolabeled derivative thereof, when the structural unit

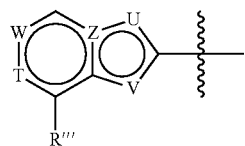

is

Formula I-(a)

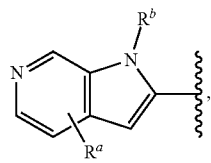

comprising the steps of
(i) reacting compound 1 with compound 2 to give compound 3 at −78° C. in an organic solvent and in the presence of a base;
(ii) reacting the compound 3 obtained from step (i) with compound 4 in an organic solvent and in the presence of a base and a Pd catalyst at 80° C.;

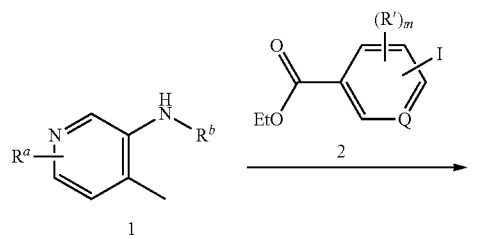

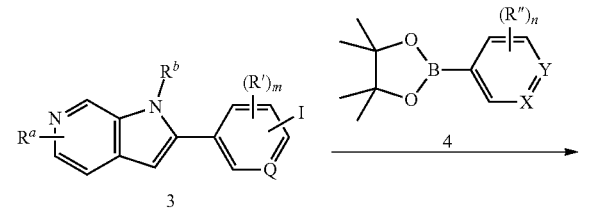

-continued

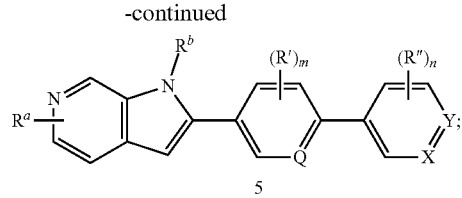

when the structural unit

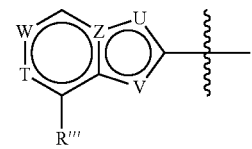

is

Formula I-(b)

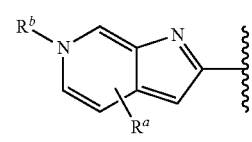

and $R^b$ is

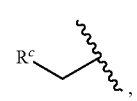

comprising reacting compound 5 with compound 11 at 60° C. in an organic solvent and in the presence of a base;

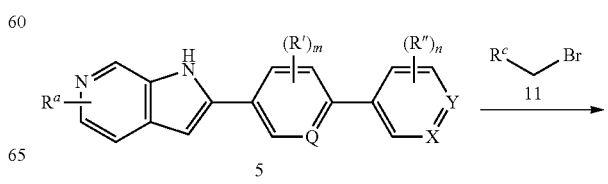

-continued

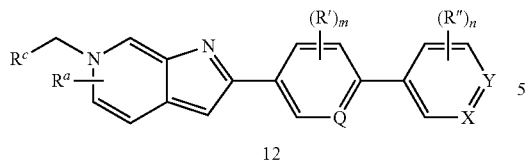

wherein $R^c$ is H, $C_{1-5}$ alkyl, $C_{1-5}$ alkoxycarbonyl, $C_{1-2}$ alkylcarbonyl and phenyl, and the $C_{1-5}$ alkyl, $C_{1-5}$ alkoxycarbonyl, $C_{1-2}$ alkylcarbonyl and phenyl of which is optionally substituted by halogen, OH, $C_{1-3}$ alkoxy, $C_{3-6}$ heterocycloalkyloxy or toluenesulfonyloxy;

when the structural unit

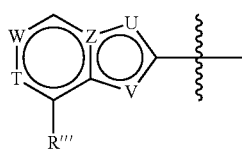

is

Formula I-(b)

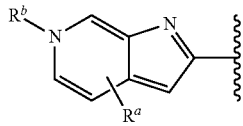

and $R^b$ is

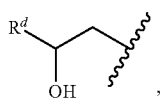

comprising reacting compound 5 with compound 13 at 50° C. in an organic solvent and in the presence of a base;

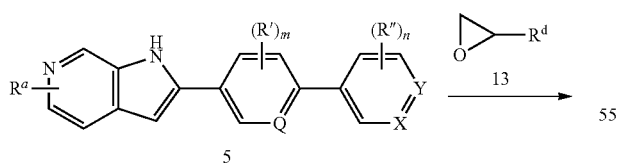

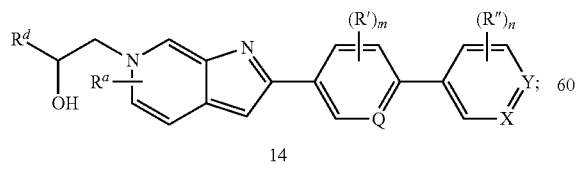

wherein $R^d$ is H or $C_{1-3}$ alkyl;
when the structural unit

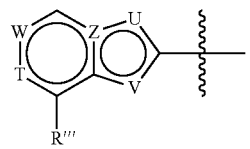

is

Formula I-(c)

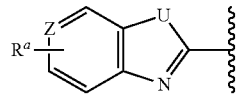

where U is O and Z is N, comprising reacting compound 15 with compound 16 at 120° C. in polyphosphoric acid (PPA);

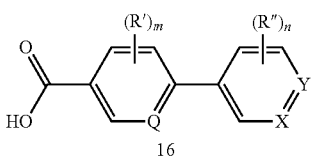

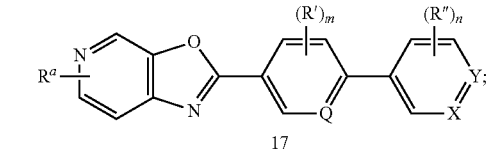

when the structural unit

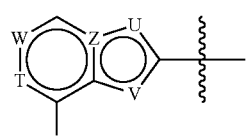

is

Formula I-(c)

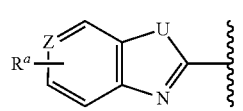

where U is S and Z is C, comprising reacting compound 18 with compound 19 at 90° C. in an organic solvent and in the presence of a base and a Pd catalyst;

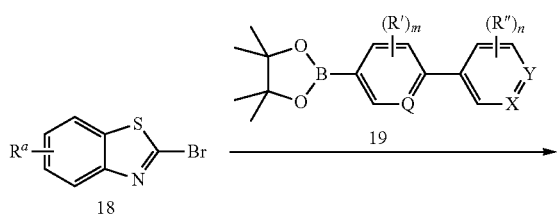

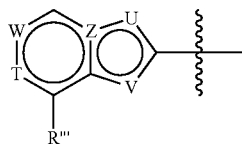

when the structural unit

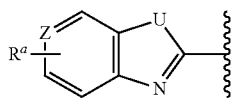

is

Formula I-(c)

where U is NH and Z is N, comprising the steps of i) reacting compound 21 with compound 22 to form compound 23 in polyphosphoric acid at 130° C.;

ii) reacting the compound 23 obtained from step i) with compound 19 to form compound 25 in a mixed solvent of MeCN and H$_2$O and in the presence of a Pd catalyst and a base at 60° C.;

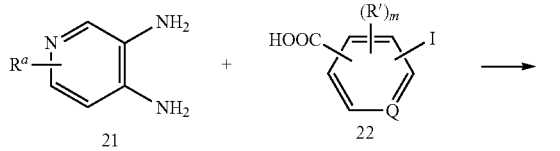

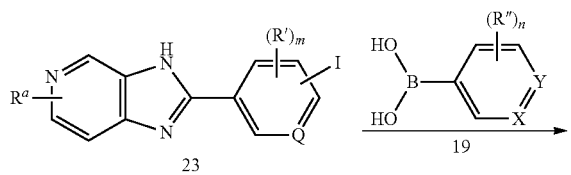

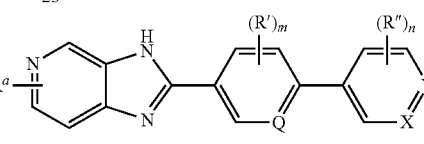

when the structural unit

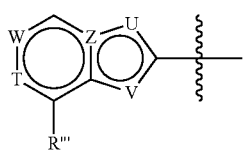

is

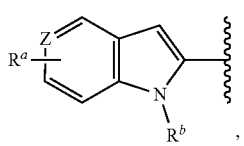

Formula I-(d)

wherein R$^b$ is H, comprising the steps of i) reacting compound 26 with compound 27 to form compound 28 in an organic solvent and in the presence of a Pd catalyst, CuI and an organic base at room temperature;

ii) reacting the compound 28 obtained from step i) with DBU to form compound 29 in a mixed solvent of MeOH and H$_2$O at 80° C.;

iii) reacting the compound 29 obtained from step ii) with compound 30 to form compound 31 in an organic solvent and in the presence of a Pd catalyst and a base at 80° C.;

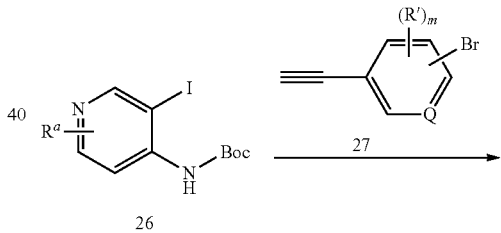

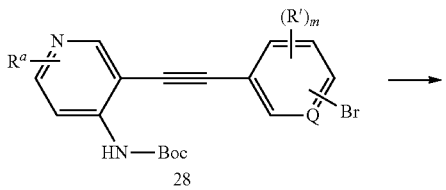

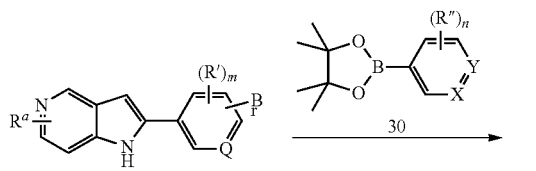

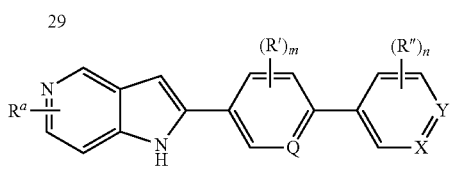

when the structural unit

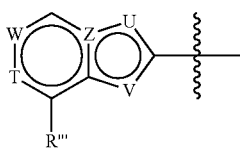

is

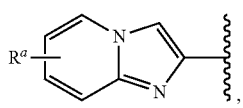   Formula I-(e)

comprising the steps of
i) reacting compound 32 with compound 33 to form compound 34 in an alcoholic solvent and in the presence of a base at 80° C.;
ii) reacting the compound 34 obtained from step i) with compound 30 in an organic solvent and in the presence of a base and a Pd catalyst at 80° C.;

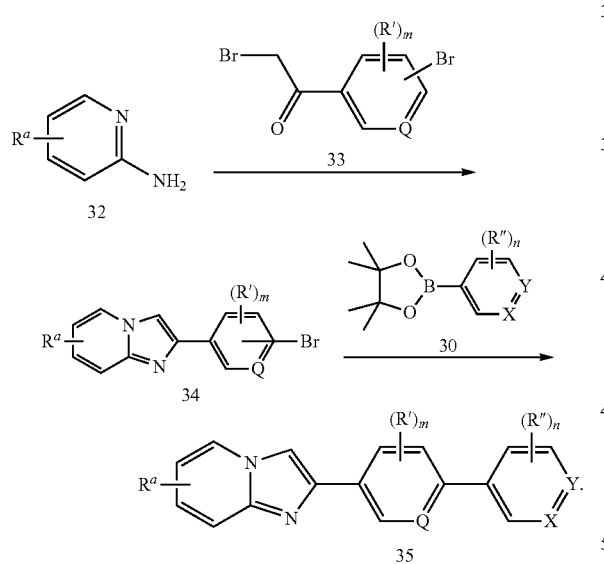

Preferably, the process for preparing the heteroaryl compounds having a structure of formula (I), or a pharmaceutically acceptable salt, a solvate, a hydrate, an isotopically labeled derivative or a radiolabeled derivative thereof, when the structural unit

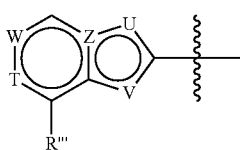

is

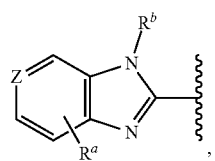   Formula I-(a)

comprising the steps of
(i) reacting compound 1 with compound 2 to give compound 3 at −78° C. in THF and in the presence of s-butyllithium;
(ii) reacting the compound 3 obtained from step (i) with compound 4 in DMF and in the presence of Na$_2$CO$_3$ and Pd(PPh$_3$)$_4$ at 80° C.;
when the structural unit

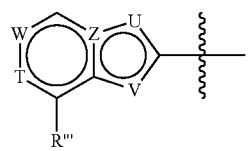

is

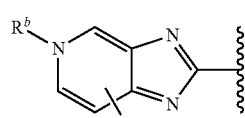   Formula I-(b)

and R$^b$ is

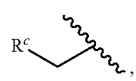, comprising reacting compound 5 with compound 11 at 60° C. in DMF and in the presence of Cs$_2$CO$_3$; wherein R$^c$ is a C$_{1-3}$ alkyl or a halogenated C$_{1-3}$ alkyl;
when the structural unit

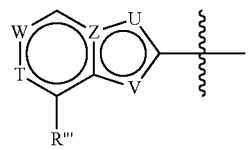

is

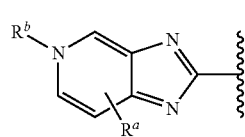   Formula I-(b)

and $R^b$ is

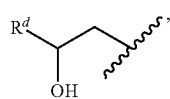

comprising reacting compound 5 with compound 13 at 50° C. in DMF and in the presence of $K_2CO_3$;
when the structural unit

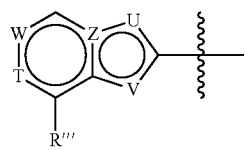

is

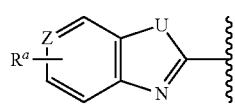

where U is O and Z is N, comprising reacting compound 15 with compound 16 at 120° C. in polyphosphoric acid (PPA);
when the structural unit

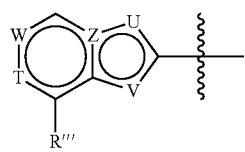

is

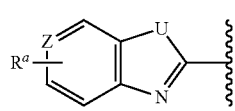

where U is S and Z is C, comprising reacting compound 18 with compound 19 at 90° C. in $CH_3CN$ and in the presence of $K_2CO_3$ and $Pd(PPh_3)_4$;
when the structural unit

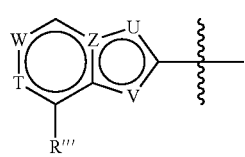

is

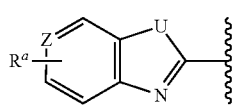

where U is NH and Z is N, comprising the steps of
i) reacting compound 21 with compound 22 to form compound 23 in polyphosphoric acid at 130° C.;
ii) reacting the compound 23 obtained from step i) with compound 19 to form compound 25 in a mixed solvent of MeCN and $H_2O$ and in the presence of $Pd(dppf)Cl_2$ and $Na_2CO_3$ at 60° C.;
when the structural unit

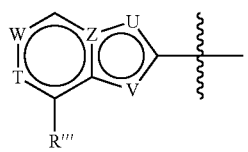

is

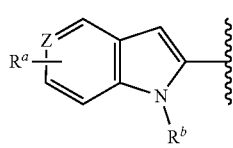

wherein $R^b$ is H, comprising the steps of
i) reacting compound 26 with compound 27 to form compound 28 in DMF and in the presence of $Pd(PPh_3)_2Cl_2$, CuI and triethanolamine at room temperature;
ii) reacting the compound 28 obtained from step i) with DBU to form compound 29 in a mixed solvent of MeOH and $H_2O$ at 80° C.;
iii) reacting the compound 29 obtained from step ii) with compound 30 to form compound 31 in DMF and in the presence of $Pd(PPh_3)_4$ and $Na_2CO_3$ at 80° C.;
when the structural unit

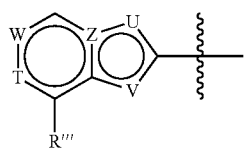

is

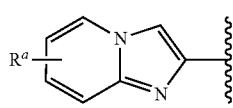

comprising the steps of
i) reacting compound 32 with compound 33 to form compound 34 in EtOH and in the presence of $NaHCO_3$ at 80° C.;

ii) reacting the compound 34 obtained from step i) with compound 30 in DMF and in the presence of $K_2CO_3$ and $Pd(PPh_3)_4$ at 80° C.

The present invention also provides a pharmaceutical composition comprising a compound of formula (I), or a pharmaceutically acceptable salt, solvate, hydrate, isotopically labeled derivative or radiolabeled derivative thereof, as described herein, and optionally a pharmaceutically acceptable excipient.

The pharmaceutical composition described herein can be prepared by any method known in the art of pharmacology. In general, such preparatory methods include the steps of bringing the compound of formula (I) into association with a carrier and/or one or more other accessory ingredients, and if necessary and/or desirable, shaping and/or packaging the product into a desired single- or multi-dose unit.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary preservatives include antioxidants, chelating agents, antimicrobial preservatives, antifungal preservatives, alcohol preservatives, acidic preservatives, and other preservatives. The preservative is preferably an antioxidant or a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

The radiolabeled compound of formula (I), as described herein, may bind to Tau aggregates and aid in identifying the amount of Tau aggregates present which in turn may correlate with the stage of AD.

The present invention also provides a use of the heteroaryl compound having a structure of formula (I), or a pharmaceutically acceptable salt, solvate, hydrate, isotopically labeled derivative or a radiolabeled derivative thereof in detecting Tau aggregates in vitro, ex vivo, and in vivo.

The present invention also provides a use of the heteroaryl compound having a structure of formula (I), or a pharmaceutically acceptable salt, solvate, hydrate, isotopically labeled derivative or a radiolabeled derivative thereof in manufacturing an imaging agent for Tau aggregates.

Also within the scope of this disclosure are (a) pharmaceutical compositions comprising inventive compounds described herein; and (b) uses of the just-described pharmaceutical compositions in manufacturing imaging agents or medicaments for neurological disorders like Alzheimer's disease.

The present disclosure further provides a method of using the inventive compounds and pharmaceutical compositions for imaging tau proteins that accumulate in the brain.

The present disclosure provides methods of using the inventive compounds and pharmaceutical compositions for detecting neurological disorders associated with accumulated tau proteins, such as Alzheimer's disease (AD).

The present invention thus provides a method of detecting tau aggregates. This imaging can be performed by molecular imaging methods such as positron emission tomography (PET), fluorescence microscopy measurement, multi-photon imaging, two-photon imaging, near-infrared fluorescence imaging, autoradiography, and single-photon emission computed tomography (SPECT). Also, this imaging includes in vitro, ex vivo, and in vivo imaging.

The imaging method comprises the step of administering a radiolabeled compound of formula (I) to a subject and detecting said radiolabeled compound of the invention in said subject. The present invention further provides a method of detecting Tau aggregates in vitro or in vivo using a radiolabeled compound of formula (I), as described herein. Hence, the present invention provides useful tools for early detection and diagnosis of Alzheimer's disease. The present invention also provides useful tools for monitoring the progression of Alzheimer's disease and the effect of treatment.

A method of Tau imaging, comprising the steps of
(a) administering to a subject an effective amount of (i) the heteroaryl compound having a structure of formula (I), or a pharmaceutically acceptable salt, a solvate, a hydrate, an isotopically labeled derivative or a radiolabeled derivative thereof, or (ii) the pharmaceutical composition of the present invention; and
(b) imaging the brain of the subject.

The imaging method preferably comprises the steps of (a) administering to a subject a radiolabeled compound of the invention as defined herein; (b) allowing said radiolabeled compound of the invention to bind to Tau in said subject; (c) detecting signals emitted by said radioisotope in said bound radiolabeled compound of the invention; (d) generating an image representative of the location and/or amount of said signals; and (e) determining the distribution and extent of said Tau aggregates in said subject.

The step of "administering" a radiolabeled compound of the invention is preferably carried out parenterally, and most preferably intravenously. The intravenous route represents the most efficient way to deliver the compound throughout the body of the subject. Intravenous administration neither represents a substantial physical intervention nor a substantial health risk to the subject. The radiolabeled compound of the invention is preferably administered as the radiopharmaceutical composition of the invention, as defined herein. The administration step is not required for a complete definition of the imaging method of the invention. As such, the imaging method of the invention can also be understood as comprising the above-defined steps (b)-(e) carried out on a subject to whom a radiolabeled compound of the invention has been pre-administered.

Following the administering step and preceding the detecting step, the radiolabeled compound of the invention is allowed to bind to the Tau aggregates. For example, when the subject is an intact mammal, the radiolabeled compound of the invention will dynamically move through the mammal's body, coming into contact with various tissues therein. Once the radiolabeled compound of the invention comes into contact with the Tau aggregates it will bind to the Tau aggregates.

The "detecting" step of the method of the invention involves detection of signals emitted by the radioisotope comprised in the radiolabeled compound of the invention by means of a detector sensitive to said signals, e.g., a PET camera. This detection step can also be understood as the acquisition of signal data.

The "generating" step of the method of the invention is carried out by a computer which applies a reconstruction algorithm to the acquired signal data to yield a dataset. This dataset is then manipulated to generate images showing the location and/or amount of signals emitted by the radioisotope. The signals emitted directly correlate with the amount of enzyme or neoplastic tissue such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human.

The "disease state associated with the Tau aggregates" can be MCI (mild cognitive impairment), dementia or Alzheimer's disease.

An amount of the isotopically labeled derivative and radiolabeled derivative of the compound for administration one or more times a day to a 70 kg adult human may comprises about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of the compound per unit dosage form.

The compound of formula (I) or the pharmaceutically acceptable salt, solvate, hydrate, isotopically labeled derivative and radiolabeled derivative thereof may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Also encompassed by the invention are kits (e.g., pharmaceutical packs). The inventive kits may be useful for detecting Tau aggregates. The kit provided may comprise an inventive pharmaceutical composition or heteroaryl compound of formula (I), or a pharmaceutically acceptable salt, solvate, hydrate, isotopically labeled derivative and radiolabeled derivative thereof, and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or heteroaryl compound of formula (I), or a pharmaceutically acceptable salt, solvate, hydrate, isotopically labeled derivative or radiolabeled derivative thereof. In some embodiments, the inventive pharmaceutical composition or heteroaryl compound of formula (I), or pharmaceutically acceptable salt, solvate, hydrate, isotopically labeled derivative or radiolabeled derivative thereof provided in the container and the second container are combined to form one unit dosage form.

Thus, in one aspect, provided are kits including a first container comprising the heteroaryl compound described herein, or a pharmaceutically acceptable salt, solvate, hydrate, isotopically labeled derivative or radiolabeled derivative, or a pharmaceutical composition thereof. The kit of the invention preferably includes a first container comprising the heteroaryl compound described herein, or a pharmaceutically acceptable salt thereof, or a pharmaceutical composition thereof. The kits are useful in preventing and/or treating a proliferative disease in a subject. Preferably, the kits further include instructions for administering the compound, or the pharmaceutically acceptable salt, solvate, hydrate thereof, or the pharmaceutical composition thereof, to a subject to identify the amount of Tau aggregates present which in turn may correlate with the stage of AD.

Chemical Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having indicated number of carbon atoms. In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

"Heterocyclo" refers to a radical of a 3- to 10-membered non-aromatic ring or aromatic ring system having indicated ring carbon atoms (such as 2 to 6 ring carbon atoms) and 1 to 4 ring heteroatoms, wherein each heteroatom is independently selected from nitrogen, oxygen and sulfur ("$C_{2-6}$ heterocyclo"). In heterocyclo groups that contain one or more nitrogen atoms, the point of attachment can be a carbon or nitrogen atom, as valency permits. A heterocyclo group can either be monocyclic ("monocyclic heterocyclo") or a fused, bridged or spiro ring system such as a bicyclic system ("bicyclic heterocyclo"), and can be saturated or partially unsaturated. Heterocyclo bicyclic ring systems can include one or more heteroatoms in one or both rings. "Heterocyclo" also includes ring systems wherein the heterocyclic ring, as defined above, is fused with one or more carbocyclic groups wherein the point of attachment is either on the carbocyclic or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

In some embodiments, a heterocyclo group is a 5-10 membered non-aromatic ring system or aromatic ring system having indicated ring carbon atoms and 1-4 ring heteroatoms, wherein each heteroatom is independently selected from nitrogen, oxygen, and sulfur. In some embodiments, a heterocyclo group is a 5-6 membered non-aromatic ring system or aromatic ring system having indicated ring carbon atoms and 1-4 ring heteroatoms, wherein each heteroatom is independently selected from nitrogen, oxygen, and sulfur ("5-6 membered heterocyclo"). In some embodiments, the 5-6 membered heterocyclo has 1-3 ring heteroatoms selected from nitrogen, oxygen, and sulfur. In some embodiments, the 5-6 membered heterocyclo has 1-2 ring heteroatoms selected from nitrogen, oxygen, and sulfur. In some embodiments, the 5-6 membered heterocyclo has one ring heteroatom selected from nitrogen, oxygen, and sulfur.

Exemplary 3-membered heterocyclo groups containing one heteroatom include, without limitation, azirdinyl, oxiranyl, and thiorenyl. Exemplary 4-membered heterocyclo groups containing one heteroatom include, without limitation, azetidinyl, oxetanyl, and thietanyl. Exemplary 5-membered heterocyclo groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclo groups containing two heteroatoms include, without limitation, dioxolanyl, oxasulfuranyl, disulfuranyl, and oxazolidin-2-one. Exemplary 5-membered heterocyclo groups containing three heteroatoms include, without limitation, triazolinyl, oxadiazolinyl, and thiadiazolinyl. Exemplary 6-membered heterocyclo groups containing one heteroatom include, without limitation, piperidinyl, tetrahydropyranyl, dihydropyridinyl, and thianyl. Exemplary 6-membered heterocyclo groups containing two heteroatoms include, without limitation, piperazinyl, morpholinyl, dithianyl, and dioxanyl. Exemplary 6-membered heterocyclo groups containing two heteroatoms include, without limitation, triazinanyl. Exemplary 7-membered heterocyclo groups containing one heteroatom include, without limitation, azepanyl, oxepanyl, and thiepanyl. Exemplary 8-membered heterocyclo groups containing one heteroatom include, without limitation, azocanyl, oxecanyl, and thiocanyl. Exemplary 5-membered heterocyclo groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclo groups fused to an aryl ring (also referred to herein as a 6,6-bicyclic heterocyclic ring) include, without limitation, tetrahydroquinolinyl, tetrahydroisoquinolinyl, and the like.

"Partially unsaturated" refers to a group that includes at least one double or triple bond. A "partially unsaturated" ring system is further intended to encompass rings having multiple sites of unsaturation. Likewise, "saturated" refers to a group that does not contain a double or triple bond, i.e., it contains all single bonds.

As used herein, the term "optionally substituted" refers to a substituted or unsubstituted moiety.

"Halo" or "halogen" refers to fluorine (fluoro, —F), chlorine (chloro, —Cl), bromine (bromo, —Br), or iodine (iodo, —I).

"Halogenated" refers to a substituent is substituted with a halogen atom.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —$OR^{aa}$, —$N(R^{cc})_2$, —CN, —C(=O)$R^{aa}$, —C(=O)N$(R^{cc})_2$, —$CO_2R^{aa}$, —$SO_2R^{aa}$, —C(=N$R^{bb}$)$R^{aa}$, —C(=N$R^{cc}$)O$R^{aa}$, —C(=N$R^{cc}$)N$(R^{cc})_2$, —$SO_2N(R^{cc})_2$, —$SO_2R^{cc}$, —$SO_2OR^{cc}$, —$SOR^{aa}$, —C(=S)N$(R^{cc})_2$, —C(=O)S$R^{cc}$, —C(=S)S$R^{cc}$, —P(=O)$_2R^{aa}$, —P(=O)$(R^{aa})_2$, —P(=O)$_2N(R^{cc})_2$, —P(=O)$(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two Rec groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
  each instance of $R^{bb}$ is, independently, selected from hydrogen, —OH, —$OR^{aa}$, —$N(R^{cc})_2$, —CN, —C(=O)$R^{aa}$, —C(=O)N$(R^{cc})_2$, —$CO_2R^{aa}$, —$SO_2R^{aa}$, —C(=N$R^{cc}$)O$R^{aa}$, —C(=N$R^{cc}$)N$(R^{cc})_2$, —$SO_2N(R^{cc})_2$, —$SO_2R^{cc}$, —$SO_2OR^{cc}$, —$SOR^{aa}$, —C(=S)N$(R^{cc})_2$, —C(=O)S$R^{cc}$, —C(=S)S$R^{cc}$, —P(=O)$_2R^{aa}$, —P(=O)$(R^{aa})_2$, —P(=O)$_2N(R^{cc})_2$, —P(=O)$(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
  each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
  each instance of $R^{dd}$ is, independently, selected from halogen, —CN, —$NO_2$, —$N_3$, —$SO_2H$, —$SO_3H$, —OH, —$OR^{cc}$, —ON$(R^{ff})_2$, —$N(R^{ff})_2$, —$N(R^{ff})_3^+X^-$, —N(O$R^{ee}$)$R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)N$(R^{ff})_2$, —OC(=O)N$(R^{ff})_2$, —$NR^{ff}$C(=O)$R^{ee}$, —$NR^{ff}CO_2R^{ee}$, —$NR^{ff}$C(=O)N$(R^{ff})_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N$(R^{ff})_2$, —OC(=N$R^{ff}$)N$(R^{ff})_2$, —$NR^{ff}$C(=N$R^{ff}$)N$(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —Si$(R^{ee})_3$, —Osi$(R^{ee})_3$, —C(=S)N$(R^{ff})_2$, —C(=O)S$R^{ee}$, —C(=S)S$R^{ee}$, —SC(=S)S$R^{ee}$, —P(=O)$_2R^{ee}$, —P(=O)$(R^{ee})_2$, —OP(=O)$(R^{ee})_2$, —OP(=O)(O$R^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two $R^{dd}$ substituents can be joined to form =O or =S;
  each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;
  each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and
  each instance of $R^{gg}$ is, independently, halogen, —CN, —$NO_2$, —$N_3$, —$SO_2H$, —$SO_3H$, —OH, —$OC_{1-6}$ alkyl, —ON$(C_{1-6}$ alkyl$)_2$, —N$(C_{1-6}$ alkyl$)_2$, —N$(C_{1-6}$ alkyl$)_3^+X^-$, —NH$(C_{1-6}$ alkyl$)_2^+X^-$, —$NH_2(C_{1-6}$ alkyl$)^+X^-$, —$NH_3^+X^-$, —N(O$C_{1-6}$ alkyl)($C_{1-6}$ alkyl), —N(OH)($C_{1-6}$ alkyl), —NH (OH), —SH, —$SC_{1-6}$ alkyl, —SS($C_{1-6}$ alkyl), —C(=O) ($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N ($C_{1-6}$ alkyl$)_2$, —OC(=O)NH($C_{1-6}$ alkyl), —NHC(=O) ($C_{1-6}$ alkyl), —N($C_{1-6}$ alkyl)C(=O)($C_{1-6}$ alkyl), —$NHCO_2$ ($C_{1-6}$ alkyl), —NHC(=O)N($C_{1-6}$ alkyl$)_2$, —NHC(=O)NH ($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH) NH($C_{1-6}$ alkyl), —OC(NH)$NH_2$, —NHC(NH)N($C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl$)_3$, —Osi($C_{1-6}$ alkyl$)_3$ —C(=S)N($C_{1-6}$ alkyl$)_2$, C(=S)NH($C_{1-6}$ alkyl), C(=S) $NH_2$, —C(=O)S($C_{1-6}$ alkyl), —C(=S)S$C_{1-6}$ alkyl, —SC (=S)S$C_{1-6}$ alkyl, —P(=O)$_2(C_{1-6}$ alkyl), —P(=O)($C_{1-6}$ alkyl$)_2$, —OP(=O)($C_{1-6}$ alkyl$)_2$, —OP(=O)(O$C_{1-6}$ alkyl$)_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two $R^{gg}$ substituents can be joined to form =O or =S; wherein $X^-$ is a counterion.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o)-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-Adamantyl)-1-methylethyl (Adpoc), 1,1-dimethyl-2-haloethyl carbamate, 1,1-dimethyl-2,2-dibromoethyl carbamate (DB-1-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, 1-amyl carbamate, S-benzyl thiocarbamate, p cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o)-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4 (4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-hydroxyl, N-methylamine, N-allylamine, N-[2-(trimethylsilyl)ethoxy]methylamine (SEM), N-3-acetoxypropylamine, N (1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N p-methoxybenzylideneamine, N-diphenylmethyleneamine, N-[(2-pyridyl)mesityl]methyleneamine, N-(N',N' dimethylaminomethylene)amine, N,N'-isopropylidenediamine, N p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

The term "pharmaceutically acceptable salt" means a salt that is not harmful to mammals, especially humans. Pharmaceutically acceptable salts can be formed using non-toxic acids or bases, including mineral acids or inorganic bases, or organic acids or organic bases. Examples of pharmaceutically acceptable salts include metal salts formed with aluminum, calcium, lithium, magnesium, potassium, sodium, zinc and so on, and organic salts formed with lysine, N,N'-dibenzylethylenediamine, chloroprocaine, choline, diethanolamine, ethylenediamine, meglumine (N-methylglucamine), procaine and so on. Also, pharmaceutically acceptable salts contain acid-addition salts and base-addition salts.

The term "pharmaceutically acceptable carriers" means pharmaceutically acceptable materials, compositions, or vehicles such as physiological saline solutions, liquid or solid fillers, diluents, solvents, or encapsulants. Examples of pharmaceutically acceptable carriers include water, saline water, physiological saline water or phosphate buffered saline water (PBS), sodium chloride injection solution, Ringer's injection solution, isotonic dextrose injection solution, sterile water injection solution, dextrose, and lactated Ringer's injection solution.

The term "effective dose" refers to the amount of a compound or a composition which will have a targeted effect. For example, in some embodiments, the effective dose may refer to the amount of a compound or a composition which will enable tau imaging.

The term "solvate" means a solvent-containing compound that is formed by association of one or a plurality of solvent molecules to the compounds of the present invention. Solvates include, for example, monosolvates, disolvates, trisolvates, and tetrasolvates. Also, solvates include hydrates. The term "hydrate" means a compound further containing a stoichiometric or a non-stoichiometric amount of water constrained by non-covalent bonding intermolecular force, or a salt thereof. Hydrates include monohydrates, dihydrates, trihydrates, and tetrahydrates.

The term "treatment" means moderating or remitting the progress, severity and/or period of a disease or condition. The term "prevention" means reducing the danger of catching or making worse a predetermined disease or condition, or reducing or suppressing the recurrence, start or progress of a predetermined disease or condition, or one or a plurality of symptoms.

The term "tau imaging" means imaging tau proteins that accumulate in the brain. This imaging may be performed by positron emission tomography (PET), fluorescence microscopy measurement, multi-photon imaging, two-photon imaging, near-infrared fluorescence imaging, autoradiography, and single-photon emission computed tomography (SPECT).

DETAILED DESCRIPTION OF THE PREFERRED EMBODIMENT

Figure 1:
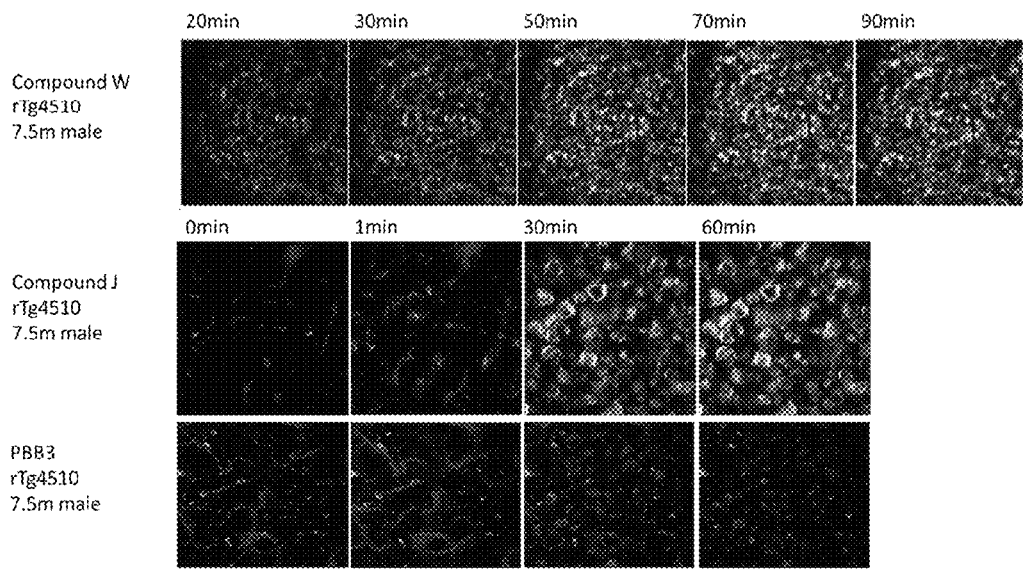
FIG. 1 are the images generated in rTg4510 mice using two photon imaging for compound J and compound W in comparison with PBB3.

Embodiments of the present invention will be described below. These embodiments will be described only to deepen the understanding of the claims of the present invention, and are by no means intended to limit the claims of the present invention.

General Method

Most of chemicals were purchased from Sinopharm Chemical Reagent Co. (SCRC), Sigma-Aldrich, Alfa or other vendors.

1H NMR or 19F NMR spectra were recorded on Bruker AVIII 400 or Bruker AVIII 500.

LCMS measurement was run on Agilent 1200 HPLC/6100 SQ System using the follow conditions:

Method A: Mobile Phase: A: Water (0.01% TFA) B: CAN (0.01% TFA); Gradient Phase: 5% B increase to 95% B within 1.4 min, 95% B with 1.6 min (total runtime: 3 min); Flow Rate: 2.3 mL/min; Column: SunFire C18, 4.6*50 mm, 3.5 μm; Column Temperature: 50° C. Detectors: ADC ELSD, DAD (214 nm and 254 nm), ES-API.

Method B: Mobile Phase: A: Water (10 mM NH4HCO3) B: Acetonitrile; Gradient Phase: 5% to 95% B within 1.5 min, 95% B with 1.5 min (total runtime: 3 min); Flow Rate: 2.0 mL/min; Column: XBridge C18, 4.6*50 mm, 3.5 μm; Column Temperature: 40° C. Detectors: ADC ELSD, DAD (214 nm and 254 nm), MSD (ES-API).

Method C: Mobile Phase: A: Water (10 mM NH4HCO3) B: Acetonitrile; Gradient Phase: 5% to 95% B within 1.5 min, 95% B with 1.5 min (total runtime: 3 min); Flow Rate: 2.0 mL/min; Column: XBridge C18, 4.6*50 mm, 3.5 μm; Column Temperature: 40° C. Detectors: ADC ELSD, DAD (214 nm and 254 nm), MSD (ES-API).

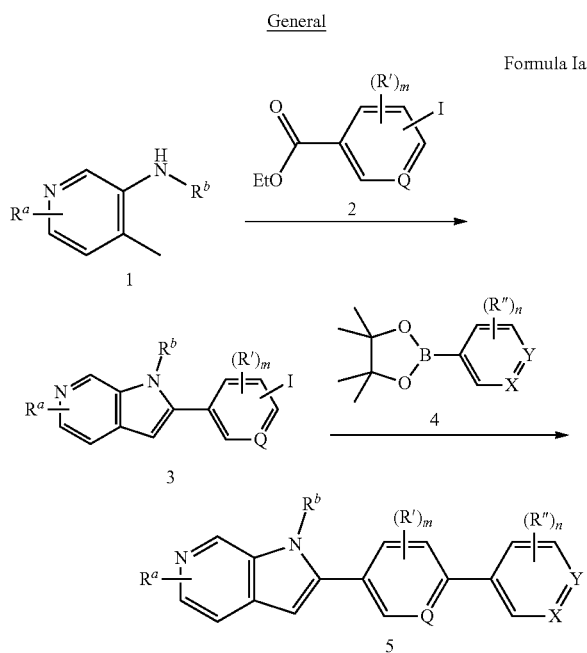

General

Formula Ia

To a solution of amino-aniline 1 (7.94 mmol) in tetrahydrofuran (15 mL) was added s-butyllithium (1.40 M in hexane, 17.01 mL, 23.81 mmol) at −78° C. dropwise. Then the mixture was warmed to room temperature and stirred for 3 h. The mixture was cooled to −78° C., then added iodo-aryl ethyl ester 2 (3.18 mmol) within 20 min. The resulting mixture was stirred at −78° C. for 1 h. The reaction mixture was quenched with methanol (5 mL) at −78° C. and stirred for another 1 h at room temperature. Water was added to the mixture and extracted with ethyl acetate (50 mL×3). The organic phase was washed with brine (50 mL×3), dried over anhydrous sodium sulfate and concentrated in vacuo. The residue was purified by flash column chromatography (dichloromethane/methanol=10/1) to give iodo aryl pyrrolopyrdine 3.

A mixture of iodo-aryl pyrrolopyridine 3 (0.29 mmol), aryl boronate 4 (0.44 mmol), sodium carbonate (a.q.) (0.73 mL, 1.45 mmol, 2M a.q.) and tetrakis(triphenylphosphine)palladium (35 mg, 0.03 mmol) in N,N-dimethylformamide (10 mL) was stirred at 80° C. for 4 h under nitrogen atmosphere. The mixture was filtered and the filtrate was concentrated to dryness. The residue was resolved with ethyl acetate (40 mL×3) and washed with brine (40 mL×3), dried over anhydrous sodium sulfate and evaporated in vacuo. The residue was then purified by flash column chromatography (dichloromethane/methanol=10/1) to give pyrrolopyridine 5.

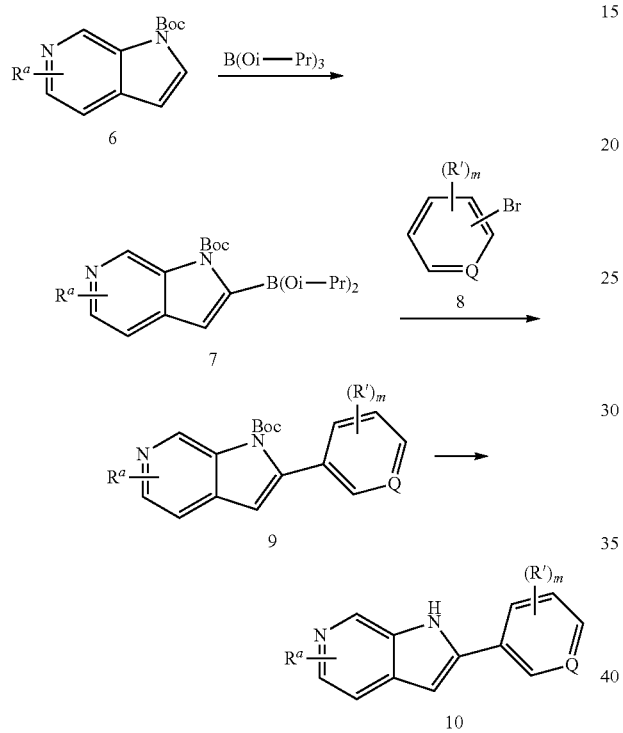

To a solution of Boc-pyrrolopyridine 6 (0.20 mmol) and tripropan-2-yl borate (0.12 mL, 0.50 mmol) in tetrahydrofuran (1 mL) was added lithium diisopropylamide (0.3 mL, 0.60 mmol) dropwise at 0° C. The reaction mixture was stirred for 10 min at 0° C. The mixture was quenched with water (1 mL) and filtered. The filtrate was concentrated to give boronate 7 which was used to next step without any purification.

A mixture of boronate 7 (0.20 mmol), aryl boronate 8 (0.14 mmol), potassium phosphate (88 mg, 0.41 mmol) and [1,1'-bis(diphenylphosphino)ferrocene] dichloropalladium (II) (9 mg, 0.01 mmol) in water (0.5 mL), tetrahydrofuran (1 mL) and 1,4-dioxane (5 mL) was stirred at 80° C. overnight under nitrogen atmosphere. After cooling to room temperature, the mixture was filtered and the filtrate was concentrated. The residue was purified by column chromatography (dichloromethane/methanol=97/3) to give aryl pyrrolopyridine 9. To 9 in acetic acid (3 mL) was added hydrogen bromide (3.0 mL). The resulting mixture was stirred at 110° C. for 16 h in a sealed tube. The mixture was filtered and the filtrate cake was washed with sodium bicarbonate (a.q.) to give crude target compound 10.

Synthesis of Compound A

Step 1: tert-Butyl 2-[4-(3-aminophenyl)phenyl]pyrrolo[2,3-c]pyridine-1-carboxylate A mixture of tert-butyl 2-(4-iodophenyl)pyrrolo[2,3-c]pyridine-1-carboxylate (100 mg, 0.24 mmol), 3-(4,4,5,5-tetramethyl-1,3,2-dioxaborolan-2-yl)aniline (156 mg, 0.71 mmol), sodium carbonate (126 mg, 1.19 mmol) and [1,1'-bis(diphenylphosphino)ferrocene]dichloropalladium(II) (18 mg, 0.02 mmol) in 1,4-dioxane (10 mL) and water (2 mL) was stirred at 80° C. for 3 h under nitrogen atmosphere. The reaction mixture was concentrated to dryness. The residue was taken up in ethyl acetate (20 mL), washed with water and brine, dried over sodium sulfate and concentrated. The residue was purified by flash column chromatography (dichloromethane/methanol=from 1% to 25%) to give tert-butyl 2-[4-(3-aminophenyl)phenyl]pyrrolo[2,3-c]pyridine-1-carboxylate (230 mg, 75% yield) as a brownish solid, which was used the next step without purification. LCMS (ESI) [M+H]+=386.2.

Step 2: 3-[4-(1H-Pyrrolo[2,3-c]pyridin-2-yl)phenyl]aniline

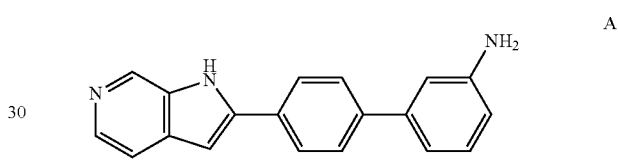

To a solution of tert-butyl 2-[4-(3-aminophenyl)phenyl]pyrrolo[2,3-c]pyridine-1-carboxylate (110 mg, 0.29 mmol) in methanol (6 mL) and water (1.2 mL) was added lithium hydroxide (36 mg, 0.86 mmol). The resulting mixture was stirred at 50° C. for 1 h. After cooling to room temperature, solid was isolated. The mixture was filtered and the filtrate cake was dried to give 3-[4-(1H-pyrrolo[2,3-c]pyridin-2-yl)phenyl]aniline (10.7 mg, 13% yield) as an off-white solid. LCMS (ESI) [M+H]+=286.1; 1H NMR (400 MHZ, DMSO-$d_6$) δ 12.10 (s, 1H), 8.75 (s, 1H), 8.10-8.09 (d, J=4.8 Hz, 1H), 8.01-7.99 (d, J=7.6 Hz, 2H), 7.72-7.70 (d, J=7.6 Hz, 2H), 7.52-7.50 (d, J=4.4 Hz, 1H), 7.15-7.11 (t, J=7.8 Hz, 1H), 7.01 (s, 1H), 6.92 (s, 1H), 6.88-6.86 (d, J=6.4 Hz, 1H), 6.60-6.59 (d, J=7.6 Hz, 1H), 5.20 (s, 2H).

Synthesis of Compound B

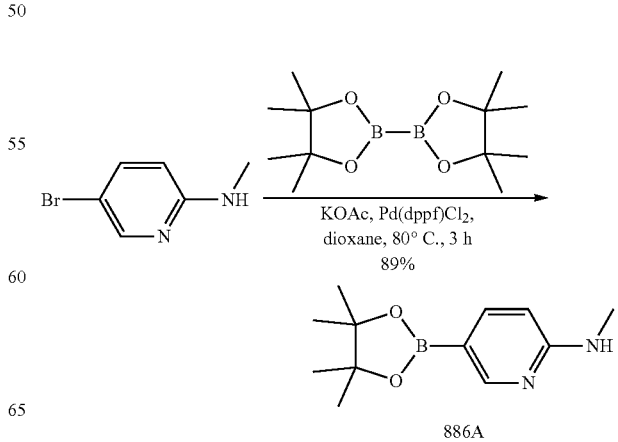

81

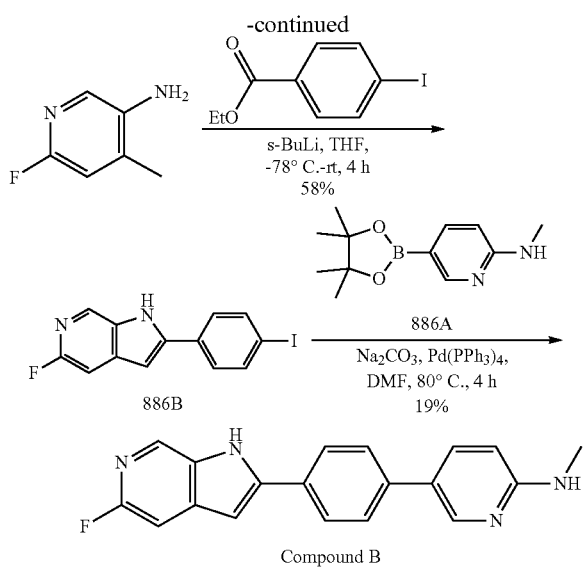

Compound B

Step 1: N-Methyl-5-(4,4,5,5-tetramethyl-1,3,2-dioxaborolan-2-yl)pyridin-2-amine

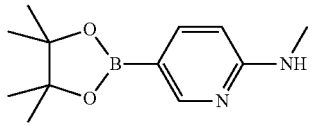

A mixture of 5-bromo-N-methylpyridin-2-amine (500 mg, 2.69 mmol) bis(pinacolato)diboron (887 mg, 3.49 mmoL), potassium acetate (791 mg, 8.07 mmoL) and [1,1'-bis(diphenylphosphino)ferrocene]dichloropalladium(II) (102 mg, 0.14 mmoL) in 1,4-dioxane (10 mL) was stirred at 100° C. for 3 h under nitrogen atmosphere. The mixture was treat with water and extracted with ethyl acetate (50 mL×3). The organic phase was washed with (50 mL×3), dried over anhydrous sodium sulfate and concentrated in vacuo to give N-methyl-5-(4,4,5,5-tetramethyl-1,3,2-dioxaborolan-2-yl)pyridin-2-amine (560 mg, 89% yield), which was used to the next step without further purification. LCMS (ESI) [M+H]+=235; $R_T$=1.70 min (Method B).

Step 2: 5-Fluoro-2-(4-iodophenyl)-1H-pyrrolo[2,3-c]pyridine

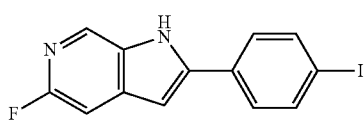 [SMILES: Fc1cc2cc(-c3ccc(I)cc3)[nH]c2cn1]

To a solution of 6-fluoro-4-methylpyridin-3-amine (1.0 g, 7.94 mmol) in tetrahydrofuran (15 mL) was added s-butyllithium (1.40 M in hexane, 17.01 mL, 23.81 mmoL) at −78° C. dropwise. Then the mixture was warmed to room temperature and stirred for 3 h. The mixture was cooled to −78° C., then added ethyl 4-iodanylbenzoate (877 mg, 3.18 mmoL) within 20 min. The resulting mixture was stirred at

82

−78° C. for 1 h. The reaction mixture was quenched with methanol (5 mL) at −78° C. and stirred for another 1 h at room temperature. Water was added to the mixture and extracted with ethyl acetate (50 mL×3). The organic phase was washed with brine (50 mL×3), dried over anhydrous sodium sulfate and concentrated in vacuo. The residue was purified by flash column chromatography (dichloromethane/methanol=10/1) to give 5-fluoro-2-(4-iodophenyl)-1H-pyrrolo[2,3-c]pyridine (630 mg, 58% yield) as a yellow solid. LCMS (ESI) [M+H]+=339; $R_T$=1.99 min (Method A).

Step 3: 5-(4-(5-Fluoro-1H-pyrrolo[2,3-c]pyridin-2-yl)phenyl)-N-methylpyridin-2-amine

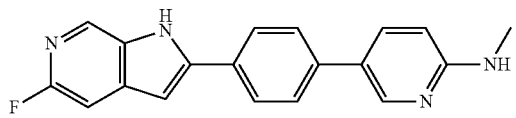 [SMILES: CNc1ccc(-c2ccc(-c3cc4cc(F)ncc4[nH]3)cc2)cn1]

A mixture of 5-fluoro-2-(4-iodophenyl)-1H-pyrrolo[2,3-c]pyridine (100 mg, 0.29 mmol), N-methyl-5-(4,4,5,5-tetramethyl-1,3,2-dioxaborolan-2-yl)pyridin-2-amine (104 mg, 0.44 mmol), sodium carbonate (a.q.) (0.73 mL, 1.45 mmol, 2 M a.q.) and tetrakis(triphenylphosphine)palladium (35 mg, 0.03 mmol) in N,N-dimethylformamide (10 mL) was stirred at 80° C. for 4 h under nitrogen atmosphere. The mixture was filtered and the filtrate was concentrated to dryness. The residue was resolved with ethyl acetate (40 mL×3) and washed with brine (40 mL×3), dried over anhydrous sodium sulfate and evaporated in vacuo. The residue was then purified by flash column chromatography (dichloromethane/methanol=10/1) to give 5-(4-(5-Fluoro-1H-pyrrolo[2,3-c]pyridin-2-yl)phenyl)-N-methylpyridin-2-amine (18.0 mg, 19% yield) as a yellow solid. LCMS (ESI) [M+H]+=319; $R_T$=1.68 min (Method B); $^1$H NMR (400 MHZ, DMSO-$d_6$) δ 12.13 (s, 1H), 8.45 (s, 1H), 8.33 (s, 1H), 7.97 (d, J=8.4 Hz, 2H), 7.82 (d, J=8.4 Hz, 1H), 7.75 (d, J=8.4 Hz, 1H), 7.15 (s, 1H), 7.01 (s, 1H), 6.73 (q, J=4.8 Hz, 1H), 6.56 (d, J=8.4 Hz, 1H), 2.83 (d, J=4.8 Hz, 3H).

Synthesis of Compound C

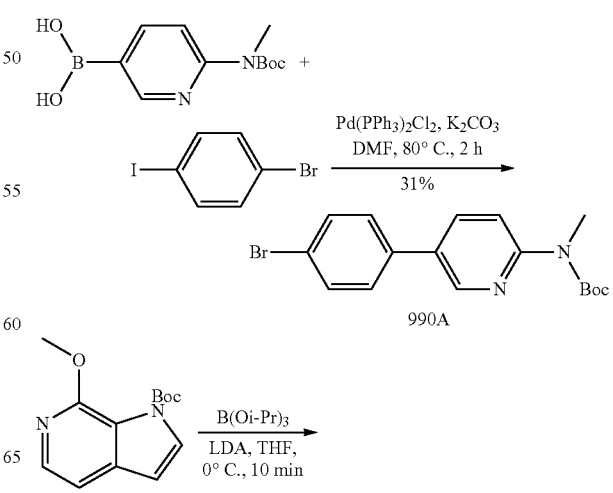

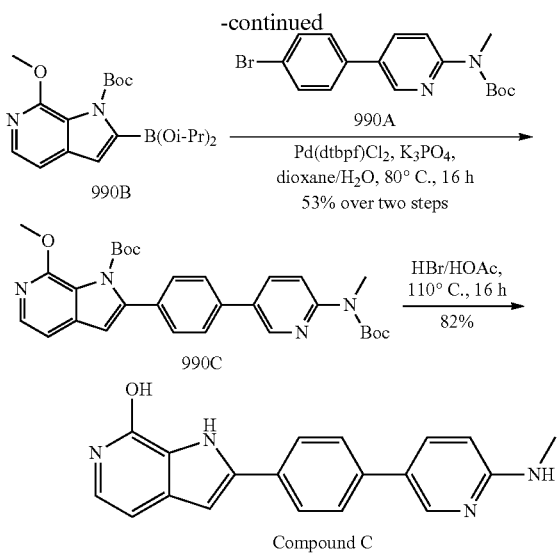

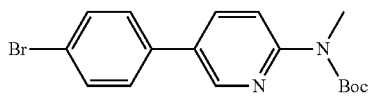 [SMILES: CN(C(=O)OC(C)(C)C)c1ccc(-c2ccc(Br)cc2)cn1]

Step 1: tert-Butyl 5-(4-bromophenyl)pyridin-2-yl(methyl)carbamate

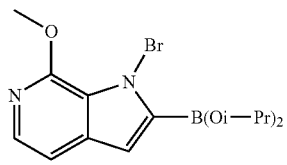

A mixture of 1-bromanyl-4-iodanyl-benzene (689 mg, 2.43 mmol), [6-[methyl-[(2-methylpropan-2-yl)oxycarbonyl]amino]pyridin-3-yl]boronic acid (510 mg, 2.02 mmol), bis(triphenylphosphine)palladium(II) chloride (59 mg, 0.08 mmol) and potassium carbonate (465 mg, 3.37 mmol) in N,N-dimethylformamide (10 mL) was stirred at 80° C. for 2 h. The reaction mixture was treated with water (30 mL) and extracted with ethyl acetate (30 mL×3). The combined organic layer was washed with brine (30 mL), dried over anhydrous sodium sulfate and concentrated. The residue was purified by column chromatography (petroleum ether/ethyl acetate=100/5) to give tert-butyl 5-(4-bromophenyl)pyridin-2-yl(methyl)carbamate (240 mg, 31% yield) as white solid. LCMS (ESI) [M+H]$^+$=326.9; $R_T$=2.501 min (Method A).

Step 2: tert-Butyl 2-di(propan-2-yloxy)boranyl-7-methoxy-pyrrolo[2,3-c]pyridine-1-carboxylate

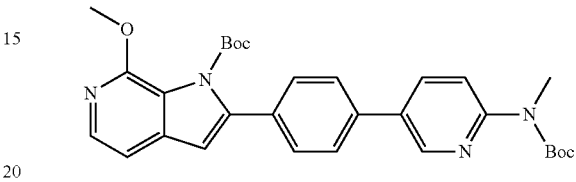

To a solution of tert-butyl 7-methoxypyrrolo[2,3-c]pyridine-1-carboxylate (50 mg, 0.20 mmol) and tripropan-2-yl borate (0.12 mL, 0.50 mmol) in tetrahydrofuran (1 mL) was added lithium diisopropylamide (0.3 mL, 0.60 mmol) dropwise at 0° C. The reaction mixture was stirred for 10 min at 0° C. The mixture was quenched with water (1 mL) and filtered. The filtrate was concentrated to give tert-butyl 2-di(propan-2-yloxy)boranyl-7-methoxy-pyrrolo[2,3-c]pyridine-1-carboxylate (90 mg, crude), which was used to next step without any purification. LCMS (ESI) [M-i-Pr+H]$^+$=292.9; $R_T$=1.434 min (Method B).

Step 3: tert-Butyl 2-(4-(6-(tert-butoxycarbonyl(methyl)amino)pyridin-3-yl)phenyl)-7-methoxy-1H-pyrrolo[2,3-c]pyridine-1-carboxylate

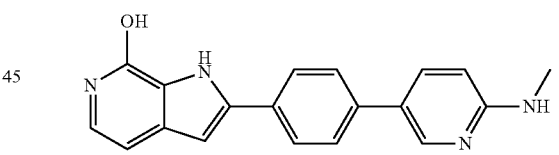

A mixture of tert-butyl 2-di(propan-2-yloxy)boranyl-7-methoxy-pyrrolo[2,3-c]pyridine-1-carboxylate (90 mg, 0.20 mmol), tert-butyl N-[5-(4-bromophenyl)pyridin-2-yl]-N-methyl-carbamate (50 mg, 0.14 mmol), potassium phosphate (88 mg, 0.41 mmol) and [1,1'-bis(diphenylphosphino)ferrocene] dichloropalladium(II) (9 mg, 0.01 mmol) in water (0.5 mL), tetrahydrofuran (1 mL) and 1,4-dioxane (5 mL) was stirred at 80° C. overnight under nitrogen atmosphere. After cooling to room temperature, the mixture was filtered and the filtrate was concentrated. The residue was purified by column chromatography (dichloromethane/methanol=97/3) to give tert-butyl 2-(4-(6-(tert-butoxycarbonyl(methyl)amino)pyridin-3-yl)phenyl)-7-methoxy-1H-pyrrolo[2,3-c]pyridine-1-carboxylate (60 mg, 53% yield over two steps) as oil. LCMS (ESI) [M+H]$^+$=531.0; $R_T$=2.644 min (Method A).

Step 4: 2-(4-(6-(Methylamino)pyridin-3-yl)phenyl)-1H-pyrrolo[2,3-c]pyridin-7-ol To a solution of tert-butyl 7-methoxy-2-[4-[6-[methyl-[(2-methylpropan-2-yl)oxycarbonyl]amino]pyridin-3-yl]phenyl]pyrrolo[2,3-c]pyridine-1-carboxylate (180 mg, 0.34 mmol) in acetic acid (3 mL) was added hydrogen bromide (3.0 mL). The resulting mixture was stirred at 110° C. for 16 h in a sealed tube. The mixture was filtered and the filtrate cake was washed with sodium bicarbonate (a.q.) to give crude target compound, which was slurry with methanol to give 2-(4-(6-(methylamino)pyridin-3-yl)phenyl)-1H-pyrrolo[2,3-c]pyridin-7-ol (88 mg, 82% yield) as a yellow solid. LCMS (ESI) [M+H]$^+$=317.0; $R_T$=1.420 min (Method A). 1H NMR (400 MHZ, DMSO-d$_6$) δ 12.28 (s, 1H), 10.90 (s, 1H), 8.40 (d, J=2.4 Hz, 1H), 7.90 (d, J=8.4 Hz, 2H), 7.79-7.77 (dd, J=8.8 Hz, J=2.4 Hz, 1H), 7.64 (d, J=8.4 Hz, 2H), 6.92-6.88 (m, 1H), 6.79 (s, 1H), 6.68-6.67 (m, 1H), 6.54 (d, J=8.8 Hz, 1H), 6.45 (d, J=6.8 Hz, 1H), 2.82 (d, J=4.8 Hz, 3H).

Synthesis of Compound D

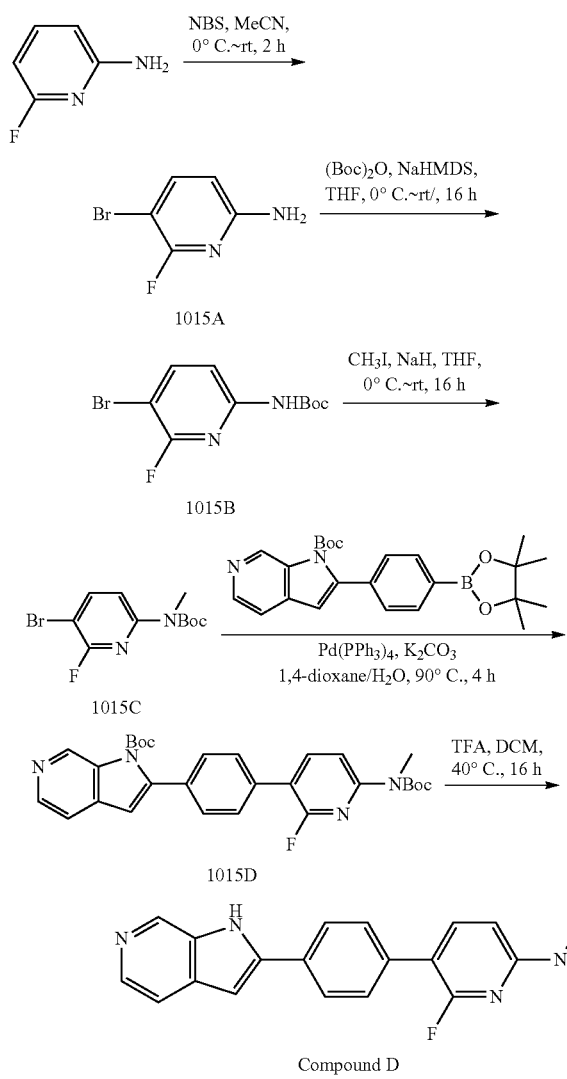

Step 1: 5-Bromo-6-fluoropyridin-2-amine

A mixture of 6-fluoranylpyridin-2-amine (2.8 g, 24.98 mmol) and N-bromosuccinimide (4.67 g, 26.22 mmol) in acetonitrile (50 mL) was stirred at 25 °C for 2 h. and concentrated. The residue was purified by column chromatography (petroleum ether=100% to petroleum ether/ethyl acetate=10/1) to give 5-bromanyl-6-fluoranyl-pyridin-2-amine (3.91 g, 82% yield) as a red solid. LCMS (ESI) [M+H]$^+$=193.0; $R_T$=1.64 min (Method B).

Step 2: tert-Butyl 5-bromo-6-fluoropyridin-2-ylcarbamate

To a solution of 5-bromanyl-6-fluoranyl-pyridin-2-amine (585 mg, 3.06 mmol) in tetrahydrofuran (15 mL) at 0° C. was added sodium bis(trimethylsilyl)amide (3.06 mL, 2 M in tetrahydrofuran, 6.13 mmol) and the mixture was stirred at this temperature for 0.5 h. tert-Butyl (2-methylpropan-2-yl)oxycarbonyl carbonate (1.0 mg, 4.59 mmol) was added. The resulting mixture was stirred at room temperature until the starting materials were consumed completely and quenched with water, extracted with ethyl acetate (50 mL×3), dried over with anhydrous sodium sulfate, filtered and concentrated under reduced pressure. The residue was purified by flash column chromatography (petroleum ether/ethyl acetate=3/1) to give tert-butyl N-(5-bromanyl-6-fluoranyl-pyridin-2-yl) carbamate (420 mg, 47% yield) as a solid. LCMS (ESI) [M–55]$^+$=236.9; $R_T$=2.02 min (Method B).

Step 3: tert-Butyl 5-bromo-6-fluoropyridin-2-yl(methyl)carbamate

To a solution of tert-butyl N-(5-bromanyl-6-fluoranyl-pyridin-2-yl)carbamate (300 mg, 1.03 mmol) in N,N-dimethylformamide (5 mL) at 0° C. was added sodium hydride (60% dispersion in mineral oil, 37 mg, 1.55 mmol). The mixture was stirred at this temperature for 0.5 h. Iodomethane (222 mg, 1.55 mmol) was added to the mixture. The resulting mixture was stirred at room temperature until the starting materials were consumed completely. The mixture was quenched with water and extracted with ethyl acetate (50 mL×3). The organic layer was washed with brine and water, dried over with anhydrous sodium sulfate, filtered and concentrated under reduced pressure. The residue was purified by flash column chromatography (dichloromethane/methanol=30/1) to give tert-butyl N-(5-bromanyl-6-fluoranyl-pyridin-2-yl)-N-methyl-carbamate (260 mg, 83% yield) as a solid. LCMS (ESI) [M–55]$^+$=248.6; $R_T$=2.25 min (Method A).

Step 4: tert-Butyl 2-(4-(6-(tert-butoxycarbonyl(methyl)amino)-2-fluoropyridin-3-yl)phenyl)-1H-pyrrolo[2,3-c]pyridine-1-carboxylate

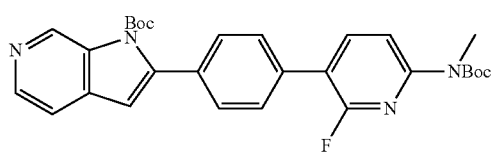 [SMILES: CN(C(=O)OC(C)(C)C)c1ccc(-c2ccc(-c3cc4ccncc4n3C(=O)OC(C)(C)C)cc2)c(F)n1]

A mixture of tert-butyl N-(5-bromanyl-6-fluoranyl-pyridin-2-yl)-N-methyl-carbamate (200 mg, 0.66 mmol), tert-butyl 2-[4-(4,4,5,5-tetramethyl-1,3,2-dioxaborolan-2-yl)phenyl]pyrrolo[2,3-c]pyridine-1-carboxylate (441 mg, 1.05 mmol), potassium carbonate (226 mg, 1.64 mmol) and tetrakis(triphenylphosphine)palladium (75 mg, 0.07 mmol) were in 1,4-dioxane (5 mL) and water (1 mL) were stirred at 90 °C for 4 h under nitrogen atmosphere. The mixture was filtered and the filtrate was concentrated under reduced pressure. The residue was diluted with ethyl acetate (50 mL), washed with brine and water, dried over with anhydrous sodium sulfate, filtered and concentrated under reduced pressure. The residue was purified by flash column chromatography (dichloromethane/methanol=100/15) to give tert-butyl 2-[4-[2-fluoranyl-6-[methyl-[(2-methylpropan-2-yl)oxycarbonyl]amino]pyridin-3-yl]phenyl]pyrrolo[2,3-c]pyridine-1-carboxylate (44 mg, 13% yield) as a yellow solid. LCMS (ESI) [M+H]$^+$=518.7, $R_T$=2.22 min (Method A).

Step 5: 5-(4-(1H-Pyrrolo[2,3-c]pyridin-2-yl)phenyl)-6-fluoro-N-methylpyridin-2-amine

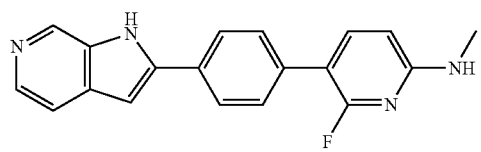 [SMILES: CNc1ccc(-c2ccc(-c3cc4ccncc4[nH]3)cc2)c(F)n1]

To a solution of tert-butyl 2-[4-[2-fluoranyl-6-[methyl-[(2-methylpropan-2-yl)oxycarbonyl]amino]pyridin-3-yl]phenyl]pyrrolo[2,3-c]pyridine-1-carboxylate (65 mg, 0.13 mmol) in dichloromethane (5 mL) was added trifluoroacetic acid (143 mg, 1.25 mmol). The mixture was stirred under reflux until the starting materials were consumed completely. The solvent was removed under reduced pressure and the residue was purified by Pre-HPLC to give 6-fluoranyl-N-methyl-5-[4-(1H-pyrrolo[2,3-c]pyridin-2-yl)phenyl]pyridin-2-amine (24 mg, 60% yield) as a solid. LCMS (ESI) [M+H]$^+$=319.0; $R_T$=1.48 min (Method C). $^1$H NMR (400 MHZ, DMSO-$d_6$) δ 12.09 (s, 1H), 8.75 (s, 1H), 8.21 (s, 1H), 8.10 (d, J=5.1 Hz, 1H), 7.98 (d, J=8.2 Hz, 2H), 7.87-7.74 (m, 1H), 7.63 (d, J=7.9 Hz, 2H), 7.51 (d, J=5.2 Hz, 1H), 7.11 (d, J=4.3 Hz, 1H), 7.00 (s, 1H), 6.48 (d, J=8.0 Hz, 1H), 2.76 (d, J=4.8 Hz, 3H).

Synthesis of Compound E

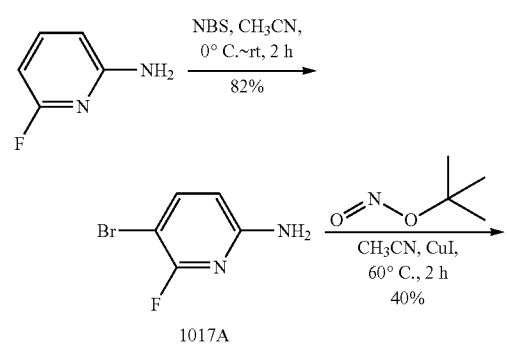

Step 1: 5-Bromo-6-fluoropyridin-2-amine

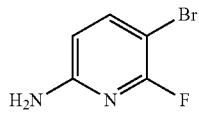

A mixture of 6-fluoranylpyridin-2-amine (2.8 g, 24.98 mmol) and N-bromosuccinimide (4.67 g, 26.22 mmol) in acetonitrile (50 mL) was stirred at 25° C. for 2 h. The mixture was concentrated and the residue was purified by column chromatography (petroleum ether/methanol=10/1) to give 5-bromo-6-fluoropyridin-2-amine (3.91 g, 82% yield) as a red solid. LCMS (ESI) [M+H]$^+$=193.0, $R_T$=1.64 min (Method B).

Step 2: 3-Bromo-2-fluoro-6-iodopyridine

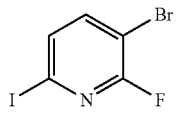

A mixture of 5-bromo-6-fluoropyridin-2-amine (3.3 g, 17.28 mmol), tert-butyl nitrite (2.67 g, 25.92 mmol) and cuprous iodide (4.94 g, 25.92 mmol) in acetonitrile (30 mL) was heated to 60° C. for 2 h. After cooling to room temperature, the mixture was filtered and the filtrate was concentrated. The residue was purified by column chroma-

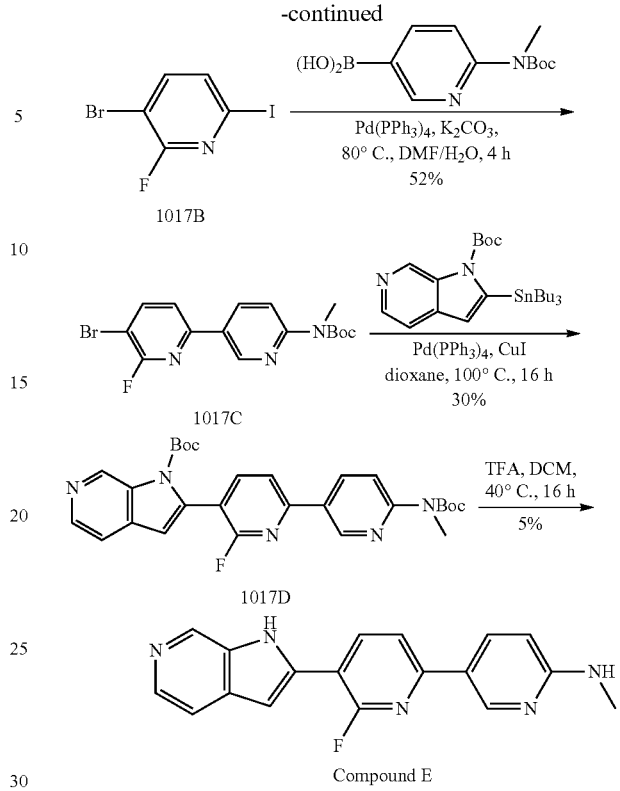

Step 3: tert-Butyl 5-bromo-6-fluoro-2,3'-bipyridin-6'-yl(methyl)carbamate

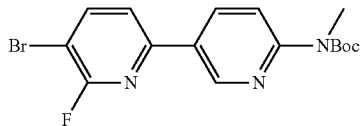

A mixture of 3-bromo-2-fluoro-6-iodopyridine (1.1 g, 3.64 mmol), [6-[methyl-[(2-methylpropan-2-yl)oxycarbonyl]amino]pyridin-3-yl]boronic acid (0.87 g, 3.46 mmol), potassium carbonate (1.26 g, 9.11 mmol) and tetrakis(triphenylphosphine)palladium (0.42 g, 0.36 mmol) in N,N-dimethylformamide (5 mL) and water (1 mL) was stirred at 80° C. under nitrogen atmosphere for 4 h. The mixture was filtered and the filtrate was concentrated under reduced pressure. The residue was diluted with ethyl acetate (100 mL), washed with brine and water, dried over with anhydrous sodium sulfate, filtered and concentrated under reduced pressure. The residue was purified by flash column chromatography (dichloromethane/methanol=100/15) to give tert-butyl 5-bromo-6-fluoro-2,3'-bipyridin-6'-yl(methyl)carbamate (723 mg, 52% yield) as a yellow solid. LCMS (ESI) [M+H]$^+$=383.8, $R_T$=2.31 min (Method A).

Step 4: tert-Butyl 2-(6'-(tert-butoxycarbonyl(methyl)amino)-6-fluoro-2,3'-bipyridin-5-yl)-1H-pyrrolo[2,3-c]pyridine-1-carboxylate

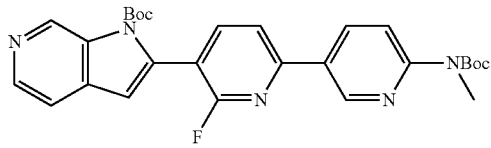 [SMILES: CN(C(=O)OC(C)(C)C)c1ccc(-c2ccc(-c3cc4ccncc4n3C(=O)OC(C)(C)C)c(F)n2)cn1]

A mixture of tert-butyl 5-bromo-6-fluoro-2,3'-bipyridin-6'-yl(methyl)carbamate (400 mg, 1.05 mmol), tert-butyl 2-tributylstannylpyrrolo[2,3-c]pyridine-1-carboxylate (584 mg, 1.15 mmol), cuprous iodide (20 mg, 0.1 mmol) and tetrakis(triphenylphosphine)palladium (121 mg, 0.1 mmol) in 1,4-dioxane (6 mL) was stirred at 100° C. overnight under nitrogen atmosphere. After cooling to room temperature, the mixture was filtered and the filtrate was concentrated to. The residue was purified by column chromatography (petroleum ether/methanol=100/35) to give tert-butyl 2-(6'-(tert-butoxycarbonyl(methyl)amino)-6-fluoro-2,3'-bipyridin-5-yl)-1H-pyrrolo[2,3-c]pyridine-1-carboxylate (161 mg, 30% yield) as oil. LCMS (ESI) [M+H]$^+$=520.3, $R_T$=2.22 min (Method B).

Step 5: 6-Fluoro-N-methyl-5-(1H-pyrrolo[2,3-c]pyridin-2-yl)-2,3'-bipyridin-6'-amine

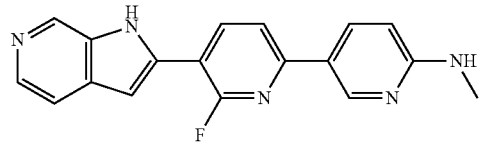 [SMILES: CNc1ccc(-c2ccc(-c3cc4ccncc4[nH]3)c(F)n2)cn1]

To a solution of tert-butyl 2-(6'-(tert-butoxycarbonyl(methyl)amino)-6-fluoro-2,3'-bipyridin-5-yl)-1H-pyrrolo[2,3-c]pyridine-1-carboxylate (160 mg, 0.31 mmol) in dichloromethane (5 mL) was added trifluoroacetic acid (351 mg, 3.08 mmol). The mixture was stirred at 40° C. overnight. The solvent was removed under reduced pressure and the residue was purified by Pre-HPLC to 6-fluoro-N-methyl-5-(1H-pyrrolo[2,3-c]pyridin-2-yl)-2,3'-bipyridin-6'-amine (5 mg, 5% yield) as a solid. LCMS (ESI) [M+H]$^+$=320.0, $R_T$=1.20 min (Method C). $^1$H NMR (400 MHZ, DMSO-d$_6$) δ 12.18 (s, 1H), 9.17 (s, 1H), 8.90 (s, 1H), 8.19 (d, J=7.7 Hz, 2H), 7.94 (d, J=13.5 Hz, 2H), 7.04 (s, 1H), 6.88 (s, 1H), 6.57 (d, J=7.7 Hz, 2H), 2.85 (d, J=3.9 Hz, 3H).

General

Formula Ib

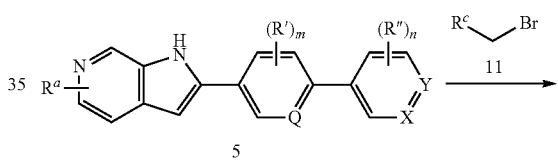

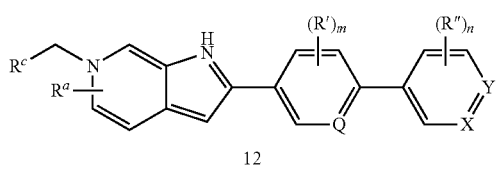

A mixture of aryl pyrrolopyridine 5 (0.67 mmol) 2-bromoalkyl 11 (6.7 mmol) and cesium carbonate (437 mg, 1.34 mmol) in N,N-dimethylformamide (10 mL) was stirred at 60 °C for 15 h. Water was added and the reaction mixture was extracted with ethyl acetate (40 mL×3). The organic phase was washed with brine (30 mL×3), dried over anhydrous sodium sulfate and evaporated in vacuo. The residue was then purified by flash column chromatography (dichloromethane/nethanol=10/1) to give pyrrolopyridine 12.

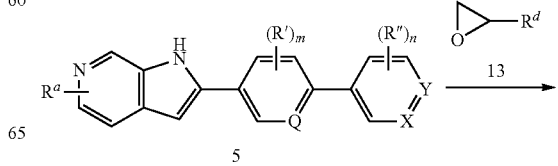

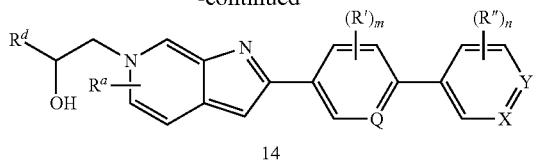

A mixture of aryl pyrrolopyridine 5 (0.25 mmol), epoxide 13 (1.78 mmol) and potassium carbonate (70 mg, 0.51 mmol) in N,N-dimethylformamide (2 mL) was heated at 50° C. overnight. The mixture was quenched by water and a precipitate was formed. The mixture was filtered and the filtrate cake was recrystallized with methanol to give 14.

Synthesis of Compound F

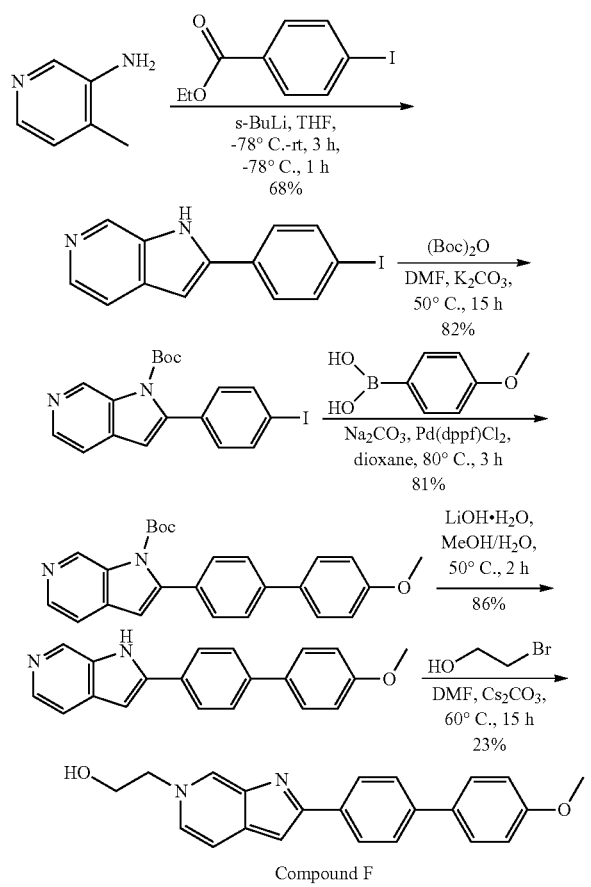

Step 1: 2-(4-Iodophenyl)-1H-pyrrolo[2,3-c]pyridine

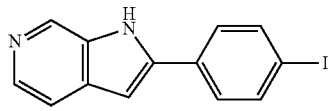

To a solution of 4-methylpyridin-3-amine (1.0 g, 9.26 mmol) in tetrahydrofuran (15 mL) was added s-butyllithium (1.40 M in hexane, 19.84 mL, 27.78 mmoL) dropwise at −78° C. The mixture was warmed to room temperature and stirred for 3 h. The mixture was cooled to −78° C., ethyl 4-iodanylbenzoate (1.02 g, 3.70 mmol) was added within 5 min and stirred at −78° C. for 1 h. The reaction mixture was quenched by methanol (5 mL) and extracted with ethyl acetate (50 mL×3). The organic phase was washed with brine (50 mL×3), dried over anhydrous sodium sulfate and concentrated in vacuo. The residue was purified by flash column chromatography (dichloromethane/methanol=10/1) to give 2-(4-iodophenyl)-1H-pyrrolo[2,3-c]pyridine (800 mg, 68% yield) as a yellow solid. LCMS (ESI) m/z=321 [M+H]$^+$; R$_T$=1.48 min (Method A).

Step 2: tert-Butyl 2-(4-iodophenyl)-1H-pyrrolo[2,3-c]pyridine-1-carboxylate

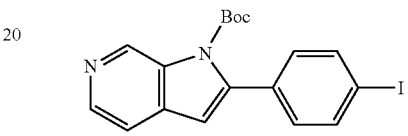

A mixture of 2-(4-iodophenyl)-1H-pyrrolo[2,3-c]pyridine (500 mg, 1.56 mmol), di-tert-butyl dicarbonate (1.02 g, 4.69 mmol), potassium carbonate (430 mg, 3.12 mmol) and 4-dimethylaminopyridine (20 mg, 0.156 mmol) in N,N-dimethylformamide (10 mL) was stirred at 50° C. for 15 h. Water was added and the mixture was extracted with ethyl acetate (40 mL×3). The organic phase was washed with brine (40 mL×3), dried over anhydrous sodium sulfate and evaporated in vacuo. The residue was then purified by flash column chromatography (dichloromethane/methanol=10/1) to give tert-butyl 2-(4-iodophenyl)-1H-pyrrolo[2,3-c]pyridine-1-carboxylate (540 mg, 82% yield) as yellow solid. LCMS (ESI) m/z=421 [M+H]$^+$; R$_T$=2.20 min (Method B); $^1$H NMR (400 MHZ, DMSO-d$_6$) δ 9.31 (s, 1H), 8.39 (d, J=5.2 Hz, 1H), 7.85 (d, J=8.0 Hz, 2H), 7.63 (d, J=5.2 Hz, 1H), 7.33 (d, J=8.0 Hz, 2H), 6.83 (s, 1H), 1.35 (s, 9H).

Step 3: tert-Butyl 2-(4'-methoxybiphenyl-4-yl)-1H-pyrrolo[2,3-c]pyridine-1-carboxylate

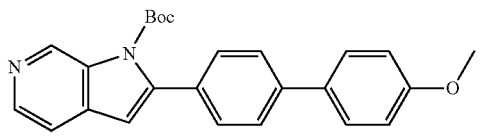 [SMILES: COc1ccc(-c2ccc(-c3cc4ccncc4n3C(=O)OC(C)(C)C)cc2)cc1]

A mixture of tert-butyl 2-(4-iodophenyl)-1H-pyrrolo[2,3-c]pyridine-1-carboxylate (500 mg, 1.19 mmol) 4-methoxyphenylboronic acid (542.86 mg, 3.57 mmol), sodium carbonate (630 mg, 5.95 mmol) and [1,1'-bis(diphenylphosphino)ferrocene]dichloropalladium(II) (87.72 mg, 0.12 mmol) in 1,4-dioxane (15 mL) and water (3 mL) was stirred at 80° C. for 3 h under nitrogen atmosphere. The mixture was filtered and the filtrate was concentrated to dryness. The residue was diluted in ethyl acetate (50 mL) and washed with brine (50 mL×3), dried over anhydrous sodium sulfate and evaporated in vacuo. The residue was purified by flash column chromatography (dichloromethane/methanol=10/1) to give tert-butyl 2-(4'-methoxybiphenyl-4-yl)-1H-pyrrolo[2,3-c]pyridine-1-carboxylate (380 mg, 80% yield) as a yellow solid. LCMS (ESI) m/z=401 [M+H]⁺; R$_T$=1.79 min (Method B); ¹H NMR (400 MHZ, CDCl₃) δ 9.48 (s, 1H), 8.45 (d, J=5.2 Hz, 1H), 7.66-7.59 (m, 4H), 7.52-7.50 (m, 3H), 7.03 (d, J=8.4 Hz, 2H), 6.62 (s, 1H), 3.89 (s, 3H), 1.43 (s, 9H).

Step 4: 2-(4'-Methoxybiphenyl-4-yl)-1H-pyrrolo[2,3-c]pyridine

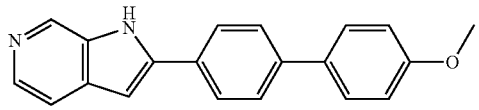 [SMILES: COc1ccc(-c2ccc(-c3cc4ccncc4[nH]3)cc2)cc1]

To a solution of tert-butyl 2-(4'-methoxybiphenyl-4-yl)-1H-pyrrolo[2,3-c]pyridine-1-carboxylate (380 mg, 0.96 mmol) in methanol (10 mL) and water (2 mL) was added lithium hydroxide (121 mg, 2.88 mmol). The mixture was stirred at 50° C. for 2 h and extracted with ethyl acetate (50 mL×3). The organic phase was washed with brine (50 mL×3), dried over anhydrous sodium sulfate and evaporated in vacuo to give 2-(4'-methoxybiphenyl-4-yl)-1H-pyrrolo[2,3-c]pyridine (250 mg, 86% yield), which was used to the next step without further purification. LCMS (ESI) m/z=301 [M+H]⁺; R$_T$=1.68 min (Method A); ¹H NMR (400 MHZ, DMSO-d₆) δ 12.06 (s, 1H), 8.74 (s, 1H), 8.09-7.99 (m, 3H), 7.78-7.71 (m, 4H), 7.50 (s, 1H), 7.05-7.01 (m, 3H), 3.81 (s, 3H).

Step 5: 2-(2-(4'-Methoxybiphenyl-4-yl)-6H-pyrrolo[2,3-c]pyridine-6-yl)ethanol (Compound F)

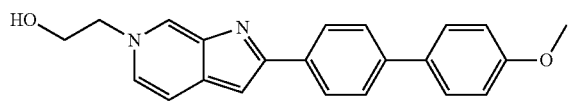 [SMILES: COc1ccc(-c2ccc(-c3cc4ccn(CCO)cc-4n3)cc2)cc1]

A mixture of 2-(4'-methoxybiphenyl-4-yl)-1H-pyrrolo[2,3-c]pyridine (200 mg, 0.67 mmol) 2-bromoethanol (831 mg, 6.7 mmol) and cesium carbonate (437 mg, 1.34 mmol) in N,N-dimethylformamide (10 mL) was stirred at 60° C. for 15 h. Water was added and the reaction mixture was extracted with ethyl acetate (40 mL×3). The organic phase was washed with brine (30 mL×3), dried over anhydrous sodium sulfate and evaporated in vacuo. The residue was then purified by flash column chromatography (dichloromethane/nethanol=10/1) to give 2-(2-(4'-methoxybiphenyl-4-yl)-6H-pyrrolo[2,3-c]pyridine-6-yl)ethanol (52.0 mg, 23% yield) as a yellow solid. LCMS (ESI) m/z=345.1 [M+H]⁺; R$_T$=1.61 min (Method A); 1H NMR (400 MHZ, DMSO-d₆) δ 9.06 (s, 1H), 8.35 (d, J=6.8 Hz, 1H), 8.17 (d, J=8.4 Hz, 2H), 8.10 (d, J=6.8 Hz, 1H), 7.90 (d, J=8.4 Hz, 2H), 7.77 (d, J=6.8 Hz, 2H), 7.48 (s, 1H), 7.08 (d, J=6.8 Hz, 2H), 5.23 (t, J=5.2 Hz, 1H), 4.68 (t, J=5.2 Hz, 2H), 3.89-3.86 (m, 2H), 3.83 (s, 3H).

Synthesis of Compound G

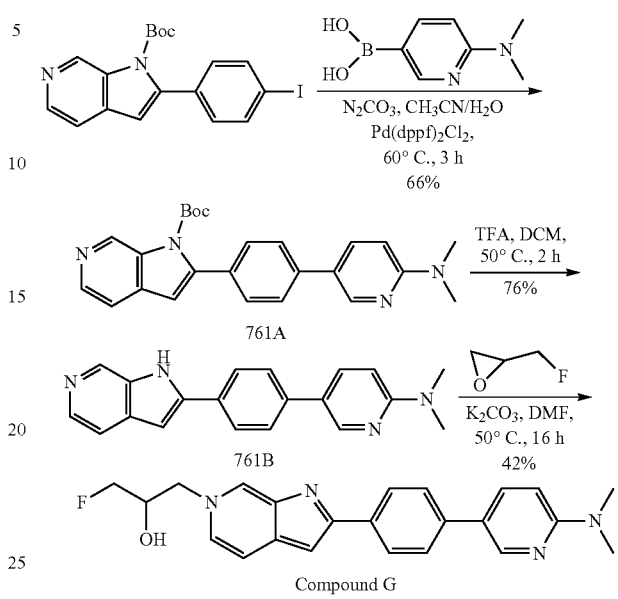

Step 1: tert-Butyl 2-(4-(6-(dimethylamino)pyridin-3-yl)phenyl)-1H-pyrrolo[2,3-c]pyridine-1-carboxylate

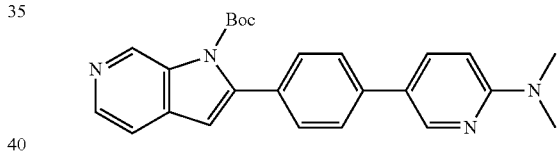

A mixture of [6-(dimethylamino)pyridin-3-yl]boronic acid (172 mg, 1.04 mmol), tert-butyl2-(4-iodophenyl)pyrrolo[2,3-c]pyridine-1-carboxylate (290 mg, 0.69 mmol), sodium carbonate (219 mg, 2.07 mmol), [1,1'-bis(diphenylphosphino)ferrocene]dichloropalladium(II) (51 mg, 0.07 mmol) in acetonitrile (10 mL) and water (2 mL) was stirred at 60° C. for 3 h under nitrogen atmosphere. The reaction mixture was concentrated to dryness and the residue was purified by chromatography (dichloromethane/methanol=100/1) to give tert-Butyl 2-(4-(6-(dimethylamino)pyridin-3-yl)phenyl)-1H-pyrrolo[2,3-c]pyridine-1-carboxylate (190 mg, 66% yield) as a white solid. LCMS (ESI) m/z=415.2 [M+H]⁺; R$_T$=1.306 min (Method A).

Step 2: 5-(4-(1H-Pyrrolo[2,3-c]pyridin-2-yl)phenyl)-N,N-dimethylpyridin-2-amine

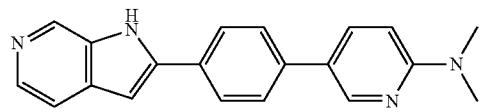

To a solution of tert-butyl 2-[4-[6-(dimethylamino)pyridin-3-yl]phenyl] pyrrolo[2,3-c]pyridine-1-carboxylate (190 mg, 0.46 mmol) in dichloromethane (2 mL) was added trifluoroacetic acid (2 mL). The mixture was stirred at 50° C. for 2 h. The reaction was concentrated to dryness and the crude was purified by column chromatography (dichloromethane/methanol=97/3) to give 5-(4-(1H-pyrrolo[2,3-c]pyridin-2-yl)phenyl)-N,N-dimethylpyridin-2-amine (110 mg, 76% yield) as a yellow solid. LCMS (ESI) m/z=315.1 [M+H]⁺; R$_T$=1.243 min (Method A).

Step 3: 1-(2-(4-(6-(Dimethylamino)pyridin-3-yl)phenyl)-6H-pyrrolo[2,3-c]pyridin-6-yl)-3-fluoropropan-2-ol

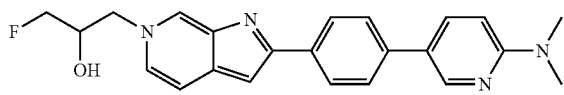

A mixture of N,N-dimethyl-5-[4-(1H-pyrrolo[2,3-c]pyridin-2-yl)phenyl]pyridin-2-amine (80 mg, 0.25 mmol), 2-(fluoranylmethyl)oxirane (135 mg, 1.78 mmol) and potassium carbonate (70 mg, 0.51 mmol) in N,N-dimethylformamide (2 mL) was heated at 50° C. overnight. The mixture was quenched by water and a precipitate was formed. The mixture was filtered and the filtrate cake was recrystalled with methanol to give 1-(2-(4-(6-(dimethylamino)pyridin-3-yl)phenyl)-6H-pyrrolo[2,3-c]pyridin-6-yl)-3-fluoropropan-2-ol (44 mg, 42% yield) as a yellow solid. LCMS (ESI) m/z=391.1 [M+H]⁺; R$_T$=1.887 min (Method B); ¹H NMR (400 MHz, DMSO-d$_6$) δ 8.56 (s, 1H), 8.51 (d, J=1.6 Hz, 1H), 8.16 (d, J=8.0 Hz, 2H), 7.91-7.88 (dd, J=8.8 Hz, J=2.0 Hz, 1H), 7.67 (d, J=8.4 Hz, 2H), 7.61 (d, J=6.8 Hz, 1H), 7.52 (d, J=6.8 Hz, 1H), 7.03 (s, 1H), 6.73 (d, J=8.8 Hz, 1H), 5.68 (brs, 1H), 4.53-4.48 (m, 2H), 4.40-4.36 (m, 1H), 4.27-4.22 (m, 1H), 4.17-4.11 (m, 1H), 3.07 (s, 6H).

General

Formula Ic

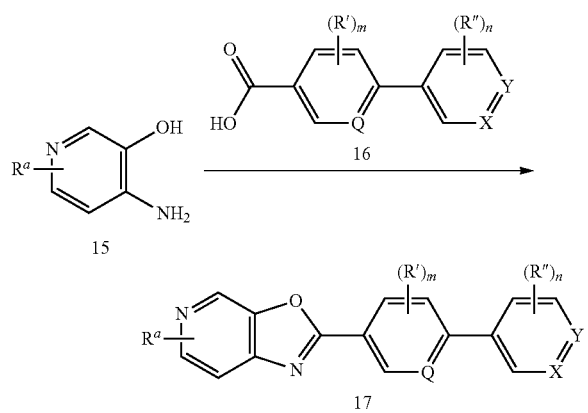

A mixture of aminophenol 15 (0.32 mmol), aryl acid 16 (0.16 mmol) in polyphosphoric acid (2 mL) was stirred at 120° C. for 16 h. The reaction mixture was poured into water and adjusted to pH=7 with saturated sodium hydroxide. Then the mixture was extracted with ethyl acetate (10 mL×4). The combined organic phase was concentrated and the residue was purified by flash chromatography (dichloromethane/methanol=100/3) to give 17.

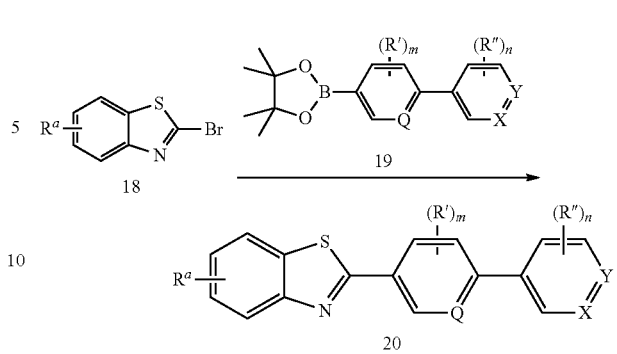

A mixture aryl bromide 18 (3.9 mmol), aryl boronic ester 19 (4.68 mmol), tetrakis(triphenylphosphine)palladium (340 mg, 0.3 mmol) and potassium carbonate (1.38 g, 10 mmol) in acetonitrile (15 mL) and water (3.0 mL) was stirred at 90° C. for 16 h under nitrogen atmosphere. Water (50 ml) was added and solid was isolated. The mixture was filtered and the filtrate cake was washed with water and ethyl acetate, dried under vacuum to provide 20.

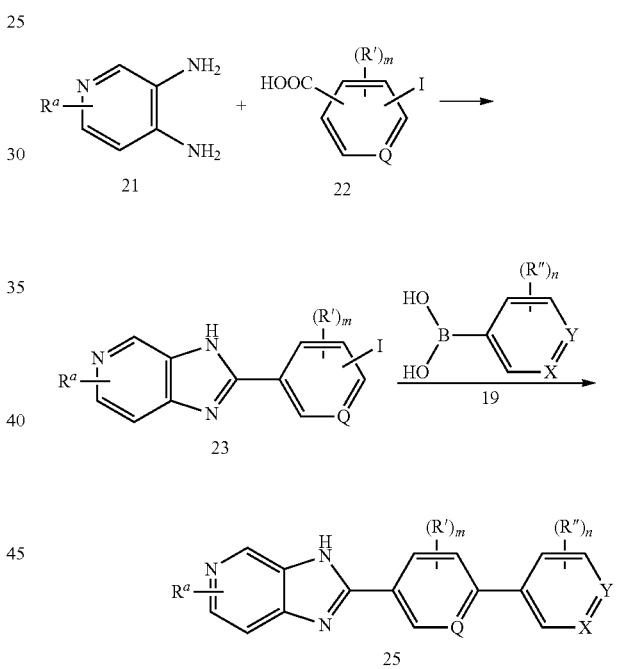

Pyridine-3,4-diamine 21 (1.83 mmol), 4-iodanyl aryl benzoic acid (2.02 mmol) were mixed in PPA (10 mL) and stirred at 130° C. for 16 h. The reaction mixture was poured into water. The mixture was adjusted to pH 9 with saturated aq NaOH. The precipitate was filtered to give the imidazole product 23 (1.74 mmol).

A mixture of Na$_2$CO$_3$ (3.61 mmol), iodo-imidazole 23 (1.2 mmol), aryl boronic acid 24 (1.2 mmol) and Pd(dppf)Cl$_2$ (40 mg, 0.05 mmol) in MeCN (50 mL) and water (10 mL) was heated at 60° C. for 3 h. The reaction was concentrated to dryness and diluted with water (20 mL), filtered to get white solid. The crude product was purified by flash chromatography (DCM/MeOH=20/1 to 10/1) to give 25 (0.31 mmol) as a white solid.

Synthesis of Compound H

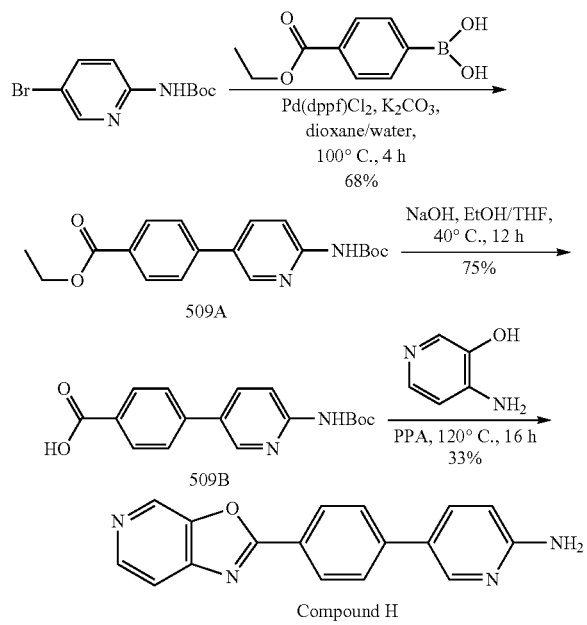

Step 1: Ethyl 4-(6-((tert-butoxycarbonyl)amino) pyridin-3-yl)benzoate

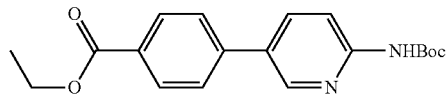

A mixture of tert-butyl 5-bromopyridin-2-ylcarbamate (500 mg, 1.84 mmol), 4-(ethoxycarbonyl)phenylboronic acid (356 mg, 1.84 mmol), potassium carbonate (762 mg, 5.52 mmol) and [1,1'-bis(diphenylphosphino)ferrocene]dichloropalladium (II) (132 mg, 0.18 mmol) in 1,4-dioxane (8 mL) and water (2 mL) was stirred at 100° C. for 4 h under nitrogen atmosphere. The mixture was filtered and the filtrate was extracted with ethyl acetate (40 mL×3). The organic layer was washed with brine (30 mL×3), dried over anhydrous sodium sulfate and evaporated in vacuo. The residue was purified by flash chromatography (dichloromethane/methanol=15/1) to give ethyl 4-(6-(tert-butoxycarbonylamino)pyridin-3-yl)benzoate (427 mg, 68% yield) as a yellow solid. LCMS (ESI) [M+H]$^+$=343.1; R$_T$=2.37 min (Method B).

Step 2: 4-(6-(((tert-Butoxycarbonyl)amino)pyridin-3-yl)benzoic acid

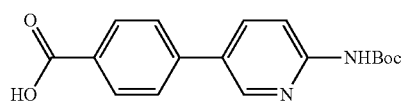

To a solution of ethyl 4-(6-(tert-butoxycarbonylamino) pyridin-3-yl)benzoate (250 mg, 0.73 mmol) in ethanol/tetrahydrofuran (v/v=1/1, 6 mL) was added sodium hydroxide (92 mg, 0.42 mmol) at 25° C. The mixture was stirred at 40° C. overnight. Water (30 mL) was added to the mixture and extracted with ethyl acetate (30 mLv3). The organic phase was washed with brine (30 mL×3), dried over anhydrous sodium sulfate and evaporated in vacuo. The residue was purified by flash chromatography (dichloromethane/methanol=10/1) to give 4-(6-(tert-butoxycarbonylamino) pyridin-3-yl)benzoic acid (172 mg, 75% yield) as a yellow solid. LCMS (ESI) [M+H]$^+$=315.2; R$_T$=1.61 min. (Method A)

Step 3: 5-(4-(Oxazolo[5,4-c]pyridin-2-yl)phenyl) pyridin-2-amine

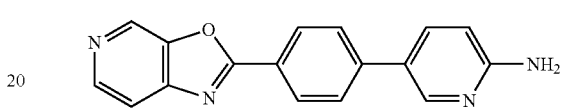

A mixture of 4-azanylpyridin-3-ol (35 mg, 0.32 mmol), 4-[6-[(2-methylpropan-2-yl) oxycarbonylamino]pyridin-3-yl]benzoic acid (50 mg, 0.16 mmol) in polyphosphoric acids (2 mL) was stirred at 120° C. for 16 h. The reaction mixture was poured into water and adjusted to pH=7 with saturated sodium hydroxide. Then the mixture was extracted with ethyl acetate (10 mL×4). The combined organic phase was concentrated and the residue was purified by flash chromatography (dichloromethane/methanol=100/3) to give 5-[4-([1,3]oxazolo[5,4-c]pyridin-2-yl)phenyl]pyridin-2-amine (15 mg, 33% yield) as a white solid. LCMS (ESI) [M+H]$^+$=289.1; R$_T$=1.62 min (Method B); $^1$H NMR (400 MHZ, DMSO-d$_6$) δ 9.13 (d, J=1.2 Hz, 1H), 8.57 (d, J=5.6 Hz, 1H), 8.42 (d, J=2.4 Hz, 1H), 8.26-8.28 (m, 2H), 7.84-7.89 (m, 4H), 6.57 (d, J=8.8 Hz, 1H), 6.30 (s, 2H).

Synthesis of Compound I

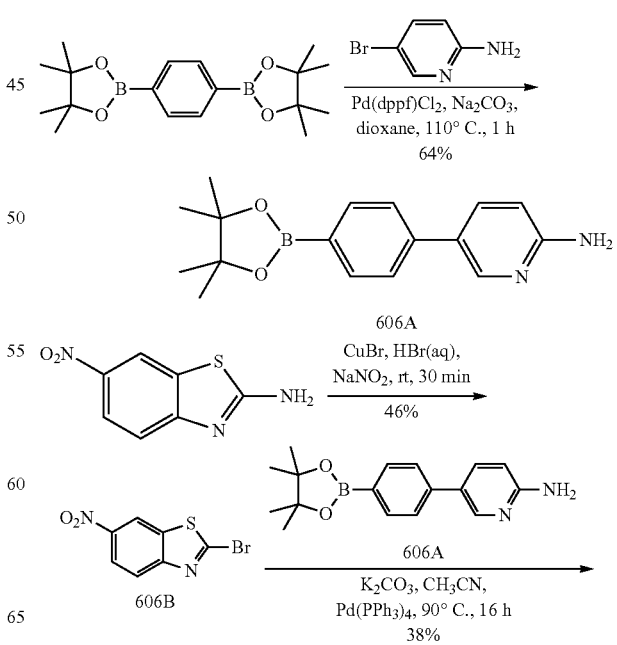

-continued

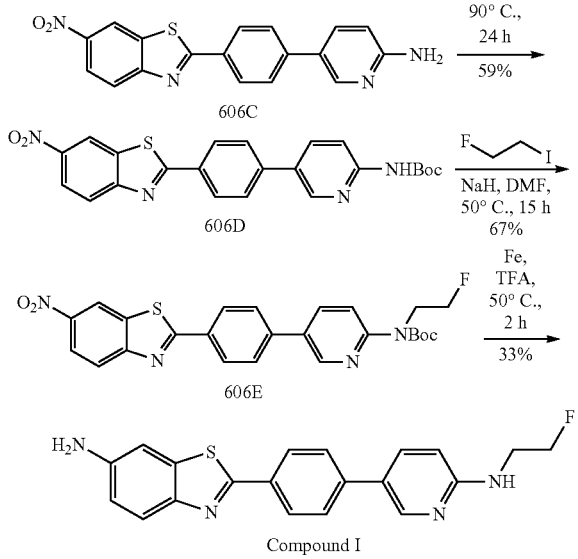

Step 1: 5-(4-(4,4,5,5-Tetramethyl-1,3,2-dioxaborolan-2-yl)phenyl)pyridin-2-amine

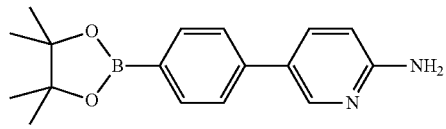 [SMILES: CC1(C)OB(c2ccc(-c3ccc(N)nc3)cc2)OC1(C)C]

A mixture of 5-bromo-pyridin-2-ylamine (500 mg, 2.89 mmol), 1,4-benzenediboronic acid bis(pinacol)ester (1.40 g, 4.25 mmol) and [1,1'-bis(diphenylphosphino)ferrocene]dichloropalladium (II) (116 mg, 0.143 mmol) in 1 M sodium carbonate solution (5.7 mL) and acetonitrile (10 mL) was stirred at 120° C. under microwave for 1 h under nitrogen atmosphere. The reaction mixture was filtered and the filtrate was concentrated. The residue was purified by flash chromatography to give 5-(4-(4,4,5,5-tetramethyl-1,3,2-dioxaborolan-2-yl)phenyl)pyridin-2-amine (534 mg, 64%) as a white solid. LCMS (ESI) [M+H]$^+$=297.1; $R_T$=1.992 min (Method B).

Step 2: 2-Bromo-6-nitrobenzo[d]thiazole

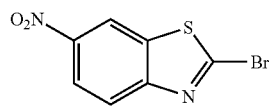 [SMILES: O=[N+]([O-])c1ccc2nc(Br)sc2c1]

To a solution of 2-amino-6-nitrobenzthiazole (3.0 g, 15.3 mmol) and copper (I) bromide (260 mg, 1.83 mmol) in hydrogen bromide (30 mL, 18% in water) and water (27 mL) was added sodium nitrite (9.0 g, 130 mmol) slowly. The mixture was stirred at room temperature for 30 min. The white precipitate was filtered and dried to afford 2-bromo-6-nitrobenzo[d]thiazole (1.8 g, 46%). $^1$H NMR (400 MHZ, DMSO-d$_6$) 9.19 (d, J=2.2 Hz, 1H), 8.36 (dd, J=9.0, 2.4 Hz, 1H), 8.20 (d, J=9.2 Hz, 1H).

Step 3: 5-(4-(6-Nitrobenzo[d]thiazol-2-yl)phenyl)pyridin-2-amine

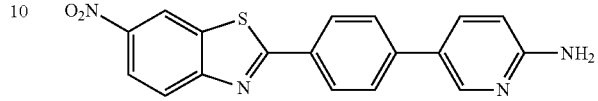

A mixture of 2-Bromo-6-nitrobenzo[d]thiazole (1.0 g, 3.9 mmol), 5-(4-(4,4,5,5-tetramethyl-1,3,2-dioxaborolan-2-yl)phenyl)pyridin-2-amine (1.38 g, 4.68 mmol), tetrakis(triphenylphosphine)palladium (340 mg, 0.3 mmol) and potassium carbonate (1.38 g, 10 mmol) in acetonitrile (15 mL) and water (3.0 mL) was stirred at 90° C. for 16 h under nitrogen atmosphere. Water (50 ml) was added and solid was isolated. The mixture was filtered and the filtrate cake was washed with water and ethyl acetate, dried under vacuum to provide 5-(4-(6-nitrobenzo[d]thiazol-2-yl)phenyl)pyridin-2-amine (500 mg, 38%) as a yellow solid. LCMS (ESI) [M+H]$^+$=349.0; $R_T$=1.93 min (Method B).

Step 4: tert-Butyl (5-(4-(6-nitrobenzo[d]thiazol-2-yl)phenyl)pyridin-2-yl)carbamate

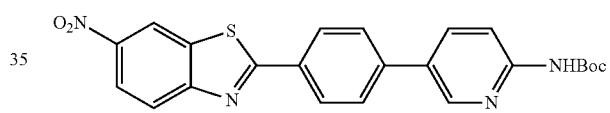

A mixture of di-tert-butyl dicarbonate (920 mg, 4.2 mmol) and 5-(4-(6-nitrobenzo[d]thiazol-2-yl)phenyl)pyridin-2-amine (500 mg, 1.44 mmol) in tetrahydrofuran (40 mL) was stirred at 90° C. for 24 h. The mixture was concentrated to afford tert-butyl (5-(4-(6-nitrobenzo[d]thiazol-2-yl)phenyl)pyridin-2-yl)carbamate (380 mg, 59%) as yellow oil, which was directly used to the next step without purification. LCMS (ESI) [M+H]$^+$=449.0; $R_T$=2.23 min (Method B).

Step 5: tert-Butyl (2-fluoroethyl)(5-(4-(6-nitrobenzo[d]thiazol-2-yl)phenyl)pyridin-2-yl)carbamate

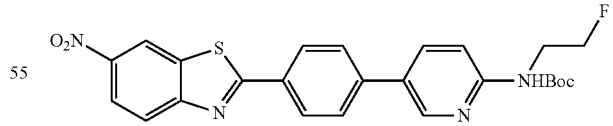

To a solution of tert-butyl (5-(4-(6-nitrobenzo[d]thiazol-2-yl)phenyl)pyridin-2-yl)carbamate (200 mg, 0.45 mmol) and 1-fluoranyl-2-iodanyl-ethane (150 mg, 0.9 mmol) in N,N-dimethylformamide (10 mL) was added sodium hydride (3 mg, 60% dispersion in mineral oil, 0.13 mmol). The reaction mixture was stirred at 50° C. for 15 h and poured into ice water, extracted with ethyl acetate. The organic layer was washed with brine, dried over anhydrous sodium sulfate and evaporated to give tert-butyl (2-fluoroethyl)(5-(4-(6-nitrobenzo[d]thiazol-2-yl)phenyl)pyridin-2-yl)carbamate (150 mg, 67%) as a yellow solid. LCMS (ESI) [M+H]⁺=438.9; $R_T$=2.25 min (Method B).

Step 6: 2-(4-(6-((2-Fluoroethyl)amino)pyridin-3-yl)phenyl)benzo[d]thiazol-6-amine

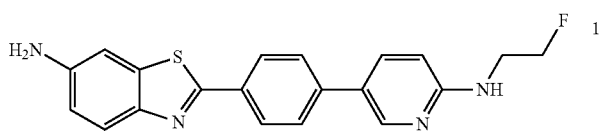

To a stirred solution of tert-butyl (2-fluoroethyl)(5-(4-(6-nitrobenzo[d]thiazol-2-yl)phenyl)pyridin-2-yl)carbamate (150 mg, 0.30 mmol) in trifluoroacetic acid (10.0 mL) was added iron powder (500 mg). The mixture was stirred at 50° C. for 2 h. After cooling to room temperature, the mixture was filtered and the filtrate was poured into water (30 mL). The precipitate was filtered and washed with water to give the crude product, which was purified by flash chromatography (dichloromethane/methanol=100/1) to give 2-(4-(6-((2-fluoroethyl)amino)pyridin-3-yl)phenyl)benzo[d]thiazol-6-amine (36 mg, 33%) as a yellow solid. LCMS (ESI) [M+H]⁺=365.0; $R_T$=1.83 min. (Method B); ¹H NMR (400 MHZ, DMSO-$d_6$) δ 8.43 (s, 1H), 7.98 (d, J=8.2 Hz, 2H), 7.91-7.60 (m, 4H), 7.09 (d, J=10.7 Hz, 2H), 6.80 (d, J=8.6 Hz, 1H), 6.66 (d, J=8.6 Hz, 1H), 5.51 (s, 2H), 4.57 (dt, J=47.7, 5.1 Hz, 2H), 3.63 (dd, J=26.3, 5.0 Hz, 2H).

Synthesis of Compound J

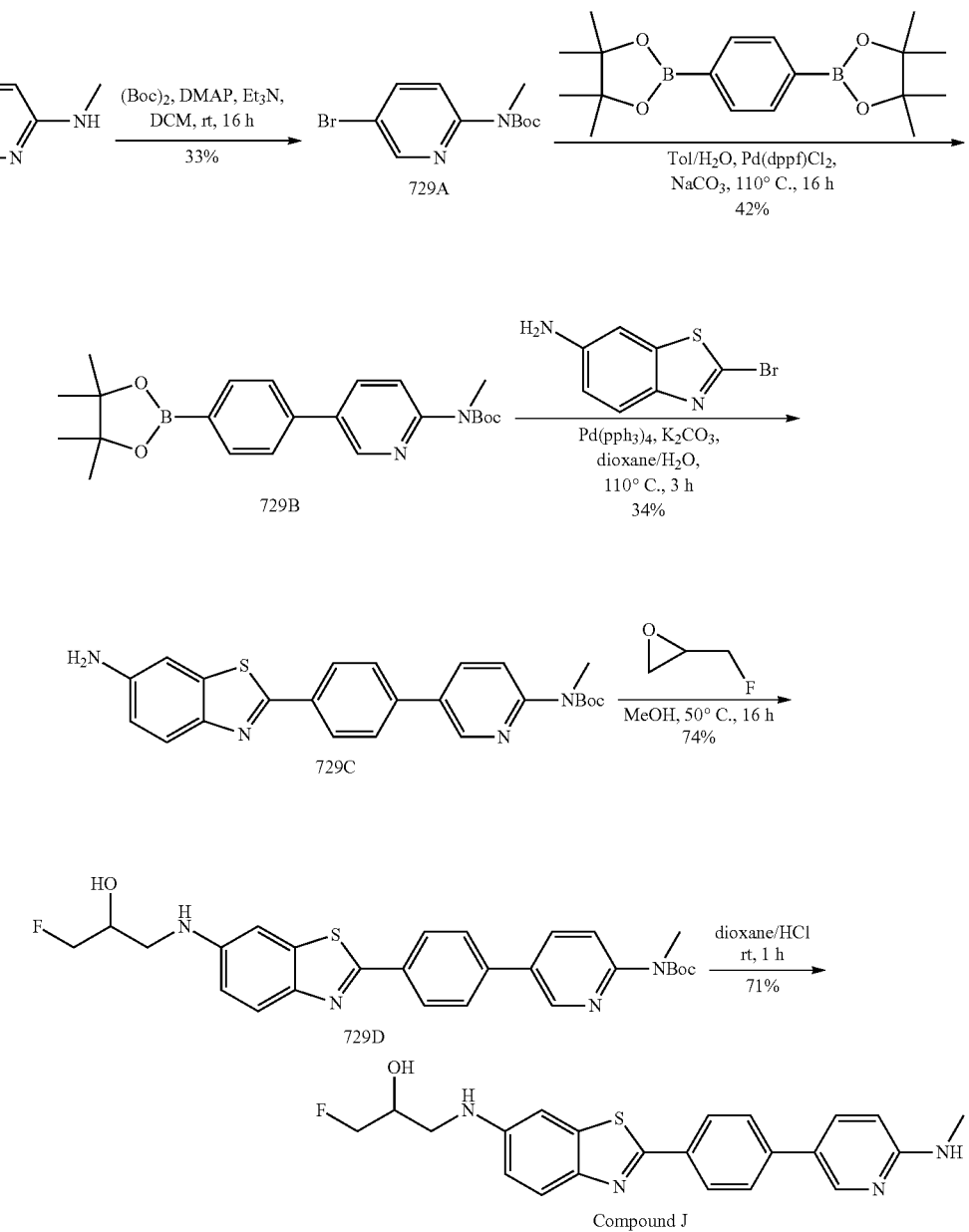

Step 1: tert-Butyl N-(4-bromophenyl)-N-methyl-carbamate

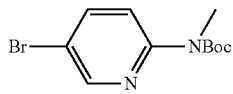

A mixture of 4-bromanyl-N-methyl-aniline (600 mg, 3.22 mmol), tert-butyl (2-methyl propan-2-yl)oxycarbonyl carbonate (2.1 g, 9.67 mmol), 4-dimethylaminopyridine (39 mg, 0.32 mmol) and triethanolamine (977 mg, 9.67 mmol) in dichloromethane (6 mL) was stirred at room temperature for 16 h. Then water was added and the precipitate was filtered. The filtrate cake was dried to give tert-butyl N-(4-bromophenyl)-N-methyl-carbamate (350 mg, 38% yield). LCMS (ESI) m/z=285 [M+H]$^+$, $R_T$=1.617 min.

Step 2: tert-Butyl N-methyl-N-[4-[4-(4,4,5,5-tetramethyl-1,3,2-dioxaborolan-2-yl)phenyl] phenyl]carbamate

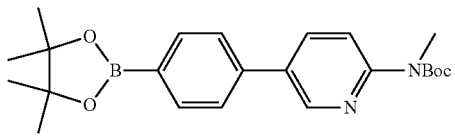

A mixture of 4,4,5,5-tetramethyl-2-[4-(4,4,5,5-tetramethyl-1,3,2-dioxaborolan-2-yl)phenyl]-1,3,2-dioxaborolane (1.15 g, 3.49 mmol), tert-butyl N-(4-bromophenyl)-N-methyl-carbamate (500 mg, 1.75 mmol), sodium carbonate (370 mg, 3.49 mmol) and [1,1'-bis(diphenylphosphino)ferrocene]dichloropalladium(II) (129 mg, 0.17 mmol) in toluene (10 mL) was stirred at 110° C. for 16 h. Then water was added to the mixture and a precipitate was formed. The precipitate was filtered and dried to give tert-butyl N-methyl-N-[4-[4-(4,4,5,5-tetramethyl-1,3,2-dioxaborolan-2-yl)phenyl]phenyl]carbamate (300 mg, 42% yield). LCMS (ESI) m/z=409 [M+H]$^+$, $R_T$=2.14 min.

Step 3: tert-Butyl N-[5-[4-(6-azanyl-1,3-benzothiazol-2-yl)phenyl]pyridin-2-yl]-N-methyl-carbamate

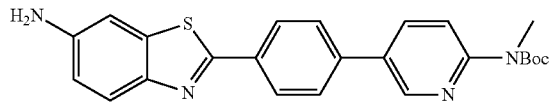 [SMILES: CN(C(=O)OC(C)(C)C)c1ccc(-c2ccc(-c3nc4ccc(N)cc4s3)cc2)cn1]

A mixture of 2-bromanyl-1,3-benzothiazol-6-amine (62 mg, 0.27 mmol), tert-butyl N-methyl-N-[5-[4-(4,4,5,5-tetramethyl-1,3,2-dioxaborolan-2-yl)phenyl]pyridin-2-yl]carbamate (110 mg, 0.27 mmol), potassium carbonate (85 mg, 0.81 mmol) and tetrakis(triphenylphosphine)palladium (20 mg, 0.03 mmol) in 1,4-dioxane (4 mL) and water (1 mL) was stirred at 110° C. for 3 h. The mixture was filtered and the filtrate was concentrated to give the product tert-butyl N-[5-[4-(6-azanyl-1,3-benzothiazol-2-yl)phenyl]pyridin-2-yl]-N-methyl-carbamate (40 mg, 34% yield). LCMS (ESI) m/z=431 [M+H]$^+$, $R_T$=1.806 min.

Step 4: tert-Butyl N-[5-[4-[6-[(3-fluoranyl-2-oxidanyl-propyl)amino]-1,3-benzothiazol-2-yl]phenyl]pyridin-2-yl]-N-methyl-carbamate

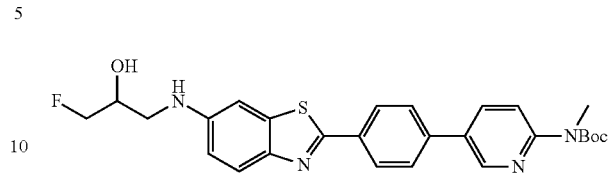

A mixture of tert-butyl N-[5-[4-(6-azanyl-1,3-benzothiazol-2-yl)phenyl]pyridin-2-yl]-N-methyl-carbamate (40 mg, 0.09 mmol) and 2-(fluoranylmethyl)oxirane (70 mg, 0.93 mmol) in methanol (3 mL) was stirred at 50° C. for 16 h. The mixture was concentrated and the residue was purified by flash column chromatography to give tert-butyl N-[5-[4-[6-[(3-fluoranyl-2-oxidanyl-propyl)amino]-1,3-benzothiazol-2-yl]phenyl]pyridin-2-yl]-N-methyl-carbamate (35 mg, 74% yield). LCMS (ESI) m/z=508 [M+H]$^+$.

Step 5: 1-Fluoranyl-3-[[2-[4-[6-(methylamino)pyridin-3-yl]phenyl]-1,3-benzothiazol-6-yl]amino]propan-2-ol

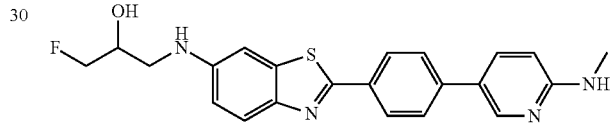

A mixture of tert-butyl N-[5-[4-[6-[(3-fluoranyl-2-oxidanyl-propyl)amino]-1,3-benzothiazol-2-yl]phenyl]pyridin-2-yl]-N-methyl-carbamate (35 mg, 0.07 mmol) in 1,4-dioxane/hydrochloric acid was stirred at room temperature for 1 h. The mixture was filtered and the filtrate cake was dried to give 1-fluoranyl-3-[[2-[4-[6-(methylamino)pyridin-3-yl]phenyl]-1,3-benzothiazol-6-yl]amino]propan-2-ol (20 mg, 71% yield). LCMS (ESI) m/z=408 [M+H]$^+$, $R_T$=1.4 min; $^1$H NMR (400 MHZ, DMSO-$d_6$) δ 8.44 (s, 1H), 7.99 (t, J=8.1 Hz, 2H), 7.80 (d, J=8.9 Hz, 2H), 7.73 (d, J=8.7 Hz, 3H), 7.26 (d, J=85.4 Hz, 1H), 6.89 (d, J=10.4 Hz, 1H), 6.76 (s, 1H), 6.56 (d, J=8.7 Hz, 1H), 6.10 (s, 1H), 5.41-5.27 (m, 1H), 4.43 (dd, J=47.8, 14.7 Hz, 3H), 3.96 (s, 2H), 3.17 (d, J=35.0 Hz, 2H), 2.83 (d, J=4.7 Hz, 3H).

Synthesis of Compound K

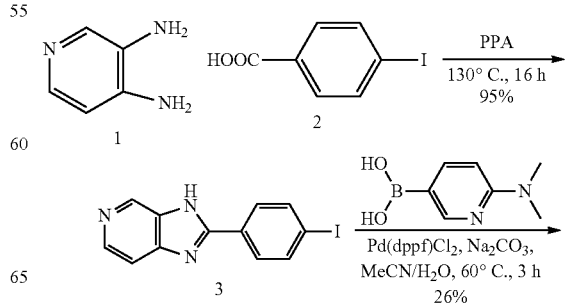

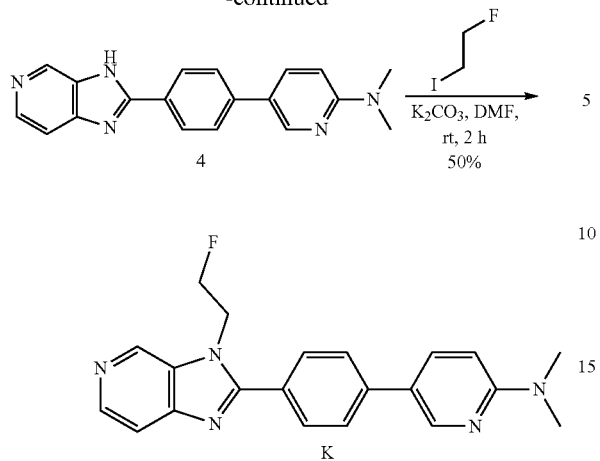

Step 1: Synthesis of 3

Pyridine-3,4-diamine (200 mg, 1.83 mmol), 4-iodanyl-benzoic acid (500 mg, 2.02 mmol) were mixed in PPA (10 mL) and stirred at 130° C. for 16 h. The reaction mixture was poured into water. The mixture was adjusted to pH 9 with saturated aq NaOH. The precipitate was filtered to give the product 2-(4-iodophenyl)-3H-imidazo[4,5-c]pyridine (560 mg, 1.74 mmol, 95.1% yield) as white solid. LCMS: ESI-MS: m/z: 322.0 [M+H]$^+$; R$_T$=1.42 (Method A)

Step 2: Synthesis of 4

A mixture of Na$_2$CO$_3$ (383 mg, 3.61 mmol), 2-(4-iodo-phenyl)-1H-imidazo[4,5-c]pyridine (386 mg, 1.2 mmol), [6-(dimethylamino)pyridin-3-yl]boronic acid (200 mg, 1.2 mmol) and Pd(dppf)Cl$_2$ (40 mg, 0.05 mmol) in MeCN (50 mL) and water (10 mL) was heated at 60° C. for 3 h. The reaction was concentrated to dryness and diluted with water (20 mL), filtered to get white solid. The crude product was purified by flash chromatography (DCM/MeOH=20/1 to 10/1) to give 5-[4-(1H-imidazo[4,5-c]pyridin-2-yl)phenyl]-N,N-dimethyl-pyridin-2-amine (100 mg, 0.31 mmol, 26.3% yield) as a white solid. LCMS: ESI-MS: m/z: 316.1 [M+H]$^+$; R$_T$=1.11 (Method B)

Step 3: Synthesis of K

To a solution of 5-[4-(3H-imidazo[4,5-c]pyridin-2-yl)phenyl]-N,N-dimethyl-pyridin-2-amine (70 mg, 0.22 mmol) in DMF (2 mL) was added K$_2$CO$_3$ (153 mg, 1.11 mmol) and 1-fluoranyl-2-iodanyl-ethane (193 mg, 1.11 mmol). The mixture was stirred at 25° C. for 2 h. The reaction was concentrated to dryness and the residue was purified by flash chromatography (DCM/MeOH=100/1 to 30/1) to give 5-[4-[3-(2-fluoranylethyl)imidazo[4,5-c]pyridin-2-yl]phenyl]-N,N-dimethyl-pyridin-2-amine (40 mg, 0.11 mmol, 49.8% yield) as a yellow solid.

LCMS: ESI-MS: m/z: 362.1 [M+H]$^+$; R$_T$=1.68 (Method A); $^1$H NMR (400 MHZ, DMSO-d6) δ 8.94 (s, 1H), 8.53 (d, J=2.4 Hz, 1H), 8.40 (d, J=8.4 Hz, 2H), 8.09 (d, J=6.4 Hz, 1H), 7.91-7.93 (m, 1H), 7.72-7.76 (m, 3H), 6.75 (d, J=9.2 Hz, 1H), 4.96-4.98 (m, 1H), 4.82-4.86 (m, 2H), 4.75-4.77 (m, 1H), 3.08 (s, 6H) ppm.

General

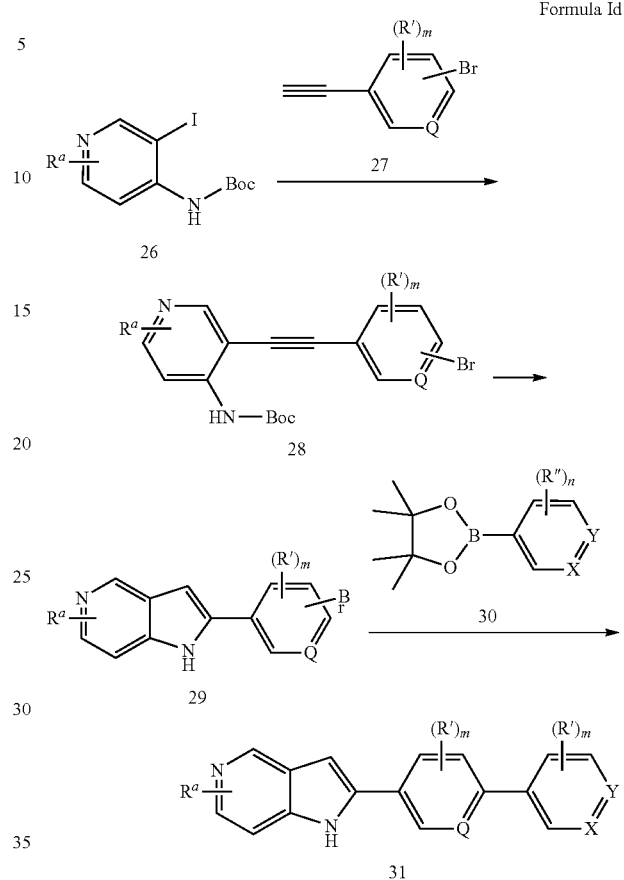

A mixture of ethynl aryl 22 (1.72 mmol), iodo pyridine 21 (1.56 mmol), cuprous iodide (30 mg, 0.16 mmol) and bis(triphenylphosphine)palladium(II) chloride (55 mg, 0.08 mmol) in N,N-dimethylformamide (2 mL) and triethanolamine (948 mg, 9.37 mmol) was stirred at room temperature overnight under nitrogen atmosphere. The reaction mixture was treated with ammonium chloride (10 mL) and extracted with ethyl acetate (15 mL×3). The combined organic layer was washed with brine (10 mL), dried over anhydrous sodium sulfate and concentrated. The residue was purified by column chromatography (petroleum ether/ethyl acetate=1/4) to give 23.

To a solution of 23 (1.38 mmol) in methanol (6 mL) and water (2 mL) was added 1,8-diazabicyclo[5.4.0]undec-7-ene (1.05 g, 6.9 mmol). The reaction mixture was stirred at 80° C. overnight. The reaction was diluted with water and methanol, and then concentrated. The residue was purified by column chromatography (dichloromethane/methanol=1/10) to give 24.

A mixture of aryl boronate 25 (1.68 mmol), and 24 (0.84 mmol), sodium carbonate (268 mg, 2.53 mmol) and tetrakis(triphenylphosphine)palladium (49 mg, 0.04 mmol) in N,N-dimethylformamide (10 mL) and water (1 mL) was heated at 80° C. for 5 h. The mixture was quenched with water and a precipitate was formed. The mixture was filtered and the filtrate cake was purified by column chromatography (dichloromethane/methanol=7/100) to give 26.

107
Synthesis of Compound L

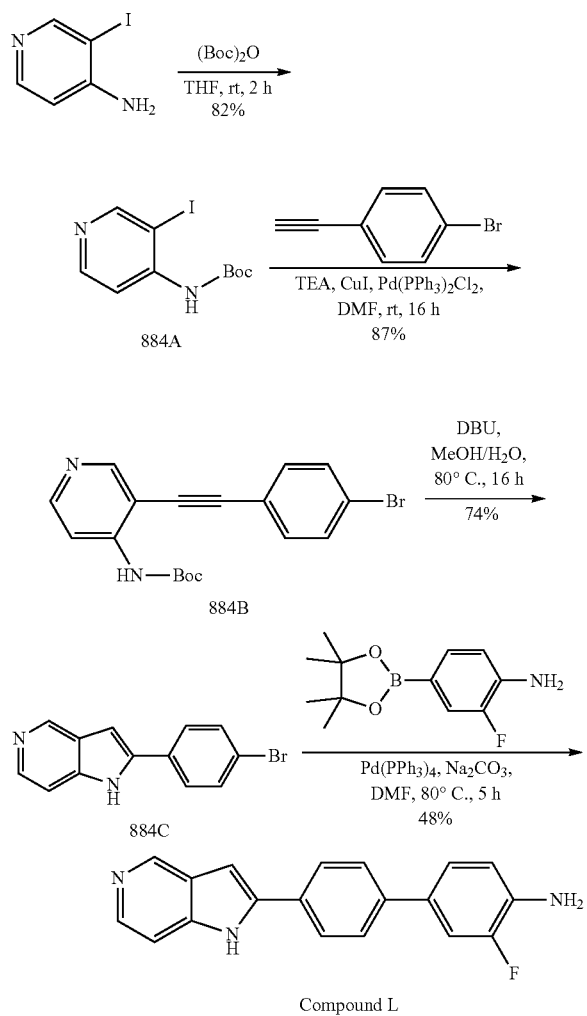

Step 1: tert-Butyl 3-iodopyridin-4-ylcarbamate

A mixture of di-tert-butyl dicarbonate (1.09 g, 5 mmol) and 3-iodanylpyridin-4-amine (1.0 g, 4.55 mmol) in tetrahydrofuran (20 mL) was stirred at room temperature for 2 h and concentrated. The residue was diluted with ethyl acetate (50 mL) and washed with saturated sodium bicarbonate solution (30 mL) and brine (30 mL), dried over sodium sulfate, filtered and concentrated. The residue is purified by column chromatography (dichloromethane/ethyl acetate/petroleum ether=38/12/50) give tert-butyl 3-iodopyridin-4-ylcarbamate (1.2 g, 82% yield) as white solid. LCMS (ESI) [M+H]$^+$=320.9; $R_T$=1.65 min (Method A).

108
Step 2: tert-Butyl 3-((4-bromophenyl)ethynyl)pyridin-4-ylcarbamate

A mixture of 1-bromanyl-4-ethynyl-benzene (311 mg, 1.72 mmol), tert-butyl N-(3-iodanylpyridin-4-yl)carbamate (500 mg, 1.56 mmol), cuprous iodide (30 mg, 0.16 mmol) and bis(triphenylphosphine)palladium(II) chloride (55 mg, 0.08 mmol) in N,N-dimethylformamide (2 mL) and triethanolamine (948 mg, 9.37 mmol) was stirred at room temperature overnight under nitrogen atmosphere. The reaction mixture was treated with ammonium chloride (10 mL) and extracted with ethyl acetate (15 mL×3). The combined organic layer was washed with brine (10 mL), dried over anhydrous sodium sulfate and concentrated. The residue was purified by column chromatography (petroleum ether/ethyl acetate=1/4) to give tert-butyl 3-((4-bromophenyl)ethynyl)pyridin-4-ylcarbamate (515 mg, 87% yield) as a white solid. LCMS (ESI) [M+H]$^+$=372.9; $R_T$=1.899 min (Method A).

Step 3: 2-(4-Bromophenyl)-1H-pyrrolo[3,2-c]pyridine

To a solution of tert-butyl N-[3-[2-(4-bromophenyl)ethynyl]pyridin-4-yl]carbamate (515 mg, 1.38 mmol) in methanol (6 mL) and water (2 mL) was added 1,8-diazabicyclo[5.4.0]undec-7-ene (1.05 g, 6.9 mmol). The reaction mixture was stirred at 80° C. overnight. The mixture was diluted with water and methanol, and then concentrated. The residue was purified by column chromatography (dichloromethane/methanol=1/10) to give 2-(4-bromophenyl)-1H-pyrrolo[3,2-c]pyridine (280 mg, 74% yield) as a pale yellow solid. LCMS (ESI) [M+H]$^+$=274.8; $R_T$=1.697 min (Method A).

Step 4: 3-Fluoro-4'-(1H-pyrrolo[3,2-c]pyridin-2-yl)biphenyl-4-amine

A mixture of 2-fluoranyl-4-(4,4,5,5-tetramethyl-1,3,2-dioxaborolan-2-yl)aniline (399 mg, 1.68 mmol), 2-(4-bromophenyl)-1H-pyrrolo[3,2-c]pyridine (230 mg, 0.84 mmol), sodium carbonate (268 mg, 2.53 mmol) and tetrakis(triphenylphosphine)palladium (49 mg, 0.04 mmol) in N,N-dimethylformamide (10 mL) and water (1 mL) was heated at 80° C. for 5 h. The mixture was quenched with water and a precipitate was formed. The mixture was filtered and the filtrate cake was purified by column chromatography (dichloromethane/methanol=7/100) to give 3-fluoro-4'-(1H-pyrrolo[3,2-c]pyridin-2-yl)biphenyl-4-amine (123 mg, 48% yield) as a pale yellow solid. LCMS (ESI) [M+H]+=303.9; $R_T$=1.747 min (Method A); $^1$H NMR (400 MHZ, DMSO-$d_6$) δ 12.07 (s, 1H), 8.84 (s, 1H), 8.18 (d, J=5.6 Hz, 1H), 7.92 (d, J=8.0 Hz, 2H), 7.73 (d, J=8.4 Hz, 2H), 7.48-7.33 (m, 3H), 7.08 (s, 1H), 6.88-6.83 (m, 1H), 5.37 (s, 2H).

Synthesis of Compound M

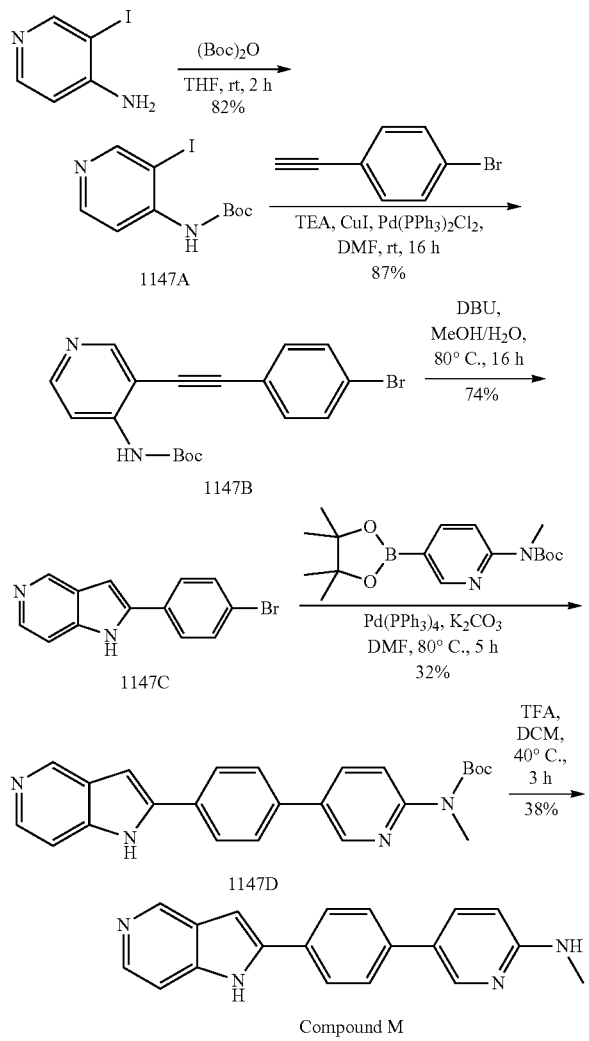

Step 1: tert-Butyl 3-iodopyridin-4-ylcarbamate

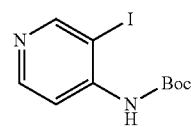

A mixture of di-tert-butyl dicarbonate (1.09 g, 5 mmol) and 3-iodanylpyridin-4-amine (1.0 g, 4.55 mmol) in tetrahydrofuran (20 mL) was stirred for 2 h at room temperature and concentrated. The residue was diluted with ethyl acetate (50 mL) and washed with saturated sodium bicarbonate solution (30 mL) and brine (30 mL). The organic layer was dried over sodium sulfate, filtered and concentrated. The residue was purified by column chromatography (ethyl acetate/dichloromethane=12/100) to give tert-butyl 3-iodopyridin-4-ylcarbamate (1.2 g, 82% yield) as a white solid. LCMS (ESI) [M+H]+=320.9; $R_T$=1.65 min (Method A).

Step 2: tert-Butyl 3-((4-bromophenyl)ethynyl)pyridin-4-ylcarbamate

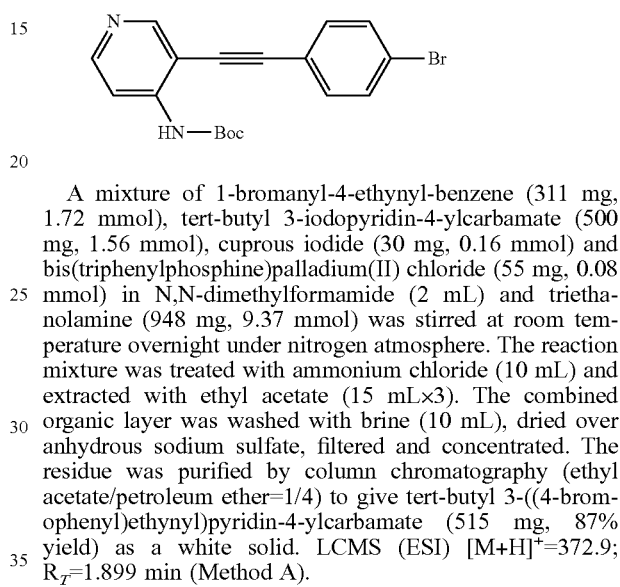

A mixture of 1-bromanyl-4-ethynyl-benzene (311 mg, 1.72 mmol), tert-butyl 3-iodopyridin-4-ylcarbamate (500 mg, 1.56 mmol), cuprous iodide (30 mg, 0.16 mmol) and bis(triphenylphosphine)palladium(II) chloride (55 mg, 0.08 mmol) in N,N-dimethylformamide (2 mL) and triethanolamine (948 mg, 9.37 mmol) was stirred at room temperature overnight under nitrogen atmosphere. The reaction mixture was treated with ammonium chloride (10 mL) and extracted with ethyl acetate (15 mL×3). The combined organic layer was washed with brine (10 mL), dried over anhydrous sodium sulfate, filtered and concentrated. The residue was purified by column chromatography (ethyl acetate/petroleum ether=1/4) to give tert-butyl 3-((4-bromophenyl)ethynyl)pyridin-4-ylcarbamate (515 mg, 87% yield) as a white solid. LCMS (ESI) [M+H]+=372.9; $R_T$=1.899 min (Method A).

Step 3: 2-(4-Bromophenyl)-1H-pyrrolo[3,2-c]pyridine

To a solution of tert-butyl 3-((4-bromophenyl)ethynyl)pyridin-4-ylcarbamate (515 mg, 1.38 mmol) in methanol (6 mL) and water (2 mL), 1,8-diazabicyclo[5.4.0]undec-7-ene (1.05 g, 6.9 mmol) was added, then the reaction mixture was stirred at 80° C. overnight. The mixture was concentrated. The residue was purified by column chromatography (dichloromethane/methanol=10/1) to give 2-(4-bromophenyl)-1H-pyrrolo[3,2-c]pyridine (280 mg, 74% yield) as pale yellow solid. LCMS (ESI) [M+H]+=274.8; $R_T$=1.697 min (Method A).

tert-Butyl (5-(4-(1H-pyrrolo[3,2-c]pyridin-2-yl)phenyl)pyridin-2-yl)(methyl)carbamate

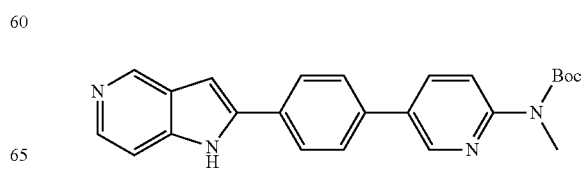

A mixture of 2-fluoranyl-4-(4,4,5,5-tetramethyl-1,3,2-dioxaborolan-2-yl)aniline (150 mg, 0.63 mmol), 2-(4-bromophenyl)-1H-pyrrolo[3,2-c]pyridine (210 mg, 0.63 mmol), sodium carbonate (268 mg, 2.53 mmol) and tetrakis(triphenylphosphine)palladium (72 mg, 0.063 mmol) in N,N-dimethylformamide (15 mL) and water (3.0 mL) was heated at 80° C. for 5 h. The mixture was quenched with water and a precipitate was formed. The mixture was filtered and the filtrate cake was purified by column chromatography (dichloromethane/methanol=20/1) to give tert-butyl (5-(4-(1H-pyrrolo[3,2-c]pyridin-2-yl)phenyl)pyridin-2-yl)(methyl)carbamate (70 mg, 32% yield) as a yellow solid. LCMS ESI-MS: m/z: 401.1 [M+H]$^+$; R$_T$=1.643 min (Method A).

Step 5: 5-(4-(1H-Pyrrolo[3,2-c]pyridin-2-yl)phenyl)-N-methylpyridin-2-amine

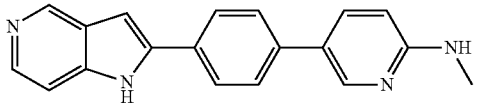 [SMILES: CNc1ccc(-c2ccc(-c3cc4cnccc4[nH]3)cc2)cn1]

A mixture of tert-butyl (5-(4-(1H-pyrrolo[3,2-c]pyridin-2-yl)phenyl)pyridin-2-yl)(methyl)carbamate (70 mg, 0.17 mmol), trifluoroacetic acid (1.0 mL) in dichloromethane (3.0 mL). The solution was heated at 40° C. for 3 h. The mixture was quenched with water and a precipitate was formed. The mixture was filtered and the filtrate cake was purified by reverse phase pre-HPLC to afford 5-(4-(1H-pyrrolo[3,2-c]pyridin-2-yl)phenyl)-N-methylpyridin-2-amine as a white solid (20 mg, 38% yield) as a white solid. LCMS (ESI) [M+H]$^+$=301.0; R$_T$=1.246 min (Method A); $^1$H NMR (400 MHZ, DMSO-d$_6$) δ 8.82 (s, 1H), 8.42 (t, J=5.5 Hz, 1H), 8.34-8.12 (m, 3H), 7.94 (d, J=8.3 Hz, 2H), 7.80 (dd, J=8.7, 2.5 Hz, 1H), 7.72 (d, J=8.4 Hz, 2H), 7.39 (d, J=5.3 Hz, 1H), 7.07 (s, 1H), 6.68 (t, J=13.6 Hz, 1H), 6.55 (d, J=8.7 Hz, 1H), 2.83 (d, J=4.5 Hz, 3H).

General

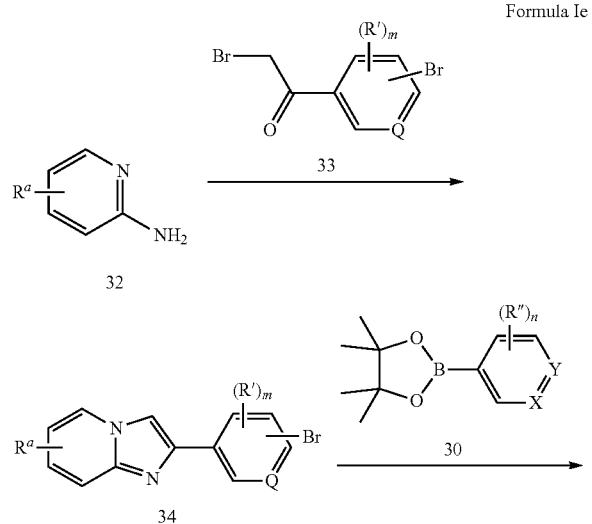

Formula Ie

A mixture of amino pyridine 27 (8.06 mmol), alpha-bromoketo-bromoaryl (8.86 mmol) and sodium bicarbonate (744 mg, 8.86 mmol) in ethanol (50 mL) was stirred at 80° C. for 3 h. The reaction mixture was diluted with water and extracted with ethyl acetate. The organic layer was dried and concentrated. The residue was purified by chromatography (petroleum ether/ethyl acetate=4/1) to give imidazopyridine 29.

A mixture of imidazopyridine 29 (3.3 mmol), arylboronate 25 (3.96 mmol), potassium carbonate (1.37 g, 9.9 mmol) and tetrakis(triphenylphosphine)palladium (241 mg, 0.33 mmol) in N,N-dimethylformamide (20 mL) and water (4 mL) was stirred at 80° C. for 16 h. The reaction mixture was diluted with water and extracted with ethyl acetate (100 mL×3). The organic layer was dried over sodium sulfate and concentrated. The residue was purified by flash chromatography (petroleum ether/ethyl acetate=2/1) to give 30.

Synthesis of Compound N

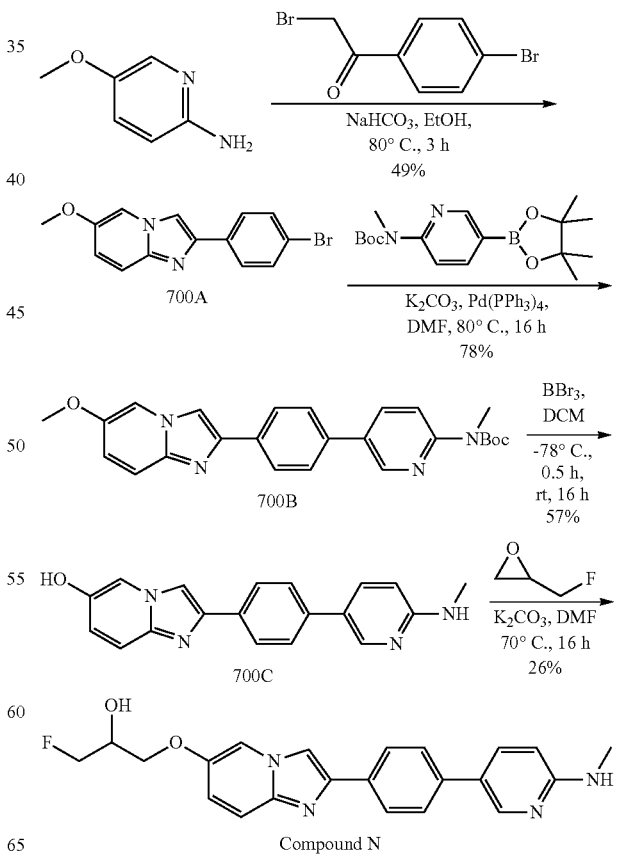

Compound N

Step 1: 2-(4-Bromophenyl)-6-methoxyimidazo[1,2-a]pyridine

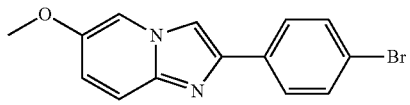

A mixture of 5-methoxypyridin-2-amine (1.0 g, 8.06 mmol), 2-bromanyl-1-(4-bromophenyl)ethanone (2.46 g, 8.86 mmol) and sodium bicarbonate (744 mg, 8.86 mmol) in ethanol (50 mL) was stirred at 80° C. for 3 h. The reaction mixture was diluted with water and extracted with ethyl acetate. The organic layer was dried and concentrated. The residue was purified by chromatography (petroleum ether/ethyl acetate=4/1) to give 2-(4-bromophenyl)-6-methoxy-imidazo[1,2-a]pyridine (1.5 g, 49% yield) as a yellow solid. LCMS (ESI) [M+H]$^+$=303.

Step 2: tert-Butyl 5-(4-(6-methoxyimidazo[1,2-a]pyridin-2-yl)phenyl)pyridin-2-yl(methyl)carbamate

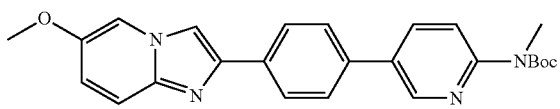

A mixture of 2-(4-bromophenyl)-6-methoxy-imidazo[1,2-a]pyridine (1.0 g, 3.3 mmol), tert-butyl N-methyl-N-[5-(4,4,5,5-tetramethyl-1,3,2-dioxaborolan-2-yl)pyridin-2-yl]carbamate (1.32 g, 3.96 mmol), potassium carbonate (1.37 g, 9.9 mmol) and tetrakis(triphenylphosphine)palladium (241 mg, 0.33 mmol) in N,N-dimethylformamide (20 mL) and water (4 mL) was stirred at 80° C. for 16 h. The reaction mixture was diluted with water and extracted with ethyl acetate (100 mL×3). The organic layer was dried over sodium sulfate and concentrated. The residue was purified by flash chromatography (petroleum ether/ethyl acetate=2/1) to give tert-butyl 5-(4-(6-methoxyimidazo[1,2-a]pyridin-2-yl)phenyl)pyridin-2-yl(methyl)carbamate (1.3 g, 78% yield) as a yellow solid. LCMS (ESI) m/z=431[M+H]$^+$.

Step 3: 2-(4-(6-(Methylamino)pyridin-3-yl)phenyl)imidazo[1,2-a]pyridin-6-ol

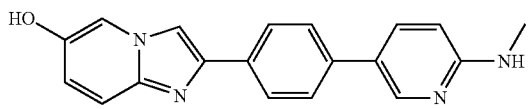

A solution of tert-butyl N-[5-[4-(6-methoxyimidazo[1,2-a]pyridin-2-yl)phenyl]pyridin-2-yl]-N-methyl-carbamate (1.5 g, 3.48 mmol) in dichloromethane (10 mL) was stirred at −78° C. for 0.5 h. Then boron tribromide (8.7 mL, 17.4 mmol) was added and the reaction mixture was stirred at −78° C. for another 0.5 h. The reaction mixture was slowly warmed to room temperature and stirred overnight. The mixture was quenched by methanol and concentrated. The residue was purified by column chromatography (dichloromethane/methanol=10/1) to give 2-[4-[6-(methylamino) pyridin-3-yl]phenyl]imidazo[1,2-a]pyridin-6-ol (800 mg, 57% yield) as a white solid. LCMS (ESI) m/z=317 [M+H]$^+$.

Step 4: 1-Fluoro-3-(2-(4-(6-(methylamino)pyridin-3-yl)phenyl)imidazo[1,2-a]pyridin-6-yloxy)propan-2-ol

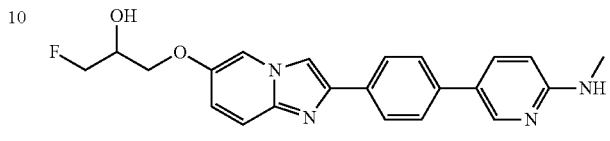

A mixture of 2-[4-[6-(methylamino)pyridin-3-yl]phenyl]imidazo[1,2-a]pyridin-6-ol (600 mg, 1.9 mmol), 2-(fluoranylmethyl)oxirane (1.44 g, 18.97 mmol) and potassium carbonate (785 mg, 5.69 mmol) in N,N-dimethylformamide (2 mL) was stirred at 70° C. for 16 h. The reaction mixture was filtered and the filtrate was concentrated. The residue was purified by column chromatography (dichloromethane/methanol=10/1) to give 1-fluoranyl-3-[2-[4-[6-(methylamino) pyridine-3-yl]phenyl]imidazo[1,2-a]pyridin-6-yl]oxy-propan-2-ol (201 mg, 26% yield) as a yellow solid. LCMS (ESI) m/z=393[M+H], R$_T$=1.653 min; $^1$H NMR (400 MHZ, DMSO-d$_6$) δ 8.41 (d, J=1.6 Hz, 1H), 8.29 (s, 1H), 7.96 (d, J=8.0 Hz, 2H), 7.76 (dd, J=8.4 Hz, 2.4 Hz, 1H), 7.64 (d, J=8.4 Hz, 2H), 7.52 (d, J=9.6 Hz, 1H), 7.07 (dd, J=9.6 Hz, 2.0 Hz, 1H), 6.705 (d, J=4.8 Hz, 2H), 6.55 (d, J=4.8 Hz, 1H), 5.59 (s, 1H), 4.56 (m, 1H), 4.44 (m, 1H), 4.02 (m, 1H), 3.97 (m, 2H), 2.833 (d, J=4.8 Hz, 3H).

Synthesis of Compound O

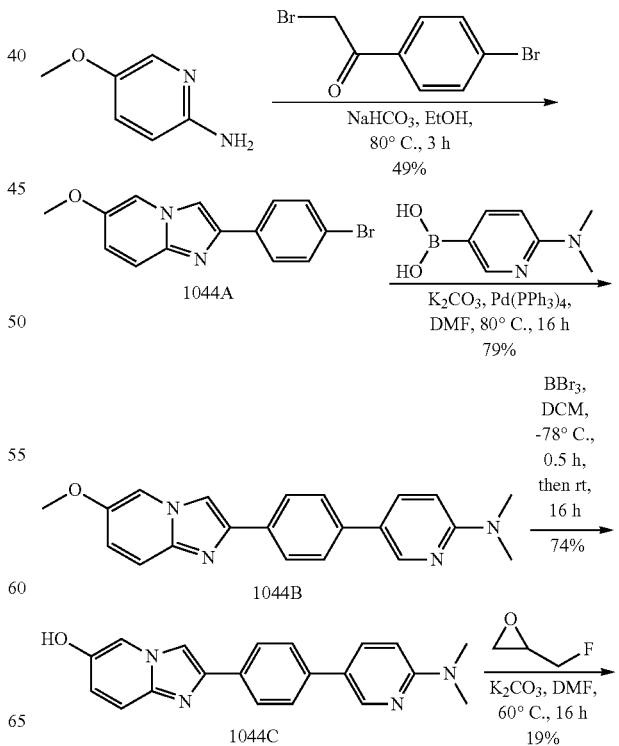

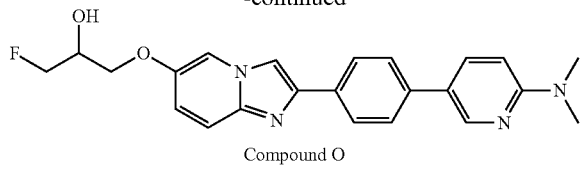

Compound O

Step 1: 2-(4-Bromophenyl)-6-methoxyimidazo[1,2-a]pyridine

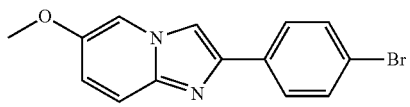 [SMILES: COc1ccc2nc(-c3ccc(Br)cc3)cn2c1]

A mixture of 5-methoxypyridin-2-amine (1.0 g, 8.06 mmol), 2-bromanyl-1-(4-bromophenyl)ethanone (2.5 mg, 8.86 mmol) and sodium bicarbonate (744 mg, 8.86 mmol) in ethanol (50 mL) was stirred at 80° C. for 3 h. The reaction mixture was added to water and extracted with ethyl acetate (100 mL×3). The organic layer was dried and concentrated. The residue was purified by column chromatography (petroleum ether/ethyl acetate=4/1) to give 2-(4-bromophenyl)-6-methoxy-imidazo[1,2-a]pyridine (1.5 g, 49% yield) as a yellow solid. LCMS (ESI) [M+H]$^+$=303.

Step 2: 5-(4-(6-Methoxyimidazo[1,2-a]pyridin-2-yl)phenyl)-N,N-dimethylpyridin-2-amine

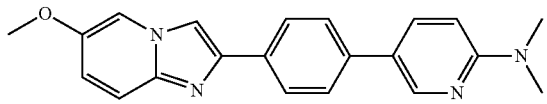

A mixture of N,N-dimethyl-5-(4,4,5,5-tetramethyl-1,3,2-dioxaborolan-2-yl)pyridin-2-amine (196 mg, 0.79 mmol), 2-(4-bromophenyl)-6-methoxy-imidazo[1,2-a]pyridine (200 mg, 0.66 mmol), potassium carbonate (273 mg, 1.98 mmol) and tetrakis(triphenylphosphine)palladium (48 mg, 0.07 mmol) in N,N-dimethylformamide (4 mL) and water (0.6 mL) was stirred at 80° C. for 16 h. The reaction mixture was concentrated and the residue was purified by column chromatography (petroleum ether/ethyl acetate=2/1) to give 5-[4-(6-methoxyimidazo[1,2-a]pyridin-2-yl)phenyl]-N,N-dimethyl-pyridin-2-amine (200 mg, 79% yield) as a white solid. LCMS (ESI) [M+H]$^+$=345.

Step 3: 2-(4-(6-(Dimethylamino)pyridin-3-yl)phenyl)imidazo[1,2-a]pyridin-6-ol

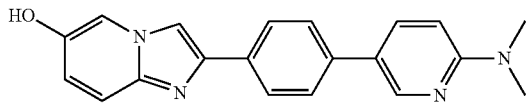 [SMILES: CN(C)c1ccc(-c2ccc(-c3cn4cc(O)ccc4n3)cc2)cn1]

To a solution of 5-[4-(6-methoxyimidazo[1,2-a]pyridin-2-yl)phenyl]-N,N-dimethyl-pyridin-2-amine (200 mg, 0.58 mmol) in dichloromethane (2 mL) was added boron tribromide (1.5 mL, 2.9 mmol) at −78° C. The reaction mixture was stirred at −78° C. for 0.5 h, then warmed to room temperature slowly and stirred at room temperature overnight. The reaction mixture was quenched with methanol and concentrated. The residue was purified by column chromatography (dichloromethane/methanol=10/1) to give 2-[4-[6-(dimethylamino)pyridin-3-yl]phenyl]imidazo[1,2-a]pyridin-6-ol (180 mg, 74% yield) as a white solid. LCMS (ESI) [M+H]$^+$=331.

Step 4: 1-(2-(4-(6-(Dimethylamino)pyridin-3-yl)phenyl)imidazo[1,2-a]pyridin-6-yloxy)-3-fluoropropan-2-ol

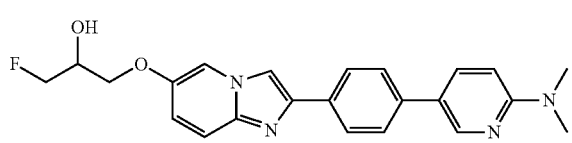 [SMILES: CN(C)c1ccc(-c2ccc(-c3cn4cc(OCC(O)CF)ccc4n3)cc2)cn1]

A mixture of 2-[4-[6-(dimethylamino)pyridin-3-yl]phenyl]imidazo[1,2-a]pyridin-6-ol (130 mg, 0.39 mmol), 2-(fluoranylmethyl)oxirane (299 mg, 3.93 mmol) and potassium carbonate (163 mg, 1.18 mmol) in N,N-dimethylformamide (2 mL) was stirred at 60° C. for 16 h. The reaction mixture was filtered and the filtrate was concentrated. The residue was purified by column chromatography (dichloromethane/methanol=10/1) to give 1-[2-[4-[6-(dimethylamino)pyridin-3-yl]phenyl]imidazo[1,2-a]pyridin-6-yl]oxy-3-fluoranyl-propan-2-ol (30 mg, 19% yield) as a yellow solid. LCMS (ESI) [M+H]$^+$=407, R$_T$=1.805 min; $^1$H NMR (400 MHz, DMSO-d$_6$) δ 8.50 (d, J=2.4 Hz, 1H), 8.29 (m, 2H), 7.96 (d, J=8.8 Hz, 2H), 7.87 (dd, J=8.8 Hz, 2.4 Hz, 1H), 7.67 (d, J=8.0 Hz, 1H), 7.50 (d, J=10.0 Hz, 1H), 7.05 (dd, J=9.2 Hz, 2.4 Hz, 1H), 6.73 (d, J=8.8 Hz, 1H), 5.53 (d, J=4.8 Hz, 1H), 4.56 (m, 1H), 4.45 (m, 1H), 4.06 (m, 1H), 4.00 (m, 1H), 3.08 (s, 6H).

Synthesis of Compound P

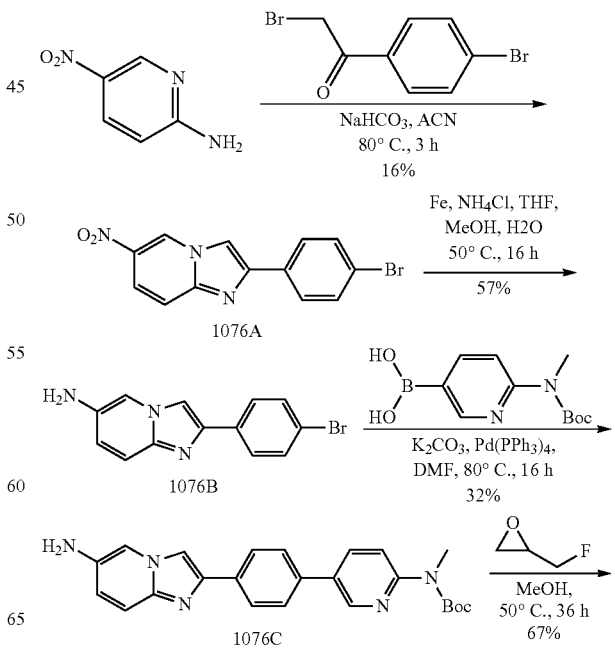

-continued

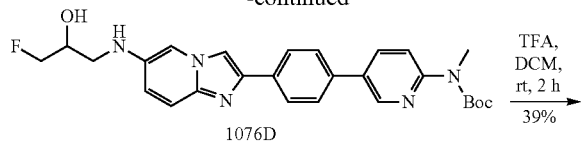
1076D

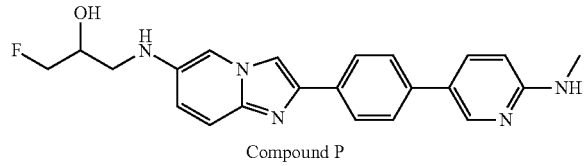
Compound P

Step 1: 2-(4-Bromophenyl)-6-nitroimidazo[1,2-a]pyridine

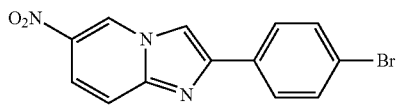

A mixture of 5-nitropyridin-2-amine (1.0 g, 7.19 mmol), 2-bromo-1-(4-bromophenyl)ethan-1-one (2.2 g, 7.91 mmol) and sodium bicarbonate (664 mg, 7.91 mmol) in acetonitrile (50 mL) was stirred at 80° C. for 3 h. The reaction mixture was added to water and extracted with ethyl acetate (100 mL×3). The organic layer was dried and concentrated. The residue was purified by column chromatography (petroleum ether/ethyl acetate=4/1) to give 2-(4-bromophenyl)-6-nitro-imidazo[1,2-a]pyridine (800 mg, 16% yield) as a yellow solid. LCMS (ESI) [M+H]$^+$=318.

Step 2: 2-(4-Bromophenyl)imidazo[1,2-a]pyridin-6-amine

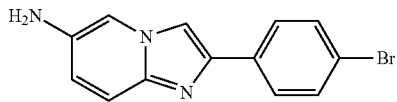 [SMILES: O=[N+]([O-])c1ccc2nc(-c3ccc(Br)cc3)cn2c1]

A mixture of 2-(4-bromophenyl)-6-nitro-imidazo[1,2-a]pyridine (800 mg, 2.51 mmol), iron (704 mg, 12.57 mmol), ammonium chloride (673 mg, 12.57 mmol) and in tetrahydrofuran (10 mL), methanol (5 mL) and water (5 mL) was stirred at 50° C. for 16 h. The reaction mixture was concentrated and the residue was purified by column chromatography (dichloromethane/methanol=20/1) to give 2-(4-bromophenyl)imidazo[1,2-a]pyridin-6-amine (500 mg, 57% yield) as a brown solid. LCMS (ESI) [M+H]$^+$=288.

Step 3: tert-Butyl 5-(4-(6-aminoimidazo[1,2-a]pyridin-2-yl)phenyl)pyridin-2-yl(methyl)carbamate

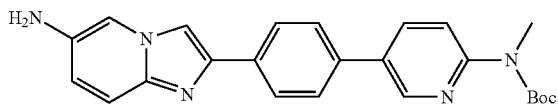 [SMILES: CN(C(=O)OC(C)(C)C)c1ccc(-c2ccc(-c3cn4cc(N)ccc4n3)cc2)cn1]

A mixture of 2-(4-bromophenyl)imidazo[1,2-a]pyridin-6-amine (500 mg, 1.74 mmol), [6-[methyl-[(2-methylpropan-2-yl)oxycarbonyl]amino]pyridin-3-yl]boronic acid (569 mg, 2.26 mmol), potassium carbonate (718 mg, 5.21 mmol) and tetrakis(triphenylphosphine)palladium (127 mg, 0.17 mmol) in N,N-dimethylformamide (4 mL) and water (0.6 mL) was stirred at 80° C. for 16 h. The reaction mixture was concentrated and the residue was purified by column chromatography (dichloromethane/methanol=20/1) to give tert-butyl 5-(4-(6-aminoimidazo[1,2-a]pyridin-2-yl)phenyl)pyridin-2-yl(methyl)carbamate (400 mg, 32% yield) as a white solid. LCMS (ESI) [M+H]$^+$=416.

Step 4: tert-Butyl 5-(4-(6-(3-fluoro-2-hydroxypropylamino)imidazo[1,2-a]pyridin-2-yl)phenyl)pyridin-2-yl(methyl)carbamate

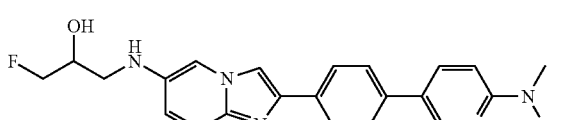

A mixture of 2-(fluoranylmethyl)oxirane (183 mg, 2.41 mmol), tert-butyl 5-(4-(6-aminoimidazo[1,2-a]pyridin-2-yl)phenyl)pyridin-2-yl(methyl)carbamate (100 mg, 0.24 mmol) and in methanol (2 mL) was stirred at 50° C. for 36 h. The reaction mixture was filtered. The filtrate was concentrated and the residue was purified by column chromatography (dichloromethane/methanol=10/1) to give tert-butyl 5-(4-(6-(3-fluoro-2-hydroxypropylamino)imidazo[1,2-a]pyridin-2-yl)phenyl)pyridin-2-yl(methyl)carbamate (80 mg, 67% yield) as a yellow solid. LCMS (ESI) [M+H]$^+$=492.

Step 5: 1-Fluoro-3-(2-(4-(6-(methylamino)pyridin-3-yl)phenyl)imidazo[1,2-a]pyridin-6-ylamino)propan-2-ol

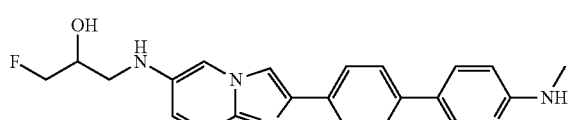

A mixture of tert-butyl 5-(4-(6-(3-fluoro-2-hydroxypropylamino)imidazo[1,2-a]pyridin-2-yl)phenyl)pyridin-2-yl(methyl)carbamate (100 mg, 0.2 mmol), trifluoroacetic acid (70 mg, 0.61 mmol) and in dichloromethane (2 mL) was stirred at 25° C. for 2 h. The reaction mixture was filtered. The filtrate was concentrated and the residue was purified by column chromatography (dichloromethane/methanol=10/1) to give 1-fluoro-3-(2-(4-(6-(methylamino)pyridin-3-yl)phenyl)imidazo[1,2-a]pyridin-6-ylamino)propan-2-ol (31 mg, 39% yield) as a yellow solid. LCMS (ESI) [M+H]$^+$=392, $R_T$=1.647 min. $^1$H NMR (400 MHZ, DMSO-$d_6$) δ 8.39 (s, 1H), 8.25 (s, 1H), 7.90 (d, J=8.4 Hz, 2H), 7.79 (d, J=8.8 Hz, 1H), 7.66 (m, 3H), 7.43 (d, J=9.6 Hz, 1H), 7.10 (m, 1H), 6.745 (m, 1H), 6.56 (d, J=8.8 Hz, 1H), 5.72 (s, 1H), 5.35 (d, J=4.8 Hz, 1H), 4.51 (m, 1H), 4.35 (m, 1H), 3.94 (m, 1H), 3.11 (m, 1H), 2.98 (m, 1H), 2.82 (d, J=4.4 Hz, 3H).

Synthesis of Compound Q

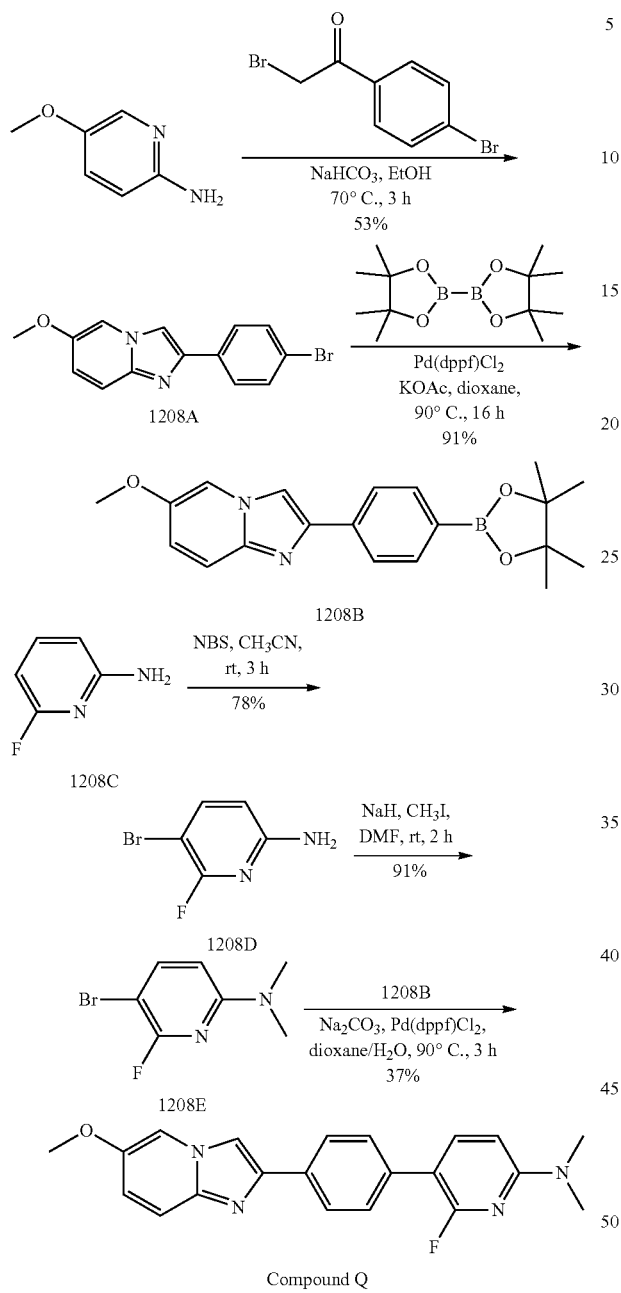

Step 1: 2-(4-Bromophenyl)-6-methoxy-imidazo[1,2-a]pyridine

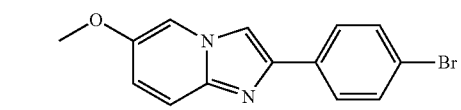 [SMILES: COc1ccc2nc(-c3ccc(Br)cc3)cn2c1]

A mixture of 5-methoxypyridin-2-amine (5 g, 40.28 mmol), 2-bromanyl-1-(4-bromo phenyl)ethanone (11.2 g, 40.3 mmol) and sodium hydrogen carbonate (3.4 g, 40.48 mmol) in ethanol (250 mL) was stirred at 70° C. for 3 h. The reaction mixture was concentrated and the residue was diluted with water (100 mL) and extracted with ethyl acetate (100 mL×3). The combined organic phase was washed with brine (100 mL), dried over sodium sulfate and concentrated. The residue was purified by slurrying in a mixture of petroleum ether/ethyl acetate (4/1) to give 2-(4-bromophenyl)-6-methoxy-imidazo[1,2-a]pyridine (6.88 g, 53% yield). LC-MS: m/z=303 (M+H)+, retention time 1.311 min (Method A).

Step 2: 6-Methoxy-2-[4-(4,4,5,5-tetramethyl-1,3,2-dioxaborolan-2-yl)phenyl]imidazo[1,2-a]pyridine A mixture of 2-(4-bromophenyl)-6-methoxy-imidazo[1,2-a]pyridine (5.8 g, 19.13 mmol), 4,4,5,5-tetramethyl-2-(4,4,5,5-tetramethyl-1,3,2-dioxaborolan-2-yl)-1,3,2-dioxaborolane (5.8 g, 22.84 mmol), potassium acetate (3.77 g, 38.47 mmol) and [1,1'-bis(diphenyl phosphino)ferrocene]dichloropalladium(II) (0.7 g, 0.96 mmol) in 1,4-dioxane (150 mL) was stirred at 90° C. for 16 h and then cooled to room temperature. The mixture was filtered and filtrate was concentrated under reduced pressure. The residue was purified by flash chromatography (dichloromethane/ethyl acetate=5/1) to give 6-methoxy-2-[4-(4,4,5,5-tetramethyl-1,3,2-dioxaborolan-2-yl)phenyl]imidazo[1,2-a]pyridine (8.5 g, 91% yield). LC-MS: m/z=351 (M+H)+, retention time 1.995 min (Method A).

Step 3: 5-Bromo-6-fluoropyridin-2-amine

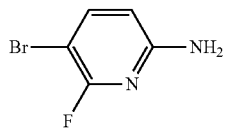

To a solution of 6-fluoranylpyridin-2-amine (6.4 g, 57.08 mmol) in acetonitrile (90 mL) was added bromosuccinimide (10.67 g, 59.94 mmol). Then the mixture was stirred at 25° C. for 3 h. The solution was poured into water and extracted with dichloromethane (150 mL×3). The combined organic layer was dried over sodium sulfate and concentrated. The residue was purified by flash chromatography (15% ethyl acetate in petroleum ether) to give 5-bromanyl-6-fluoranyl-pyridin-2-amine (8.5 g, 78% yield) as yellow solid. LC-MS: m/z=191 (M+H)+, retention time 1.506 min (Method A).

Step 4:
5-Bromo-6-fluoro-N,N-dimethylpyridin-2-amine

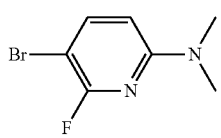

To a solution of 5-bromanyl-6-fluoranyl-pyridin-2-amine (6.2 g, 32.46 mmol) in dimethyformamide (100 mL) was added sodium hydride (3.25 g, 81.15 mmol) at 0° C. The mixture was stirred at 0° C. for 20 min, then iodanylmethane (13.82 g, 97.38 mmol) was added, and the resulting mixture was stirred at 25° C. for 2 h. The mixture was poured into water and extracted with ethyl acetate (150 mL×3). The combined organics were washed with brine (100 mL×3), dried over sodium sulfate and concentrated. The crude product was purified by flash chromatography (3% ethyl acetate in petroleum ether) to give 5-bromanyl-6-fluoranyl-N,N-dimethyl-pyridin-2-amine (6.5 g, 91% yield) as a green solid. LC-MS: m/z=219 (M+H)+, retention time 1.239 min (Method A).

Step 5: 6-Fluoranyl-5-[4-(6-methoxyimidazo[1,2-a]pyridin-2-yl)phenyl]-N,N-dimethyl-pyridin-2-amine

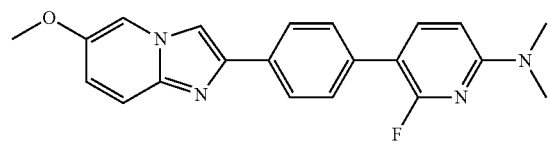

A mixture of 5-bromanyl-6-fluoranyl-N,N-dimethyl-pyridin-2-amine (1.97 g, 8.99 mmol), 6-methoxy-2-[4-(4,4,5,5-tetramethyl-1,3,2-dioxaborolan-2-yl)phenyl]imidazo[1,2-a]pyridine (3.15 g, 8.99 mmol), sodium carbonate (1.91 g, 17.99 mmol), [1, 1'-bis(diphenylphosphino)ferrocene]dichloropalladium(II) (332.79 mg, 0.45 mmol) in 1,4-dioxane (75 mL) and water (15 mL) was stirred at 90° C. for 3 h under nitrogen atmosphere. The reaction was cooled to room temperature and filtered. The filtrate was concentrated and the residue was purified by flash column chromatography (5% methanol in dichloromethane) to give 6-fluoranyl-5-[4-(6-methoxyimidazo[1,2-a]pyridin-2-yl)phenyl]-N,N-dimethyl-pyridin-2-amine (1.2 g, 37% yield) as a yellow solid. LCMS: m/z=363 (M+H)+, retention time 5.020 min (Method A). $^1$H NMR (400 MHZ, DMSO-d$_6$) δ 8.32 (s, 1H), 8.23 (s, 1H), 7.98 (d, J=8.2 Hz, 2H), 7.94-7.82 (m, 1H), 7.58 (d, J=7.8 Hz, 2H), 7.51 (d, J=9.7 Hz, 1H), 7.04 (dd, J=9.7, 2.2 Hz, 1H), 6.64 (d, J=8.5 Hz, 1H), 3.81 (s, 3H), 3.06 (s, 6H). 13C NMR (400 MHZ, DMSO-d$_6$) δ 157.65, 148.96, 144.48, 142.55, 142.05, 142.00, 134.04, 132.93, 128.57, 128.54, 125.97, 120.20, 117.39, 110.55, 109.14, 107.58, 107.30, 103.96, 56.58, 38.09.

Synthesis of Compound R

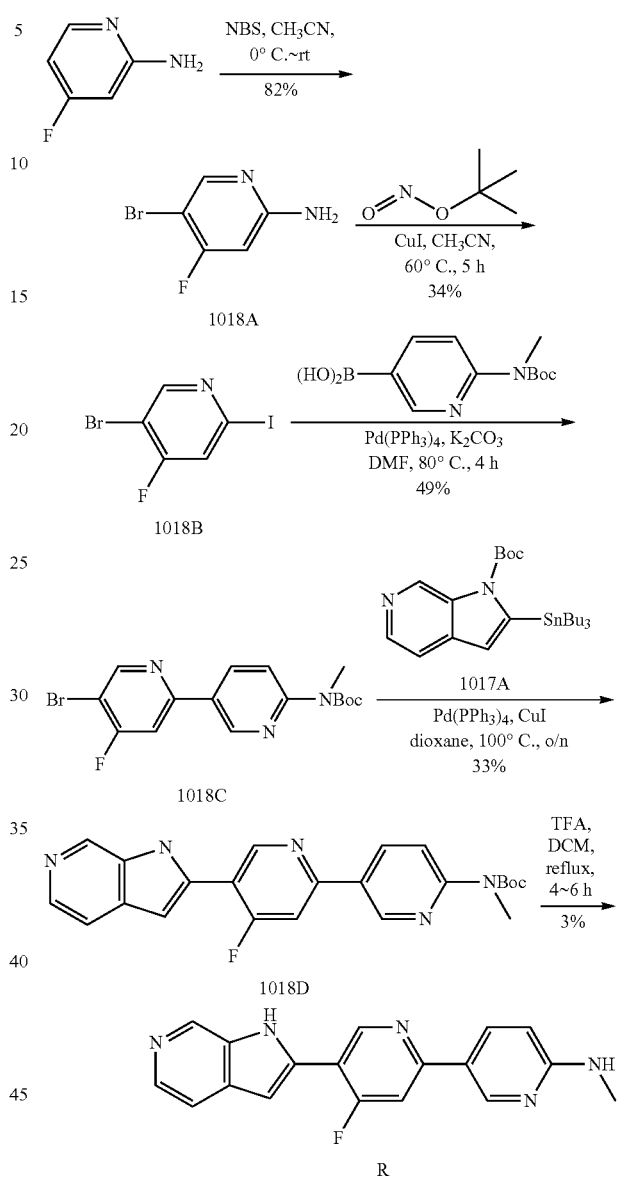

Step 1: 5-Bromo-4-fluoropyridin-2-amine

To a solution of 4-fluoranylpyridin-2-amine (2.35 g, 20.96 mmol) in acetonitrile (50 mL) was added N-bromosuccinimide (3.92 g, 22.01 mmol), then the reaction mixture was stirred at 25° C. for 2 h and concentrated. The residue was purified by flash chromatography (ethyl acetate/petroleum ether=22%) to give 5-bromanyl-4-fluoranyl-pyridin-2- amine (3.3 g, 17.277 mmol, 82.425% yield) as red solid. LCMS: m/z=250.0 (M−55)+, retention time: 2.07 min.

Step 2: 5-Bromo-4-fluoro-2-iodopyridine

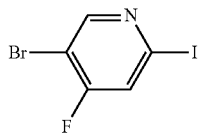

A mixture of 5-bromanyl-4-fluoranyl-pyridin-2-amine (3 g, 9.74 mmol), tert-butyl nitrite (1.51 g, 14.61 mmol) and copper (I) iodide (2.78 g, 14.61 mmol) in acetonitrile (50 mL) was heated to 60° C. for 2 h. The mixture was cooled to room temperature, filtered and concentrated. The residue was purified by flash chromatography (ethyl acetate/petroleum ether=10%) to give 5-bromanyl-4-fluoranyl-2-iodanyl-pyridine (1 g, 3.3126 mmol, 34.006% yield) as white solid. LCMS: m/z=250.0 (M−55)+, retention time: 2.16 min.

Step 3: Tert-Butyl 5-bromo-4-fluoro-2,3'-bipyridin-6'-yl(methyl)carbamate

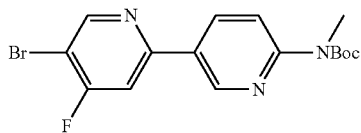

A mixture of 5-bromanyl-4-fluoranyl-2-iodanyl-pyridine (500 mg, 1.66 mmol), (6-((tert-butoxycarbonyl)(methyl) amino)pyridin-3-yl)boronic acid (396.63 mg, 1.57 mmol), potassium carbonate (571.42 mg, 4.14 mmol) and tetrakis (triphenylphosphine) palladium(0) (191.3 mg, 0.17 mmol in 1,4-dioxane (5 mL) and water (1 mL) were stirred at 90° C. under nitrogen atmosphere for 3~4 h. The mixture was filtered and the filtrate was concentrated. The residue was diluted with ethyl acetate (100 mL), washed with brine and water, dried over anhydrous sodium sulfate, filtered and concentrated. The residue was purified by flash chromatography (methanol/dichloromethane=0~15%) to give tert-butyl N-[5-(5-bromanyl-4-fluoranyl-pyridin-2-yl)pyridin-2-yl]-N-methyl-carbamate (310 mg, 0.811 mmol, 48.967% yield) as yellow solid.

LCMS: m/z=383.8 (M+H)+, retention time: 2.41 min

Step 4: Tert-Butyl 2-(6'-(tert-butoxycarbonyl (methyl)amino)-4-fluoro-2,3'-bipyridin-5-yl)-1H-pyrrolo[2,3-c]pyridine-1-carboxylate

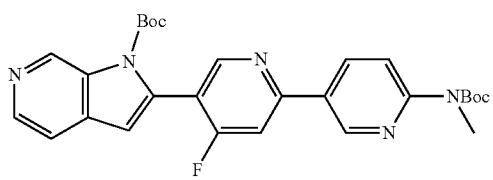 [SMILES: CN(C(=O)OC(C)(C)C)c1ccc(-c2cc(F)c(-c3cc4ccncc4n3C(=O)OC(C)(C)C)cn2)cn1]

To a solution of tert-butyl N-[5-(5-bromanyl-4-fluoranyl-pyridin-2-yl)pyridin-2-yl]-N-methyl-carbamate (310 mg, 0.81 mmol) and tert-butyl 2-tributylstannylpyrrolo[2,3-c] pyridine-1-carboxylate (452.58 mg, 0.89 mmol) in 1,4-dioxane (10 mL) was added copper (I) iodide (11.19 mg, 0.08 mmol) and tetrakis(triphenylphosphine)palladium(0) (93.67 mg, 0.08 mmol). The resulting mixture was stirred at 100° C. overnight under nitrogen atmosphere. After cooling to room temperature, the mixture was filtered and concentrated. The residue was purified by flash chromatography (ethyl acetate/petroleum ether=0~30%) to give tert-butyl 2-[4-fluoranyl-6-[6-[methyl-[(2-methylpropan-2-yl)oxycarbonyl]amino]pyridin-3-yl]pyridin-3-yl]pyrrolo[2,3-c]pyridine-1-carboxylate (140 mg, 0.2695 mmol, 33.224% yield) as oil. LCMS: m/z=520.3 (M+H)+, retention time: 2.24 min.

Step 5: 4-Fluoro-N-methyl-5-(1H-pyrrolo[2,3-c] pyridin-2-yl)-2,3'-bipyridin-6'-amine (Compound R)

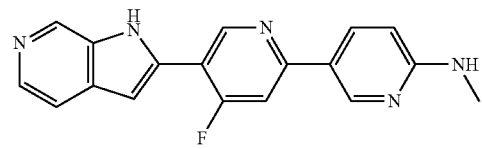 [SMILES: CNc1ccc(-c2cc(F)c(-c3cc4ccncc4[nH]3)cn2)cn1]

To a solution of tert-butyl 2-[4-fluoranyl-6-[6-[methyl-[(2-methylpropan-2-yl)oxy carbonyl]amino]pyridin-3-yl] pyridin-3-yl]pyrrolo[2,3-c]pyridine-1-carboxylate (140 mg, 0.27 mmol) in dichloromethane (3 mL) was added trifluoroacetic acid (307.23 mg, 2.69 mmol) and then the mixture was stirred under reflux until the starting materials was consumed. The solvent was removed under reduced pressure and the residue was purified by Prep-HPLC to give 5-[4-fluoranyl-5-(1H-pyrrolo[2,3-c]pyridin-2-yl)pyridin-2-yl]-N-methyl-pyridin-2-amine (3 mg, 0.0094 mmol, 3.4865% yield) as solid.

LCMS: m/z=320.1 (M+H)+, retention time: 1.70 min, purity 100% (UV 254).

1HNMR (400 MHZ, DMSO-$d_6$) δ 12.10 (s, 1H), 9.13 (d, J=11.0 Hz, 1H), 8.91~8.78 (m, 2H), 8.18 (dd, J=8.8, 2.2 Hz, 1H), 8.14 (d, J=5.4 Hz, 1H), 7.97 (d, J=13.3 Hz, 1H), 7.56 (t, J=10.6 Hz, 1H), 7.03 (s, 2H), 6.56 (d, J=8.9 Hz, 1H), 2.88 (t, J=17.8 Hz, 3H).

Synthesis of Compound S

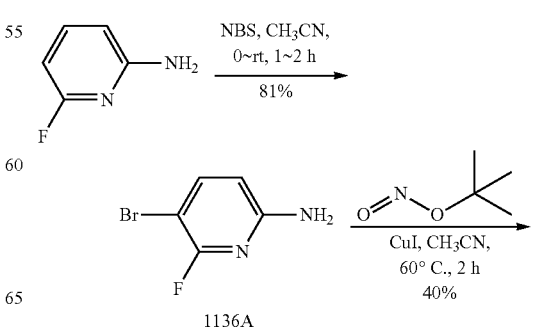

1136A

-continued

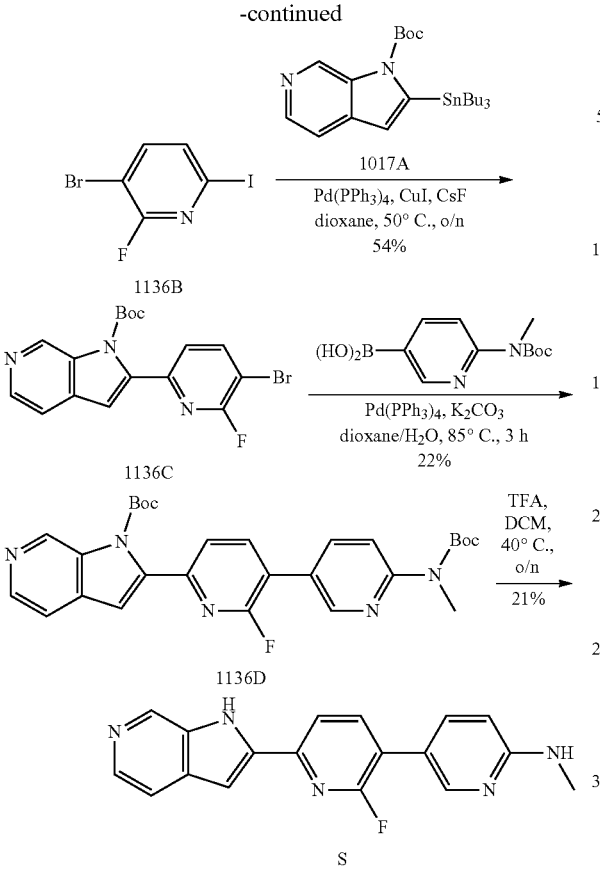

Step 1: 5-Bromo-6-fluoropyridin-2-amine

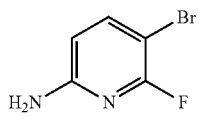

To a solution of 6-fluoranylpyridin-2-amine (2.8 g, 24.98 mmol) in acetonitrile (50 mL) was added N-bromosuccinimide (4.67 g, 26.22 mmol). Then the reaction mixture was stirred at 25° C. for 2 h and concentrated. The residue was purified by flash chromatography (ethyl acetate/petroleum ether=0~10%) to give 5-bromanyl-6-fluoranyl-pyridin-2-amine (3.91 g, 20.471 mmol, 81.965% yield) as yellow solid. LC-MS: m/z=193.0 (M+H)+, retention time: 1.64 min (Method B).

Step 2: 3-Bromo-2-fluoro-6-iodopyridine

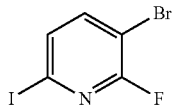

A mixture of 5-bromanyl-6-fluoranyl-pyridin-2-amine (3.3 g, 17.28 mmol), tert-butyl nitrite (2.67 g, 25.92 mmol) and copper (I) iodide (4.94 g, 25.92 mmol) in acetonitrile (30 mL) was heated to 60° C. for 2 h. The mixture was cooled to room temperature, filtered and concentrated. The residue was purified by flash chromatography (ethyl acetate/petroleum ether=0~10%) to give 3-bromanyl-2-fluoranyl-6-iodanyl-pyridine (2.1 g, 6.9564 mmol, 40.263% yield) as white solid. LC-MS: m/z=302.6 (M+H)+, retention time: 1.89 min (Method A).

Step 3: Tert-Butyl 2-(5-bromanyl-6-fluoranyl-pyridin-2-yl)pyrrolo[2,3-c]pyridine-1-carboxylate

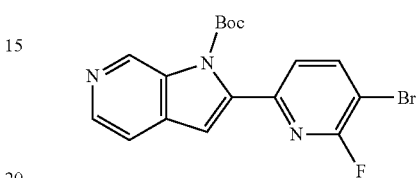

A mixture of tert-butyl 2-tributylstannylpyrrolo[2,3-c]pyridine-1-carboxylate (500 mg, 0.98 mmol), 3-bromanyl-2-fluoranyl-6-iodanyl-pyridine (357 mg, 1.18 mmol), copper (I) iodide (18 mg, 0.09 mmol), tetrakis(triphenylphosphine)palladium(0) (113 mg, 0.09 mmol) and cesium fluoride (29 mg, 0.19 mmol) in 1,4-dioxane (5 mL) were stirred at 50° C. under nitrogen atmosphere overnight. The mixture was filtered and the filtrate was concentrated under reduced pressure. The residue was diluted with ethyl acetate (100 mL), washed with brine and water, dried over with anhydrous sodium sulfate, filtered and concentrated under reduced pressure. The residue was purified by flash chromatography eluting (ethyl acetate/petroleum ether=0~10%) to give tert-butyl 2-(5-bromanyl-6-fluoranyl-pyridin-2-yl)pyrrolo[2,3-c]pyridine-1-carboxylate (400 mg, 54.84% yield) as yellow solid. LC-MS: m/z=392 (M)+, retention time: 1.991 min (Method A).

Step 4: Tert-Butyl 2-[6-fluoranyl-5-[6-[methyl-[(2-methylpropan-2-yl)oxycarbonyl] amino]pyridin-3-yl]pyridin-2-yl]pyrrolo[2,3-c]pyridine-1-carboxylate

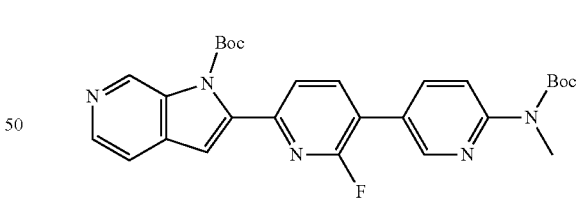

To a solution of tert-butyl 2-(5-bromanyl-6-fluoranyl-pyridin-2-yl)pyrrolo[2,3-c]pyridine-1-carboxylate (300 mg, 0.76 mmol) and [6-[methyl-[(2-methylpropan-2-yl)oxycarbonyl] amino]pyridin-3-yl]boronic acid (289 mg, 1.14 mmol) in 1,4-dioxane (20 mL) and water (5 mL) was added potassium carbonate (316 mg, 2.29 mmol) and tetrakis(triphenyl phosphine)palladium(0) (88 mg, 0.07 mmol). The resulting mixture was stirred at 85° C. for 3 h under nitrogen atmosphere. The mixture was cooled to room temperature, filtered and concentrated to get the crude product (300 mg, 22.47% yield, purity 54%) as oil, which was directly used to the next step without purification. LC-MS: m/z=520 (M+H)+, retention time: 2.220 min (Method B).

Step 5: 5-[2-Fluoranyl-6-(1H-pyrrolo[2,3-c]pyridin-2-yl)pyridin-3-yl]-N-methyl-pyridin-2-amine

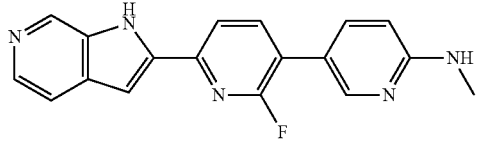 [SMILES: CNc1ccc(-c2ccc(-c3cc4ccncc4[nH]3)nc2F)cn1]

To a solution of tert-butyl 2-[6-fluoranyl-5-[6-[methyl-[(2-methylpropan-2-yl)oxy carbonyl]amino]pyridin-3-yl]pyridin-2-yl]pyrrolo[2,3-c]pyridine-1-carboxylate (200 mg, 0.384 mmol) in dichloromethane (5 mL) was added trifluoroacetic acid (5 mL) and then the mixture was stirred under reflux until the starting materials were consumed completely. The solvent was removed under reduced pressure and the residue was purified by Pre-HPLC to give 5-[2-fluoranyl-6-(1H-pyrrolo[2,3-c]pyridin-2-yl)pyridin-3-yl]-N-methyl-pyridin-2-amine (26 mg, 21.15% yield) as solid. LC-MS: m/z=320.0 (M+H)+, purity 100% (UV 254), retention time: 1.725 min (Method C); $^1$H NMR (400 MHZ, DMSO-$d_6$) δ 12.19 (s, 1H), 8.81 (s, 1H), 8.36 (s, 1H), 8.30-8.18 (m, 1H), 8.10 (dd, J=11.4, 6.6 Hz, 2H), 7.74 (d, J=8.7 Hz, 1H), 7.56 (d, J=5.1 Hz, 1H), 7.27 (s, 1H), 6.89 (d, J=4.9 Hz, 1H), 6.58 (d, J=8.8 Hz, 1H), 2.83 (d, J=4.7 Hz, 3H).

Synthesis of Compound T

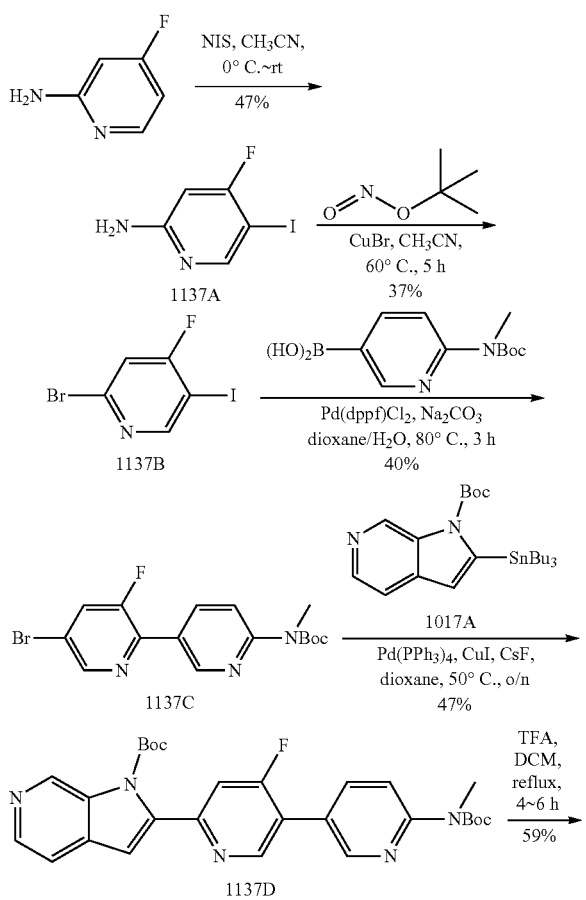

-continued

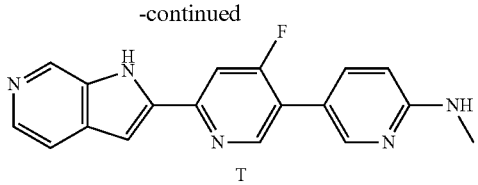

Step 1: 4-Fluoranyl-5-iodanyl-pyridin-2-amine

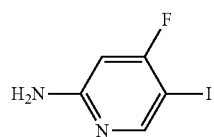

To a solution of 4-fluoranylpyridin-2-amine (2.0 g, 17.84 mmol) in acetonitrile (50 mL), was added N-iodosuccinimide (4.81 g, 21.40 mmol), then the reaction mixture was stirred at 25° C. overnight and concentrated. The residue was purified by flash chromatography (ethyl acetate/petroleum ether=0-30%) to give 4-fluoranyl-5-iodanyl-pyridin-2-amine (2.0 g, 47.10% yield) as yellow solid. LC-MS: m/z=238 (M+H)+, retention time: 1.682 min (Method B).

Step 2: 2-Bromanyl-4-fluoranyl-5-iodanyl-pyridine

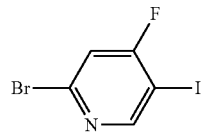

A mixture of 4-fluoranyl-5-iodanyl-pyridin-2-amine (1.5 g, 6.3 mmol), tert-butyl nitrite (3.2 g, 31.42 mmol) and copper (I) bromide (4.47 g, 31.51 mmol) in acetonitrile (30 mL) was heated to 60° C. overnight and then cooled to room temperature. The mixture was filtered and the filtrate was concentrated. The residue was purified by flash chromatography (ethyl acetate/petroleum ether=0~10%) to give 2-bromanyl-4-fluoranyl-5-iodanyl-pyridine (800 mg, 37.843% yield) as yellow solid. LC-MS: no MS, retention time: 1.89 min (Method A).

Step 3: Tert-Butyl N-[5-(6-bromanyl-4-fluoranyl-pyridin-3-yl)pyridin-2-yl]-N-methyl-carbamate

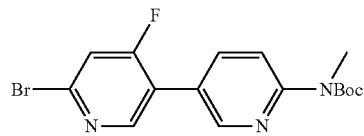

To a solution of 2-bromanyl-4-fluoranyl-5-iodanyl-pyridine (431 mg, 1.42 mmol) and [6-[methyl-[(2-methylpropan-2-yl)oxycarbonyl]amino]pyridin-3-yl]boronic acid (300 mg, 1.19 mmol) in 1,4-dioxane (20 mL) and water (5 mL) was added sodium carbonate (378 mg, 3.57 mmol) and bis(triphenylphosphine)palladium(II) chloride (137 mg, 0.11 mmol). The resulting mixture was stirred at 80° C. for 3 h under nitrogen atmosphere. The mixture was filtered and the filtrate was concentrated. The residue was diluted with ethyl acetate (100 mL), washed with brine and water, dried over with anhydrous sodium sulfate, filtered and concentrated under reduced pressure. The residue was purified by flash chromatography (ethyl acetate/petroleum ether=0-10%) to give tert-butyl N-[5-(6-bromanyl-4-fluoranyl-pyridin-3-yl)pyridin-2-yl]-N-methyl-carbamate (200 mg, 40.44% yield) as yellow solid. LC-MS: m/z=381 (M)+, retention time: 2.141 min (Method A).

Step 4: Tert-Butyl 2-[4-fluoranyl-5-[6-[methyl-[(2-methylpropan-2-yl)oxycarbonyl] amino]pyridin-3-yl]pyridin-2-yl]pyrrolo[2,3-c]pyridine-1-carboxylate

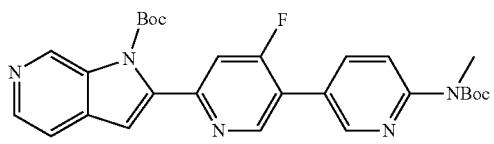 [SMILES: CN(C(=O)OC(C)(C)C)c1ccc(-c2cnc(-c3cc4ccncc4n3C(=O)OC(C)(C)C)cc2F)cn1]

A mixture of tert-butyl N-[5-(6-bromanyl-4-fluoranyl-pyridin-3-yl)pyridin-2-yl]-N-methyl-carbamate (200 mg, 0.52 mmol), tert-butyl 2-tributylstannylpyrrolo[2,3-c] pyridine-1-carboxylate (291 mg, 0.57 mmol), copper (I) iodide (7 mg, 0.05 mmol), tetrakis(triphenylphosphine)palladium (0) (60 mg, 0.05 mmol) and cesium fluoride (15.8 mg, 0.10 mmol) in 1,4-dioxane (5 mL) were stirred at 50° C. under nitrogen atmosphere overnight. The mixture was filtered and the filtrate was concentrated. The residue was diluted with ethyl acetate (100 mL), washed with brine and water, dried over with anhydrous sodium sulfate, filtered and concentrated under reduced pressure. The residue was purified by flash chromatography (methanol/dichloromethane=0-10%) to give tert-butyl 2-[4-fluoranyl-5-[6-[methyl-[(2-methyl-propan-2-yl)oxycarbonyl]amino]pyridin-3-yl]pyridin-2-yl] pyrrolo[2,3-c]pyridine-1-carboxylate (130 mg, 47.81% yield) as white solid. LC-MS: m/z=520 (M+H)+, retention time: 2.190 min (Method B).

Step 5: 5-[4-Fluoranyl-6-(1H-pyrrolo[2,3-c]pyridin-2-yl)pyridin-3-yl]-N-methyl-pyridin-2-amine

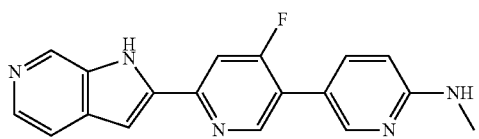 [SMILES: CNc1ccc(-c2cnc(-c3cc4ccncc4[nH]3)cc2F)cn1]

To a solution of tert-butyl 2-[4-fluoranyl-5-[6-[methyl-[(2-methylpropan-2-yl)oxy carbonyl]amino]pyridin-3-yl] pyridin-2-yl]pyrrolo[2,3-c]pyridine-1-carboxylate (110 mg, 0.217 mmol) in dichloromethane (5 mL) was added trifluoroacetic acid (5 mL) and then the mixture was stirred under reflux until the starting materials were consumed completely. The solvent was removed under reduced pressure and the residue was purified by Pre-HPLC to give 5-[4-fluoranyl-6-(1H-pyrrolo[2,3-c]pyridin-2-yl)pyridin-3-yl]-N-methyl-pyridin-2-amine (41 mg, 59.43% yield) as yellow solid. LC-MS: m/z=320.0 (M+H)+, purity: 100% (UV 254), retention time: 1.363 min (Method B); $^1$H NMR (400 MHZ, DMSO-$d_6$) δ 12.19 (s, 1H), 8.81 (s, 1H), 8.36 (s, 1H), 8.30-8.18 (m, 2H), 8.10 (dd, J=11.4, 6.6 Hz, 2H), 7.74 (d, J=8.7 Hz, 1H), 7.56 (d, J=5.1 Hz, 1H), 7.27 (s, 1H), 6.89 (d, J=4.9 Hz, 1H), 6.58 (d, J=8.8 Hz, 1H), 2.83 (d, J=4.7 Hz, 3H).

Synthesis of Compound U

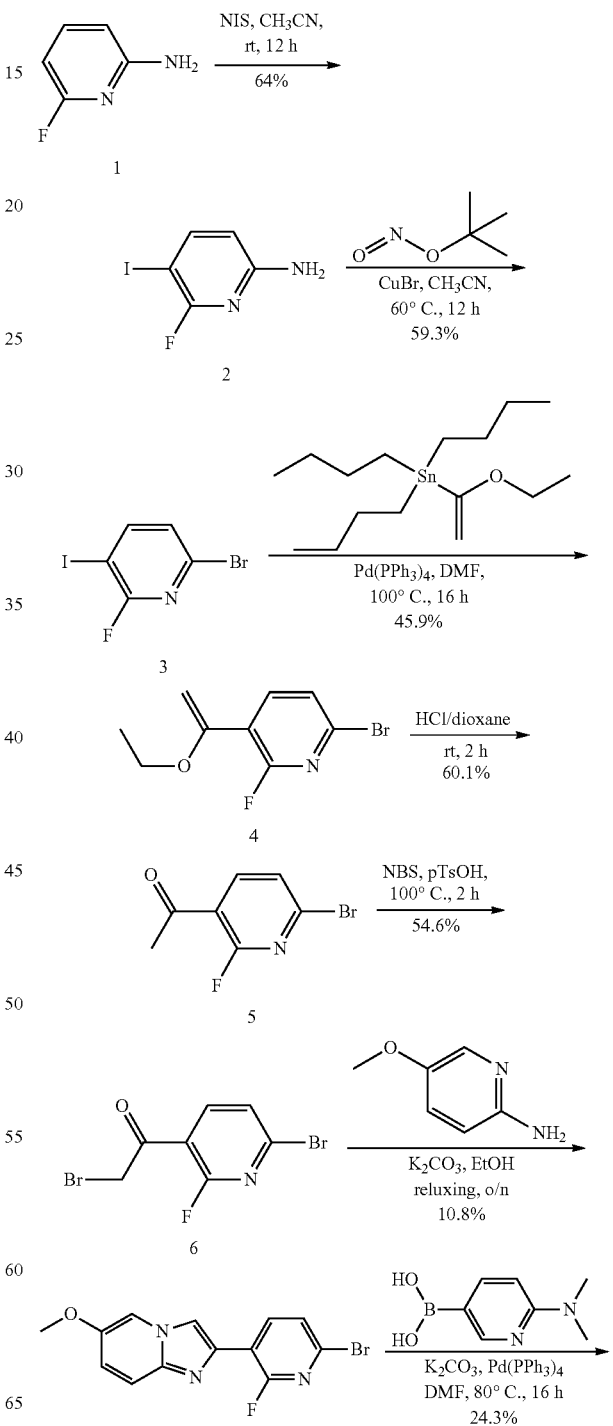

-continued

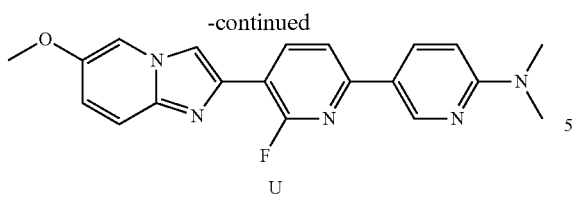

Step 1: 6-Fluoro-5-iodopyridin-2-amine

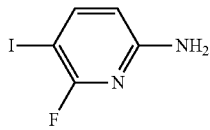

A mixture of 6-fluoranylpyridin-2-amine (500 mg, 4.46 mmol) and N-iodosuccinimide (833 mg, 4.68 mmol) in acetonitrile (10 mL) was stirred at 0° C. for 3 h. The reaction mixture was concentrated and the residue was purified by flash chromatography (petroleum ether/ethyl acetate=10/1) to give 6-fluoranyl-5-iodanyl-pyridin-2-amine (700 mg, 2.853 mmol, 64% yield) as white solid. LC-MS: m/z=239 (M+H)+.

Step 2: 6-Bromo-2-fluoro-3-iodopyridine

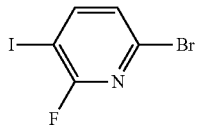

A mixture of 6-fluoranyl-5-iodanyl-pyridin-2-amine (700 mg, 2.94 mmol), tert-butylnitrite (1516 mg, 14.7 mmol) and copper (I) bromide (2117 mg, 14.71 mmol) in acetonitrile (20 mL) was stirred at 60° C. for 3 h. Water was added to the mixture. The mixture was extracted with ethyl acetate. The organic layer was dried and concentrated. The residue was purified by flash chromatography (petroleum ether/ethyl acetate=20/1) to give 6-bromo-2-fluoro-3-iodopyridine (600 mg, 1.75 mmol, 59.3% yield) as yellow solid. LC-MS: no MS.

Step 3: 6-Bromo-3-(1-ethoxyvinyl)-2-fluoropyridine

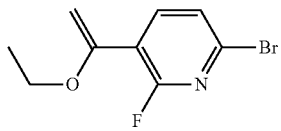

A mixture of 6-bromo-2-fluoro-3-iodopyridine (500 mg, 1.66 mmol) and tetrakis (triphenylphosphine)palladium(0) (9565 mg, 8.28 mmol) in N,N-dimethylformamide (5 mL) was stirred at 100° C. for 16 h. Water was added to the mixture. The mixture was extracted with ethyl acetate. The organic layer was dried and concentrated. The residue was purified by flash chromatography (petroleum ether/ethyl acetate=3/1) to give 6-bromo-3-(1-ethoxyvinyl)-2-fluoropyridine (200 mg, 0.761 mmol, 45.9% yield) as yellow solid. LC-MS: m/z=246 (M+H)+.

Step 4: 1-(6-Bromo-2-fluoropyridin-3-yl)ethanone

A mixture of 6-bromo-3-(1-ethoxyvinyl)-2-fluoropyridine (150 mg, 0.61 mmol) and hydrochloric acid (4 N in dioxane, 0.76 mL, 3.05 mmol) in dichloromethane (3 mL) was stirred at 90° C. for 2 h. The reaction mixture was concentrated and the residue was purified by Pre-TLC (petroleum ether/ethyl acetate=10/1) to give 1-(6-bromo-2-fluoropyridin-3-yl)ethanone (90 mg, 0.366 mmol, 60.1% yield) as yellow solid. LC-MS: no MS.

Step 5: 2-Bromo-1-(6-bromo-2-fluoropyridin-3-yl)ethanone

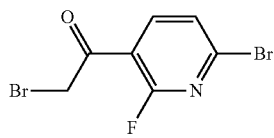 [SMILES: O=C(CBr)c1ccc(Br)nc1F]

A mixture of 1-(6-bromanyl-2-fluoranyl-pyridin-3-yl)ethanone (50 mg, 0.23 mmol), N-bromosuccinimide (41 mg, 0.23 mmol) and p-toluenesulfonic acid (4.5 mg, 0.023 mmol) was stirred at 100° C. for 2 h. Dichloromethane was added and the mixture was washed with water. The organic layer was dried and concentrated to give 2-bromanyl-1-(6-bromanyl-2-fluoranyl-pyridin-3-yl)ethanone (60 mg, 0.1253 mmol, 54.63% yield) as yellow solid. The crude product was used for next step without purification. LC-MS: no MS.

Step 6: 2-(6-Bromo-2-fluoropyridin-3-yl)-6-methoxyimidazo[1,2-a]pyridine

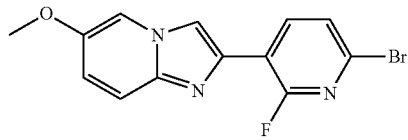 [SMILES: COc1ccc2nc(-c3ccc(Br)nc3F)cn2c1]

A mixture of 2-bromanyl-1-(6-bromanyl-2-fluoranyl-pyridin-3-yl)ethanone (132 mg, 0.44 mmol), 5-methoxypyridin-2-amine (50 mg, 0.40 mmol) and NaHCO₃ (37 mg, 0.44 mmol) in ethanol (5 mL) was stirred at 80° C. for 3 h. The reaction was quenched with water and extracted with ethyl acetate. The organic layer was dried and concentrated. The residue was purified by flash chromatography (petroleum ether/ethyl acetate=2/1) to give 2-(6-bromo-2-fluoropyridin-3-yl)-6-methoxyimidazo[1,2-a]pyridine (20 mg, 0.043 mmol, 10.8% yield) as yellow solid. LC-MS: m/z=322 (M+H)+.

Step 7: 6-Fluoro-5-(6-methoxyimidazo[1,2-a]pyridin-2-yl)-N,N-dimethyl-2,3'-bipyridin-6'-amine

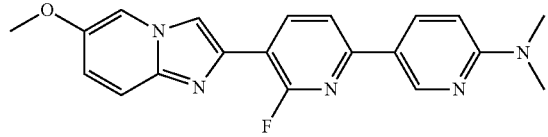

A mixture of 2-(6-bromo-2-fluoropyridin-3-yl)-6-methoxyimidazo[1,2-a]pyridine (20 mg, 0.06 mmol), [6-(dimethylamino)pyridin-3-yl]boronic acid (15.5 mg, 0.09 mmol), tetrakis (triphenylphosphine)palladium(0) (7.2 mg, 0.01 mmol) and potassium carbonate (0.09 mL, 0.19 mmol) in N,N-dimethylformamide (3 mL) was stirred at 80° C. for 3 h. Water was added to the mixture. The mixture was extracted with ethyl acetate. The organic layer was dried and concentrated. The residue was purified by flash chromatography (petroleum ether/ethyl acetate=5/1) to give 6-fluoro-5-(6-methoxyimidazo[1,2-a]pyridin-2-yl)-N,N-dimethyl-2,3'-bipyridin-6'-amine (5.5 mg, 0.015 mmol, 24.38% yield) as yellow solid. LC-MS: m/z=364 (M+H)+, purity 100% (214 nm), Rt=4.067. 1HNMR (400 MHZ, DMSO-d$_6$) δ 8.854 (d, J=1.6 Hz, 1H), 8.600 (m, 1H), 8.361 (d, J=2.0 Hz, 1H), 8.286 (d, J=4.0 Hz, 1H), 8.180 (dd, J=9.2 Hz, 2.4 Hz, 1H), 7.925 (d, J=8.0 Hz, 1H), 7.538 (d, J=9.2 Hz, 1H), 7.090 (dd, J=10.0 Hz, 2.0 Hz, 1H), 6.751 (d, J=8.8 Hz, 3H), 3.802 (s, 3H), 3.116 (s, 6H).

Synthesis of Compound V

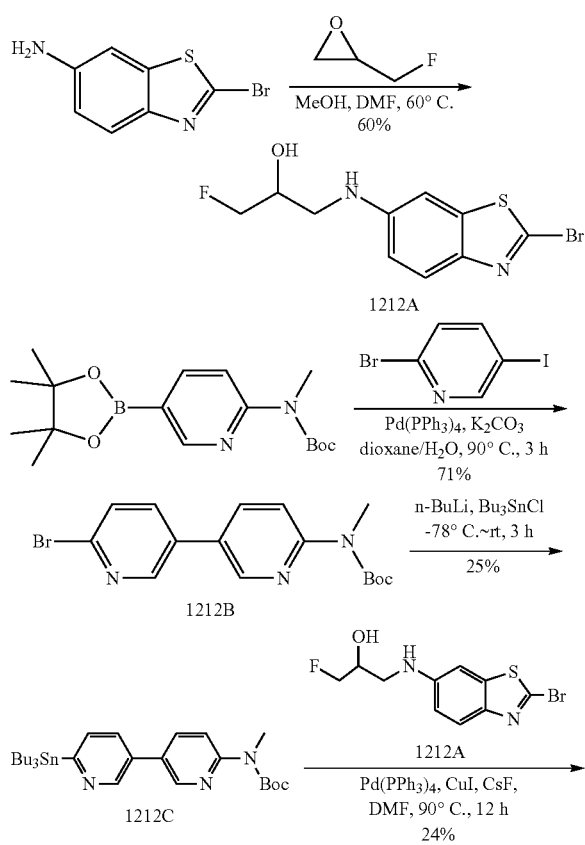

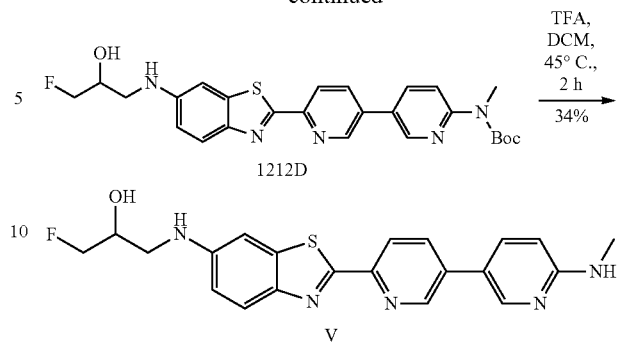

Step 1: 1-(2-Bromobenzo[d]thiazol-6-ylamino)-3-fluoropropan-2-ol

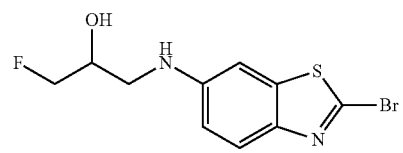 [SMILES: OC(CF)CNc1ccc2nc(Br)sc2c1]

To a solution of 2-bromobenzo[d]thiazol-6-amine (1 g, 4.58 mmol) in methanol (50 mL) was added 2-(fluoromethyl)oxirane (1.74 g, 22.9 mmol). The mixture was stirred at 60° C. overnight. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (methanol/dichloromethane=0-30%) to give (1.74 g, 75.3%, yield) as yellow solid. LC-MS: m/z=304 (M+H)+, retention time: 1.651 min (Method B).

Step 2: Tert-Butyl N-[5-(6-bromanylpyridin-3-yl)pyridin-2-yl]-N-methyl-carbamate

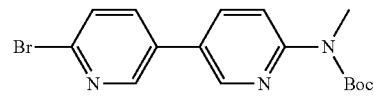

To a solution of 2-bromanyl-5-iodanyl-pyridine (637 mg, 2.24 mmol) and tert-butyl N-methyl-N-[5-(4,4,5,5-tetramethyl-1,3,2-dioxaborolan-2-yl)pyridin-2-yl]carbamate (500 mg, 1.49 mmol) in 1,4-dioxane (20 mL) and water (5 mL) was added potassium carbonate (619 mg, 4.48 mmol) and tetrakis(triphenylphosphine)palladium(0) (172 mg, 0.14 mmol). The resulting mixture was stirred at 90° C. for 3 h under nitrogen atmosphere. The mixture was filtered and the filtrate was concentrated. The residue was diluted with ethyl acetate (100 mL), washed with brine and water, dried over with anhydrous sodium sulfate, filtered and concentrated under reduced pressure. The residue was purified by flash column chromatography (ethyl acetate/petroleum ether=0-10%) to give tert-butyl N-[5-(6-bromanylpyridin-3-yl)pyridin-2-yl]-N-methyl-carbamate (400 mg, 71.93% yield) as yellow solid. LC-MS: m/z=364 (M+H)+, retention time: 2.136 min (Method B).

Step 3: Tert-Butyl N-methyl-N-[5-(6-tributylstannylpyridin-3-yl)pyridin-2-yl]carbamate

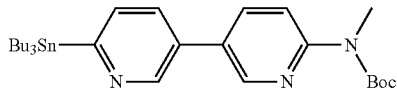

To a solution of tert-butyl N-[5-(6-bromanylpyridin-3-yl)pyridin-2-yl]-N-methyl-carbamate (380 mg, 1.04 mmol) in dry tetrahydrofuran (20 mL) was added n-butyl lithium (0.62 mL, 1.25 mmol) at −78° C., the mixture was stirred at −78° C. for 10 min, then tributylchlorostannane (509 mg, 1.56 mmol) was added to the reaction mixture. The mixture was stirred at 25° C. for 3 h. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (ethyl acetate/petroleum ether-0~10%) to give tert-butyl N-methyl-N-[5-(6-tributylstannylpyridin-3-yl)pyridin-2-yl]carbamate (180 mg, 25.53% yield) as yellow oil. LC-MS: m/z=574 (M)+, retention time: 2.101 min (Method A).

Step 4: Tert-Butyl N-[5-[6-[6-[(3-fluoranyl-2-oxidanyl-propyl)amino]-1,3-benzothiazol-2-yl]pyridin-3-yl]pyridin-2-yl]-N-methyl-carbamate

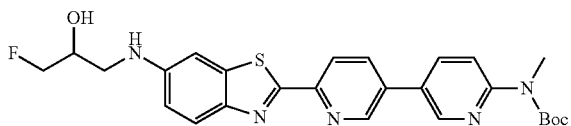 [SMILES: CN(C(=O)OC(C)(C)C)c1ccc(-c2ccc(-c3nc4ccc(NCC(O)CF)cc4s3)nc2)cn1]

A mixture of 1-[(2-bromanyl-1,3-benzothiazol-6-yl)amino]-3-fluoranyl-propan-2-ol (85 mg, 0.27 mmol), tert-butyl 2-tributylstannylpyrrolo[2,3-c]pyridine-1-carboxylate (175 mg, 0.30 mmol), copper (I) iodide (3.8 mg, 0.02 mmol), tetrakis(triphenylphosphine) palladium(0) (32 mg, 0.02 mmol) and cesium fluoride (4.23 mg, 0.02 mmol) in N,N-dimethylformamide (5 mL) were stirred at 90° C. under nitrogen atmosphere overnight. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (methanol/dichloromethane=0~30%) to give tert-butyl N-[5-[6-[6-[(3-fluoranyl-2-oxidanyl-propyl)amino]-1,3-benzothiazol-2-yl]pyridin-3-yl]pyridin-2-yl]-N-methyl-carbamate (38 mg, 24.63% yield) as yellow solid. LC-MS: m/z=510 (M)+, retention time: 1.982 min (Method A).

Step 5: 1-Fluoranyl-3-[[2-[5-[6-(methylamino)pyridin-3-yl]pyridin-2-yl]-1,3-benzothiazol-6-yl]amino]propan-2-ol

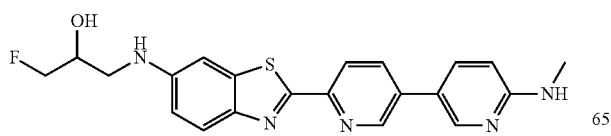

To a solution of tert-butyl N-[5-[6-[6-[(3-fluoranyl-2-oxidanyl-propyl)amino]-1,3-benzothiazol-2-yl]pyridin-3-yl]pyridin-2-yl]-N-methyl-carbamate (40 mg, 0.07 mmol) in dichloromethane (5 mL) was added trifluoroacetic acid (5 mL) and then the mixture was stirred under reflux until the starting materials were consumed completely. The solvent was removed under reduced pressure and the residue was purified by Pre-HPLC to give 1-fluoranyl-3-[[2-[5-[6-(methylamino)pyridin-3-yl]pyridin-2-yl]-1,3-benzothiazol-6-yl]amino]propan-2-ol (11 mg, 34.22% yield) as yellow solid. LC-MS: m/z=410 (M+H)+, purity 100% (UV 254), retention time: 1.570 min, (Method B); ¹H NMR (400 MHZ, DMSO-d₆) δ 8.92 (s, 1H), 8.51 (s, 1H), 8.18 (t, J=6.8 Hz, 2H), 7.90 (s, 1H), 7.82 (dd, J=41.3, 7.8 Hz, 1H), 7.16 (s, 1H), 6.89 (dd, J=23.5, 6.5 Hz, 2H), 6.58 (d, J=8.6 Hz, 1H), 6.18 (s, 1H), 5.31 (d, J=4.8 Hz, 1H), 4.69-4.46 (m, 1H), 4.42-4.34 (m, 1H), 3.93 (d, J=16.4 Hz, 1H), 3.31-3.28 (m, 1H), 3.21 (dd, J=27.9, 21.2 Hz, 1H), 2.84 (d, J=4.3 Hz, 3H).

Synthesis of Compound W

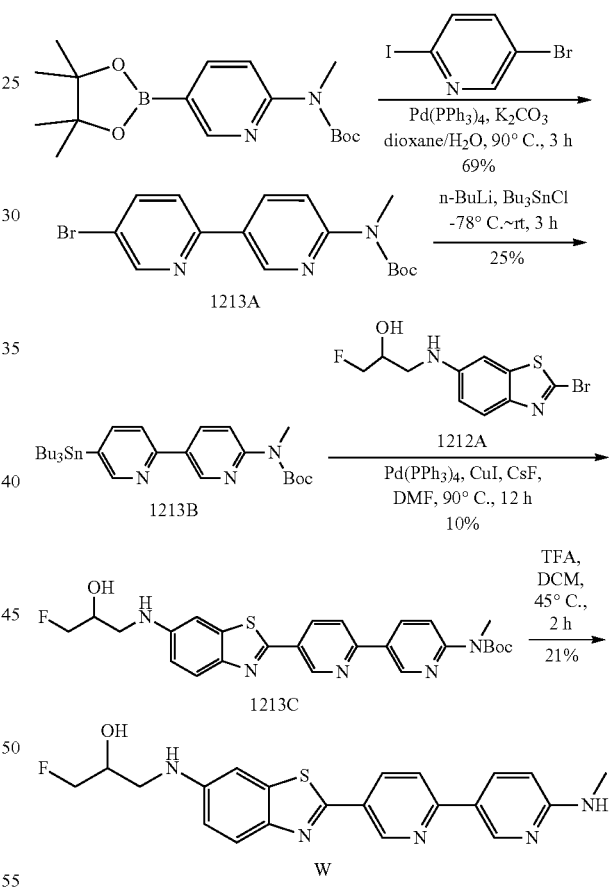

Step 1: Tert-Butyl N-[5-(5-bromanylpyridin-2-yl)pyridin-2-yl]-N-methyl-carbamate

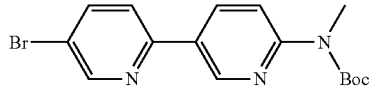 [SMILES: CN(C(=O)OC(C)(C)C)c1ccc(-c2ccc(Br)cn2)cn1]

To a solution of 5-bromo-2-iodopyridine (637 mg, 2.24 mmol) and tert-butyl N-methyl-N-[5-(4,4,5,5-tetramethyl-1,3,2-dioxaborolan-2-yl)pyridin-2-yl]carbamate (500 mg, 1.49 mmol) in 1,4-dioxane (20 mL) and water (5 mL) was added potassium carbonate (619 mg, 4.48 mmol) and tetrakis(triphenylphosphine)palladium(0) (172 mg, 0.14 mmol). The resulting mixture was stirred at 90° C. for 3 h under nitrogen atmosphere. The mixture was filtered and the filtrate was concentrated. The residue was diluted with ethyl acetate (100 mL), washed with brine and water, dried over with anhydrous sodium sulfate, filtered and concentrated under reduced pressure. The residue was purified by flash column chromatography (ethyl acetate/petroleum ether=0~10%) to give tert-butyl N-[5-(6-bromanylpyridin-3-yl)pyridin-2-yl]-N-methyl-carbamate (380 mg, 69.73% yield) as yellow solid. LC-MS: m/z=364 (M+H)+, retention time: 2.143 min (Method B).

Step 2: Tert-Butyl N-methyl-N-[5-(6-tributylstannylpyridin-3-yl)pyridin-2-yl]carbamate

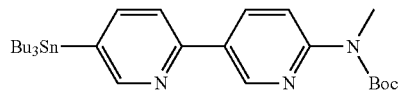

To a solution of tert-butyl N-[5-(6-bromanylpyridin-3-yl)pyridin-2-yl]-N-methyl-carbamate (380 mg, 1.04 mmol) in dry tetrahydrofuran (20 ml) was added n-butyl lithium (0.62 mL, 1.25 mmol) at −78° C., the mixture was stirred at −78° C. for 10 min, then tributylchlorostannane (509 mg, 1.56 mmol) was added to the reaction mixture. The mixture was stirred at 25° C. for 3 h. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (ethyl acetate/petroleum ether=0-10%) to give tert-butyl N-methyl-N-[5-(6-tributylstannylpyridin-3-yl)pyridin-2-yl]carbamate (150 mg, 25.03% yield) as yellow oil. LC-MS: m/z=574 (M)+, retention time: 2.277 min (Method A).

Step 3: Tert-Butyl N-[5-[5-[6-[(3-fluoranyl-2-oxidanyl-propyl)amino]-1,3-benzothiazol-2-yl]pyridin-2-yl]pyridin-2-yl]-N-methyl-carbamate

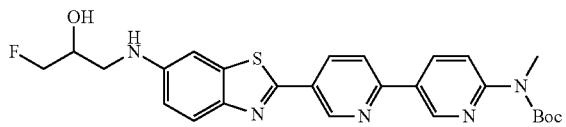

A mixture of 1-[(2-bromanyl-1,3-benzothiazol-6-yl)amino]-3-fluoranyl-propan-2-ol (85 mg, 0.27 mmol), tert-butyl 2-tributylstannylpyrrolo[2,3-c]pyridine-1-carboxylate (175 mg, 0.30 mmol), copper (I) iodide (3.8 mg, 0.02 mmol), tetrakis(triphenylphosphine) palladium(0) (32 mg, 0.02 mmol) and cesium fluoride (4.23 mg, 0.02 mmol) in N,N-dimethylformamide (5 mL) were stirred at 90° C. under nitrogen atmosphere overnight. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (methanol/dichloromethane=0-30%) to give tert-butyl N-[5-[6-[6-[(3-fluoranyl-2-oxidanyl-propyl)amino]-1,3-benzothiazol-2-yl]pyridin-3-yl]pyridin-2-yl]-N-methyl-carbamate (15 mg, 10.56% yield) as yellow solid. LC-MS: m/z=510 (M)+, retention time: 2.135 min (Method B).

Step 4: 1-Fluoranyl-3-[[2-[5-[6-(methylamino)pyridin-3-yl]pyridin-2-yl]-1,3-benzo thiazol-6-yl]amino]propan-2-ol

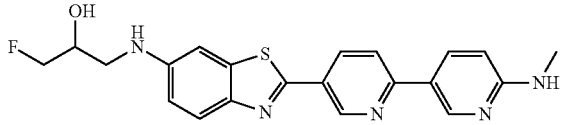 [SMILES: CNc1ccc(-c2ccc(-c3nc4ccc(NCC(O)CF)cc4s3)cn2)cn1]

To a solution of tert-butyl N-[5-[6-[6-[(3-fluoranyl-2-oxidanyl-propyl)amino]-1,3-benzothiazol-2-yl]pyridin-3-yl]pyridin-2-yl]-N-methyl-carbamate (35 mg, 0.06 mmol) in dichloromethane (5 mL) was added trifluoroacetic acid (5 mL) and then the mixture was stirred under reflux until the starting materials were consumed completely. The solvent was removed under reduced pressure and the residue was purified by Pre-HPLC to give 1-fluoranyl-3-[[2-[5-[6-(methylamino)pyridin-3-yl]pyridin-2-yl]-1,3-benzothiazol-6-yl]amino]propan-2-ol (6 mg, 21.33% yield) as yellow solid. LC-MS: m/z=410 (M+H)+, purity 100% (UV 254), retention time: 1.763 min (Method B); $^1$H NMR (400 MHZ, DMSO-d$_6$) δ 9.12 (d, J=1.8 Hz, 1H), 8.83 (d, J=2.3 Hz, 1H), 8.27 (dd, J=8.4, 2.4 Hz, 1H), 8.16 (dd, J=8.8, 2.4 Hz, 1H), 7.96 (d, J=8.2 Hz, 1H), 7.77 (d, J=8.9 Hz, 1H), 7.18 (d, J=2.2 Hz, 1H), 7.14-6.86 (m, 2H), 6.56 (d, J=8.9 Hz, 1H), 6.16 (t, J=5.8 Hz, 1H), 5.32 (d, J=5.1 Hz, 1H), 4.44 (dddd, J=24.1, 15.1, 9.6, 4.4 Hz, 2H), 3.93 (d, J=17.3 Hz, 1H), 3.30-2.88 (m, 2H), 2.85 (d, J=4.8 Hz, 3H).

Synthesis of Compound X

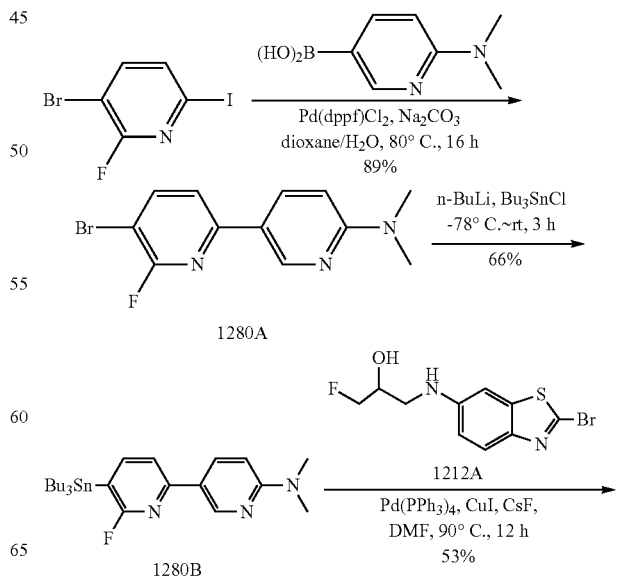

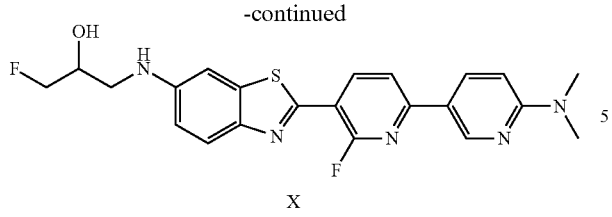

X

Step 1: 5-(5-Bromanyl-6-fluoranyl-pyridin-2-yl)-N,N-dimethyl-pyridin-2-amine

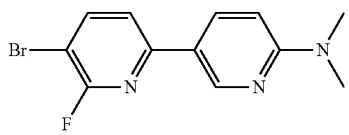 [SMILES: CN(C)c1ccc(-c2ccc(Br)c(F)n2)cn1]

A mixture of 3-bromanyl-2-fluoranyl-6-iodanyl-pyridine (500 mg, 1.60 mmol), [6-(dimethylamino)pyridin-3-yl]boronic acid (250 mg, 1.50 mmol), bis(triphenylphosphine)palladium(II) chloride (105 mg, 0.15 mmol), sodium carbonate (625 mg, 4.8 mmol) in dioxane (12 mL) and water (4 mL) was heated at 80° C. for 16 h under nitrogen atmosphere. The reaction mixture was diluted with water (30 mL) and extracted with ethyl acetate (30 mL×3). The combined organic layer was washed with brine (30 mL), dried over anhydrous sodium sulfate and concentrated. The residue was purified by flash chromatography (ethyl acetate/petroleum ether=0-10%) to give 5-(5-Bromanyl-6-fluoranyl-pyridin-2-yl)-N,N-dimethyl-pyridin-2-amine (400 mg, 89% yield) as white solid. LCMS: m/z=297[M+H]+; $R_T$=2.000 min. (Method B)

Step 2: 5-(6-Fluoranyl-5-tributylstannyl-pyridin-2-yl)-N,N-dimethyl-pyridin-2-amine

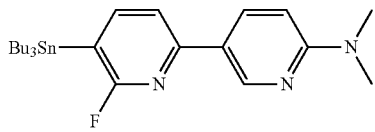

To a solution of 5-(5-bromanyl-6-fluoranyl-pyridin-2-yl)-N,N-dimethyl-pyridin-2-amine (600 mg, 2.02 mmol) in tetrahydrofuran (50 mL) was added n-butyl lithium (194 mg, 3.03 mmol) at −78° C., the mixture was stirred at −78° C. for 15 min, then tributylchlorostannane (989 mg, 3.03 mmol) was added to the reaction mixture. The mixture was stirred at 25° C. for 3 h. The reaction mixture was diluted with water (30 mL) and extracted with ethyl acetate (30 mL×3). The combined organic layer was washed with brine (30 mL), dried over anhydrous sodium sulfate and concentrated. The residue was purified by flash chromatography (ethyl acetate/petroleum ether=0-6%) to give 5-(6-fluoranyl-5-tributylstannyl-pyridin-2-yl)-N,N-dimethyl-pyridin-2-amine (800 mg, 66% yield) as yellow oil. LCMS: m/z=506 [M]+; $R_T$=2.096 min. (Method B)

Step 3: 1-[[2-[6-[6-(Dimethylamino)pyridin-3-yl]-2-fluoranyl-pyridin-3-yl]-1,3-benzo thiazol-6-yl]amino]-3-fluoranyl-propan-2-ol

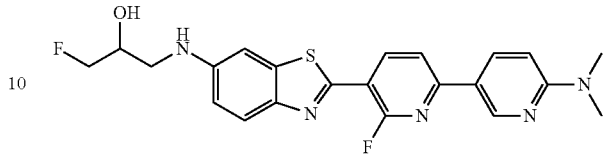

A mixture of 1-[(2-bromanyl-1,3-benzothiazol-6-yl)amino]-3-fluoranyl-propan-2-ol (56 mg, 0.27 mmol), 5-(6-fluoranyl-5-tributylstannyl-pyridin-2-yl)-N,N-dimethyl-pyridin-2-amine (100 mg, 0.195 mmol), copper (I) iodide (3.4 mg, 0.018 mmol), tetrakis(triphenyl phosphine)palladium(0) (21 mg, 0.018 mmol) and cesium fluoride (2.73 mg, 0.018 mmol) in N,N-dimethylformamide (5 mL) were stirred at 90° C. under nitrogen atmosphere overnight. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (methanol/dichloromethane=0-30%) to give 1-[[2-[6-[6-(dimethylamino)pyridin-3-yl]-2-fluoranyl-pyridin-3-yl]-1,3-benzothiazol-6-yl]amino]-3-fluoranyl-propan-2-ol (44 mg, 53.22% yield) as yellow solid.

LC-MS: m/z=442 (M+H)+, purity 100% (UV 254), retention time: 2.037 min (Method B); $^1$H NMR (400 MHZ, DMSO-$d_6$) δ 8.90 (d, J=2.3 Hz, 1H), 8.76-8.61 (m, 1H), 8.22 (dd, J=9.1, 2.4 Hz, 1H), 8.01 (d, J=8.2 Hz, 1H), 7.80 (d, J=8.9 Hz, 1H), 7.19 (d, J=1.9 Hz, 1H), 7.02-6.90 (m, 1H), 6.78 (d, J=9.2 Hz, 1H), 6.22 (t, J=5.6 Hz, 1H), 5.73-5.38 (m, 1H), 5.73-4.17 (m, 2H), 3.94 (d, J=21.0 Hz, 1H), 3.29-3.18 (m, 1H), 3.13 (s, 6H), 2.87-2.82 (m, 1H)

Synthesis of Compound Y

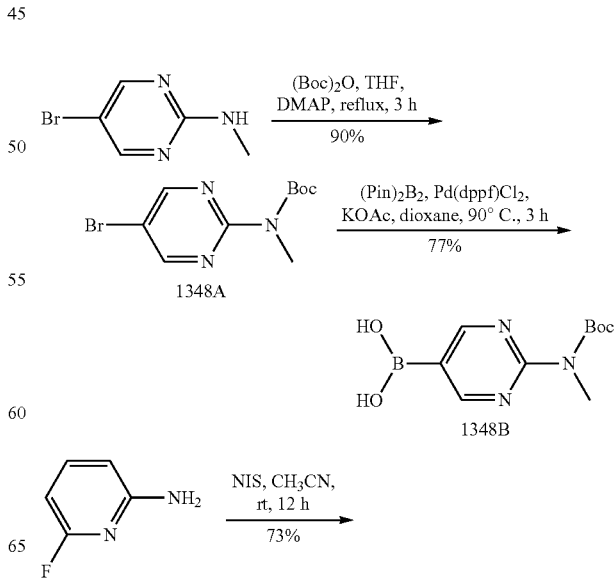

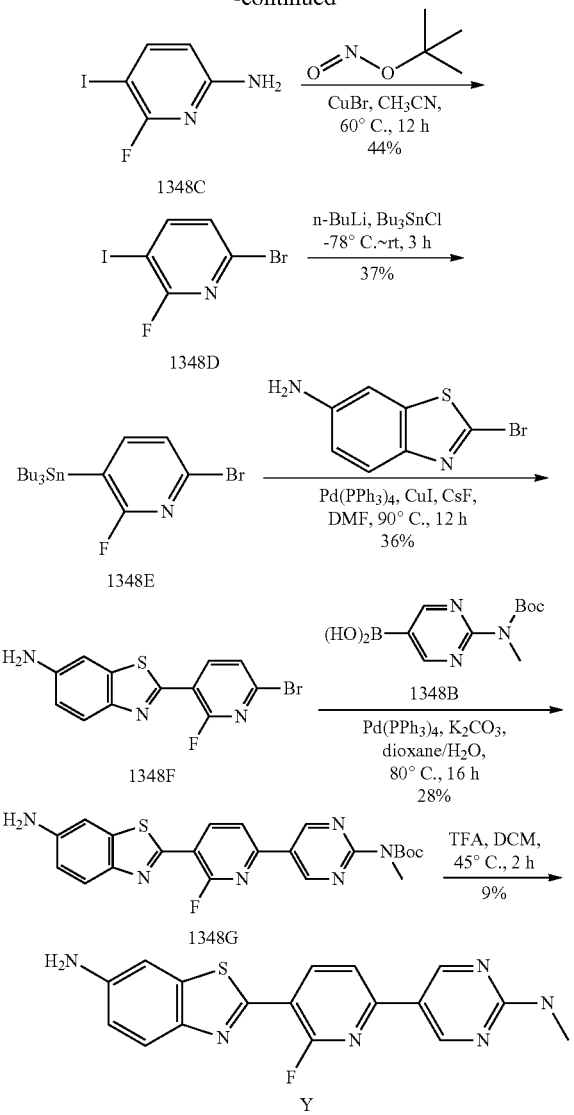

Step 1: Tert-Butyl N-(5-bromanylpyrimidin-2-yl)-N-methyl-carbamate

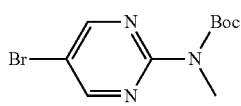

A mixture of 5-bromanyl-N-methyl-pyrimidin-2-amine (4 g, 21.27 mmol), tert-butyl (2-methylpropan-2-yl)oxycarbonyl carbonate (9 g, 42.54 mmol), 4-dimethylaminopyridine (260 mg, 2.13 mmol) and triethylamine (6 g, 63.8 mmol) in tetrahydrofuran (80 mL) was heated at 70° C. for 3 h and concentrated. The residue was purified by flash chromatography (petroleum ether/ethyl acetate=4/1) to give tert-butyl N-(5-bromanyl pyrimidin-2-yl)-N-methyl-carbamate (5.5 g, 19.0 mmol, 89.728% yield) as white solid. LC-MS: m/z=232 (M−56+H)+, purity 100% (UV 254 nm). Retention time: 2.06 min.

Step 2: (2-((Tert-Butoxycarbonyl)(methyl)amino) pyrimidin-5-yl)boronic acid

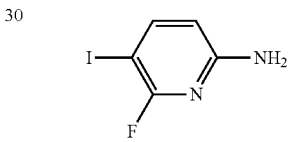

A mixture of tert-butyl N-(5-bromanyl pyrimidin-2-yl)-N-methyl-carbamate (4 g, 13.88 mmol), 4,4,5,5-tetramethyl-2-(4,4,5,5-tetramethyl-1,3,2-dioxaborolan-2-yl)-1,3,2-dioxa borolane (5.29 g, 20.82 mmol), [1,1'-bis(diphenylphosphino)ferrocene]dichloro palladium(II) (205.6 mg, 0.28 mmol), potassium acetate (4.08 g, 41.65 mmol) in 1,4-dioxane (100 mL) was stirred at 90° C. for 3 h. The mixture was cooled to room temperature, filtered and concentrated. The residue was purified by flash chromatography (petroleum ether/ethyl acetate=3/1) to give (2-((tert-butoxycarbonyl)(methyl)amino) pyrimidin-5-yl)boronic acid (3 g, 10.669 mmol, 76.857% yield). LC-MS: m/z=324 (M−56+H)+, purity 100% (UV 254 nm). Retention time: 1.31 min.

Step 3: 6-Fluoranyl-5-iodanyl-pyridin-2-amine

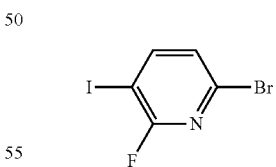

To a solution of 6-fluoranylpyridin-2-amine (3.0 g, 17.84 mmol) in acetonitrile (50 mL) was added N-iodosuccinimide (5.2 g, 29.43 mmol), then the reaction mixture was stirred at 25° C. overnight. The mixture was concentrated and the residue was purified by flash chromatography (ethyl acetate/petroleum ether=0~30%) to give 6-fluoranyl-5-iodanyl-pyridin-2-amine (5.0 g, 73.01% yield) as white solid. LC-MS: m/z=238 (M+H)+, retention time: 1.529 min (Method B).

Step 4: 6-Bromanyl-2-fluoranyl-3-iodanyl-pyridine

A mixture of 6-fluoranyl-5-iodanyl-pyridin-2-amine (4.0 g, 16.8 mmol), tert-butyl nitrite (2.5 g, 25.2 mmol) and copper (I) bromide (3.5 g, 25.2 mmol) in acetonitrile (30 mL) was heated to 60° C. overnight and then cooled to room temperature. The mixture was filtered and the filtrate was concentrated. The residue was purified by flash chromatography (ethyl acetate/petroleum ether=0~10%) to give 2-bromanyl-4-fluoranyl-5-iodanyl-pyridine (2.5 g, 44.34% yield) as yellow solid. LC-MS: no Ms, retention time: 2.088 min (Method B)

Step 5: (6-Bromanyl-2-fluoranyl-pyridin-3-yl)-tributyl-stannane

To a solution of 6-bromanyl-2-fluoranyl-3-iodanyl-pyridine (1.4 g, 4.63 mmol) in tetrahydrofuran (50 mL) was added n-butyl lithium (1.9 mL, 4.63 mmol) at −78° C., the mixture was stirred at −78° C. for 15 min, then tributylchlorostannane (2.26 g, 6.95 mmol) was added to the reaction mixture. The mixture was stirred at 25° C. for 3 h. The reaction mixture was diluted with water (30 mL) and extracted with ethyl acetate (30 mL×3). The combined organic layer was washed with brine (30 mL), dried over anhydrous sodium sulfate and concentrated. The residue was purified by flash chromatography (ethyl acetate/petroleum ether=0-6%) to give (6-bromanyl-2-fluoranyl-pyridin-3-yl)-tributyl-stannane (800 mg, 37.09% yield) as yellow oil. 1HNMR (400 MHZ, DMSO-$d_6$) δ 8.06-7.57 (m, 1H), 7.58 (dd, J=7.2, 2.4 Hz, 1H), 2.36-1.93 (m, 12H), 1.77-1.22 (m, 6H), 0.57 (dd, J=82.9, 42.7 Hz, 9H).

Step 6: 2-(6-Bromanyl-2-fluoranyl-pyridin-3-yl)-1,3-benzothiazol-6-amine

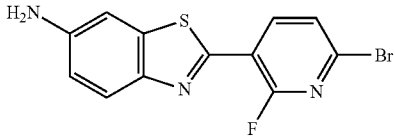 [SMILES: Nc1ccc2nc(-c3ccc(Br)nc3F)sc2c1]

A mixture of 2-bromanyl-1,3-benzothiazol-6-amine (150 mg, 0.65 mmol), (6-bromanyl-2-fluoranyl-pyridin-3-yl)-tributyl-stannane (319 mg, 0.68 mmol), copper (I) iodide (9 mg, 0.06 mmol), tetrakis(triphenyl phosphine)palladium(0) (75 mg, 0.06 mmol) and cesium fluoride (15.8 mg, 0.10 mmol) in N,N-dimethylformamide (15 mL) were stirred at 60° C. under nitrogen atmosphere overnight. The mixture was filtered and the filtrate was concentrated. The residue was diluted with ethyl acetate (100 mL), washed with brine and water, dried over with anhydrous sulfate, filtered and concentrated under reduced pressure. The residue was purified by flash column chromatography (methanol/dichloromethane=0~10%) to give 2-(6-bromanyl-2-fluoranyl-pyridin-3-yl)-1,3-benzo thiazol-6-amine (100 mg, 36.75% yield) as yellow solid. LC-MS: m/z=325 (M+H)+, retention time: 2.028 min (Method B).

Step 7: Tert-Butyl N-[5-[5-(6-azanyl-1,3-benzothiazol-2-yl)-6-fluoranyl-pyridin-2-yl]pyrimidin-2-yl]-N-methyl-carbamate

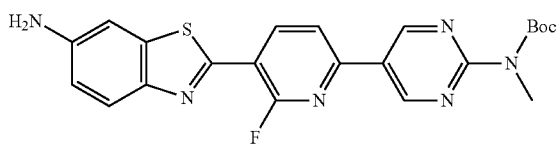 [SMILES: CN(C(=O)OC(C)(C)C)c1ncc(-c2ccc(-c3nc4ccc(N)cc4s3)c(F)n2)cn1]

A mixture of 2-(6-bromanyl-2-fluoranyl-pyridin-3-yl)-1,3-benzothiazol-6-amine (100 mg, 0.30 mmol), [2-[methyl-[(2-methylpropan-2-yl)oxycarbonyl]amino]pyrimidin-5-yl] boronic acid (117 mg, 0.46 mmol), tetrakis(triphenylphosphine)palladium(0) (35 mg, 0.03 mmol), potassium carbonate (127 mg, 0.92 mmol) in dioxane (12 mL) and water (4 mL) was heated at 80° C. for 16 h under nitrogen atmosphere. The reaction mixture was diluted with water (30 mL) and extracted with ethyl acetate (30 mL×3). The combined organic layer was washed with brine (30 mL), dried over anhydrous sodium sulfate and concentrated. The residue was purified by flash chromatography (ethyl acetate/petroleum ether=0-10%) to give tert-butyl N-[5-[5-(6-azanyl-1,3-benzothiazol-2-yl)-6-fluoranyl-pyridin-2-yl]pyrimidin-2-yl]-N-methyl-carbamate (40 mg, 28.65% yield) as yellow solid.

LCMS: m/z=453[M+H]+; $R_T$=2.026 min. (Method B)

Step 8: 2-[2-Fluoranyl-6-[2-(methylamino)pyrimidin-5-yl]pyridin-3-yl]-1,3-benzothiazol-6-amine

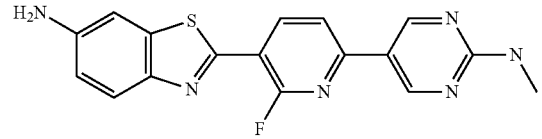

To a solution of tert-butyl N-[5-[5-(6-azanyl-1,3-benzothiazol-2-yl)-6-fluoranyl-pyridin-2-yl]pyrimidin-2-yl]-N-methyl-carbamate (40 mg, 0.08 mmol) in dichloromethane (5 mL) was added trifluoroacetic acid (5 mL) and then the mixture was stirred under reflux until the starting materials were consumed completely. The solvent was removed under reduced pressure and the residue was purified by Pre-HPLC to give 2-[2-fluoranyl-6-[2-(methylamino)pyrimidin-5-yl]pyridin-3-yl]-1,3-benzothiazol-6-amine (3 mg, 9.63% yield) as yellow solid. LC-MS: m/z=352 (M+H)+, purity 100% (UV 254), retention time: 3.360 min (Method B); $^1$H NMR (400 MHZ, DMSO-$d_6$) δ 9.05 (dd, J=76.2, 68.1 Hz, 2H), δ 8.79 (dd, J=76.2, 68.1 Hz, 1H), 8.03 (d, J=8.5 Hz, 1H), 7.87-7.72 (m, 2H), 7.14 (d, J=2.1 Hz, 1H), 6.86 (d, J=8.8 Hz, 1H), 5.62 (s, 2H), 2.89 (s, 6H).

Synthesis of Compound Z

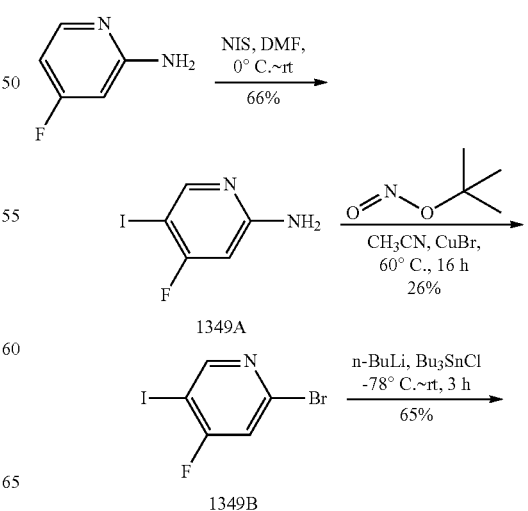

-continued

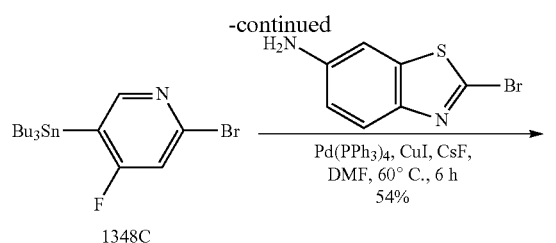

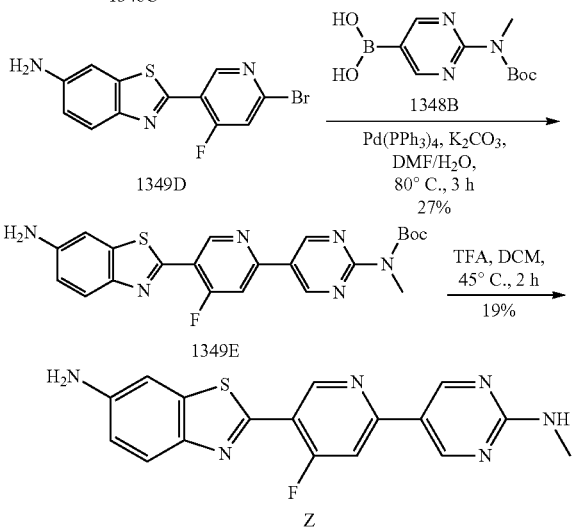

Step 1: 4-Fluoro-5-iodopyridin-2-amine

To a solution of 4-fluoranylpyridin-2-amine (500 mg, 4.46 mmol) in N,N-dimethylformamide (10 mL) was added N-iodosuccinimide (880 mg, 4.94 mmol) at 0° C. The mixture was stirred at 25° C. overnight and concentrated. The crude product was purified by flash chromatography (petroleum ether/ethyl acetate=3/1) to give 4-fluoranyl-5-iodanyl-pyridin-2-amine (700 mg, 2.9 mmol, 66% yield) as yellow solid. LC-MS: m/z=239 (M+H)+, purity 100% (UV 254 nm). Retention time: 1.70 min.

Step 2: 2-Bromo-4-fluoro-5-iodopyridine

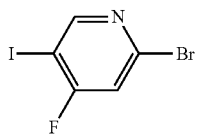

To a solution of 4-fluoranyl-5-iodanyl-pyridin-2-amine (500 mg, 2.1 mmol) in acetonitrile (15 mL) was added tert-butyl nitrite (1080 mg, 10.47 mmol) and copper (I) bromide (1490 mg, 10.5 mmol). The mixture was stirred at 60° C. for 16 h and concentrated. The crude product was purified by flash chromatography (petroleum ether/ethyl acetate=10/1) to give 2-bromanyl-4-fluoranyl-5-iodanyl-pyridine (180 mg, 0.5366 mmol, 25.54% yield) as yellow solid. LC-MS: no MS, purity 90% (UV 254 nm). Retention time 2.01 min

Step 3: 2-Bromo-4-fluoro-5-(tributylstannyl)pyridine

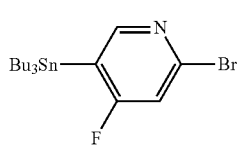

To a solution of 2-bromanyl-4-fluoranyl-5-iodanyl-pyridine (100 mg, 0.3300 mmol) in tetrahydrofuran (2 mL) was added n-butyl lithium (0.2 mL, 0.5000 mmol) at −78° C. The mixture was stirred at −78° C. for 15 min, then tributylchlorostannane (163.33 mg, 0.5000 mmol) was added to the reaction mixture, and the mixture was stirred at 25° C. for 3 h. The mixture was concentrated and the residue was purified by flash chromatography (petroleum ether/ethyl acetate=20/1) to give (6-bromanyl-4-fluoranyl-pyridin-3-yl)-tributyl-stannane (100 mg, 0.2150 mmol, 64.916% yield) as yellow oil. LC-MS: no MS. purity 90% (UV 254 nm). Retention time: 2.65 min

Step 4: 2-(6-Bromo-4-fluoropyridin-3-yl)benzo[d]thiazol-6-amine

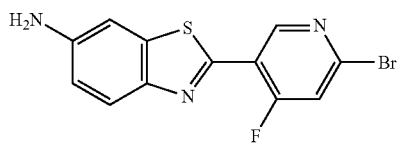 [SMILES: Nc1ccc2nc(-c3cnc(Br)cc3F)sc2c1]

To a solution of tetrakis(triphenylphosphine)palladium(0) (50 mg, 0.02 mmol) in N,N-dimethylformamide (5 mL) was added copper (I) iodide (4 mg, 0.03 mmol), cesium fluoride (4 mg, 0.0300 mmol), (6-bromanyl-4-fluoranyl-pyridin-3-yl)-tributyl-stannane (100 mg, 0.22 mmol) and 2-bromanyl-1,3-benzothiazol-6-amine (50 mg, 0.2200 mmol). The mixture was stirred at 60° C. for 6 h and cooled to room temperature. The mixture was filtered and the filtrate was concentrated. The crude product was purified by flash chromatography (petroleum ether/ethyl acetate=1/1) to give 2-(6-bromanyl-4-fluoranyl-pyridin-3-yl)-1,3-benzothiazol-6-amine (70 mg, 0.1188 mmol, 54.418% yield) as yellow solid. LC-MS: m/z=324 (M+H)+, purity 54% (UV 254 nm). Retention time: 1.81 min.

Step 5: Tert-Butyl 5-(5-(6-aminobenzo[d]thiazol-2-yl)-4-fluoropyridin-2-yl)pyrimidin-2-yl(methyl)carbamate

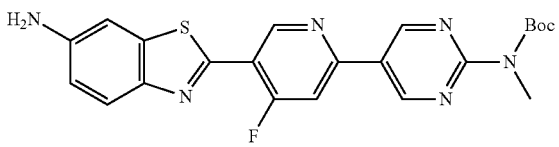

To a solution of 2-(6-bromanyl-4-fluoranyl-pyridin-3-yl)-1,3-benzothiazol-6-amine (40 mg, 0.1200 mmol) in N,N-dimethylformamide (4 mL) was added [2-[methyl-[(2-methylpropan-2-yl)oxycarbonyl]amino]pyrimidin-5-yl]boronic acid (46 mg, 0.1800 mmol), tetrakis(triphenylphosphine) palladium(0) (14 mg, 0.02 mmol) and potassium carbonate (50 mg, 0.3800 mmol). The mixture was stirred at 80° C. for 3 h and then cooled to room temperature. The mixture was filtered and the filtrate was concentrated. The crude product was purified by flash chromatography (petroleum ether/ethyl acetate=1/1) to give tert-butyl 5-(5-(6-aminobenzo[d]thiazol-2-yl)-4-fluoropyridin-2-yl)pyrimidin-2-yl(methyl)carbamate (15 mg, 0.03 mmol, 27% yield) as yellow solid. LC-MS: m/z=453 (M+H)+, purity 33% (UV 254 nm). Retention time: 2.01 min.

Step 6: 2-(4-Fluoro-6-(2-(methylamino)pyrimidin-5-yl)pyridin-3-yl)benzo[d]thiazol-6-amine

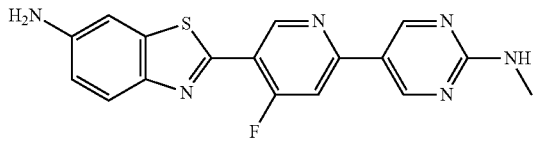

To a solution of tert-butyl N-[5-[5-(6-azanyl-1,3-benzothiazol-2-yl)-4-fluoranyl-pyridin-2-yl]pyrimidin-2-yl]-N-methyl-carbamate (15 mg, 0.0400 mmol) in dichloromethane (4 mL) was added trifluoroacetic acid (1 mL, 0.07 mmol). The mixture was stirred at 45° C. for 2 h and concentrated. The crude product was purified by flash chromatography (dichloromethane/methanol=20/1) to give 2-[4-fluoranyl-6-[2-(methylamino)pyrimidin-5-yl]pyridin-3-yl]-1,3-benzothiazol-6-amine (3 mg, 0.0083 mmol, 18.876% yield) as yellow solid. LC-MS: m/z=353 (M+H)+, purity 98% (UV 254 nm). Retention time: 3.35 min; 1HNMR (400 MHZ, DMSO-$d_6$) δ 9.34 (d, 1H), 9.10 (d, 2H), 8.08 (d, 1H), 7.79 (s, 1H), 7.70 (s, 1H), 7.14 (s, 1H), 6.86 (d, 1H), 5.64 (s, 2H), 2.89 (d, 3H).

Biological Experiments

Expression and Purification of Human Tau Protein
Materials:
  pET41a-Tau wild type
  One Shot® BL21(DE3) Chemically Competent *E. coli* (Invitrogen, C600003)
  Kanamycin sulfate (Sangon Biotech, A506636)
  IPTG (Sangon Biotech, A100487)
  Pipes buffer (100 mM Pipes, pH6.8, 1 mM EGTA, 1 mM MgSO4)
  Hepes buffer (25 mM Hepes, pH7.2, 0.1 mM EDTA, 0.5 mM DTT, 100 mM NaCl)
  Q-Sepharose Fast Flow column (GE Healthcare, 17-0510-01)
  SP-Sepharose Fast Flow column (GE Healthcare, 17-0729-01)
Procedures:
Protein Expression:
  Step 1: Transform 1 uL expression plasmid pET41a-tau wt into one One Shot® BL21(DE3) Chemically Competent *E. coli*, on ice 30 min.
  Step 2: 42° C. heat shock 90 second and on ice 2 min, 37° C. recovery for 30 min, Plate small amount on LB(Kan+) agar plate incubate overnight at 37° C.
  Step 3: Pick and resuspend a single colony in 200 mL liquid culture with 50 ug/mL Kanamycin to produce a starter culture. Inoculate starter culture and shake 200 rpm overnight at 37° C.
  Step 4: Add 100× dilution Starter into fresh culture medium (Kan+) shake 200 rpm at 37° C. until OD600=0.8.
  Step 5: Add IPTG (final conc. 1 mM) and express protein for 3 hr.
  Step 6: Collect cell pellet and store at −80° C. for purification.
Protein Purification:
  Step 1: Cell pellet was resuspended in Pipes buffer.
  Step 2: Sonication and centrifugation (15,000 rpm, 15 min at 4° C.
  Step 3: The supernatant was placed in a boiling water bath for 20 min and subsequently centrifuged. The heat-stable proteins in the supernatant were loaded onto a Q-Sepharose Fast Flow column (20 mL)
  Step 4: The flow through containing tau was loaded onto SP-Sepharose Fast Flow column (10 mL), eluted with Pipes buffer containing 0.2M NaCl.
  Step 6: Fractions containing tau were pooled, concentrated and dialyzed against Hepes buffer, stored at −80° C.
  Step 7: Reload SP-Flow through into Q-Sepharose Fast Flow column (20 mL) and SP-Sepharose Fast Flow column (10 mL) again, eluted with Pipes buffer containing 0.2M NaCl.
  Step 8: Fractions containing tau were pooled, concentrated and dialyzed against Hepes buffer, stored at −80° C. Repeat step 6-7 twice, Collect all above all elution product and concentrated.
Biological Assays
Fluorescence Quantitative Tau Binding Assay In Vitro 2 uM of recombinant tau proteins and 15 uM of heparin were fiberized in 30 mM Tris (pH 7.5) buffer by overnight incubation at 37° C. 0.04 uM of recombinant tau proteins which was diluted in 30 mM Tris buffer (pH 7.5) was then reacted with test compounds (containing 1% DMSO) for 1 h. Regarding the fluorometric data, the binding saturation curve was created and the parameter estimation method was conducted using Prism software (GraphPad). Kd values were determined for each of test compounds. Table A lists Kd values of exemplary test compounds.

TABLE A

| Compound No. | Quantitative Tau binding assay Kd (uM) |
|---|---|
| Compound A | 0.5 |
| Compound B | 0.99 |
| Compound C | 0.25 |
| Compound D | 0.69 |
| Compound E | 2.7 |
| Compound R | 1.82 |
| Compound S | 0.94 |
| Compound T | 2.51 |
| Compound F | 0.34 |
| Compound G | 0.28 |
| Compound H | 0.09 |
| Compound I | 0.8 |
| Compound J | 0.89 |
| Compound K | 3.5 |
| Compound V | 3.57 |
| Compound W | ND |
| Compound X | 0.17 |
| Compound Y | >10 |
| Compound Z | 1.45 |

TABLE A-continued

| Compound No. | Quantitative Tau binding assay Kd (uM) |
|---|---|
| Compound L | 0.54 |
| Compound M | 2.63 |
| Compound N | 0.26 |
| Compound O | 0.27 |
| Compound P | 0.37 |
| Compound U | 1.51 |
| Compound Q | 0.52 |

(ND: not determined)

Fluorescence Competitive Binding Assay In Vitro

Fluorescence competitive binding assay in vitro was performed as reported previously1. Frozen tissues derived from the temporal cortex of an Alzheimer's disease patient was homogenized in 50 mM Tris-HCl buffer, pH 7.4, containing protease inhibitor cocktail (cOmplete™, EDTA-free; Roche), and stored at −80° C. pending analyses. To assay radioligand binding with homologous or heterologous blockade, these homogenates (100 μg tissue) were incubated with 5 nM [11C]PBB3 (molar radioactivity: 100-150 GBq/μmol) in the absence or presence of unlabeled PBB3 at varying concentrations ranging from 10-11-106 M in Tris-HCl buffer containing 10% ethanol, pH 7.4, for 30 min at room temperature. Non-specific binding of [11C]PBB3 was determined in the presence of $5 \times 10^{-7}$ M PBB3. Samples were run once only and specific radioligand binding was determined as pmol/g tissue. Inhibition constant (Ki) and percentage of displacement were determined by using non-linear regression to fit a concentration-binding plot to one-site and two-site binding models derived from the Cheng-Prusoff equation with GraphPad Prism version 6.0 (GraphPad Software), followed by F-test for model selection. In a one-site homologous blockade model, dissociation constant (Kd) was calculated from homologous competitive binding using this function:

$$Kd = K_i = IC50 - Radioligand$$

where IC50 and [Radioligand] stand for the concentration of the competitor inducing 50% inhibition and radioligand concentration, respectively. Experiments with [$^{11}$C]PBB3 and unlabeled PBB3 were performed in a dimly lit condition to avoid photoconversion of the compounds. Table B lists Ki values of exemplary test compounds.

TABLE B

| Compound No. | In vitro binding assay Ki (uM) |
|---|---|
| Compound A | 0.045 |
| Compound B | 0.002 |
| Compound C | 0.025 |
| Compound D | 0.001 |
| Compound E | 0.005 |
| Compound R | 0.015 |
| Compound S | 0.015 |
| Compound T | 0.14 |
| Compound F | ND |
| Compound G | 0.01 |
| Compound H | ND |
| Compound I | 0.005 |
| Compound J | 0.005 |
| Compound K | ND |
| Compound V | 0.0075 |
| Compound W | 0.005 |
| Compound X | ND |
| Compound Y | ND |
| Compound Z | 0.005 |
| Compound L | 0.005 |

TABLE B-continued

| Compound No. | In vitro binding assay Ki (uM) |
|---|---|
| Compound M | 0.015 |
| Compound N | 0.02 |
| Compound O | 0.01 |
| Compound P | 0.045 |
| Compound U | ND |
| Compound Q | 0.005 |

(ND: not determined)

Histological Examination by Fluorescence Staining

The fluorescence binding assessment was performed as reported previously[1]. For fluorescence labeling with PBB3 and test compounds, deparaffinized temporal cortex sections of an AD brain were incubated in 50% ethanol containing 0.001% (W/V) of PBB3 or test compound at room temperature for 30 min. The samples were rinsed with 50% ethanol for 5 min, dipped into distilled water twice for 3 min, and mounted in non-fluorescent mounting media (VECTASHIELD; Vector Laboratories). Fluorescence images were captured using a DM4000 microscope (Leica) equipped with a custom filter cube for PBB3 (excitation band-pass at 391-437 nm and suppression low-pass with 458 nm cutoff). In the fluorescence binding assessment, the reactivity of compounds with tau aggregates was semiquantitatively evaluated as '0' (no labeling), '1' (faint labeling), '2' (weaker than PBB3), and '3' (equivalent to or greater than PBB3). '0.5' score describes a middle-grounded condition of two integer scores 0 and 1. '1.5' score describes a middle-grounded condition of two integer scores 1 and 2. '2.5' score describes a middle-grounded condition of two integer scores 2 and 3. Table C lists scores of exemplary test compounds.

TABLE C

| Compound No. | Fluorescent binding Tangle/Thread |
|---|---|
| Compound A | 2/2 |
| Compound B | 3/3 |
| Compound C | 2/1.5 |
| Compound D | 3/3 |
| Compound E | 3/3 |
| Compound R | 3/3 |
| Compound S | 3/3 |
| Compound T | 2.5/2.5 |
| Compound F | ND |
| Compound G | 2/0.5 |
| Compound H | ND |
| Compound I | 2/1.5 |
| Compound J | 3/3 |
| Compound K | ND |
| Compound V | 2.5/2.5 |
| Compound W | 3/3 |
| Compound X | ND |
| Compound Y | ND |
| Compound Z | 3/3 |
| Compound L | 2.5/1.5 |
| Compound M | 2.5/2 |
| Compound N | 0.5/0 |
| Compound O | 1.5/1.5 |
| Compound P | 1/0 |
| Compound U | ND |
| Compound Q | 1/0.5 |

(ND: not determined)

Live Two-Photon Imaging in Awake Animals

Live imaging in awake animals was performed by two-photon laser scanning microscopy as reported previously[2].

Figure 2:
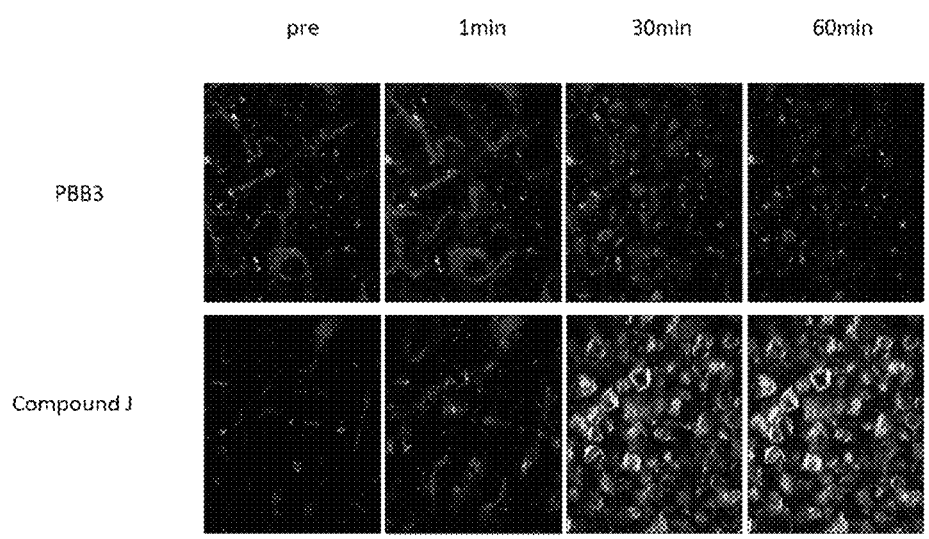
FIG. 2 are the images generated in rTg4510 mice using two photon imaging for compound J in comparison with PBB3 (top) as well as the quantification of green fluorescence signaling over time (bottom).

For the placement of a cranial window, rTg4510 tau transgenic mice[3] at 6-13 months of age were anesthetized with a mixture of air, oxygen, and isoflurane (3-5% for induction and 2% for surgery) via a facemask, and a cranial window (3-4 mm in diameter) was placed over the left somatosensory cortex, centered at 1.8 mm caudal and 2.5 mm lateral to the bregma, according to 'Seylaz-Tomita method'[4]. A custom metal plate was affixed to the skull with a 7-mm-diameter hole centered over the cranial window. The method for preparing the chronic cranial window was previously reported in detail by Takuwa et al.[5]. All imaging experiments were performed at least two weeks after the creation of the cranial window. Vessels and pathological tau inclusions were fluorescently labeled with a sulforhodamine 101 (SR101; MP Biomedicals, Irvine, CA) and either PBB3 or test compounds, respectively. SR101 was dissolved in saline to 5 mM, and either PBB3 or test compounds was dissolved in DMSO (Wako):Saline=1:1 solution to 0.05% (W/V). 100 μL of both solutions were injected intraperitoneally to the mice just right before initiation of the imaging experiments. Noted that experiments of the same experimental set (consisted of test-compounds and PBB3 experiments, respectively) were conducted sequentially with a roughly one-week-long interval on the same rTg4510 tau transgenic mouse. For imaging sessions, the awake animal was placed on a custom-made apparatus as previously described[5]. Briefly, the metal plate on the animal's head was screwed to a custom-made stereotactic apparatus, and the animal was then placed on a styrofoam ball that was floating using a stream of air, allowing the animal to exercise freely on the ball while the animal's head was fixed to the apparatus. After head fixing, real-time imaging was conducted by a two-photon laser scanning microscopy (TCS-SP5 MP, Leica Microsystems GmbH, Wetzlar, Germany) with an excitation wavelength of 900 nm. Emission signals were separated by a beam splitter (560/10 nm) and simultaneously detected with band-pass filters for SR101 (610/75 nm) and PBB3 (525/50 nm). A single image plane consisted of 1024×1024 pixels, and in-plane pixel size was 0.45 μm. Volume images were acquired with a maximum depth of 0.3-0.5 mm from the cortical surface with a z-step size of 2.5 μm. For each set of experiments conducted in the same rTg4510 tau transgenic mice, a reference image plane showing abundant and clear fluorescence-labeled tau pathologies was assigned accordingly based on the result of the control (PBB3) experiment and its equivalents in all related experiments were also extracted from the original volume image sets, respectively, for comparison. In each resultative images, fluorescence intensity from 10 randomly selected fluorescence-labeled pathologies were measured by ImageJ and the average was calculated after background normalization. Noted that the background intensity of each image was acquired by averaging the fluorescence intensity at 10 randomly selected areas where no fluorescence-labeled pathologies were found. FIG. 1 shows the results of two-photon laser fluorescence microscopy for compound J and compound W in comparison with PBB3. FIG. 2 shows the images generated in rTg4510 mice using two photon imaging for compound J in comparison with PBB3 (top), and the quantification of green fluorescence signaling over time (bottom).

REFERENCES

1. Ono M, Sahara N, Kumata K, et al. Distinct binding of PET ligands PBB3 and AV-1451 to tau fibril strains in neurodegenerative tauopathies. *Brain*. 2017; 140(3): 764-780. doi: 10.1093/brain/aww339
2. Maruyama M, Shimada H, Suhara T, et al. Imaging of Tau Pathology in a Tauopathy Mouse Model and in Alzheimer Patients Compared to Normal Controls. *Neuron*. 2013; 79(6): 1094-1108. doi: 10.1016/J.NEURON.2013.07.037
3. Santacruz K, Lewis J, Spires T, et al. Tau suppression in a neurodegenerative mouse model improves memory function. *Science*. 2005; 309(5733):476-481. doi: 10.1126/science.1113694
4. Tomita Y, Kubis N, Calando Y, et al. Long-Term in Vivo Investigation of Mouse Cerebral Microcirculation by Fluorescence Confocal Microscopy in the Area of Focal Ischemia. *J Cereb Blood Flow Metab*. 2005; 25(7): 858-867. doi:10.1038/sj.jcbfm.9600077
5. Takuwa H, Tajima Y, Kokuryo D, et al. Hemodynamic changes during neural deactivation in awake mice: A measurement by laser-Doppler flowmetry in crossed cerebellar diaschisis. *Brain Res*. 2013; 1537:350-355. doi: 10.1016/J.BRAINRES.2013.09.023

What is claimed is:

1. A heteroaryl compound having a structure of formula (I), or a pharmaceutically acceptable salt, a solvate, a hydrate, an isotopically labeled derivative or a radiolabeled derivative thereof,

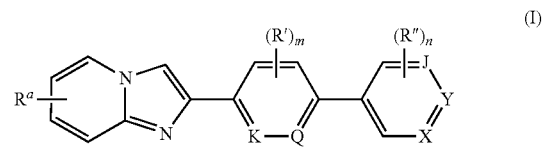

wherein,
$R^a$ is selected from the group consisting of

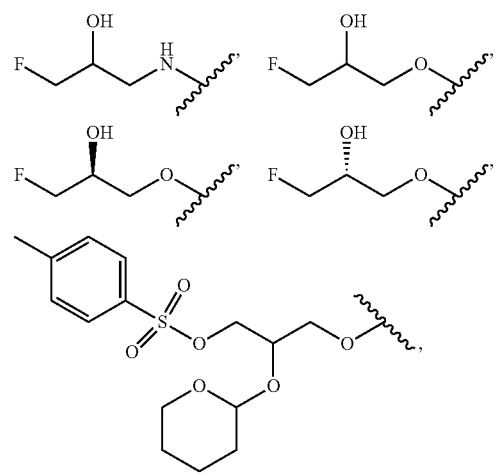

H, OH, halogen, $C_{1-3}$ alkyl, $C_{1-3}$ alkoxy, $NH_2$, $C_{1-3}$ alkylamino and $C_{1-6}$ alkoxycarbonyl, wherein said $C_{1-3}$ alkyl, said $C_{1-3}$ alkoxy, said $C_{1-3}$ alkylamino, and said $C_{1-6}$ alkoxycarbonyl are optionally substituted with OH, halogen, $C_{2-6}$ heterocycloalkyloxy or toluenesulfonyloxy;
Q is CH or N;
X is CH and Y is N, or X is N and Y is $CR^6$;
$R^6$ is selected from the group consisting of H, $NH_2$ and $C_{1-6}$ alkoxy; wherein said $NH_2$ is optionally substituted with $C_{1-3}$ alkyl, and said $C_{1-6}$ alkoxy is optionally substituted with $C_{1-3}$ alkyl or halogen;
J is CH or N;
K is CH or N; and
provided that J and Y are not N simultaneously;
R' is halogen, OH, $C_{1-6}$ alkyl, or $C_{1-6}$ alkoxy;
R" is Br, I, OH, $NH_2$,

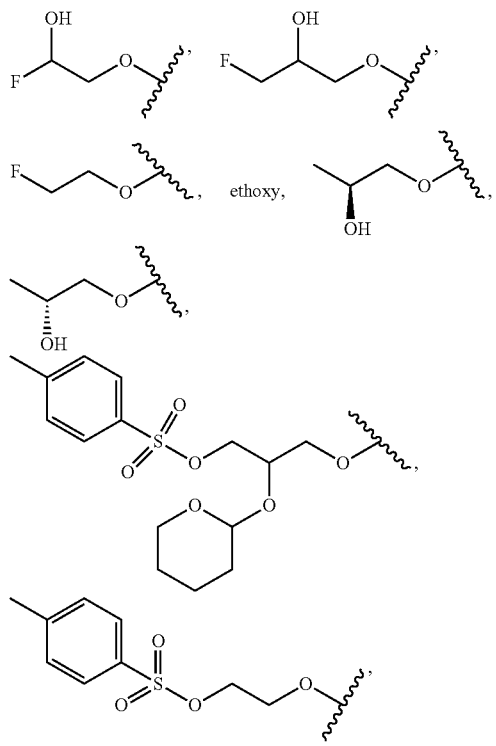

$C_{1-6}$ alkylamino or $C_{3-6}$ heterocycloalkyl; wherein said $C_{1-6}$ alkylamino and said $C_{3-6}$ heterocycloalkyl are optionally substituted with a substituent selected from the group consisting of oxo, OH, halogen, $C_{3-6}$ cycloalkyl, $C_{1-4}$ alkoxy carbonyl, $C_{3-6}$ heterocycloalkyloxy, toluenesulfonyloxy, and phenyl which is further optionally substituted with OH and/or $C_{1-3}$ alkoxy;
m is 0, 1, 2; and
n is 0, 1, or 2;
provided that:
when Y is N or CH, then n is 1 or 2; and
when Y is $CR^6$, wherein $R^6$ is $NH_2$ or $C_{1-6}$ alkoxy, and wherein said $NH_2$ is optionally substituted with $C_{1-3}$ alkyl, and said $C_{1-6}$ alkoxy is optionally substituted with $C_{1-3}$ alkyl or halogen, then n is 0.

2. The heteroaryl compound having a structure of formula (I), or a pharmaceutically acceptable salt, a solvate, a hydrate, an isotopically labeled derivative or a radiolabeled derivative thereof according to claim 1, wherein the moiety of

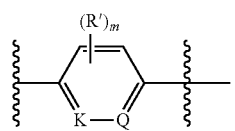

is selected from the group consisting of

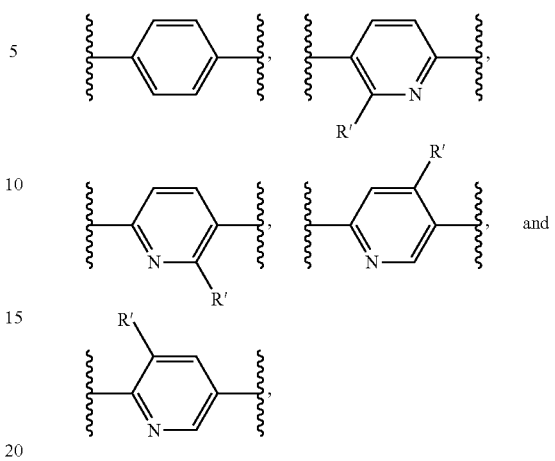

and wherein R' is H or F.

3. The heteroaryl compound having a structure of formula (I), or a pharmaceutically acceptable salt, a solvate, a hydrate, an isotopically labeled derivative or a radiolabeled derivative thereof according to claim 1, which is of the structure of formula (II),

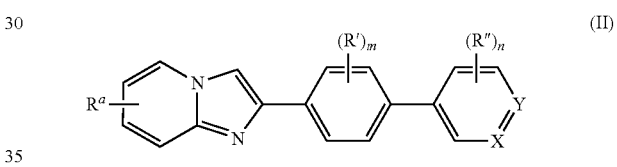

(II)

wherein, X is CH and Y is N, or X is N and Y is CH.

4. The heteroaryl compound having a structure of formula (I), or a pharmaceutically acceptable salt, a solvate, a hydrate, an isotopically labeled derivative or a radiolabeled derivative thereof according to claim 3, wherein,
$R^a$ is selected from the group consisting of H, OH, F, methoxy, ethoxy, $NH_2$,

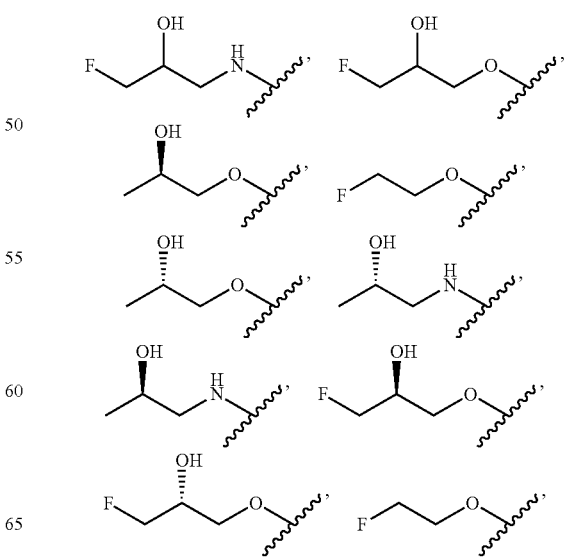

-continued

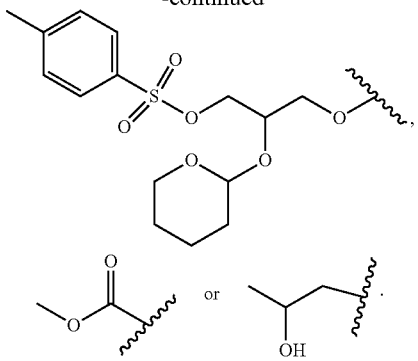

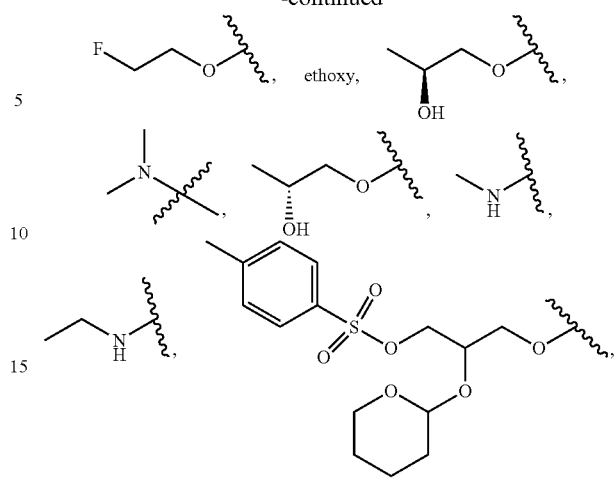

5. The heteroaryl compound having a structure of formula (I), or a pharmaceutically acceptable salt, a solvate, a hydrate, an isotopically labeled derivative or a radiolabeled derivative thereof according to claim 3, wherein,
$R^a$ is

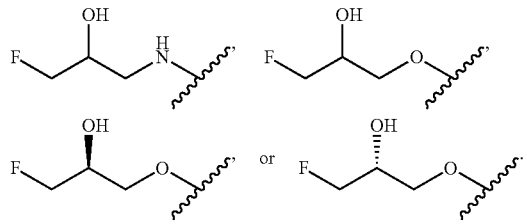

6. The heteroaryl compound having a structure of formula (I), or a pharmaceutically acceptable salt, a solvate, a hydrate, an isotopically labeled derivative or a radiolabeled derivative thereof according to claim 1, wherein
R' is F, OH, methyl or methoxy;
and/or, R" is OH, NH$_2$, methyl,

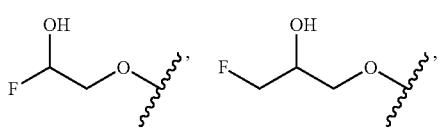

7. A heteroaryl compound having a structure of formula (I), or a pharmaceutically acceptable salt, a solvate, a hydrate, an isotopically labeled derivative or a radiolabeled derivative thereof, which is selected from the group consisting of

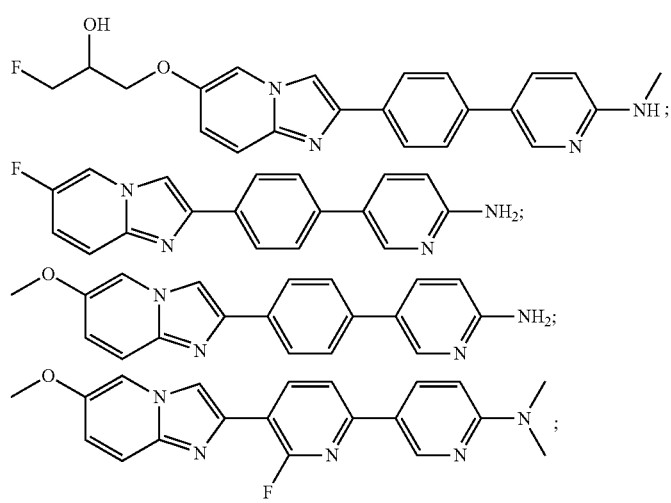

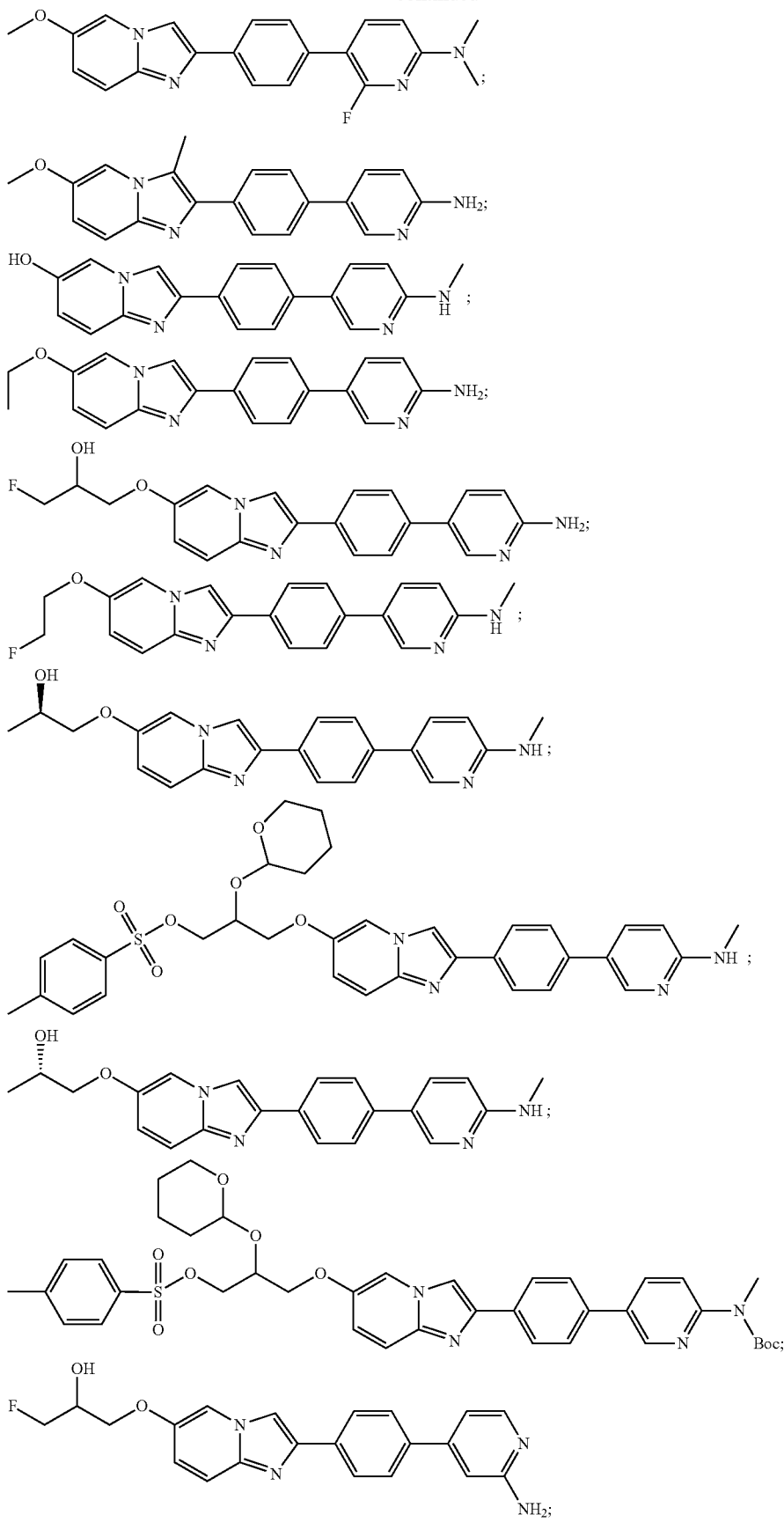

-continued
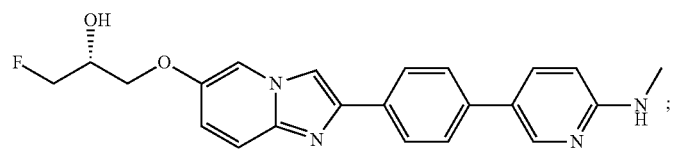
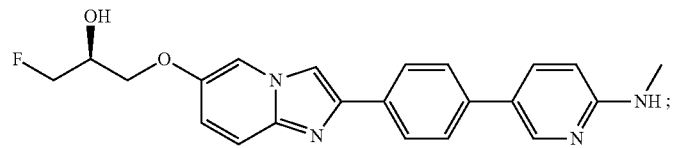
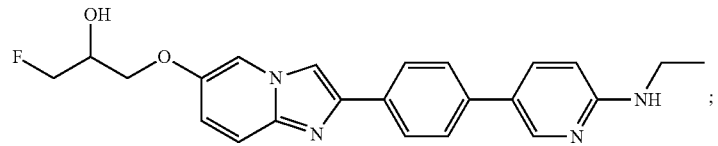
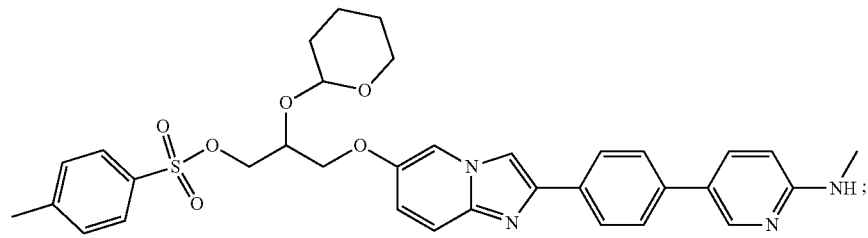
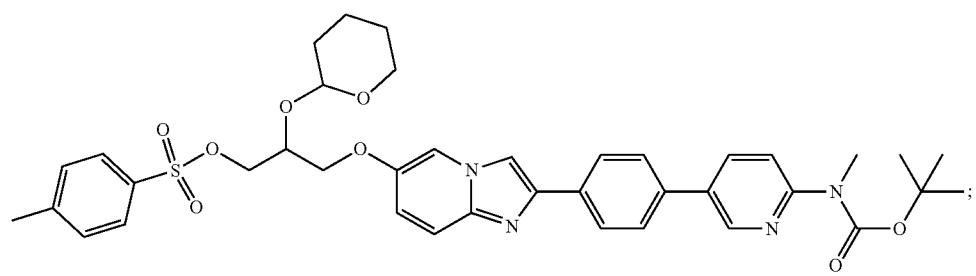
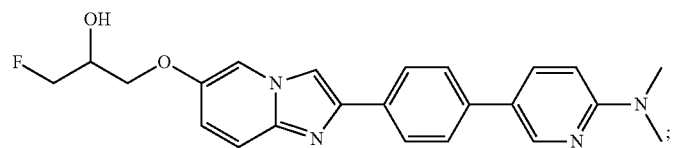
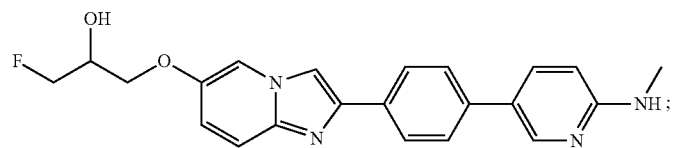
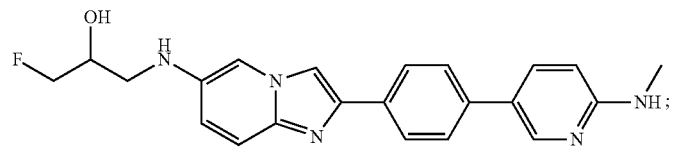
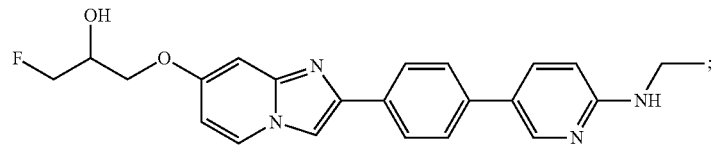
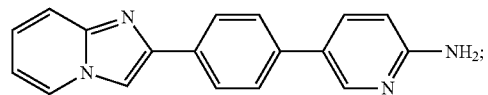

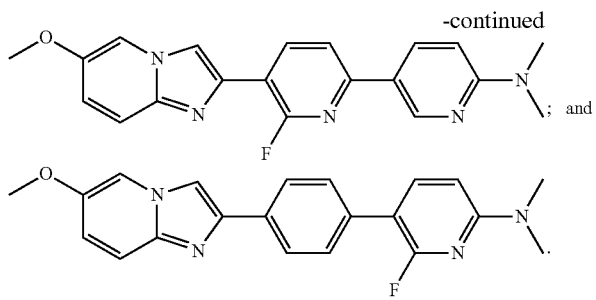
; and

8. A process for preparing the heteroaryl compound having a structure of formula (I), or a pharmaceutically acceptable salt, a solvate, a hydrate, an isotopically labeled derivative or a radiolabeled derivative thereof according to claim 1,
the process comprising the steps of
i) reacting compound 32 with compound 33 to form compound 34 in an alcoholic solvent and in the presence of a base at 80° C.;
ii) reacting the compound 34 obtained from step i) with compound 30 in an organic solvent and in the presence of a base and a Pd catalyst at 80° C.;

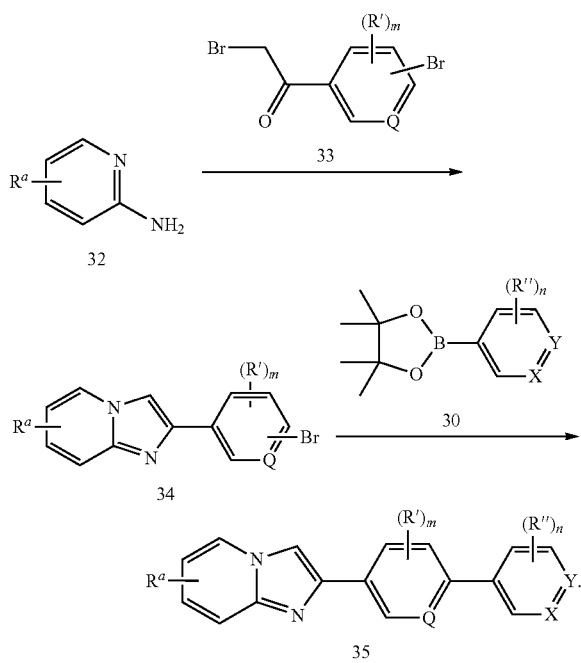

9. The process according to claim 8, wherein
the process comprises the steps of
i) reacting compound 32 with compound 33 to form compound 34 in EtOH and in the presence of NaHCO$_3$ at 80° C.;
ii) reacting the compound 34 obtained from step i) with compound 30 in DMF and in the presence of K$_2$CO$_3$ and Pd(PPh$_3$)$_4$ at 80° C.

10. A pharmaceutical composition comprising heteroaryl compound having a structure of formula (I), or pharmaceutically acceptable salt, solvate, hydrate, isotopically labeled derivative or radiolabeled derivative thereof according to claim 1, and optionally a pharmaceutically acceptable excipient.

11. The heteroaryl compound having a structure of formula (I), or a pharmaceutically acceptable salt, a solvate, a hydrate, an isotopically labeled derivative or a radiolabeled derivative thereof according to claim 1, wherein K is CH, Q is N, m is 0, X is N, Y is CR$^6$, and R$^6$ is —NH$_2$ optionally substituted with one or more C$_{1-3}$ alkyl.

12. The heteroaryl compound having a structure of formula (I), or a pharmaceutically acceptable salt, a solvate, a hydrate, an isotopically labeled derivative or a radiolabeled derivative thereof according to claim 11, wherein R$^a$ is C$_{1-3}$ alkoxy substituted with halogen.

13. An isotopically labeled derivative of the heteroaryl compound having a structure of formula (I), or the pharmaceutically acceptable salt, the solvate, or the hydrate thereof, according to claim 12.

14. An isotopically labeled derivative of the heteroaryl compound having a structure of formula (I), or the pharmaceutically acceptable salt, the solvate, or the hydrate thereof, according to claim 1.

* * * * *